(12) United States Patent
Pietersz et al.

(10) Patent No.: US 10,344,261 B2
(45) Date of Patent: Jul. 9, 2019

(54) IMMUNOMODULATORY CONJUGATES

(71) Applicant: ASCEND BIOPHARMACEUTICALS LTD, South Melbourne, Victoria (AU)

(72) Inventors: Geoffrey Alan Pietersz, Greensborough (AU); Clement Leong, Malvern (AU)

(73) Assignee: ASCEND BIOPHARMACEUTICALS LTD, South Melbourne (AU)

(*) Notice: Subject to any disclaimer, the term of this patent is extended or adjusted under 35 U.S.C. 154(b) by 1099 days.

(21) Appl. No.: 14/357,520

(22) PCT Filed: Nov. 9, 2012

(86) PCT No.: PCT/AU2012/001387
§ 371 (c)(1),
(2) Date: Oct. 9, 2014

(87) PCT Pub. No.: WO2013/067597
PCT Pub. Date: May 16, 2013

(65) Prior Publication Data
US 2015/0030626 A1  Jan. 29, 2015

(30) Foreign Application Priority Data

Nov. 9, 2011 (AU) ............................. 2011904656

(51) Int. Cl.
| | | |
|---|---|---|
| *A61K 39/395* | (2006.01) | |
| *C12N 5/0784* | (2010.01) | |
| *C07D 471/04* | (2006.01) | |
| *C07D 473/18* | (2006.01) | |
| *C07D 487/04* | (2006.01) | |
| *C07D 493/04* | (2006.01) | |
| *C08B 37/00* | (2006.01) | |
| *A61K 31/4745* | (2006.01) | |
| *A61K 31/522* | (2006.01) | |
| *C12N 5/0783* | (2010.01) | |
| *C12N 5/0786* | (2010.01) | |
| *A61K 47/60* | (2017.01) | |
| *A61K 47/61* | (2017.01) | |

(52) U.S. Cl.
CPC ........ *C12N 5/0639* (2013.01); *A61K 31/4745* (2013.01); *A61K 31/522* (2013.01); *A61K 47/60* (2017.08); *A61K 47/61* (2017.08); *C07D 471/04* (2013.01); *C07D 473/18* (2013.01); *C07D 487/04* (2013.01); *C07D 493/04* (2013.01); *C08B 37/0006* (2013.01); *C12N 5/0638* (2013.01); *C12N 5/0645* (2013.01); *C12N 2501/90* (2013.01); *Y02A 50/409* (2018.01); *Y02A 50/411* (2018.01)

(58) Field of Classification Search
None
See application file for complete search history.

(56) References Cited

U.S. PATENT DOCUMENTS

| | | | | |
|---|---|---|---|---|
| 2010/0008951 A1* | 1/2010 | Pietersz | ............... | A61K 31/715 424/209.1 |
| 2010/0092425 A1 | 4/2010 | von Andrian et al. | | |

FOREIGN PATENT DOCUMENTS

| | | |
|---|---|---|
| AU | 2001263653 B2 | 12/2001 |
| CA | 2582662 * | 10/2005 |
| WO | WO 95/18145 A1 | 7/1995 |
| WO | WO 95/34325 | 12/1995 |
| WO | WO 99/16455 A1 | 4/1999 |
| WO | WO 99/17783 A1 | 4/1999 |
| WO | WO 2005/047507 A1 | 5/2005 |
| WO | WO2006003014 * | 1/2006 |
| WO | WO 2007/100634 A2 | 9/2007 |
| WO | WO 2007/149802 A2 | 12/2007 |
| WO | WO 2008/011672 A1 | 1/2008 |
| WO | WO 2008/079924 A1 | 7/2008 |
| WO | WO 2011/140595 A2 | 11/2011 |

OTHER PUBLICATIONS

Jan. 12, 2016 Extended European European Search Report issued by the European patent Office (EPO) in connection with European Application No. 12847434.3.
Dziadek et al. (2008), "A Novel Linker Methodology for the Synthesis of Tailored Conjugate Vaccines Composed of Complex Carbohydrate Antigens and Specific $T_H$-Cell Peptide Epitopes", *Chem. Eur. J.*, 14(19), 5908-5917.
Lipinski et al. (2011), "Synthesis and Immunogenicity of a Glycopolymer Conjugate", *Bioconjugate Chem.*, 22(2), 274-281.
Paulovičová et al. (2010), "Model α-Mannoside Conjugates: Immunogenicity and Induction of Candidacidal Activity", *FEM Immunol Med. Microbiol.*, 58(3), 307-313.
Petrushina et al. (2008), "Mannan-Abeta$_{28}$ Conjugate Prevents Abeta-plaque Deposition, but Increases Microhemorrhages in the Brains of Vaccinated Tg2576 (APPsw) Mice", *J. Neuroinflamm.*, 5(1), 42.
Michon et al, (2006), "Group B Streptococcal Type II and III Conjugate Vaccines: Physicochemical Properties That Influence Immunogenicity", *Clin. Vaccine Immunol.*, 13(8), 936-943.
Paulovičová et al. (2005), "Immune Response to *Saccharomyces cerevisiae* Mennen Conjugate in Mice", *Int. Immunopharmacol.*, 5(12), 1693-1698.
Wu et al. (2005), "Synthesis of Glycoconjugate Vaccines for *Candida albicans* Using Novel Linker Methodology", *J. Org. Chem.*, 70(18), 7381-7388.

(Continued)

*Primary Examiner* — Yunsoo Kim
(74) *Attorney, Agent, or Firm* — John P. White; Cooper & Dunham LLP

(57) ABSTRACT

The present invention provides an immunomodulatory compound comprising a carbohydrate polymer comprising mannose, wherein the carbohydrate polymer is conjugated to at least one immune modulator. The present invention also provides for the use of this compound in immunomodulatory compositions for vaccination and gene therapy methods, together with processes for its preparation.

28 Claims, 61 Drawing Sheets

Figure 1:
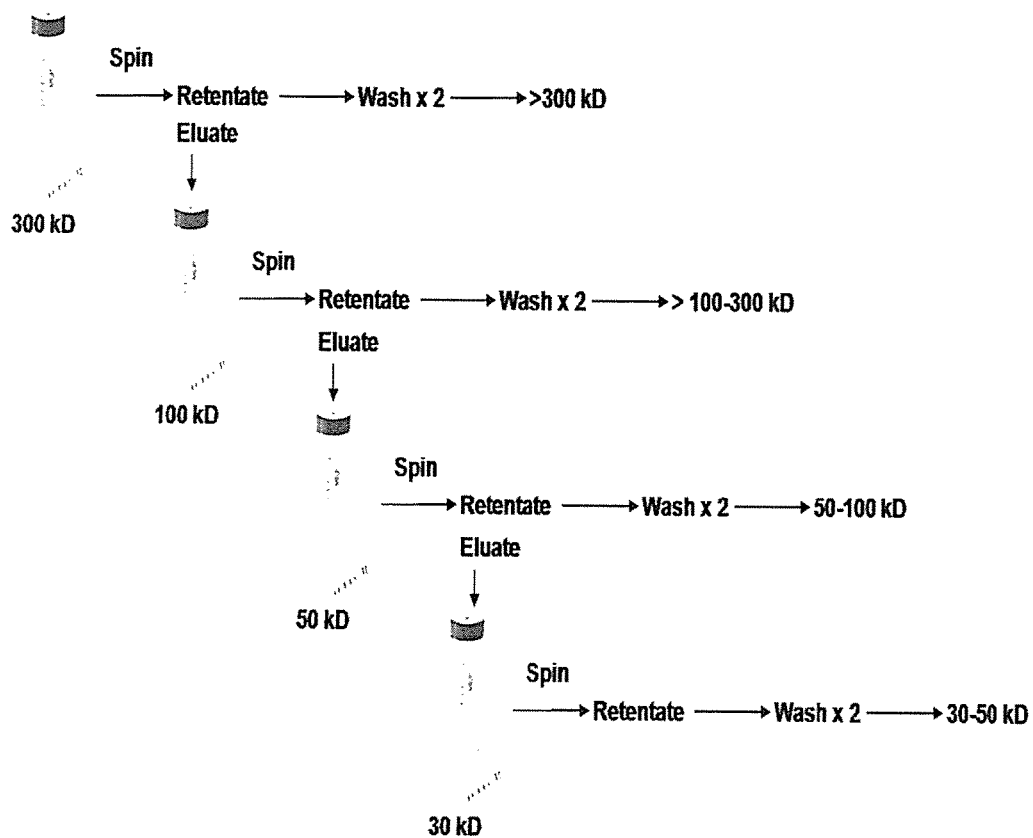

Specification includes a Sequence Listing.

(56) References Cited

OTHER PUBLICATIONS

Katsara et al. (2009), "Altered Peptide Ligands of Myelin Basic Protein ($MBP_{87-99}$) Conjugated to Reduced Mannan Modulate Immune Responses in Mice", *Immunology*, 128(4), 521-533.
Han et al. (1999), "*Candida albicans* Mannan Extract—Protein Conjugates Induce a Protective Immune Response against Experimental Candidiasis", *J. Infect. Dis.*, 179(6), 1477-1484.
Apostolopoulos, V. et al. (1995). Oxidative/reductive conjugation of mannan to antigen selects for $T_1$ or $T_2$ immune responses. *Proceedings of the National Academy of Sciences of the United States of America*, 92, 10128-10132.
Stambas, J. et al, (2002). Oxidised mannan as a novel adjuvant inducing mucosal IgA production. *Vaccine*, 20, 1068-1078.
Basith, S. et al. (2011). Toll-like receptor modulators: a patent review (2006-2010). *Expert Opinion on Therapeutic Patents*, 21(6), 927-944.
International Search Report, dated Feb. 18, 2013 in connection with PCT International Application No. PCT/AU2012/001387, filed Nov. 9, 2012.
Written Opinion of the International Searching Authority, dated Feb. 18, 2013 in connection with PCT International Application No. PCT/AU2012/001387, filed Nov. 9, 2012.
Spoljar, B.H.; et al, "A novel ELISA for determination of polysaccharide specific immunoglobulins", Vaccine, 2001, vol. 19, 7-8, pp. 924-930.
Tomasic, J., et al, "Preparation of Novel Conjugates Involving Immunmodulating Peptidoglycan Monomer", Preparative Biochemistry & Biotechnology, 1999, vol. 29, 4, pp. 385-401.

\* cited by examiner

Product Name    Mannan from Saccharomyces cerevisiae, powder
Product Number  M7504
Product Brand   SIGMA
CAS Number      9036-88-8

| TEST | SPECIFICATION | LOT 048K3810 RESULTS |
|---|---|---|
| APPEARANCE | WHITE TO LIGHT YELLOW WITH A BROWN CAST POWDER | LIGHT YELLOW POWDER |
| SOLUBILITY | CLEAR TO SLIGHTLY HAZY YELLOW TO TAN SOLUTION AT 50MG/ML IN WATER | SLIGHTLY HAZY LIGHT YELL |
| CARBON | REPORT RESULT | 40.3% (39.7%) |
| PHOSPHORUS | REPORT RESULT | 0.6% (0.5%, 0.2%) |
| SODIUM | REPORT RESULT | 0.9% (0.7%, 0.67%, 2.3%) |
| SPECIFIC ROTATION | +73 TO +82DEG (C=1 IN WATER) | +76 DEG (+80, 75.7, 78.5, 74) |
| THIN LAYER CHROMATOGRAPHY | NO LOW MOLECULAR WEIGHT SACCHARIDES DETECTED | CONFORMS |
| RECOMMENDED RETEST | 2 YEARS | MAY 2010 |
| QC RELEASE DATE |  | MAY 2008 |

Figure 18

- Batch no & size          no. of residues
                                  <u>1.</u>    <u>2.</u>    <u>3.</u>

- 102K3778 large              153    129    125
- 102K37781 large             148    128    131
- 92H3876 small               101    100    106
- 92H3876 medium              -      97     98
- 16H3843 medium              -      92     100

Figure 20

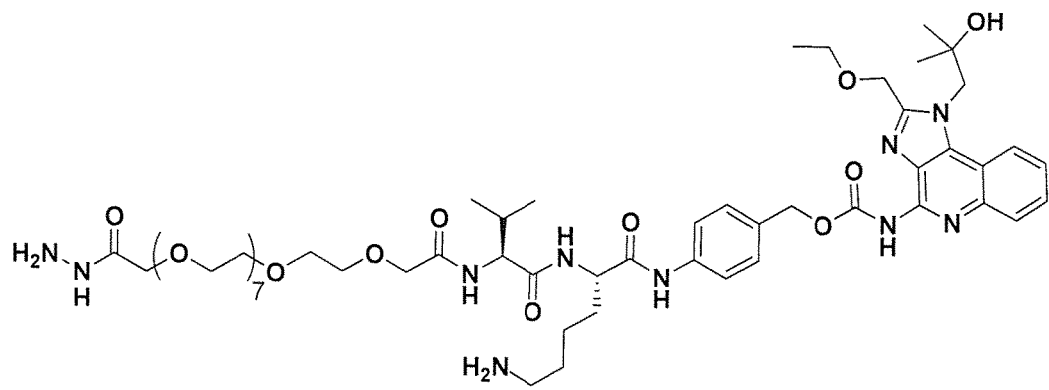
Chemical Formula: $C_{56}H_{88}N_{10}O_{17}$
Molecular Weight: 1173.35
derivative 1
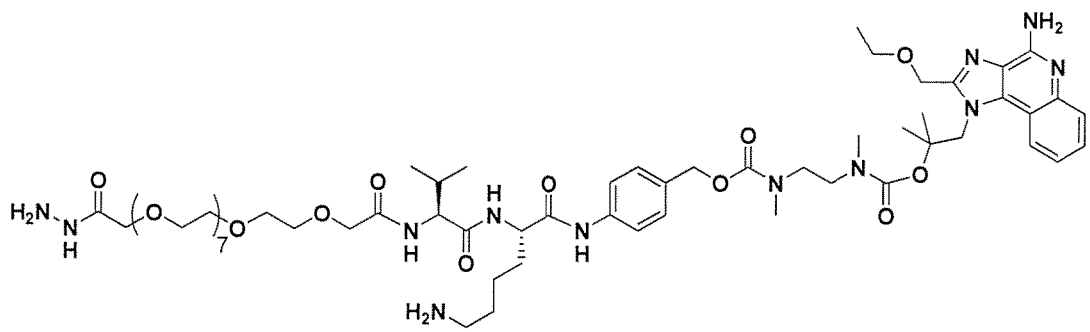
Chemical Formula: $C_{61}H_{98}N_{12}O_{18}$
Molecular Weight: 1287.50
derivative 2
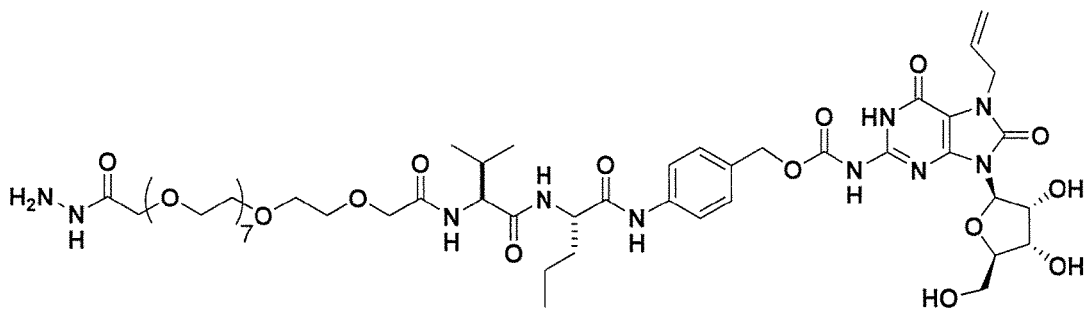
Chemical Formula: $C_{51}H_{80}N_{10}O_{21}$
Molecular Weight: 1169.24
derivative 3
Figure 30A

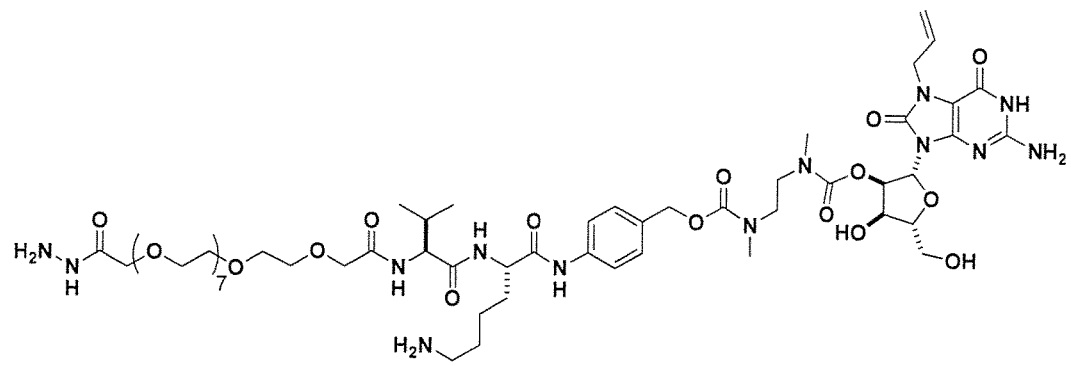
Chemical Formula: $C_{57}H_{93}N_{13}O_{22}$
Molecular Weight: 1312.42
derivative 4
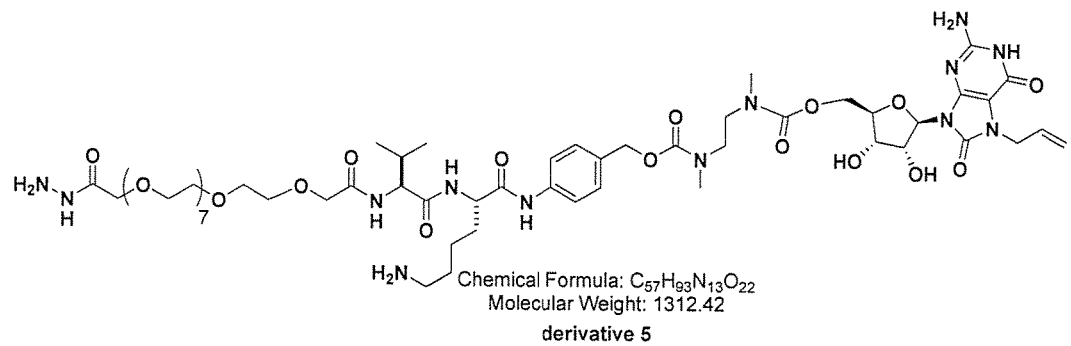
Chemical Formula: $C_{57}H_{93}N_{13}O_{22}$
Molecular Weight: 1312.42
derivative 5
Figure 30B

SEQUENCE LISTING

```
<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: peptide

<400> SEQUENCE: 1

Glu Ala Ala Gly Ile Gly Ile Leu Thr Val
1               5                   10

<210> SEQ ID NO 2
<211> LENGTH: 10
<212> TYPE: PRT
<213> ORGANISM: Artificial Sequence
<220> FEATURE:
<223> OTHER INFORMATION: peptide

<400> SEQUENCE: 2

Glu Leu Ala Gly Ile Gly Ile Leu Thr Val
1               5                   10
```

IMMUNOMODULATORY CONJUGATES

CROSS-REFERENCE TO RELATED APPLICATIONS

This application is a § 371 national stage of PCT International Application No. PCT/AU2012/001387, filed Nov. 9, 2012, claiming priority of Australian Patent Application No. 2011904656, filed Nov. 9, 2011, the contents of each of which are hereby incorporated by reference in their entirety.

REFERENCE TO SEQUENCE LISTING

This application incorporates-by-reference nucleotide and/or amino acid sequences which are present in the file named "140509_2251_86459 Substitute_Sequence_Listing_BI.txt," which is 683 bytes in size, and which was created May 7, 2014 in the IBM-PC machine format, having an operating system compatibility with MS-Windows, which is contained in the text file filed May 9, 2014 as part of this application.

FIELD OF THE INVENTION

The present invention relates to carbohydrate polymers comprising mannose conjugated to at least one immune modulator, their preparation and use in immunomodulatory and vaccine compositions.

BACKGROUND OF THE INVENTION

There has been a major effort in recent years to discover new drug compounds that act by stimulating certain key aspects of the immune system, as well as by suppressing certain other aspects. These compounds, referred to herein as immune modulators, may be useful for treating a wide variety of diseases and conditions. For example, certain immune modulators may be useful for treating viral diseases (e.g., human papilloma virus, hepatitis, herpes), neoplasias (e.g., basal cell carcinoma, squamous cell carcinoma, actinic keratosis, melanoma), and Th2-mediated diseases (e.g., asthma, allergic rhinitis, atopic dermatitis, multiple sclerosis), and are also useful as vaccine adjuvants.

Several polysaccharides (carbohydrate polymers) of mannose (e.g., mannans), β(1,3) glucose (e.g., glucans), β(1,4) acetylated mannose (acemannans), β(1,4) N-acetyl-glucosamine (chitins), and heteropolysaccharides, such as rhamnogalacturonans (pectins), have been shown to stimulate the immune system.

Binding of polysaccharides to C-type lectin receptors induces immunostimulation, as shown by the increase in phagocytosis, proliferative responses, release of cytokines, and other activities of the immune system. Because of this immunostimulatory activity, these polysaccharides have been proposed for use in vaccine compositions. Of particular interest is mannan.

Mannan is a polymannose recognized by C-type lectin receptors, such as the mannose receptor (CD206) and DC-SIGN (CD209). Because of their presence on antigen-presenting cells, these receptors have been characterized for their uptake of mannose, fucose or glucose containing compounds. Binding of mannan to the mannose receptor for instance, induces endocytosis, followed by its delivery into the endosomal pathway. Early studies on mannnosylated antigens indicated that the presence of mannose residues on antigens greatly enhanced antigen-uptake and major histocompatibility complex (MHC) class II-restricted antigen presentation by dendritic cells (DCs). Conjugation of mannan to at least one antigen also enhances its uptake and presentation.

There is a need for further immunomodulatory and vaccine compositions for use in the treatment or prevention of diseases, as well as reliable methods for the preparation thereof. Furthermore, in view of the great therapeutic potential for immune modulators, and despite the work that has already been done, there is a substantial ongoing need to expand their uses and therapeutic benefits.

SUMMARY OF THE INVENTION

The present inventors have developed new compounds for stimulating an immune response.

In a first aspect, the present invention provides an immunomodulatory compound comprising a carbohydrate polymer comprising mannose, wherein the carbohydrate polymer is conjugated to at least one immune modulator.

In an embodiment, there is more than one immune modulator and each immune modulator is the same or different. For example, the carbohydrate polymer comprises more than one functional group that can be directly conjugated or conjugated via a linker to an immune modulator. Alternatively or in addition, the carbohydrate polymer is conjugated via a branched linker to more than one immune modulator.

In an embodiment, the carbohydrate polymer is greater than about 1000 kDa.

In an embodiment, the carbohydrate polymer is oxidized. The oxidized carbohydrate polymer may have at least 150 aldehyde groups prior to conjugation to the immune modulator.

In an embodiment, the oxidized carbohydrate polymer is further conjugated to at least one antigen or nucleic acid encoding therefor. The antigen can be from any source such as viral, bacterial, protozoan, fungal, tumor antigen, a self antigen, or an allegen. The antigen may be, for example, a whole organism, a protein, or an antigenic peptide. The antigen may be conjugated directly to the oxizided mannan, optionally via a linker, or indirectly conjugated to the oxidized mannan by conjugation to the immune modulator, optionally via a linker. Similarly, the nucleic acid may be conjugated directly or indirectly (via, for example, the IRM) to the oxidized mannan.

In an embodiment, the oxidized carbohydrate polymer is covalently conjugated to the at least one antigen.

In an embodiment, the oxidized carbohydrate polymer is conjugated to the at least one nucleic acid via a polycation.

In an embodiment, the carbohydrate polymer is mannan. The mannan can be from any source, such as fungi, more preferably yeast.

In an embodiment, the size distribution of the mannan prior to conjugation to the immune modulator and/or antigen or nucleic acid encoding therefor and following labelling with aminonaphthalene-1,3,6-trisulfonic acid (ANTS) is between about 150 to about 250 kDa based on protein standards and/or is between about 800 to about 3000 kDa based on carbohydrate standards.

In an embodiment, the immune modulator is a Toll-like receptor (TLR) agonist such as, for example, a guanosine analog, a deaza-adenosine analog, an imidazoquinoline, or derivatives thereof. In a preferred embodiment, the TLR agonist is Loxoribine, Isatoribine, Imiquimod, Resiquimod, or a derivative thereof.

In an embodiment, each immune modulator is conjugated to the carbohydrate polymer via a linker, and prior to conjugation each linker comprises one or more functional groups capable of conjugation to the immune modulator or the carbohydrate polymer, and the functional groups may optionally comprise a suitable leaving group or protecting group.

In an embodiment, each functional group is selected from the group consisting of an aldehyde, ketone, formyl, hydrazine, hydrazide, amine, amide, carboxylic acid, alkyne, maleimide, sulphydryl and halogen.

In an embodiment, the protecting group of the amine is a BOC group.

In an embodiment, the leaving group of the formyl is a para-nitrophenoxy group.

In an embodiment, each immune modulator is conjugated to the carbohydrate polymer via a linker which comprises:
i) a functional group conjugated to the carbohydrate polymer (type (i) group);
ii) a functional group conjugated to the immune modulator (type (ii) group); and
iii) a spacer;
and wherein each linker may be the same or different to each other.

In an embodiment, the type (i) group is a hydrazone.

In an embodiment, the type (ii) group is a carbamate group.

In an embodiment, the spacer comprises one or more different types of linking units. In an embodiment, each linking unit may be independently selected from the group consisting of a polymer of ethylene glycol and/or propylene gycol; a polyaryl; an amino acid residue or derivative thereof; an alkyl or alkenyl chain; a phenyl containing moiety; and a saccharide.

In an embodiment, the spacer comprises a polymer comprising 1 to 100 units of ethylene glycol and/or propylene gycol. For example, the spacer may comprise a polymer comprising 1-10 units of ethylene glycol and/or propylene glycol, 1-5 amino acid residues or derivatives thereof, and a phenyl containing moiety.

In an embodiment, the linker is cleavable after conjugation. For example, the linker comprises a cleavable group selected from the group consisting of ester, carbamate, hydrazone, amide and acetal.

In a preferred embodiment, the carbohydrate polymer and the immune modulator are linked by reaction with a linker of Formula I:

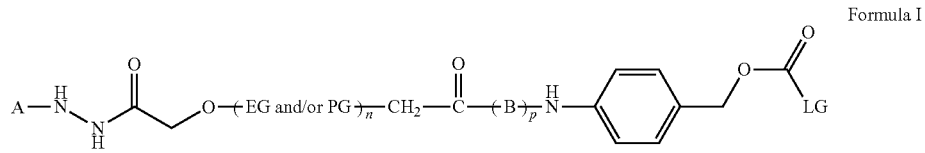

Formula I wherein,
A is a protecting group;
EG is —CH$_2$—CH$_2$—O—;
PG is —CH$_2$—CH$_2$—CH$_2$—O—;
B is an amino acid residue or derivative thereof;
n is an integer between 1 and 10;
p is an integer between 1 and 5; and
LG is a leaving group.

In an embodiment, the leaving group is a para-nitrophenoxy group.

In an embodiment, the protecting group is BOC.

In an embodiment:
i) -(EG and/or PG)$_n$- is only ethylene glycol (EG) units;
ii) -(EG and/or PG)$_n$- is only propylene glycol (PG) units; or
iii) -(EG and/or PG)$_n$- is a mixture of ethylene glycol (EG) and propylene glycol (PG) units.

In an alternate preferred embodiment, the carbohydrate polymer and the immune modulator are linked by reaction with a linker of Formula II:

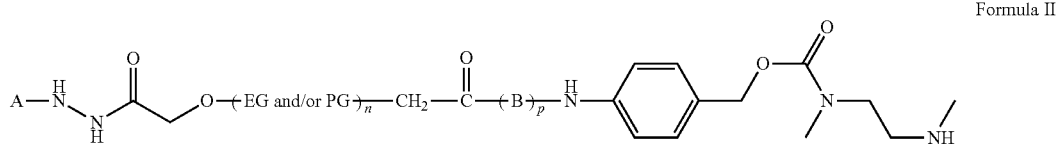

Formula II wherein,
A is a protecting group;
EG is —CH$_2$—CH$_2$—O—;
PG is —CH$_2$—CH$_2$—CH$_2$—O—;
B is an amino acid residue or derivative thereof;
n is an integer between 1 and 10; and
p is an integer between 1 and 5.

In an embodiment, the protecting group is BOC.

In another aspect, the present invention provides a compound of Formula III comprising oxidized mannan which is conjugated via a linker to at least one immune modulator:

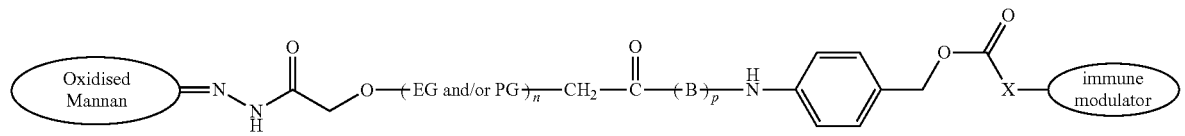

Formula III wherein,
EG is —CH$_2$—CH$_2$—O—;
PG is —CH$_2$—CH$_2$—CH$_2$—O—;
B is an amino acid residue or derivative thereof;
n is an integer between 1 and 10;
p is an integer between 1 and 5; and
X is a bond or -MeN(CH$_2$)$_2$NMeC(O)—.

In an embodiment:
i) -(EG and/or PG)$_n$- is only ethylene glycol (EG) units;
ii) -(EG and/or PG)$_n$- is only propylene glycol (PG) units; or
iii) -(EG and/or PG)$_n$- is a mixture of ethylene glycol (EG) and propylene glycol (PG) units.

In an embodiment, n is 8 and/or p is 1 to 3. In a preferred embodiment p is 2.

In an embodiment, p is greater than 1 and each amino acid residue is the same or different. Each amino acid residue may be independently selected from the group consisting of valine and lysine.

In a further embodiment, the oxidized mannan is conjugated to at least one antigen or nucleic acid encoding therefor.

In a further embodiment:
i) the immune modulator is Loxoribine or a derivative thereof;
ii) X is -MeN(CH$_2$)$_2$NMeC(O)—; and
iii) the immune modulator is conjugated to X through its primary or secondary hydroxyl group.

In an alternate embodiment:
i) the immune modulator is Resiquimod or a derivative thereof;
ii) X is -MeN(CH$_2$)$_2$NMeC(O)—; and
iii) the immune modulator is conjugated to X through a free hydroxyl group on the immune modulator.

In an embodiment, the free hydroxyl group is a tertiary hydroxyl group.

In an alternate embodiment:
i) the immune modulator is Loxoribine or Resiquimod or derivatives thereof;
ii) X is a bond; and
iii) the immune modulator is conjugated to X through a free amino group on the immune modulator.

In another aspect, there is provided a compound of Formula IV

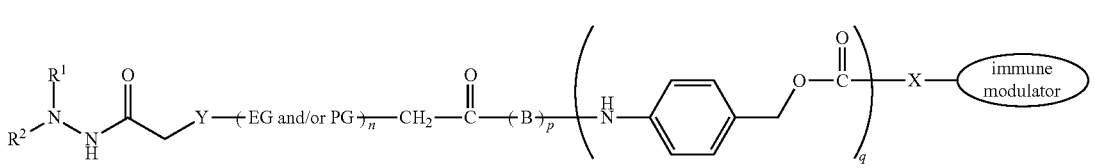

Formula IV wherein,
R$^1$ and R$^2$ are each independently selected from the group consisting of hydrogen and A
  wherein A is a protecting group;
or R$^1$ and R$^2$ are taken together to form a double bond which connects to an another moiety via a carbonyl carbon;
Y is selected from —CH$_2$— and —O—;
EG is —CH$_2$—CH$_2$—O—;
PG is —CH$_2$—CH$_2$—CH$_2$—O—;
B is an amino acid residue or derivative thereof;
n is an integer between 0 and 10;
p is an integer between 1 and 5;
q is an integer selected from 0 and 1;
X is a connecting group capable of binding to one or more hydroxyl groups of the immune modulator or a free amino group of the immune modulator.

In a preferred embodiment, R$^1$ and R$^2$ are taken together to form a double bond which connects to a carbohydrate polymer via a carbonyl carbon. Even more preferably the carbohydrate polymer is oxidized mannan.

In another aspect, the present invention provides a compound of Formula V comprising oxidized mannan which is conjugated via a linker to at least one immune modulator:

Formula V

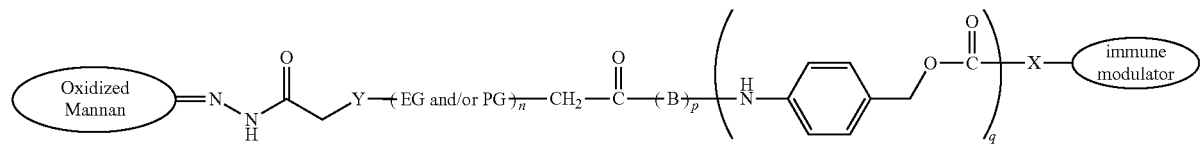

wherein,
Y is selected from —CH$_2$— and —O—;
EG is —CH$_2$—CH$_2$—O—;
PG is —CH$_2$—CH$_2$—CH$_2$—O—;
B is an amino acid residue or derivative thereof;
n is an integer between 0 and 10;
p is an integer between 1 and 5.
q is an integer selected from 0 and 1;
X is a connecting group capable of binding to one or more hydroxyl groups of the immune modulator or a free amino group of the immune modulator.

In one embodiment p is an integer between 1 and 3. In a preferred embodiment p is 2.

In an embodiment, when p is greater than 1 each amino acid residue is the same or different. In a preferred embodiment each amino acid residue is independently selected from the group consisting of valine and lysine.

In one embodiment n is 0.

In another embodiment q is 0.

In one embodiment X is a bond.

In one embodiment X is —R$^3$N(CH$_2$)$_2$NR$^4$C(O)— connected to the immune modulator via at least one hydroxyl group or free amino group of the immune modulator;
  wherein R$^3$ and R$^4$ are each independently selected from the group consisting of H and C$_{1-4}$alkyl.

In one embodiment X is connected to the immune modulator through the formation of an acetal with two hydroxyl groups of the immune modulator.

Preferably, X-immune modulator includes the following functionality:

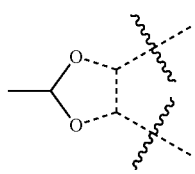

wherein the two oxygens and dotted bonds are part of the immune modulator molecule.

Even more preferably, X-immune modulator comprises a group selected from the groups consisting of:

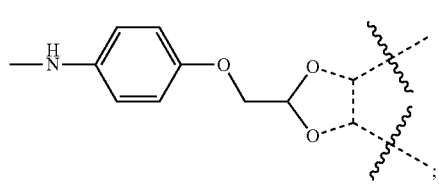

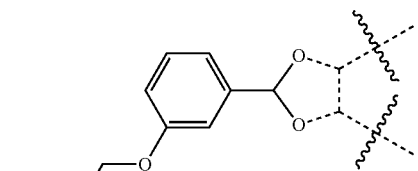

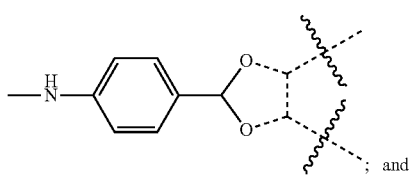

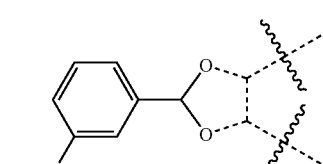

wherein R$^3$ and R$^4$ are each independently selected from the group consisting of H and C$_{1-4}$alkyl;
EG is —CH$_2$—CH$_2$—O—;
PG is —CH$_2$—CH$_2$—CH$_2$—O—; and
m is an integer between 0 and 10.

In certain embodiments, the compound of formula IV is a compound selected from the group consisting of:

derivative 1
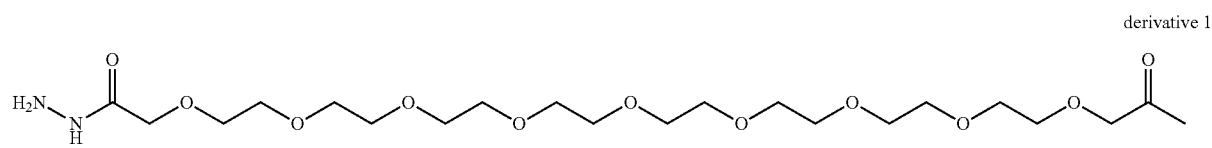
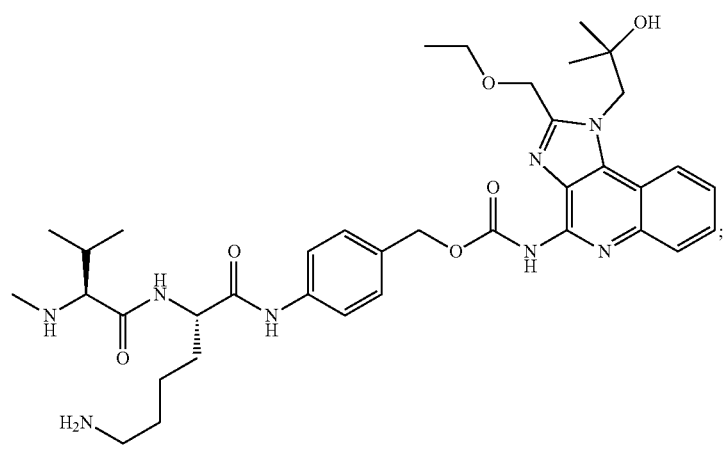
derivative 2
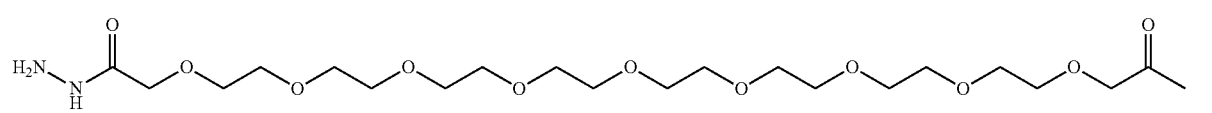
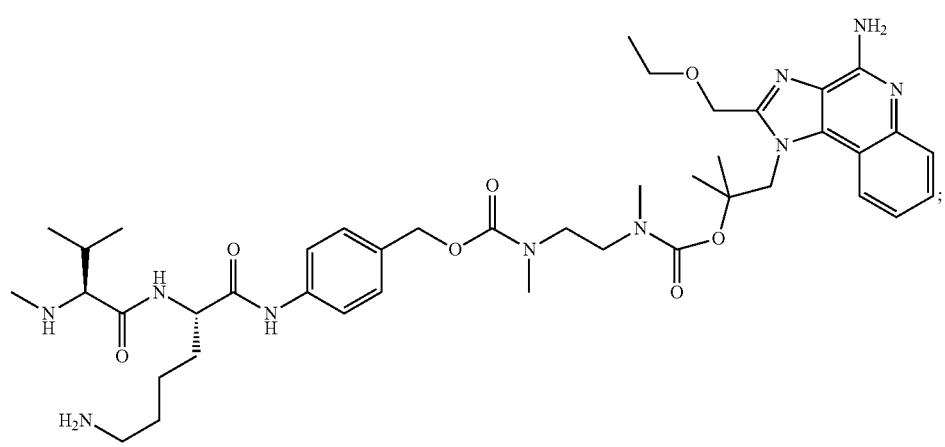
derivative 3
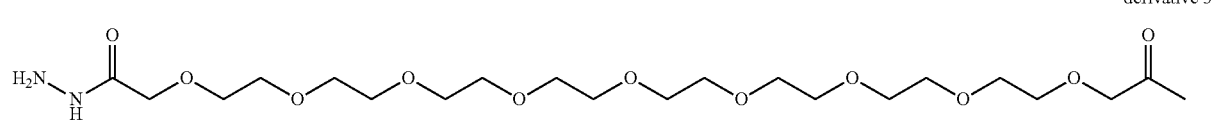
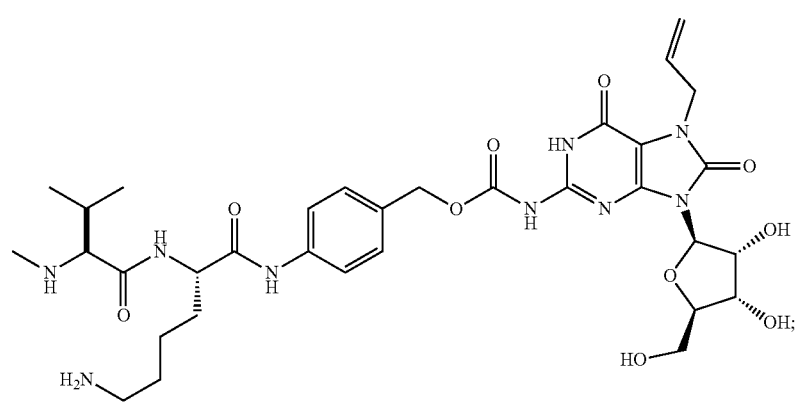

derivative 4
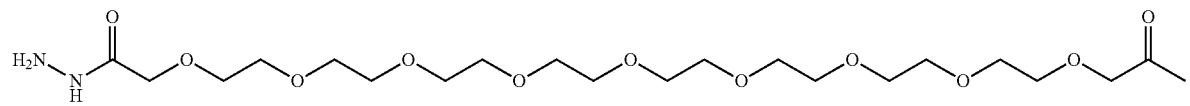
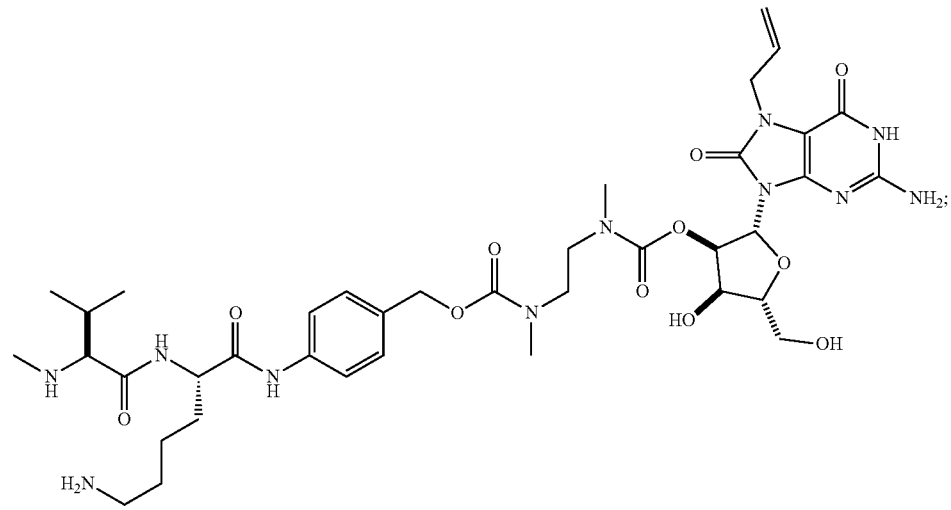
derivative 5
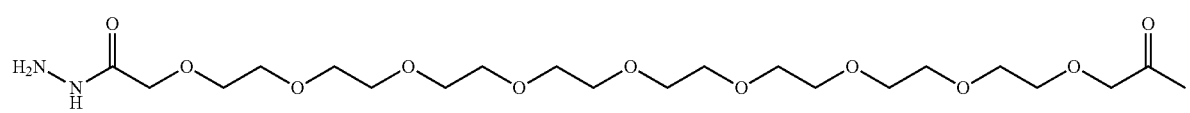
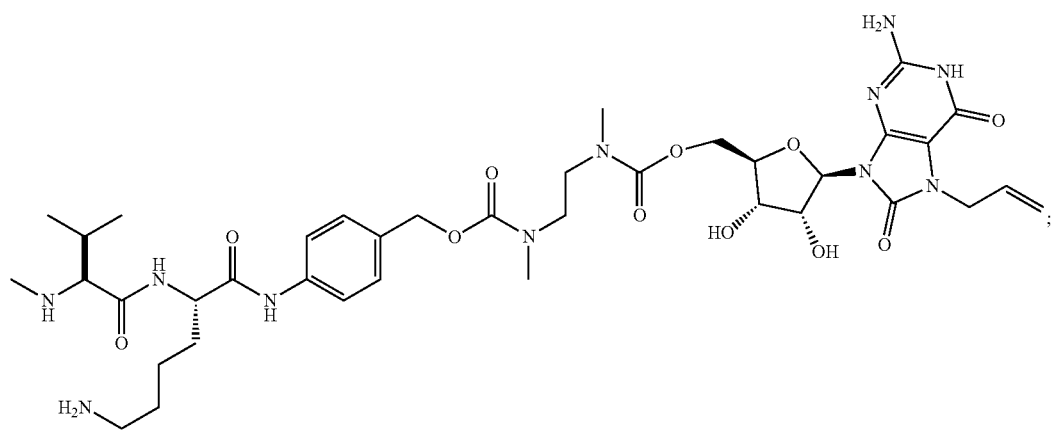
Rd2
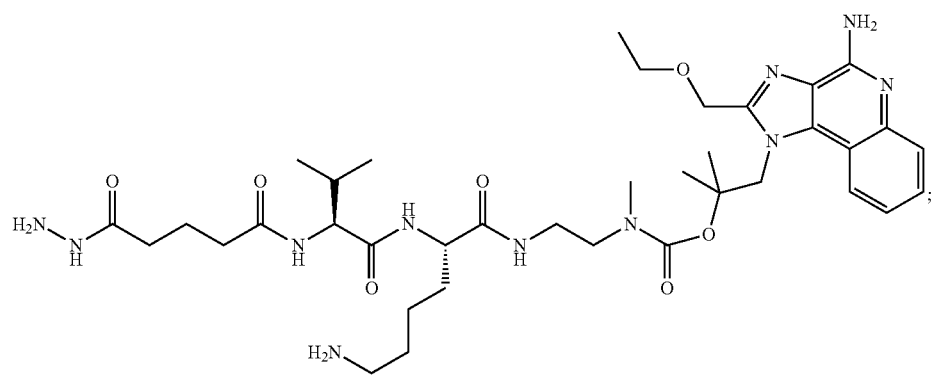

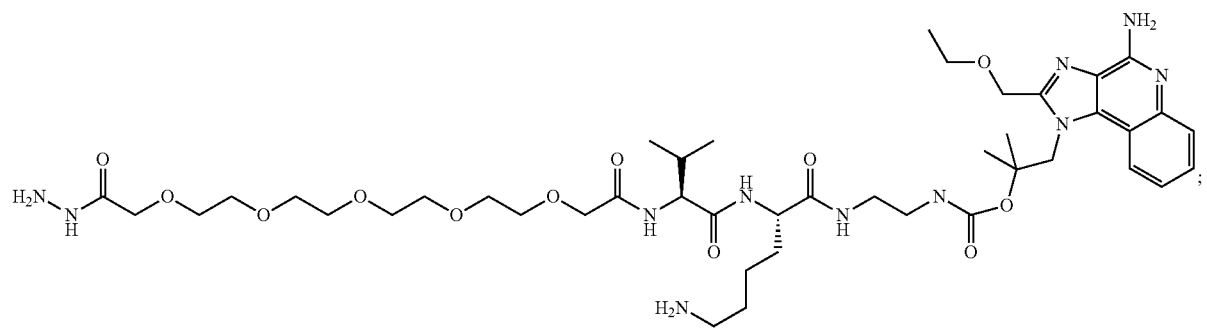
Rd3
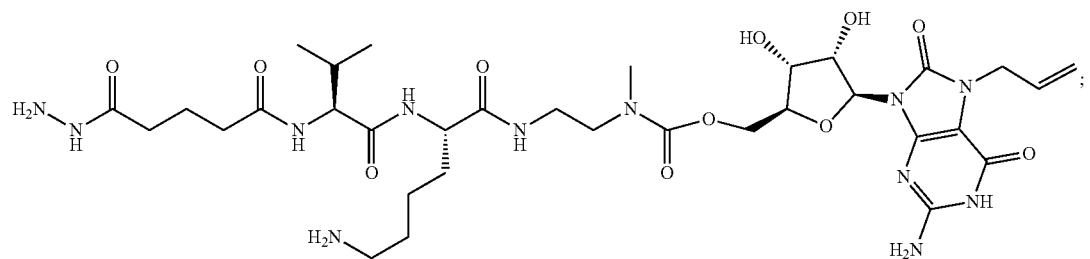
Ld2
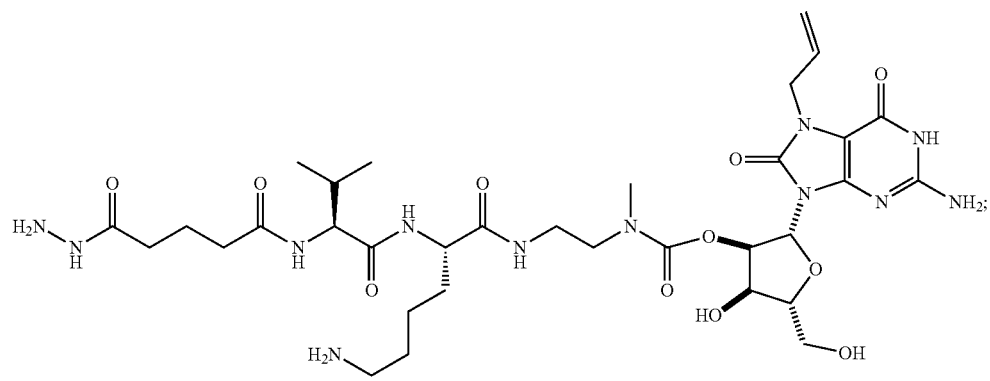
Ld3
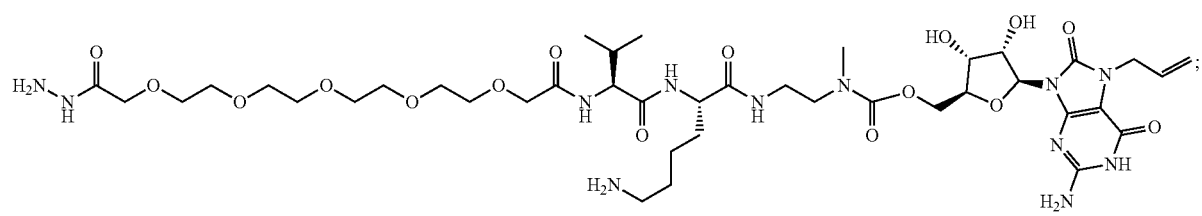
Ld4
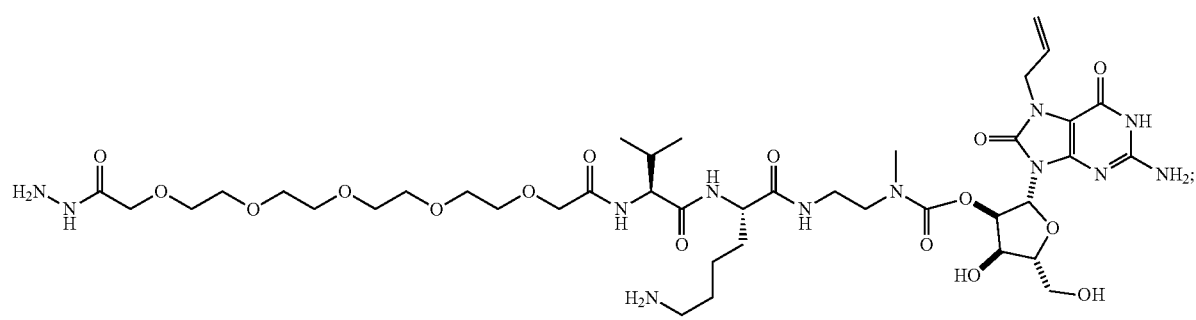
Ld5

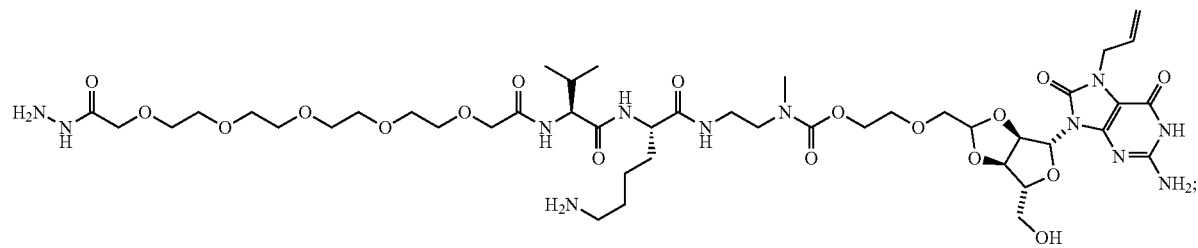
Ld8
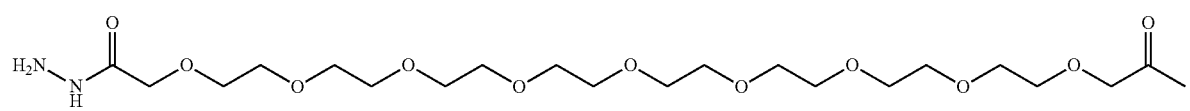
Ld9
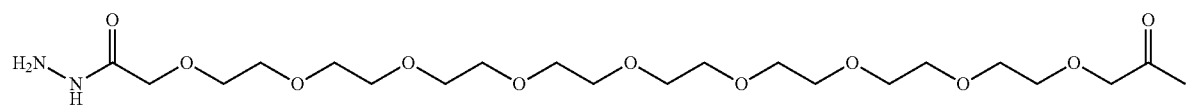
Ld10
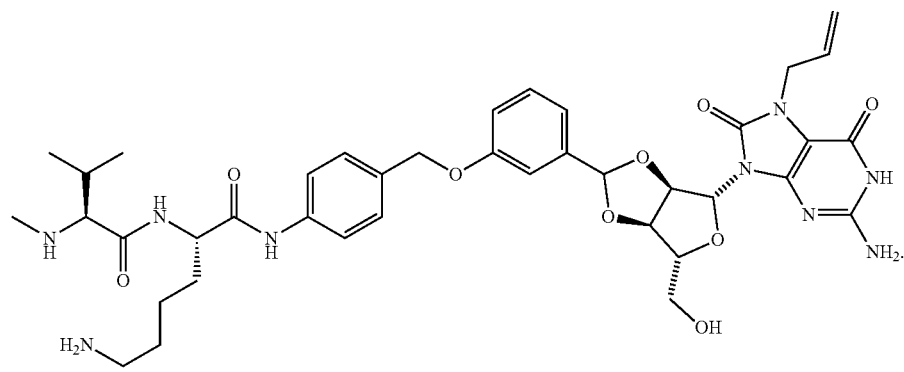

Preferably, in certain embodiments, the compound of formula IV is a compound selected from the group consisting of:
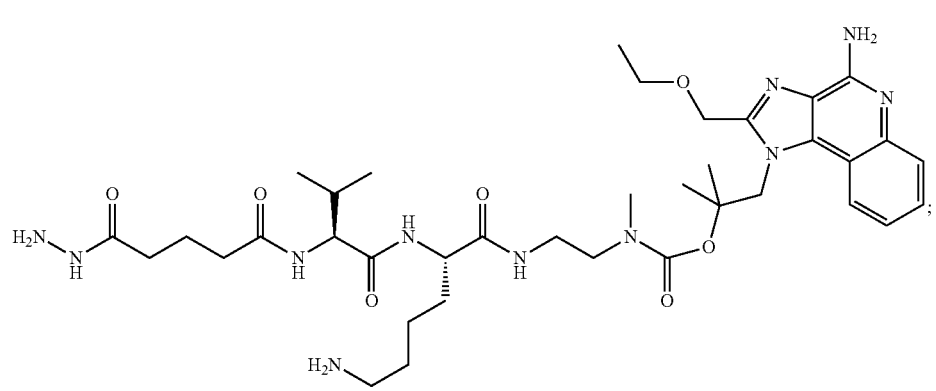
Rd2
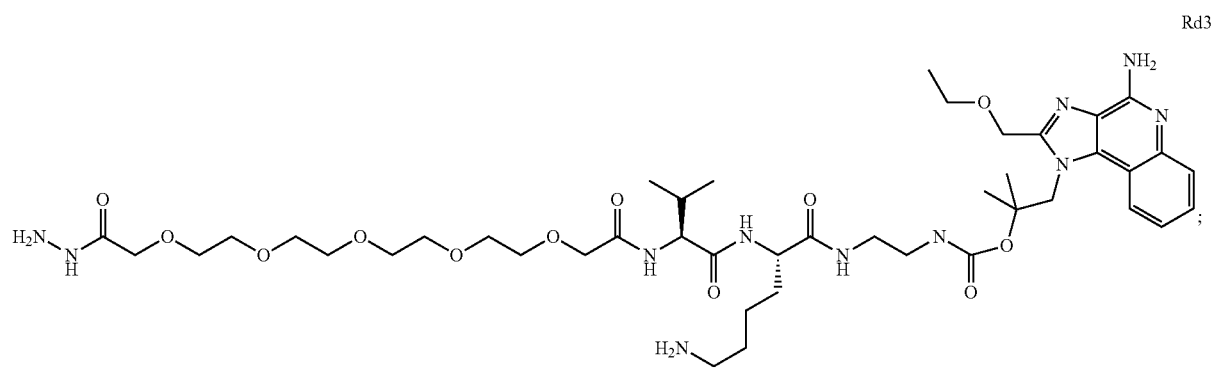
Rd3
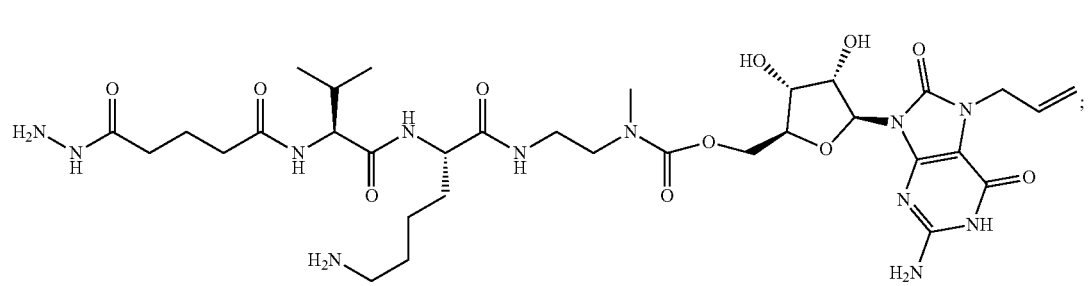
Ld2
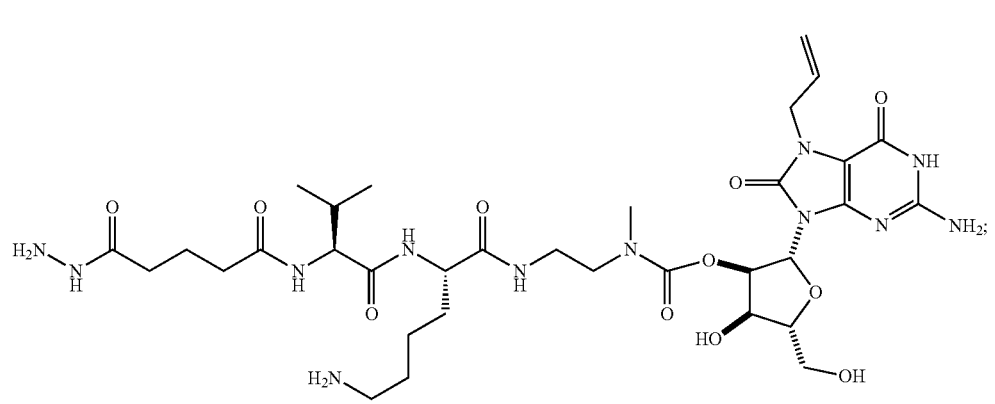
Ld3

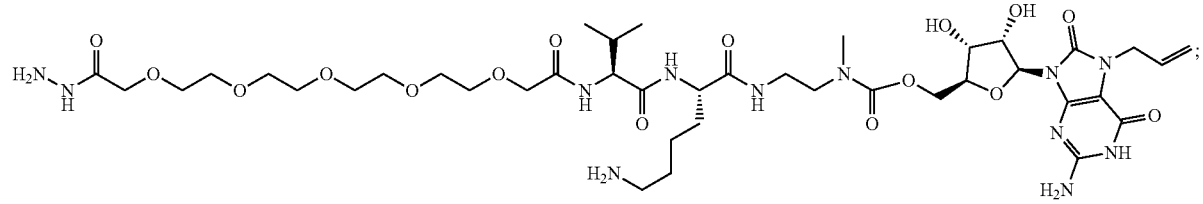
Ld4
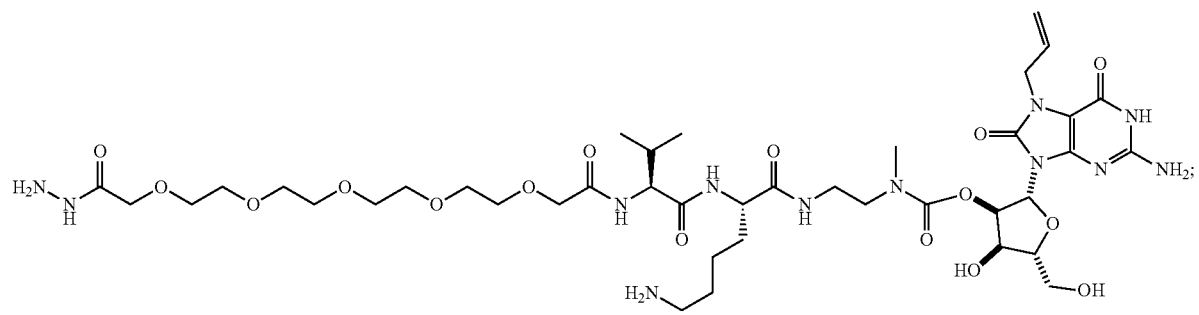
Ld5
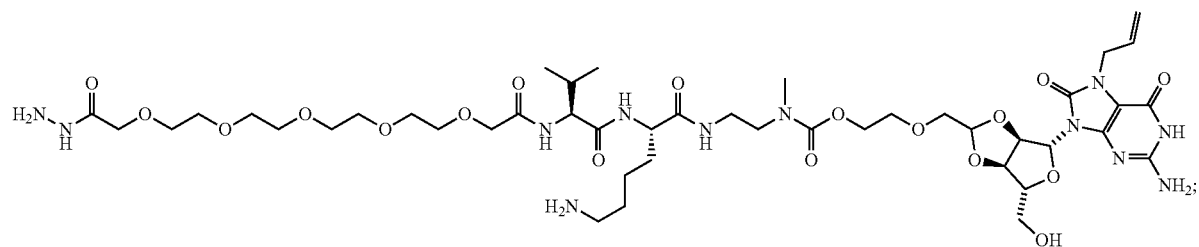
Ld8
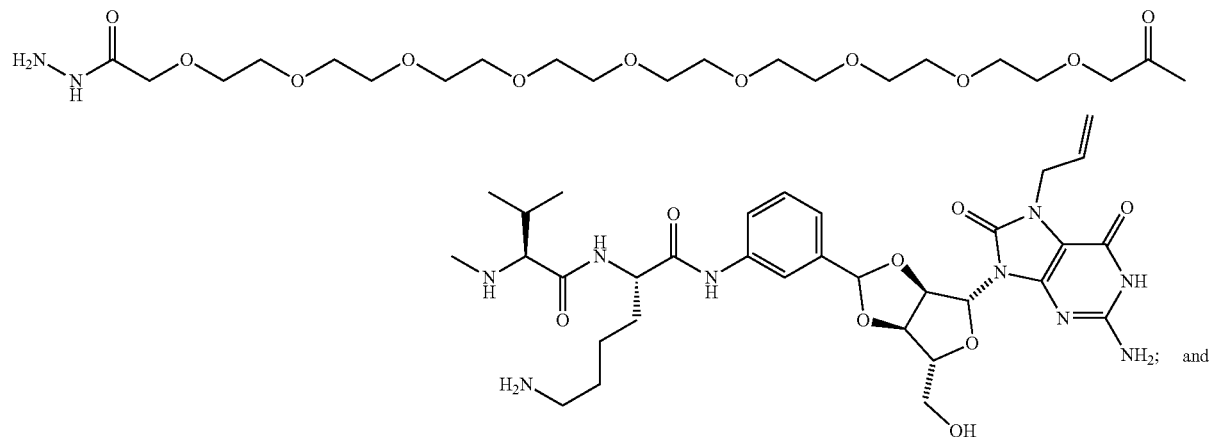
Ld9; and
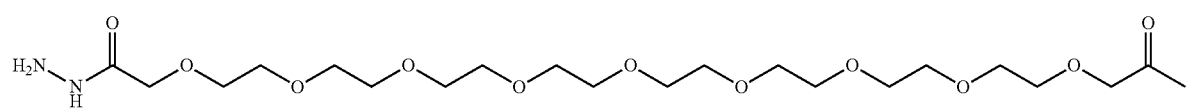
Ld10

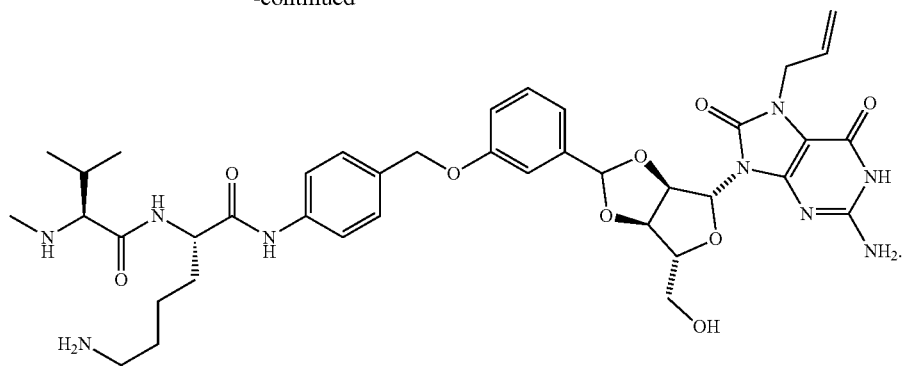

In another aspect, the present invention provides a compound of Formula VI:

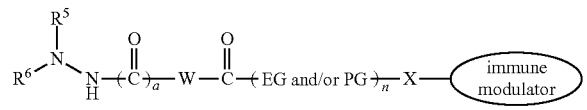

Formula VI wherein $R^5$ and $R^6$ are each independently selected from the group consisting of hydrogen and A
wherein A is a protecting group; or $R^5$ and $R^6$ are taken together to form a double bond which connects to an another moiety via a carbonyl carbon;
W is a connecting group comprising an aromatic or heteroaromatic ring
wherein the heteroatomic ring comprising 1 to 3 heteroatoms selected from the group consisting of N, O and S;
EG is —$CH_2$—$CH_2$—O—;
PG is —$CH_2$—$CH_2$—$CH_2$—O—;
n is an integer between 0 and 10;
a is an integer selected from 0 and 1;
X is a connecting group capable of binding to one or more hydroxyl groups of the immune modulator or a free amino group of the immune modulator.
In a preferred embodiment, $R^1$ and $R^2$ are taken together to form a double bond which connects to a carbohydrate polymer via a carbonyl carbon. Even more preferably the carbohydrate polymer is oxidized mannan.
In another aspect, the present invention provides a compound of Formula VII comprising oxidized mannan which is conjugated via a linker to at least one immune modulator:

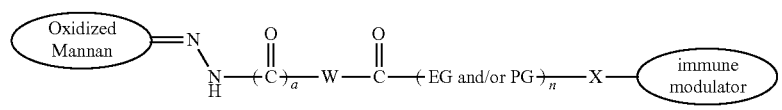

Formula VII wherein
W is a connecting group comprising an aromatic or heteroaromatic ring;
wherein the heteroatomic ring comprising 1 to 3 heteroatoms selected from the group consisting of N, O and S;
EG is —$CH_2$—$CH_2$—O—;
PG is —$CH_2$—$CH_2$—$CH_2$—O—;
n is an integer between 0 and 10;
a is an integer selected from 0 and 1;
X is a connecting group capable of binding to one or more hydroxyl groups of the immune modulator or a free amino group of the immune modulator.
In one embodiment X is connected to the immune modulator through the formation of an acetal with two hydroxyl groups of the immune modulator.
In one embodiment, X-immune modulator includes the following functionality:

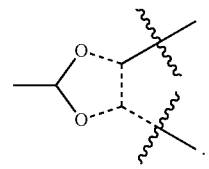

wherein the two oxygens and dotted bonds are part of the immune modulator molecule.
Preferably the X-immune modulator functionality comprises:

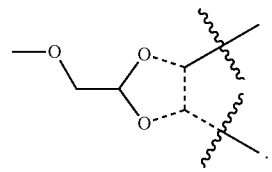

In another embodiment X is selected from the group consisting of a bond and —$CH_2$—C(O)—.

In one embodiment W is a heteroaromatic ring, preferably a pyridine ring. Even more preferably, W is

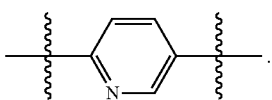

In another embodiment W is an aromatic ring, preferably a benzene ring. Even more preferably, W is

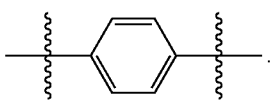

In one embodiment a is 1.
In one embodiment —(C(O))$_a$—W is

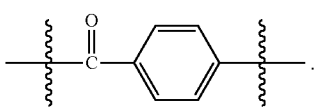 [SMILES: *C(=O)c1ccc(*)cc1]

In certain embodiments, the compound of Formula VI is selected from the group consisting of:

Rd1-a
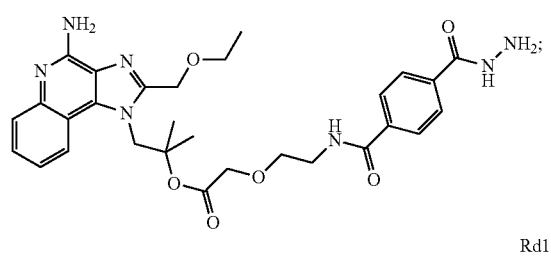

Rd1-b
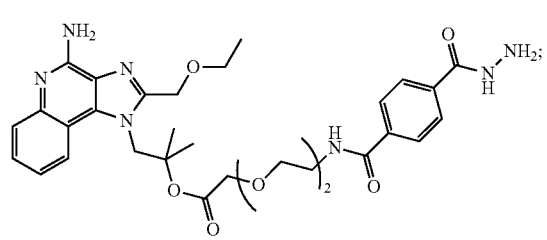

Ld1
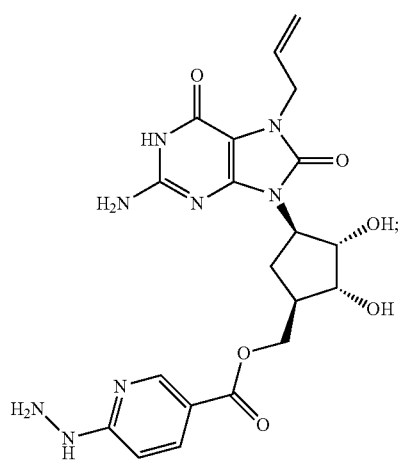

Ld6-a
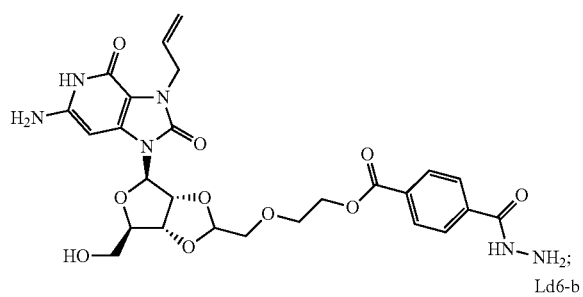

Ld6-b
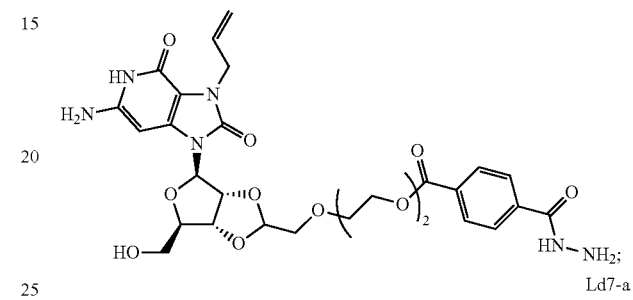

Ld7-a
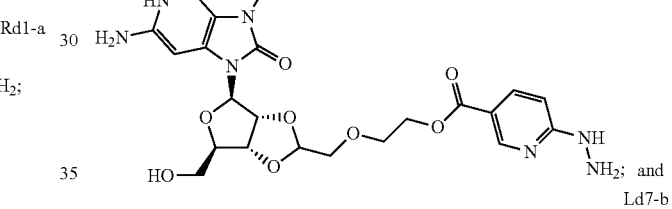

Ld7-b
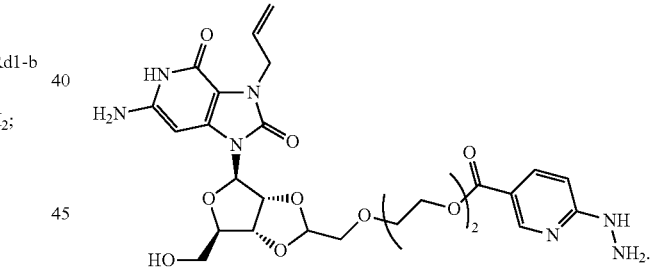

In another aspect, the present invention provides an immunomodulatory composition comprising a compound of the invention.

In another aspect, the present invention provides a vaccine composition comprising:
  i) a compound of the invention and at least one antigen or nucleic acid encoding therefor, wherein the at least one antigen or nucleic acid encoding therefor is conjugated to the carbohydrate polymer; or
  ii) a compound of the invention and at least one antigen or nucleic acid encoding therefor, wherein the at least one antigen or nucleic acid encoding therefor is not conjugated to the carbohydrate polymer.

In an embodiment, at least 75% of the carbohydrate polymers in the composition are greater than about 1000 kDa.

In an embodiment, at least 75% of the carbohydrate polymers in the composition are oxidized and have at least 150 aldehyde groups prior to conjugation to the immune modulator and/or antigen or nucleic acid encoding therefor.

In an embodiment, the composition is formulated for mucosal, topical, intradermal, intramuscular, subcutaneous, or intravenous administration.

In an embodiment, the composition further comprises at least one acceptable carrier.

In another aspect of the invention, the present invention provides a method for inducing and/or enhancing or suppressing or tolerizing an immune response in a subject, the method comprising administering to the subject a first composition according to the invention.

In an embodiment, the first composition does not comprise at least one antigen or nucleic acid encoding therefor and the method further comprises administering a second composition comprising at least one antigen or nucleic acid encoding therefor.

In an embodiment, the first and second compositions are administered sequentially or simultaneously.

In an embodiment, when the antigen is from an infectious agent or is a mutant/derivative thereof, the method immunizes the subject against a pathogen (infectious agent). In another embodiment, when the antigen is from a cancer cell or is a mutant/derivative thereof, the method is for cancer therapy.

Also provided, is the use of a compound of the invention for the manufacture of a medicament for inducing and/or enhancing or suppressing or tolerizing an immune response in a subject.

Further, provided is the use of a compound of the invention for inducing and/or enhancing or suppressing or tolerizing an immune response in a subject.

In another aspect, the present invention provides a method for activating macrophages, DCs and/or cytotoxic T lymphocytes (CTLs) in vitro or ex vivo, the method comprising contacting the cells with a compound or composition of the invention.

In another aspect, the present invention provides a linker of Formula VIII

B is an amino acid residue or derivative thereof;
n is an integer between 0 and 10;
p is an integer between 1 and 5;
q is an integer selected from 0 and 1;
X is a connecting group capable of binding to one or more hydroxyl groups or a free amino group.

In another aspect, the present invention provides a compound of Formula IX:

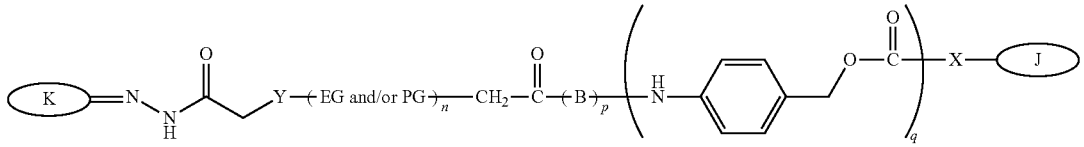

Formula IX wherein,
Y is selected from —CH$_2$— and —O—;
EG is —CH$_2$—CH$_2$—O—:
PG is —CH$_2$—CH$_2$—CH$_2$—O—;
B is an amino acid residue or derivative thereof;
n is an integer between 0 and 10;
p is an integer between 1 and 5.
q is an integer selected from 0 and 1;
X is a connecting group capable of binding to one or more hydroxyl groups of J or a free amino group of J;
J is a moiety comprising one or more hydroxyl groups and/or a free amino group; and
K is a moiety connected via a carbonyl carbon.

In another aspect, the present invention provides a linker of Formula X:

Formula X wherein $R^5$ and $R^6$ are each independently selected from the group consisting of hydrogen and A
wherein A is a protecting group; W is a connecting group comprising an aromatic or heteroaromatic ring

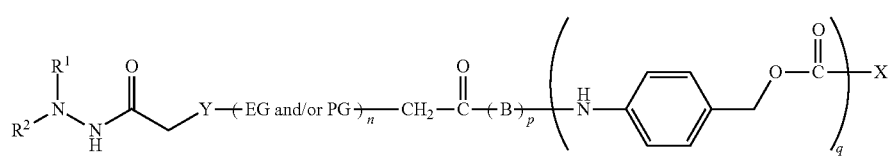

Formula VIII wherein,
$R^1$ and $R^2$ are each independently selected from the group consisting of hydrogen and A
wherein A is a protecting group;
Y is selected from —CH$_2$— and —O—;
EG is —CH$_2$—CH$_2$—O—:
PG is —CH$_2$—CH$_2$—CH$_2$—O—;

wherein the heteroatomic ring comprising 1 to 3 heteroatoms selected from the group consisting of N, O and S;
EG is —CH$_2$—CH$_2$—O—;
PG is —CH$_2$—CH$_2$—CH$_2$—O—;
n is an integer between 0 and 10;
a is an integer selected from 0 and 1;

X is a connecting group capable of binding to one or more hydroxyl groups or a free amino group.

In another aspect, the present invention provides a compound of Formula XI:

Formula XI

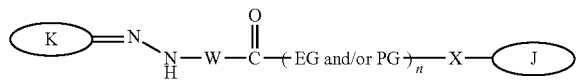

wherein
W is a connecting group comprising an aromatic or heteroaromatic ring;
wherein the heteroatomic ring comprising 1 to 3 heteroatoms selected from the group consisting of N, O and S;
EG is —CH$_2$—CH$_2$—O—;
PG is —CH$_2$—CH$_2$—CH$_2$—O—;
n is an integer between 0 and 10;
a is an integer selected from 0 and 1;
X is a connecting group capable of binding to one or more hydroxyl groups of J or a free amino group of J;
K is a moiety connected via a carbonyl carbon.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

As will be apparent, preferred features and characteristics of one aspect of the invention are applicable to many other aspects of the invention.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1: Fractionation process using Centriprep concentrators.

Figure 2:
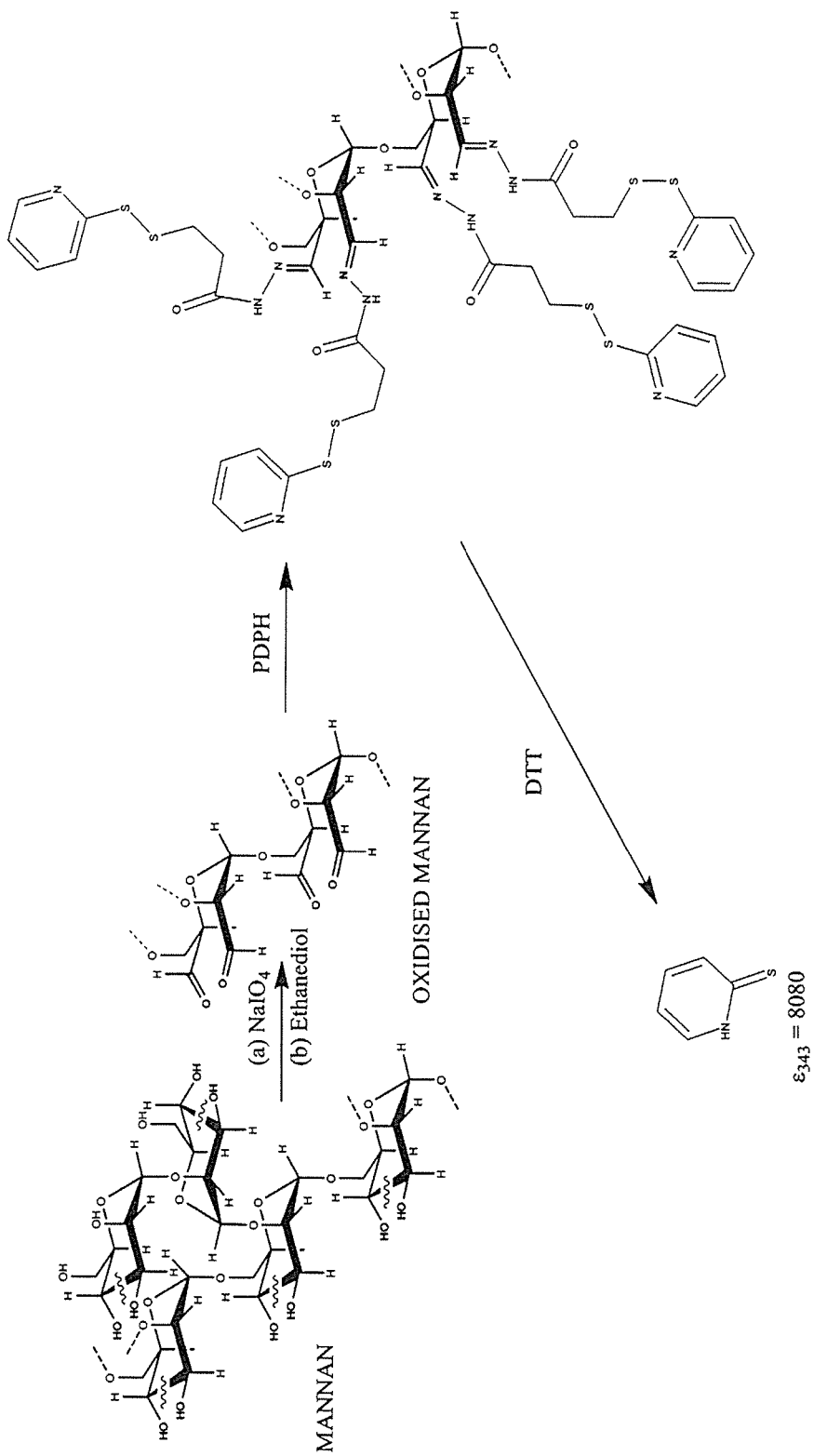

FIG. 2: Schematic depicting method for quantitating aldehyde residues in oxidized mannan.

Figure 3:
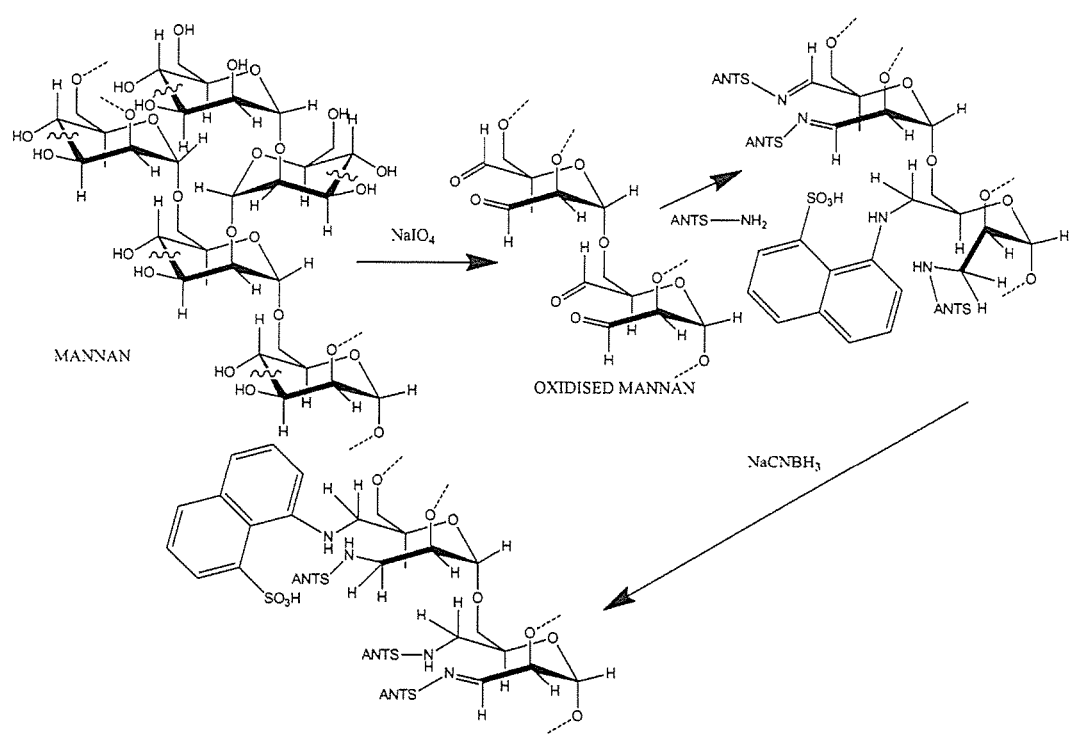

FIG. 3: Schematic depicting the modification of oxidized mannan with ANTS.

Figure 4:
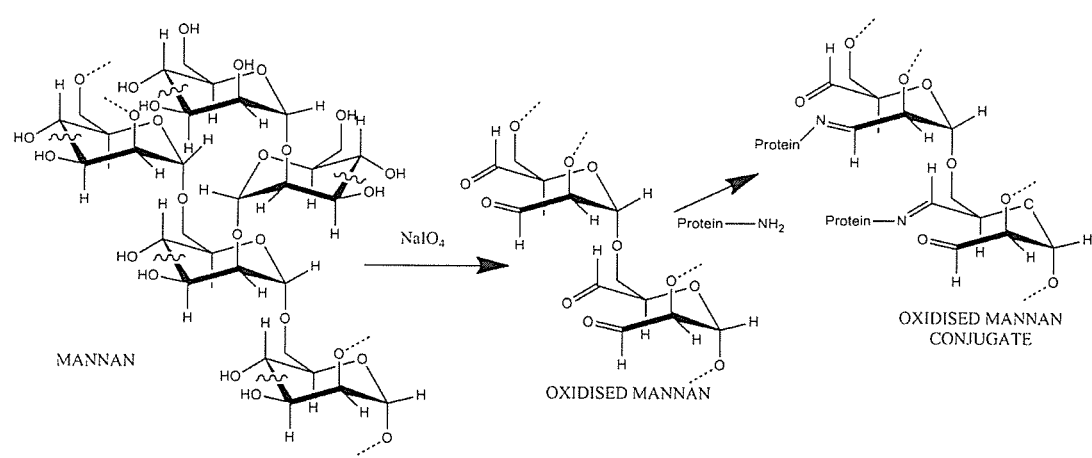

FIG. 4: Schematic depicting conjugation of proteins to oxidized mannan.

Figure 5:
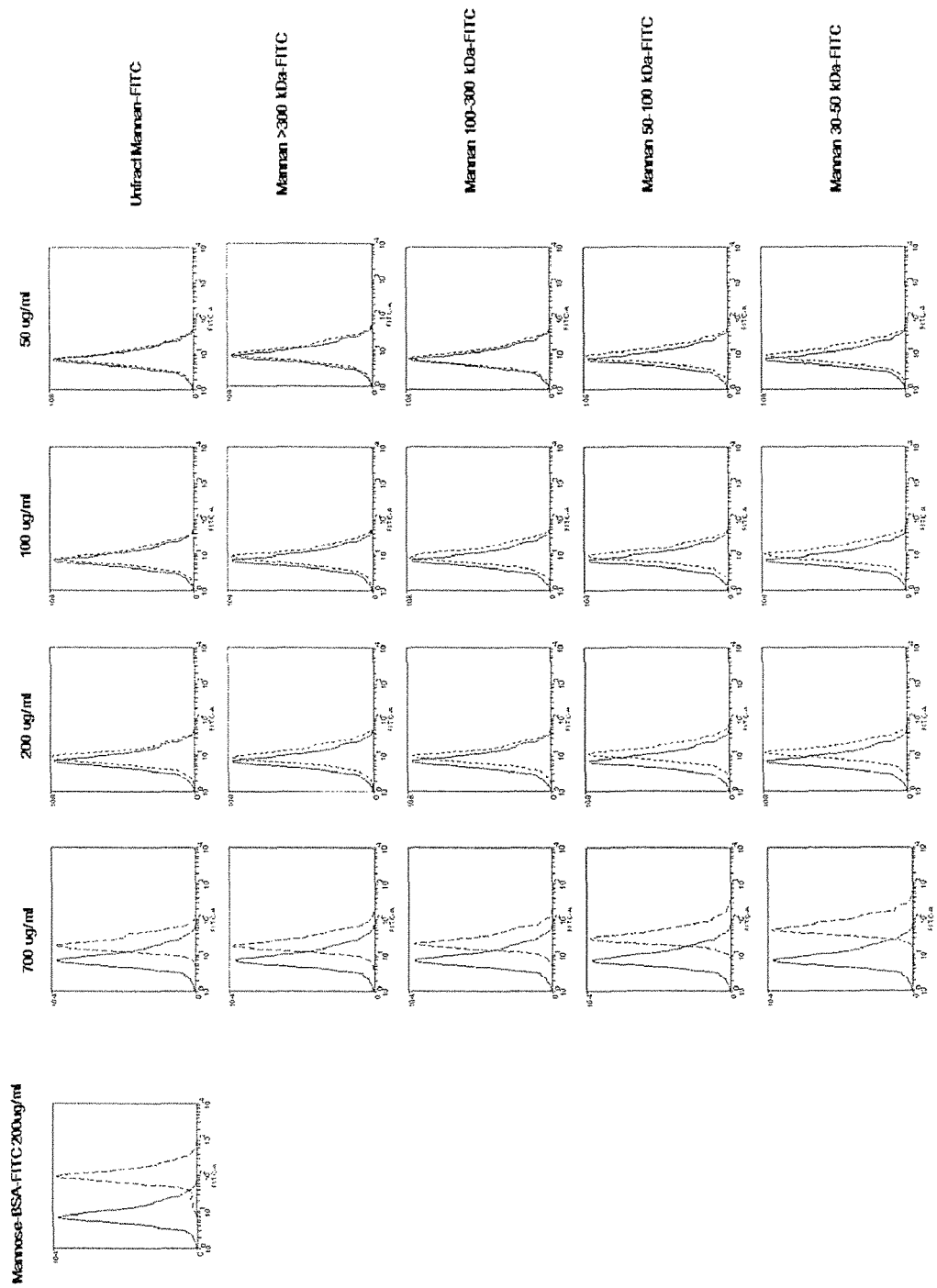

FIG. 5: Mannans were labelled with fluorocein isothiocyanate (FITC) and binding at various concentrations to huh7 human hepatoma cells was measured by flow cytometry.

Figure 6A:
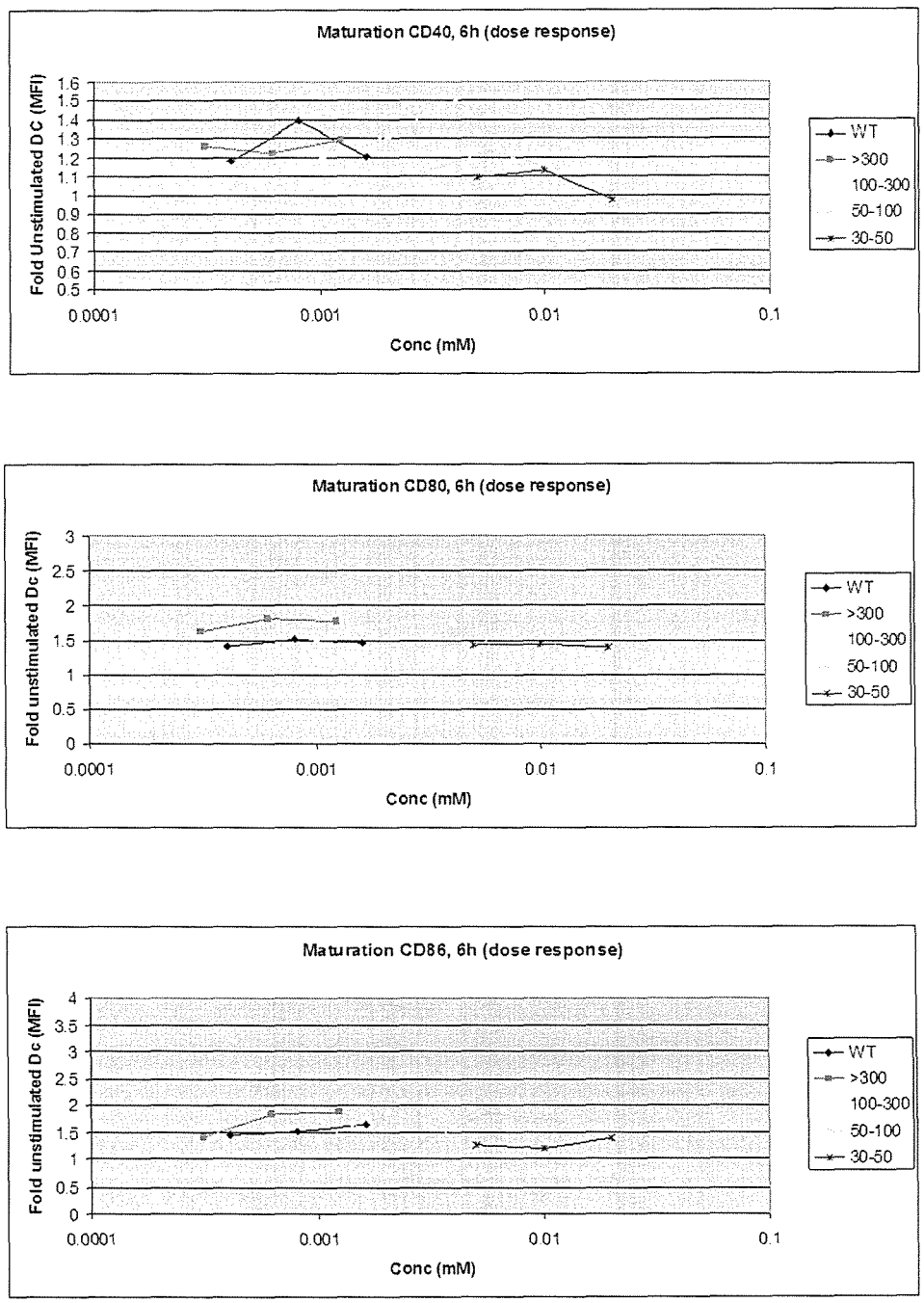
Figure 6B:
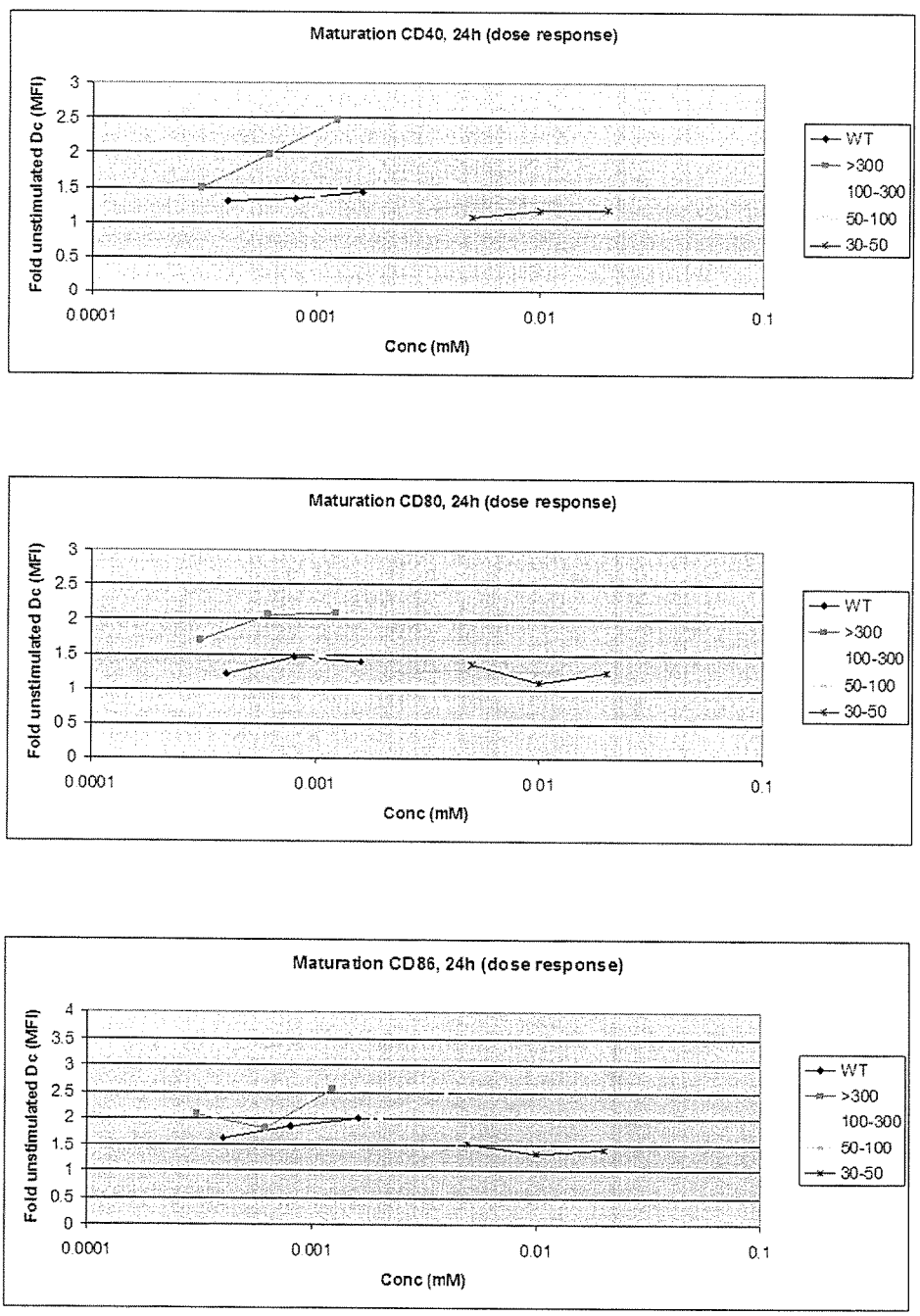
Figure 6C:
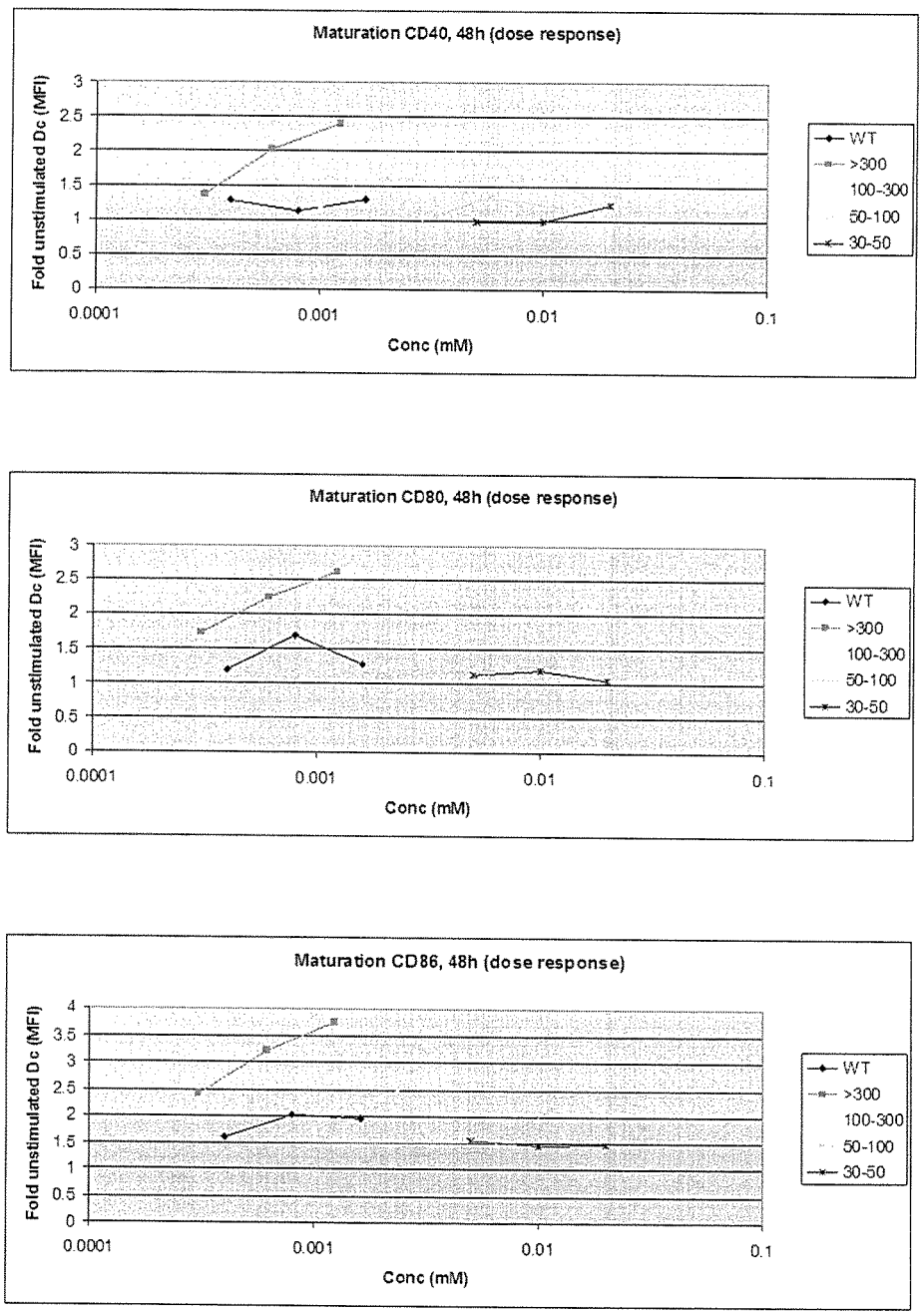

FIG. 6: Maturation of BMDCs with whole mannan and mannan fractions. The upregulation of costimulatory molecules, CD40, CD80 and CD86 was measured by flow cytometry at 6 (FIG. 6A), 24 (FIG. 6B) and 48 (FIG. 6C) hour time points. Samples were analysed at various doses.

Figure 7A:
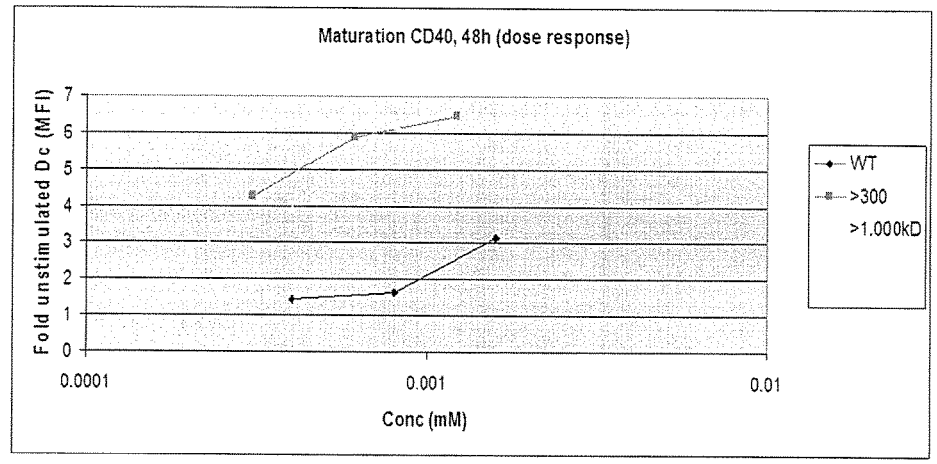
Figure 7B:
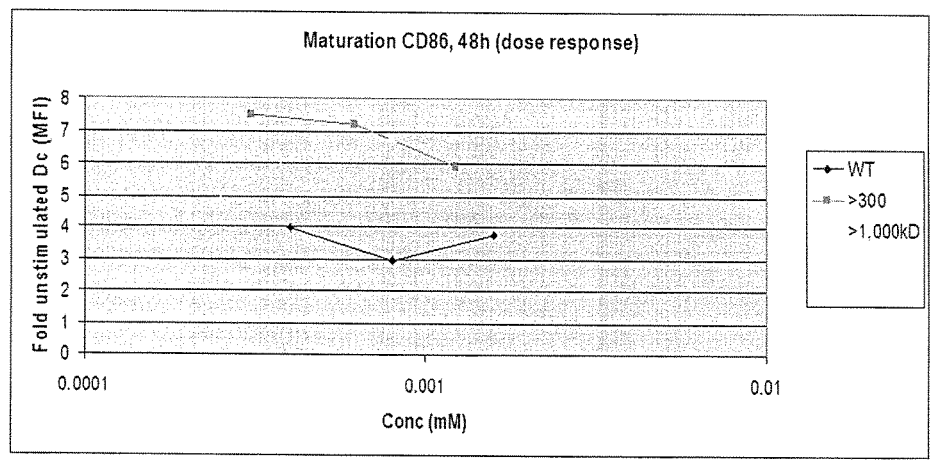

FIG. 7: Maturation of BMDCs with whole mannan, >1000 kDa mannan fraction, and >300 kDa mannan fraction. The upregulation of costimulatory molecules, CD40 (FIG. 7A) and CD86 (FIG. 7B) was measured by flow cytometry. Samples were analysed at various doses and at 48 hour time point.

Figure 8:
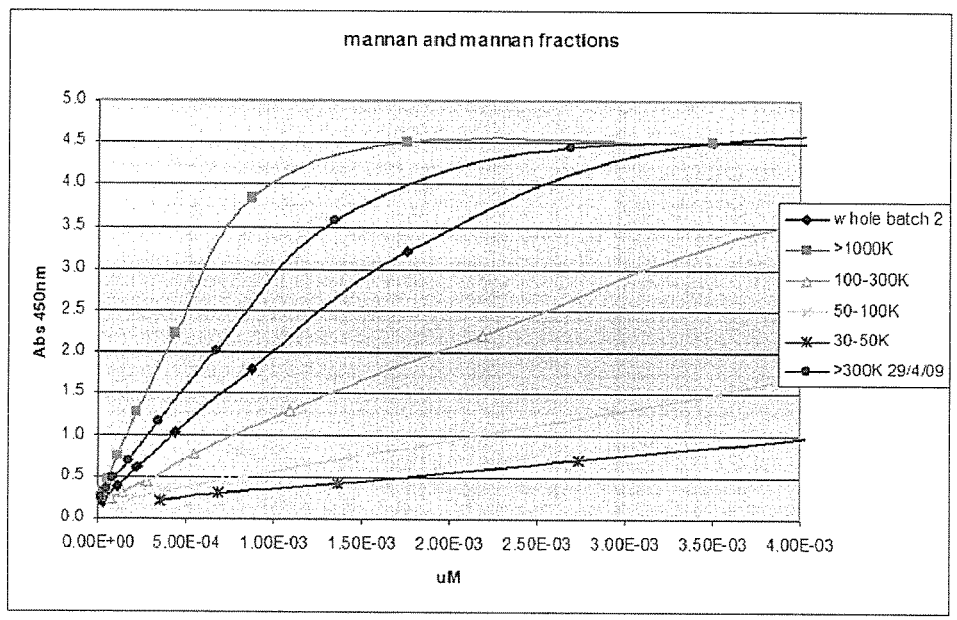

FIG. 8: Absorbance vs. concentration curve for resorcinol assay demonstrating the different mannose content of the mannan fractions.

Figure 9:
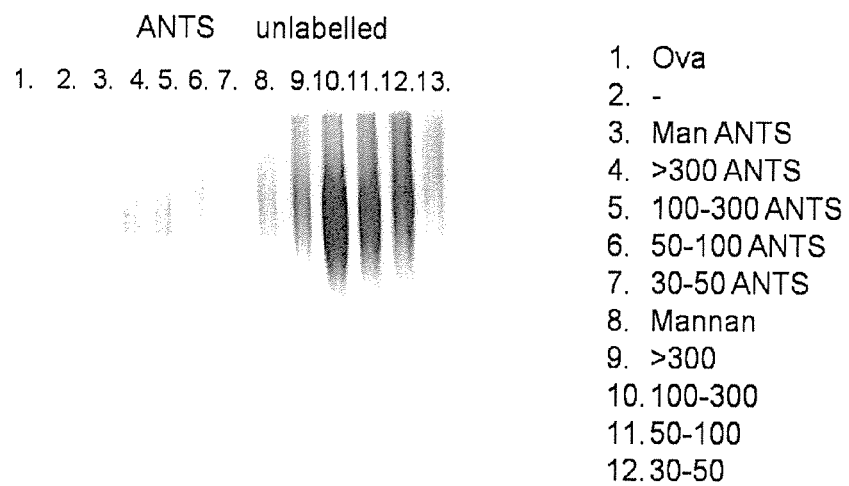

FIG. 9: Analysis of ANTS labelled mannan fractions on native PAGE gel.

Figure 10:
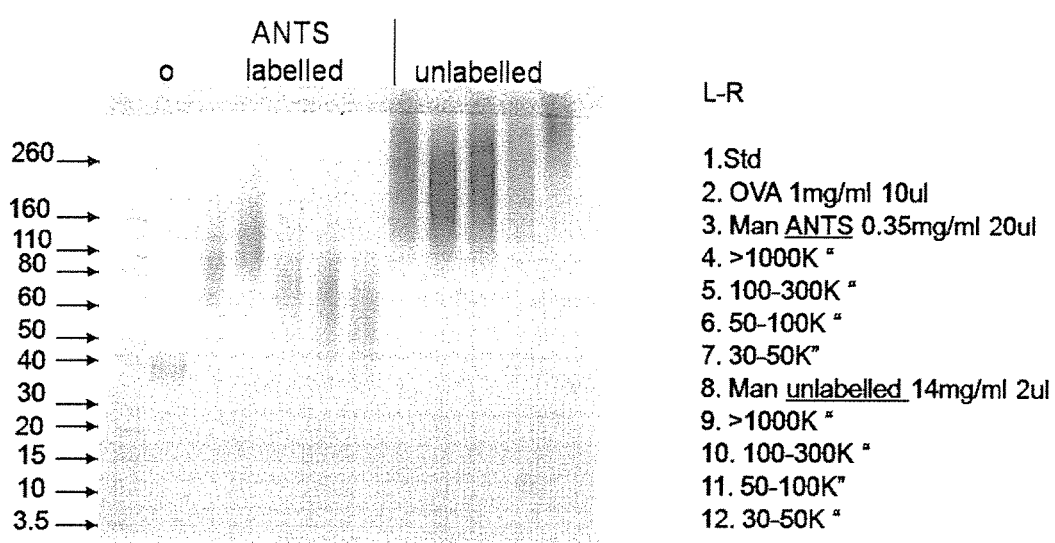

FIG. 10: Analysis of ANTS labelled mannan fractions on SDS-PAGE gel.

Figure 11A:
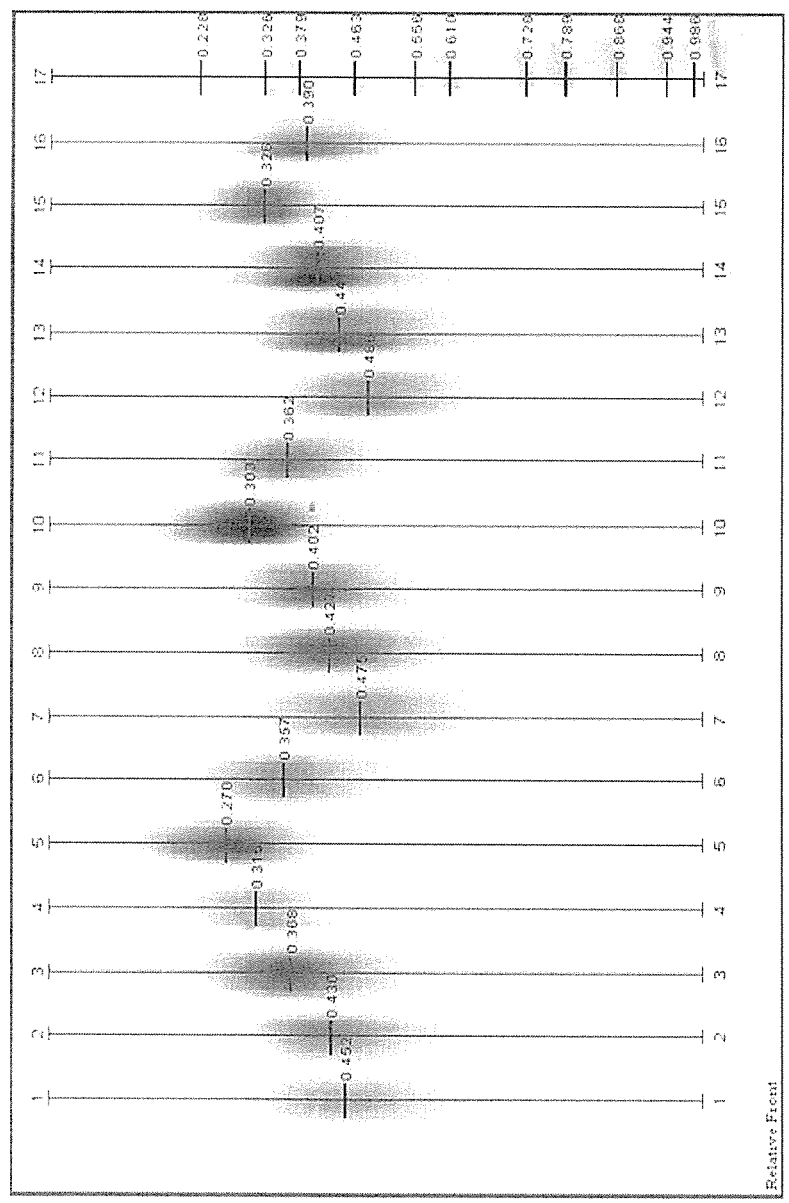
Figure 11B:
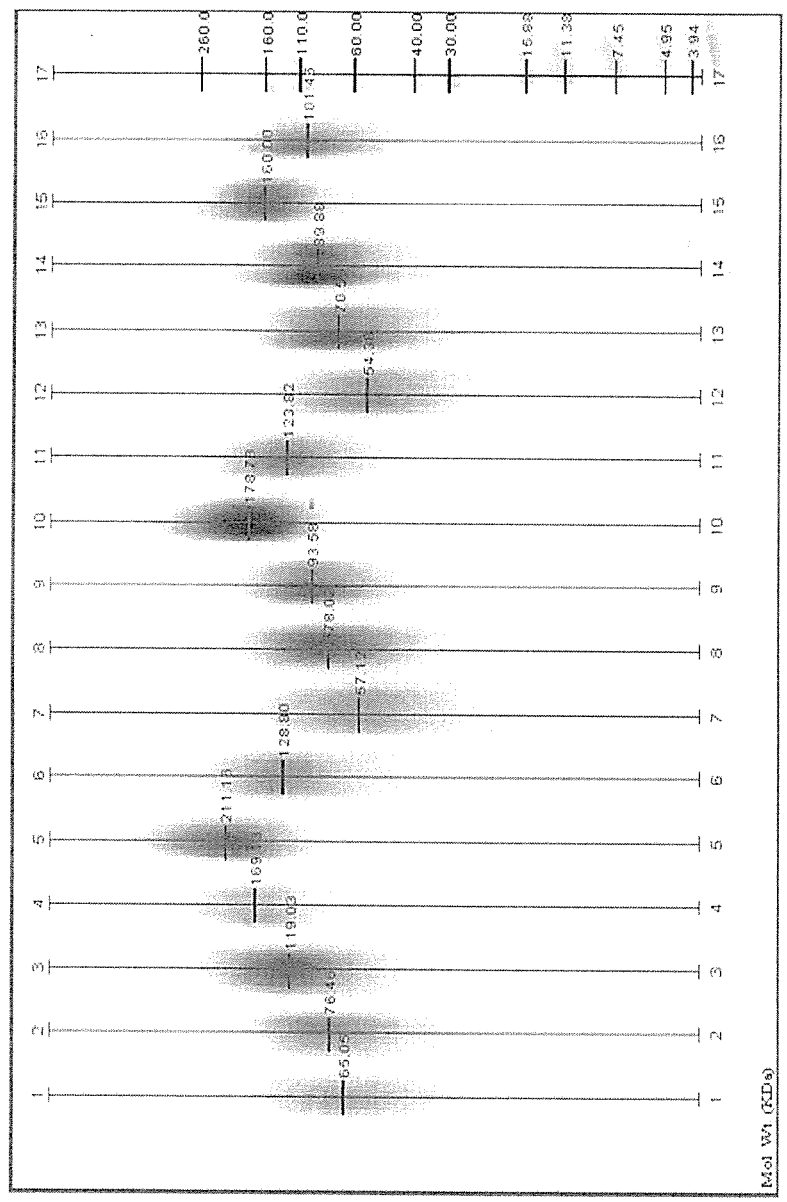

FIG. 11: Scanned SDS-PAGE gels of ANTS-labelled mannan fractions with annotated Rfs (FIG. 11A) and molecular weights (FIG. 11B).

Figure 12:
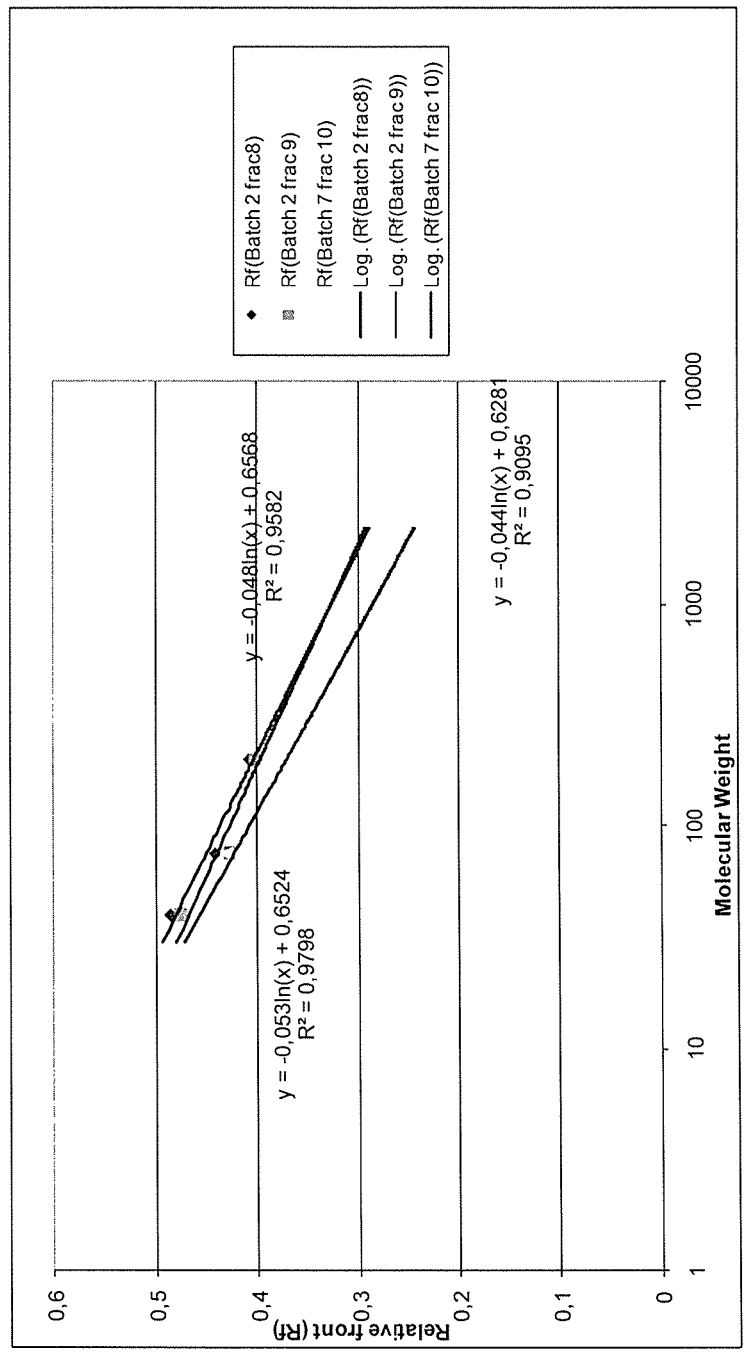

FIG. 12: Standard curves generated by Quantity one software.

Figure 13:
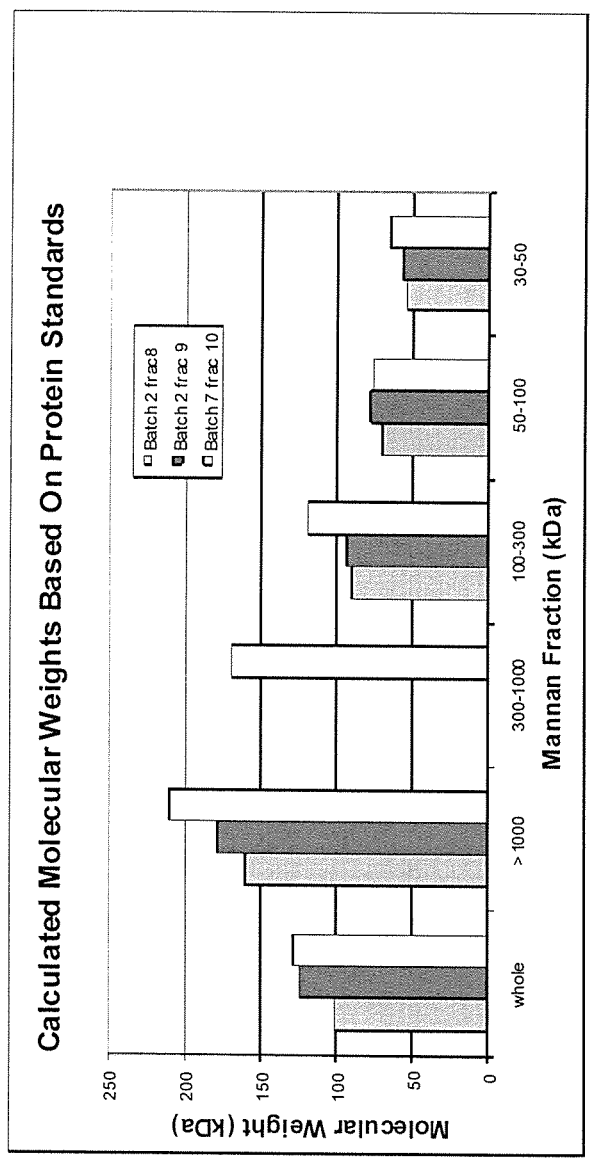

FIG. 13: Relative molecular weights based on protein standards.

Figure 14:
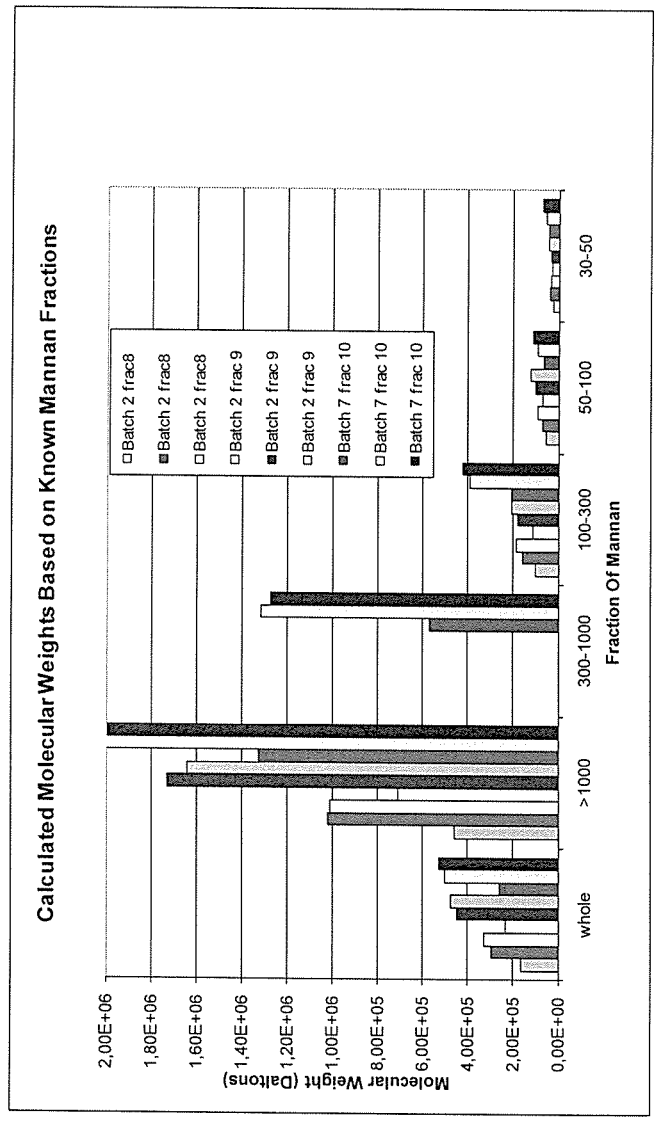

FIG. 14: Relative molecular weights based on carbohydrate standards.

Figure 15:
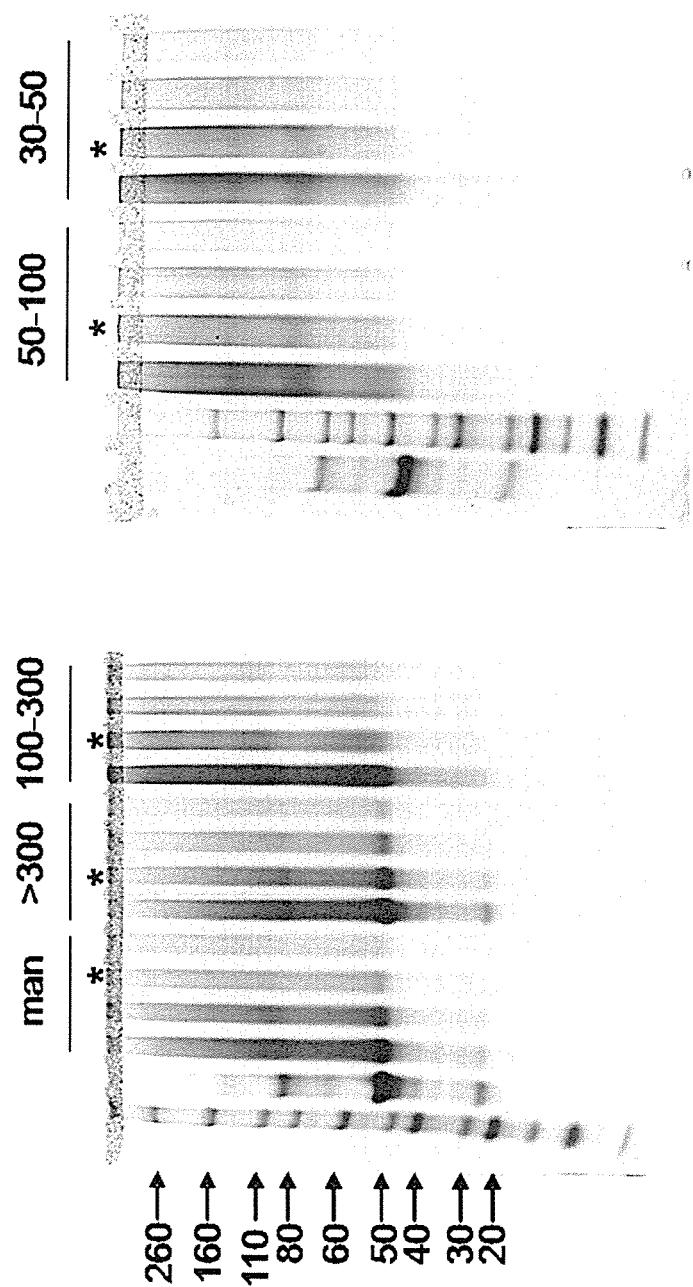

FIG. 15: Analysis of whole mannan and fractions of mannan conjugated to MUC1-FP on SDS-PAGE gels. The star denotes the conjugates incorporating the same ratio of MUC1-FP:mannan as in whole mannan-MUC1-FP conjugate.

Figure 16:
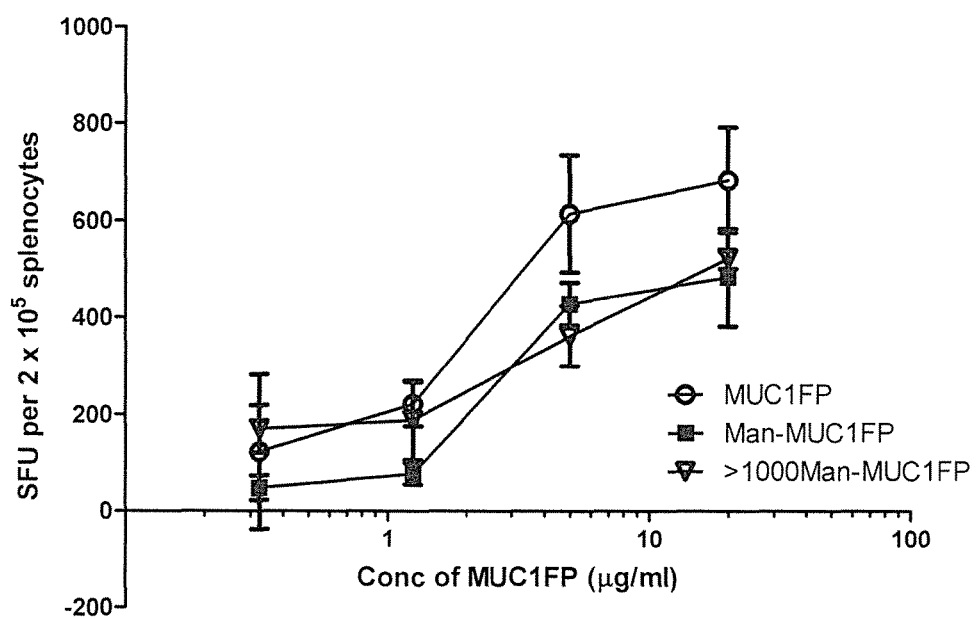

FIG. 16: MUC1-specific IFN-γ responses in splenocytes of mice immunized on day 0, 10, 17 with 10 μg of MUC1-FP, MFP or >1000MFP.

Figure 17:
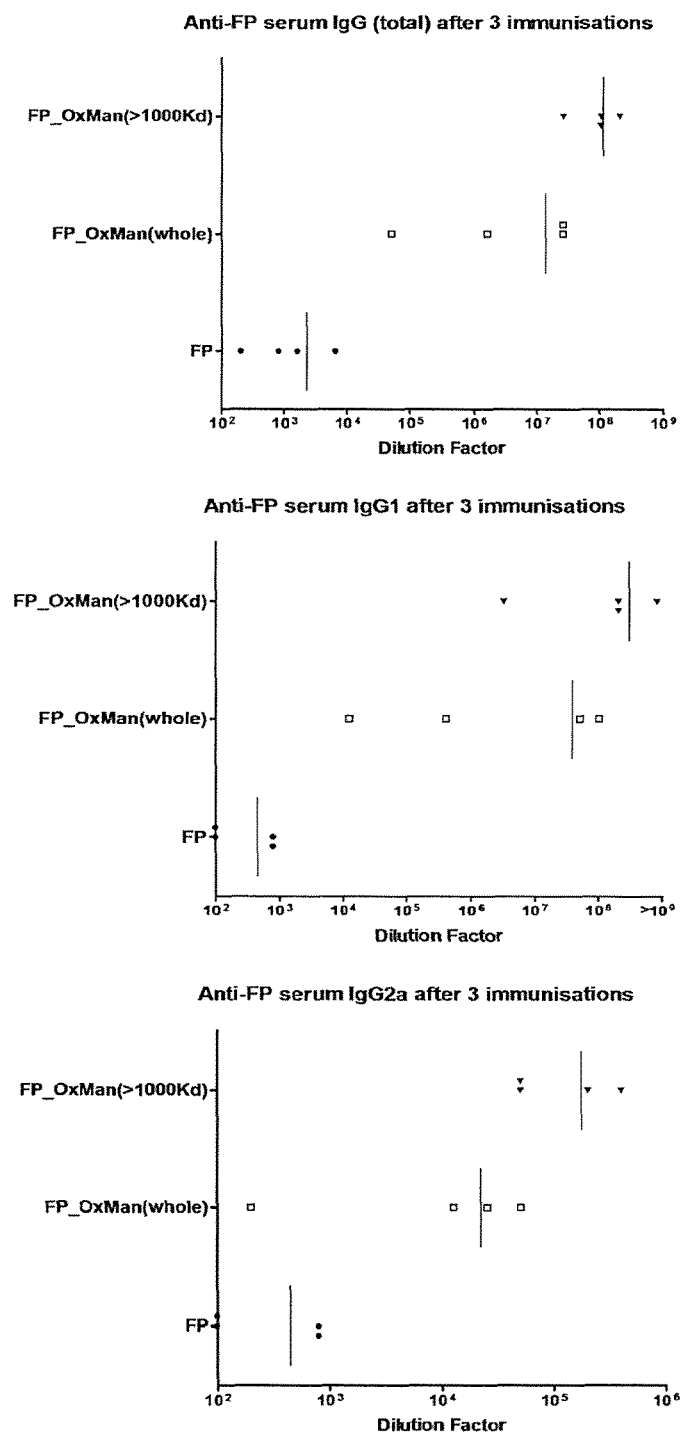

FIG. 17: Total anti-MUC1 serum IgG, IgG1 and IgG2a in mice immunized on day 0, 10, 17 with 10 gg of MUC1-FP, MFP or >1000MFP.

FIG. 18: Mannan specifications from supplier.

Figure 19A:
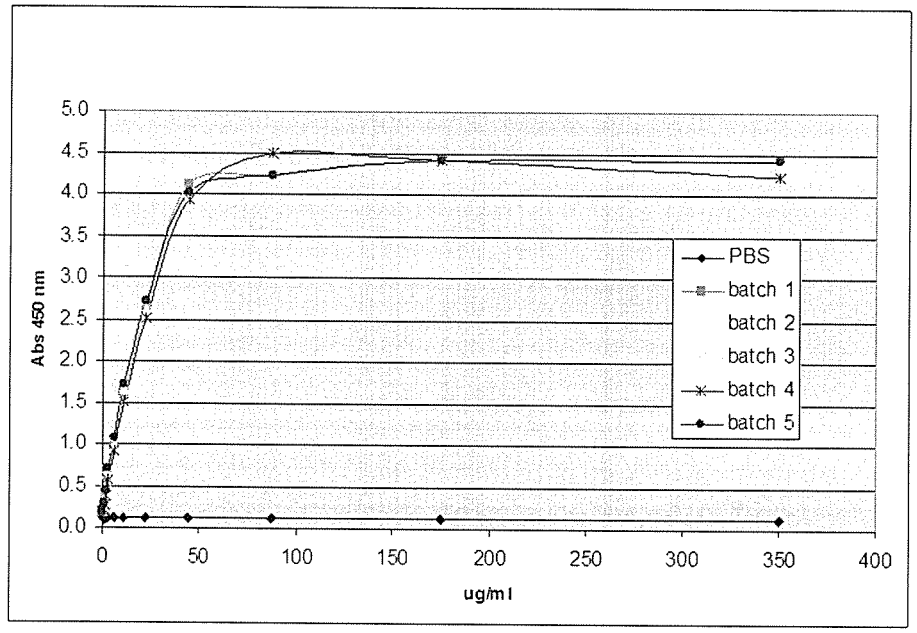

FIG. 19A: Analysis of batches of mannan using the resorcinol assay.

Figure 19B:
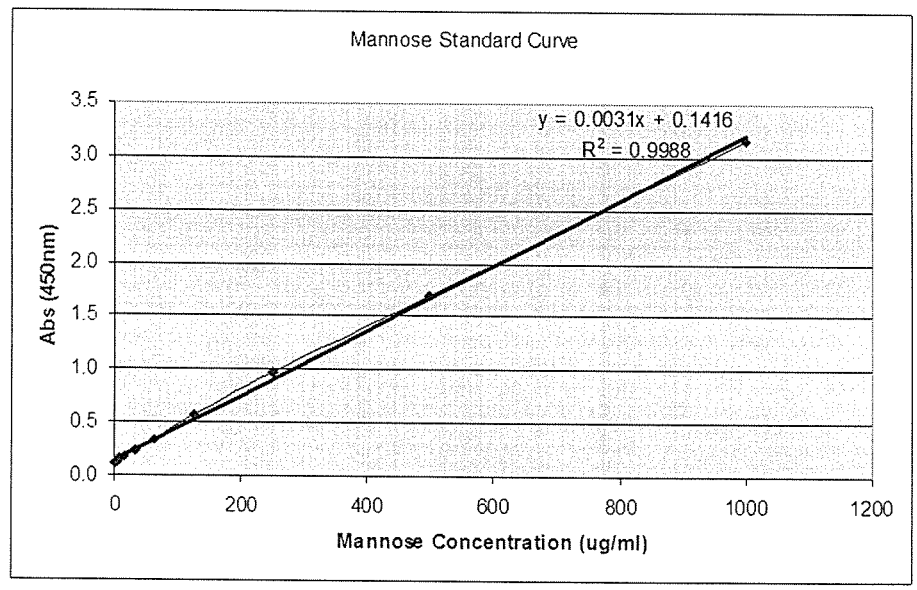

FIG. 19B: Standard curve for mannose obtained using the resorcinol assay.

FIG. 20: Comparison of various batches of mannan from Sigma by quantitating aldehyde residues after periodate oxidation.

Figure 21:
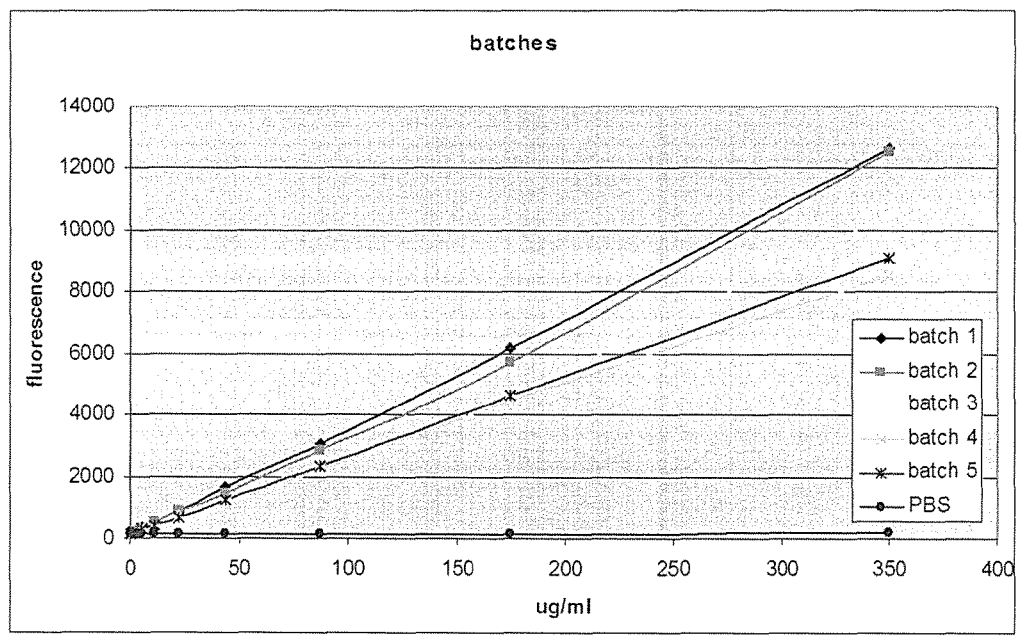

FIG. 21: Fluorescence vs. concentration curve for various batches of mannan reacted with ANTS.

Figure 22:
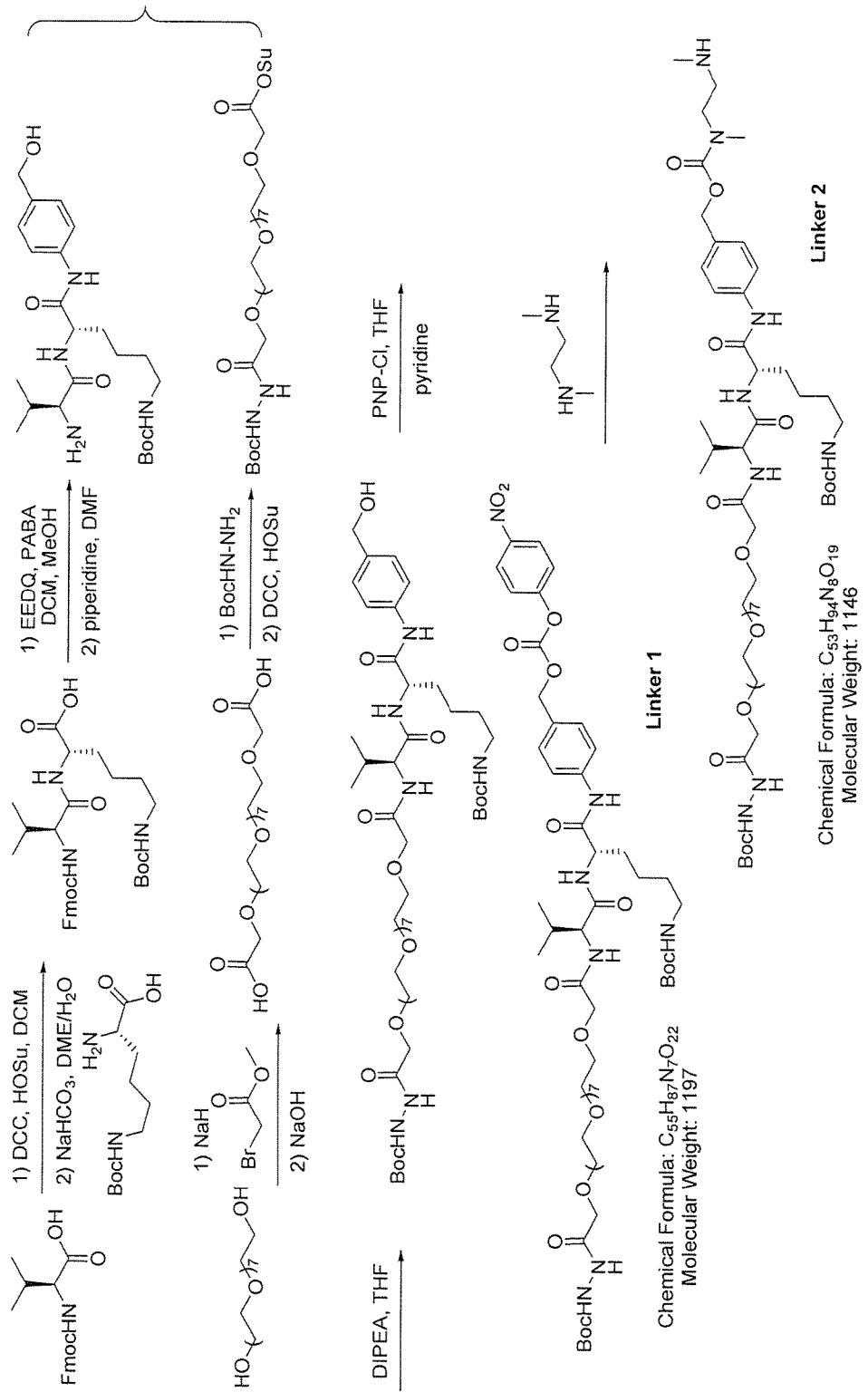
Figure 23:
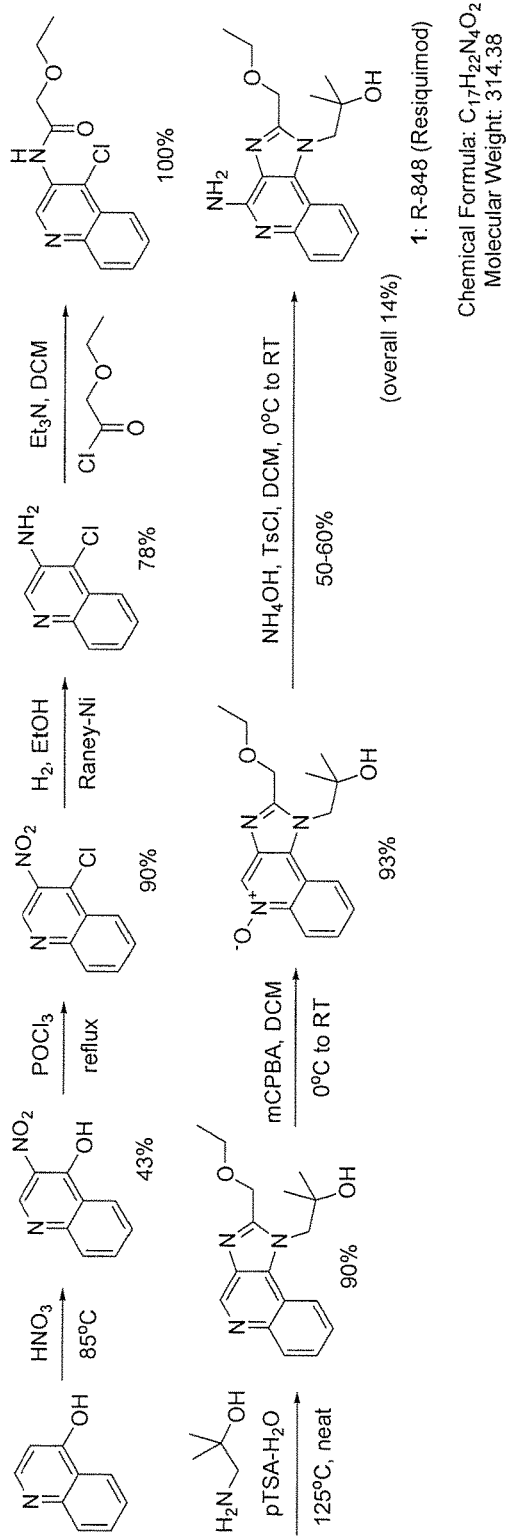
Figure 24:
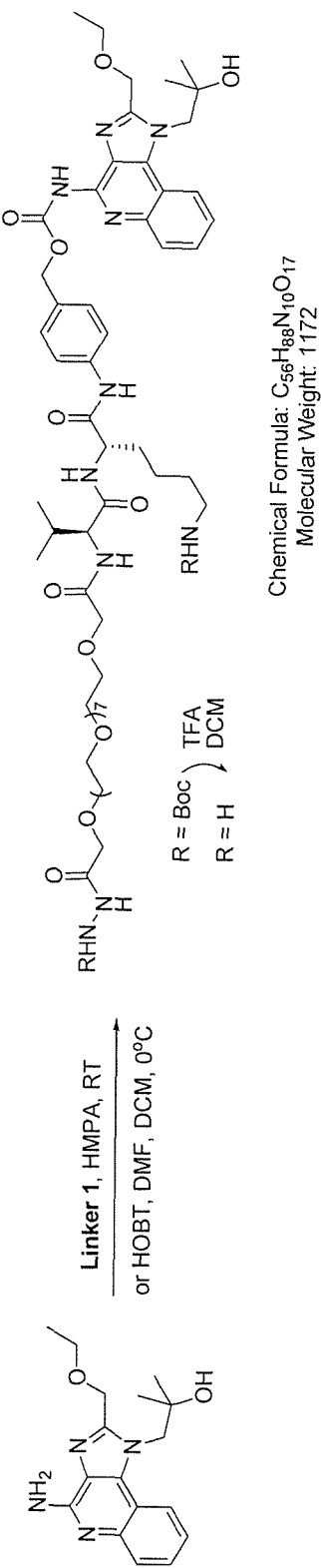
Figure 25:
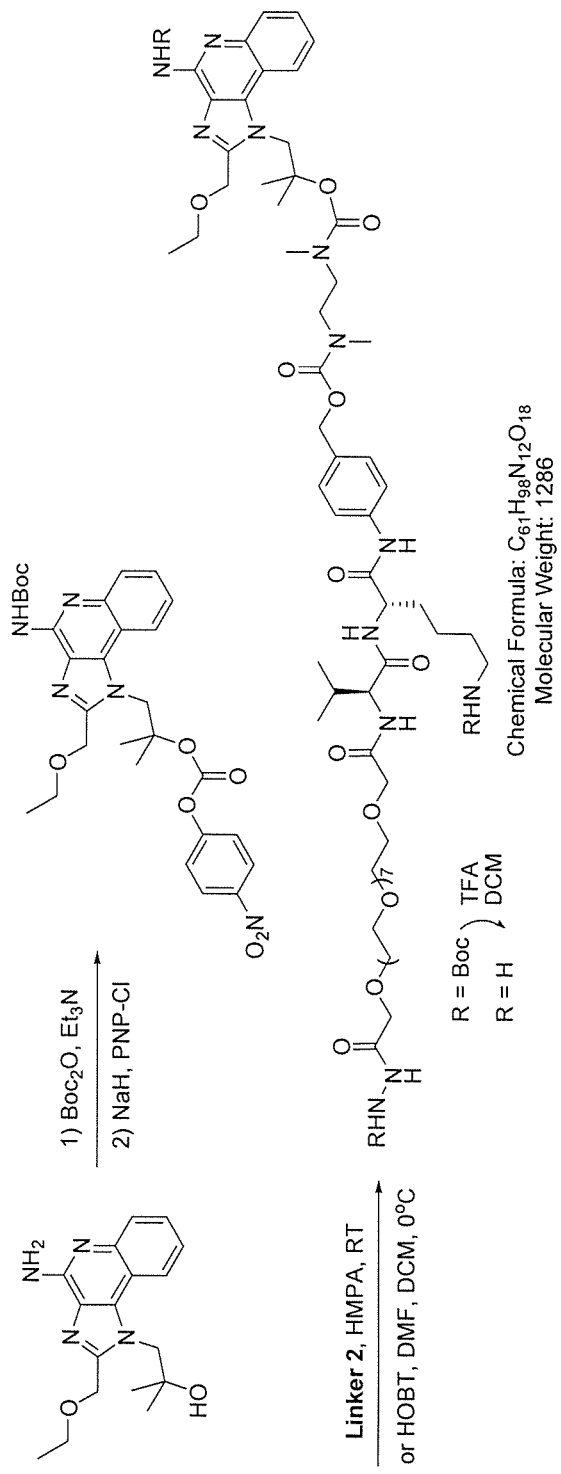
Figure 26:
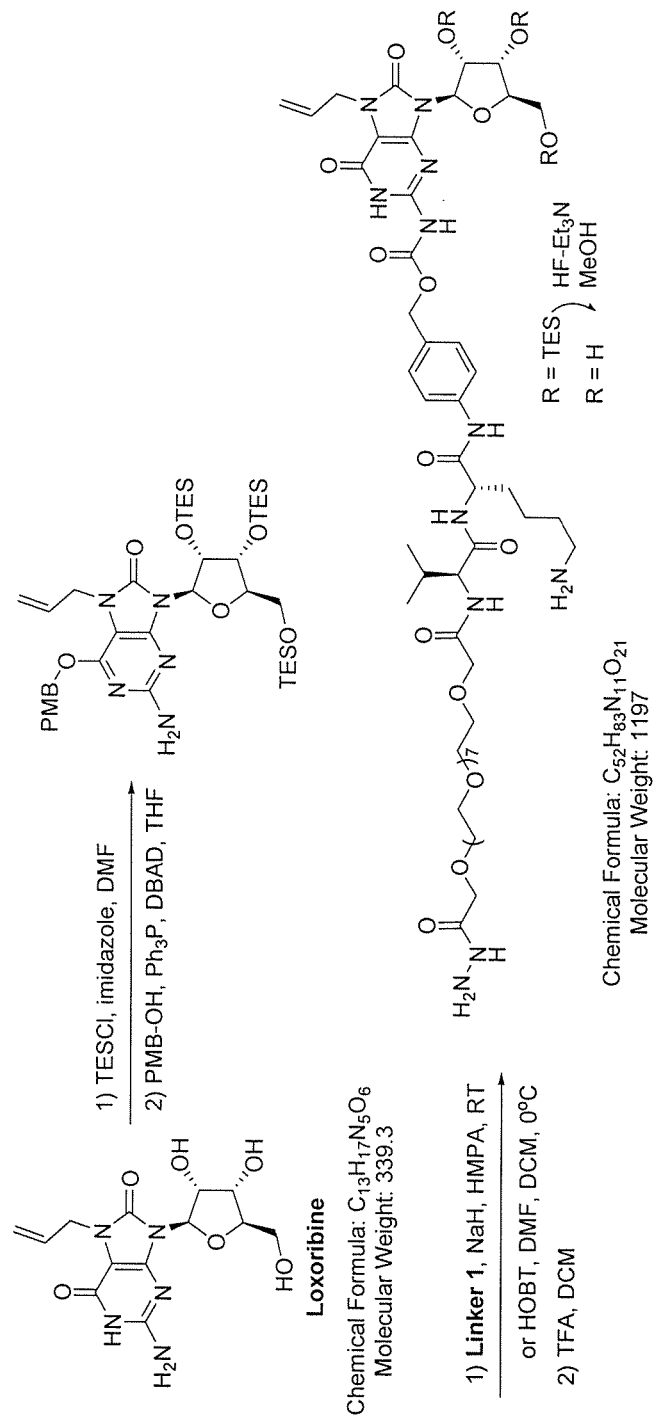
Figure 27:
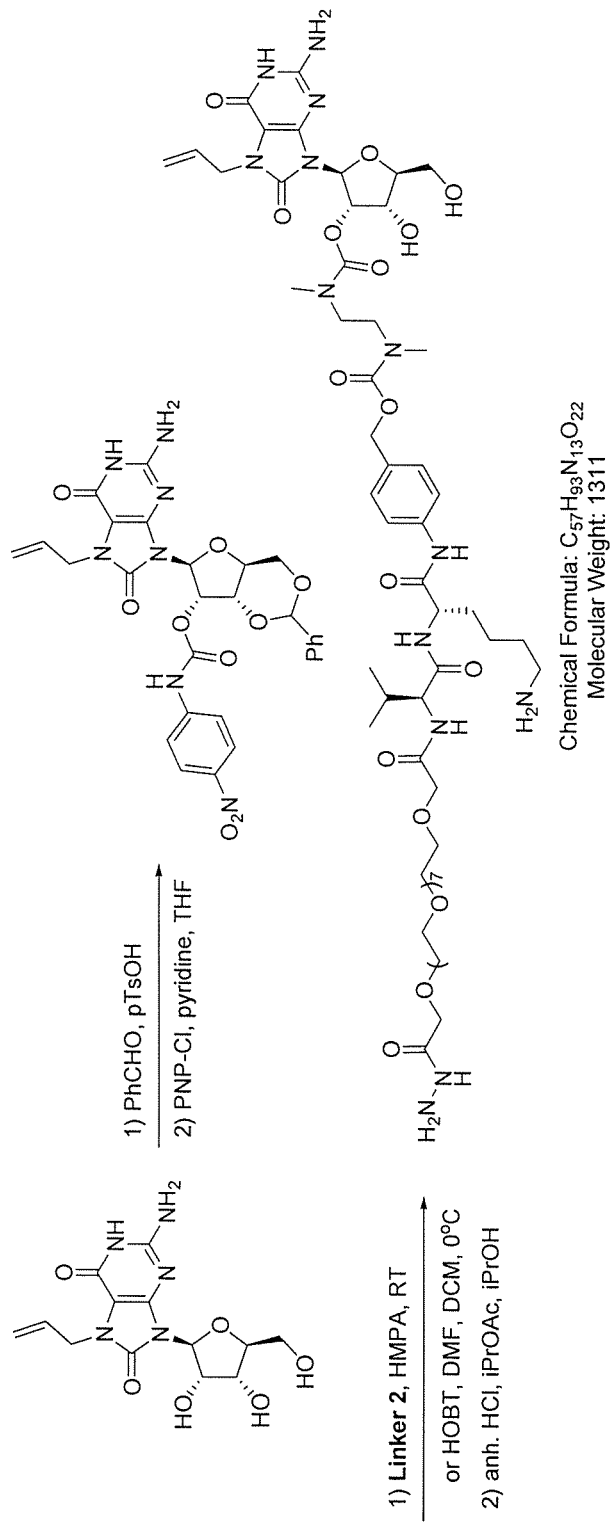
Figure 28:
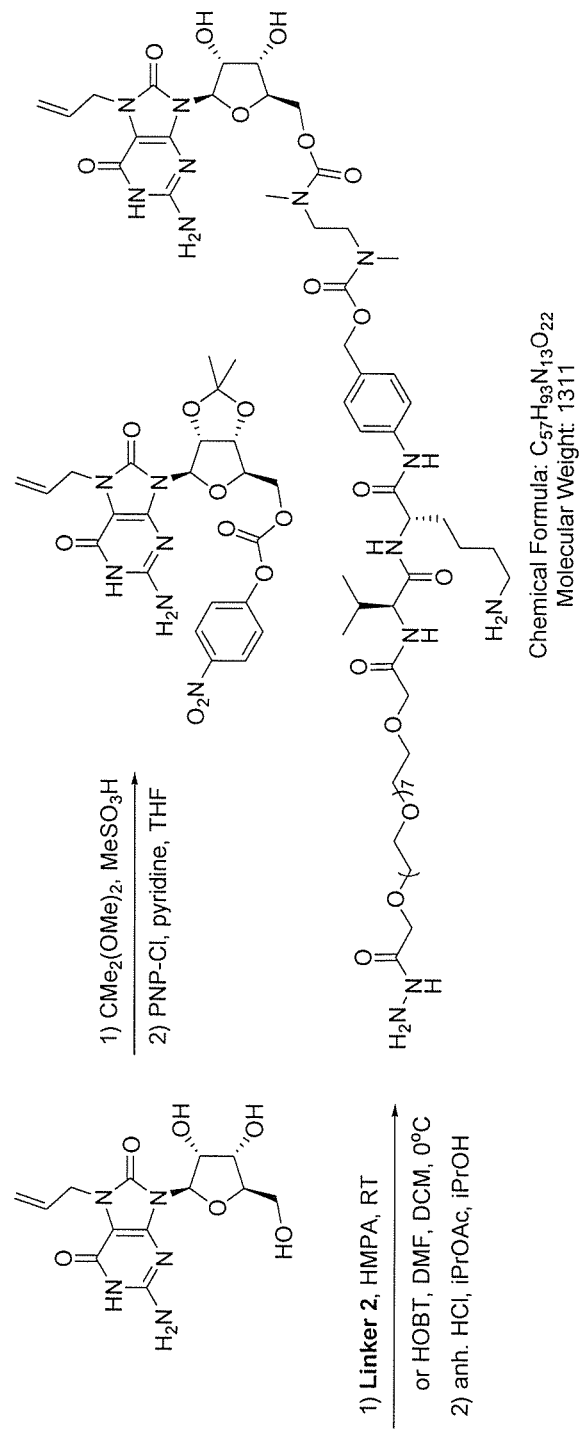
Figure 29:
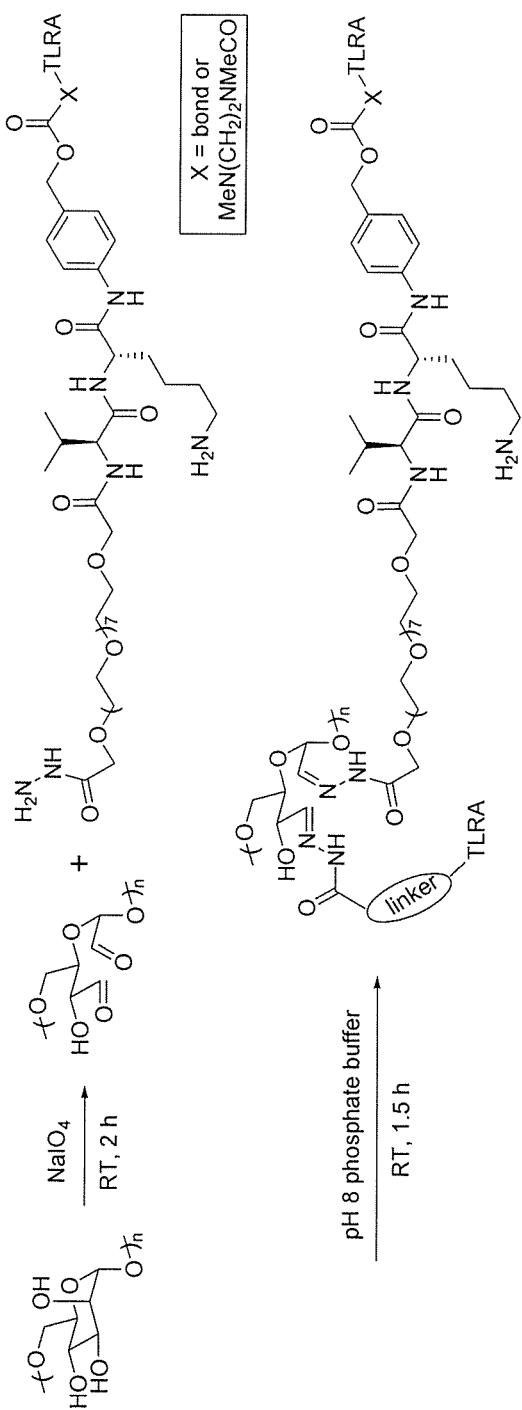
Figure 31:
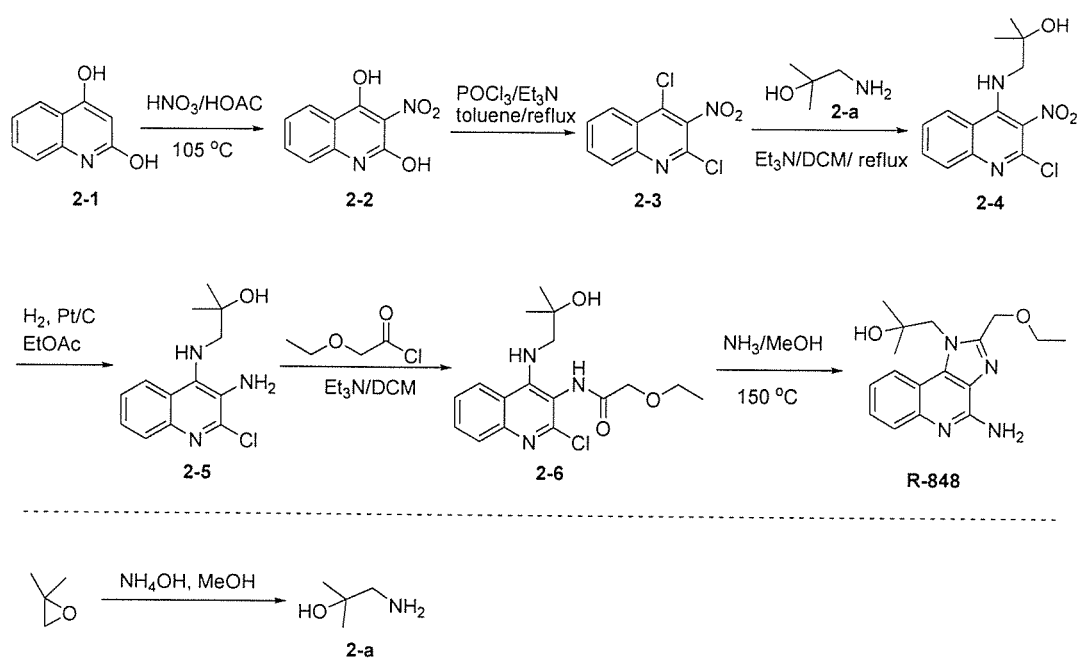
Figure 32:
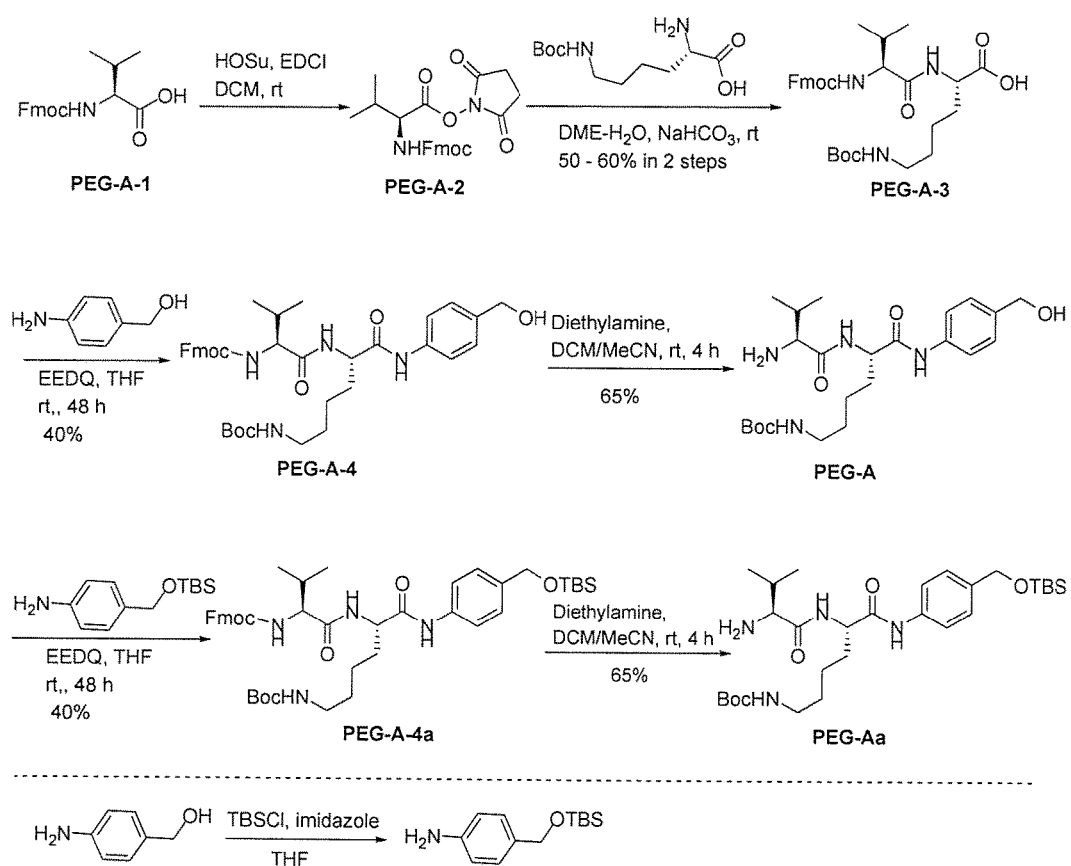
Figure 33:
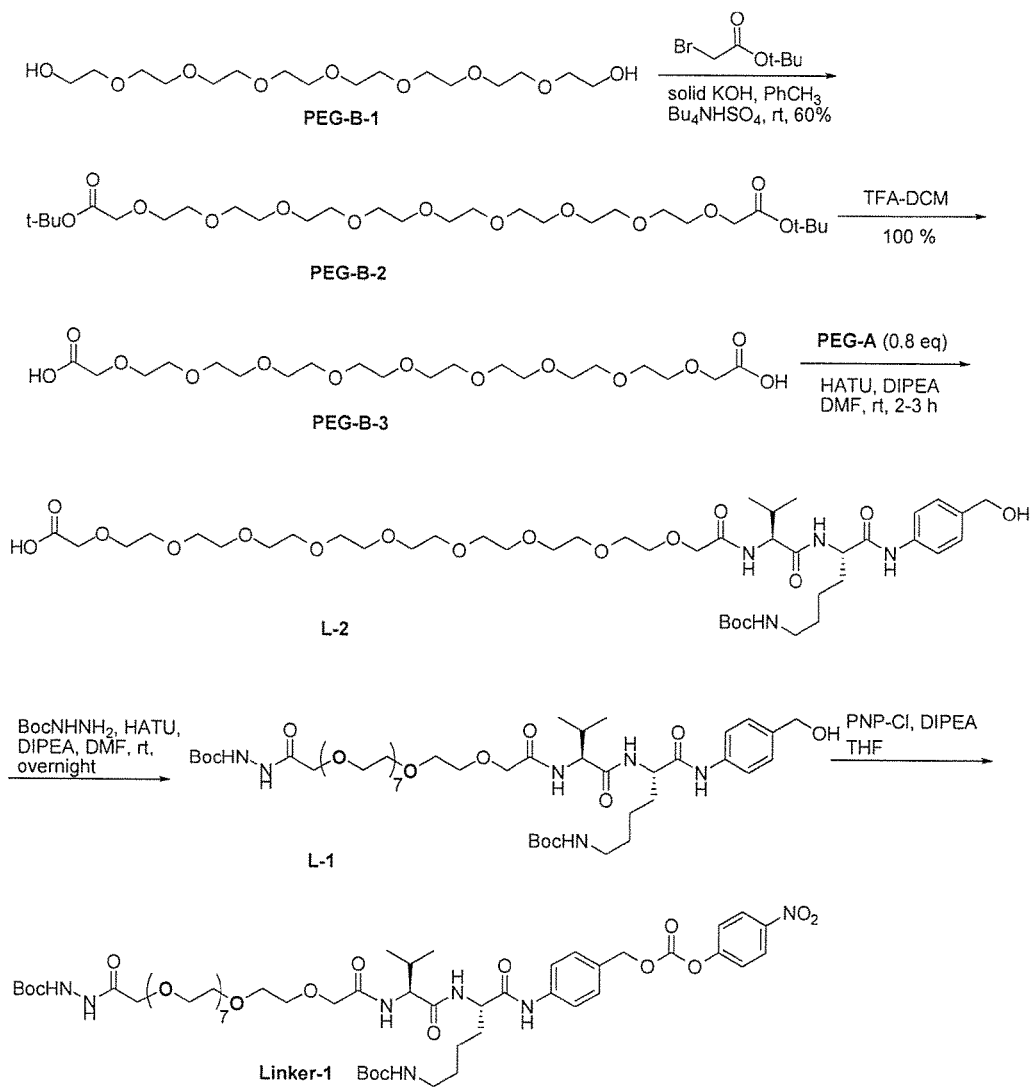
Figure 34:
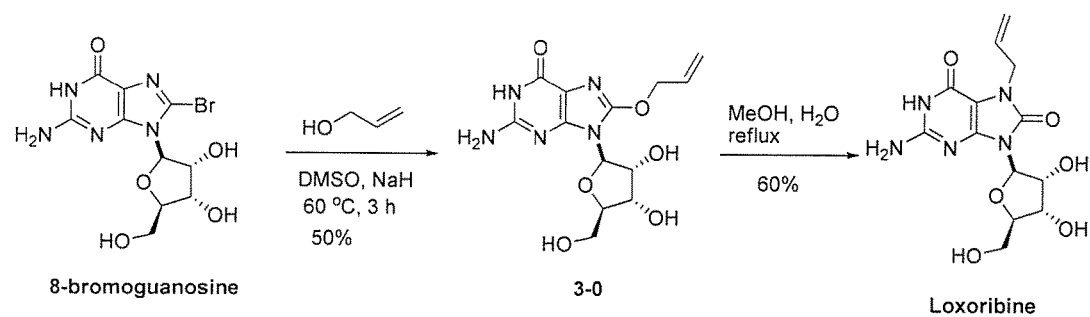
Figure 35:
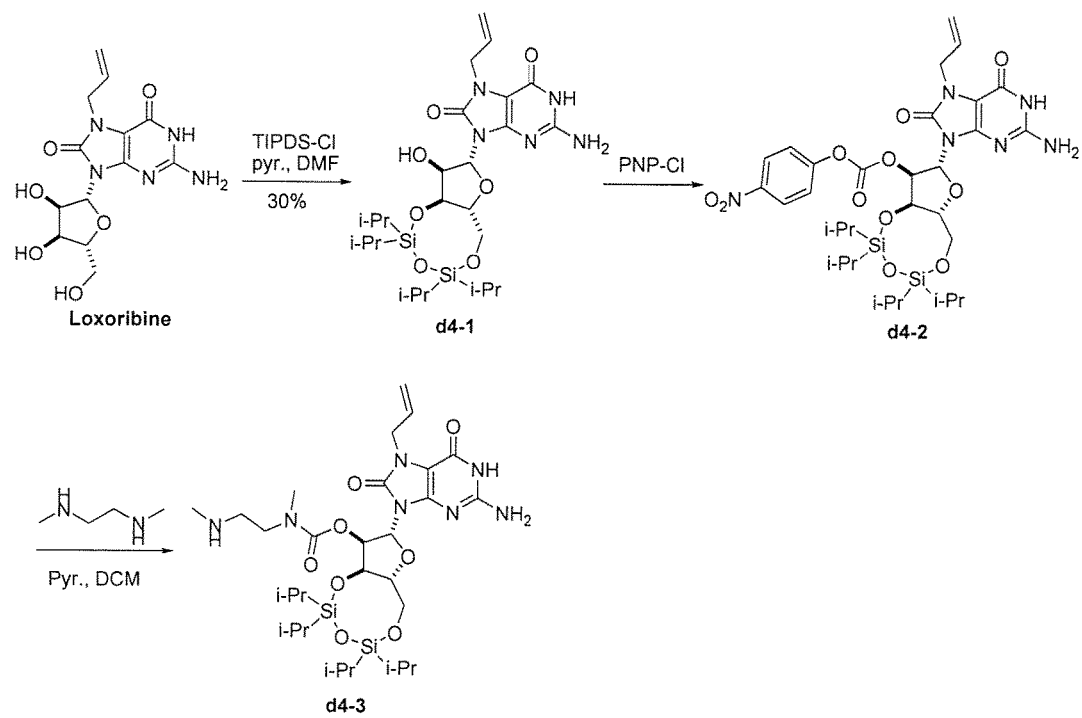
Figure 36:
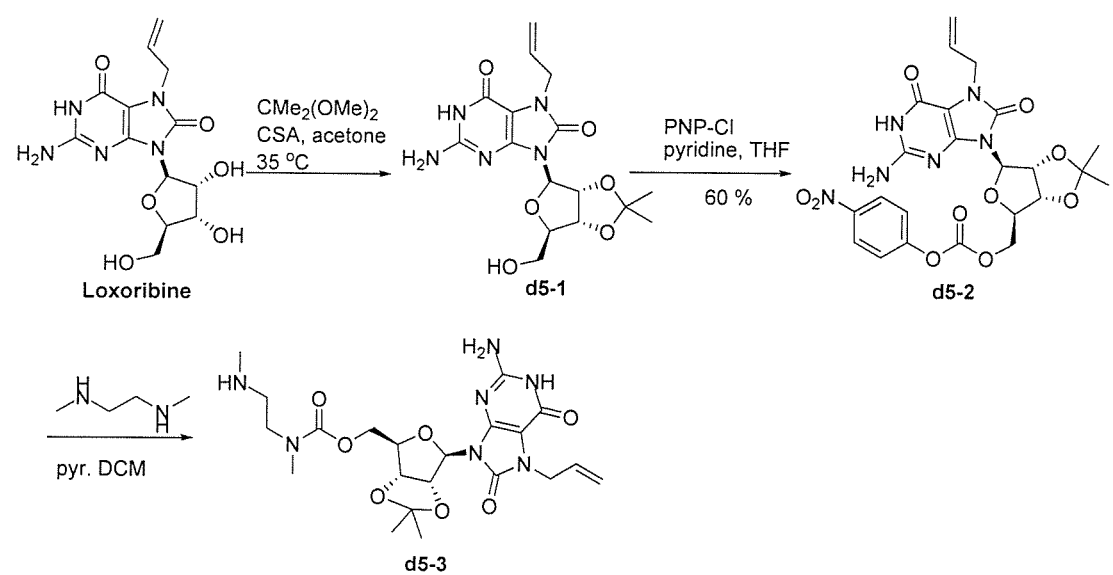
Figure 37:
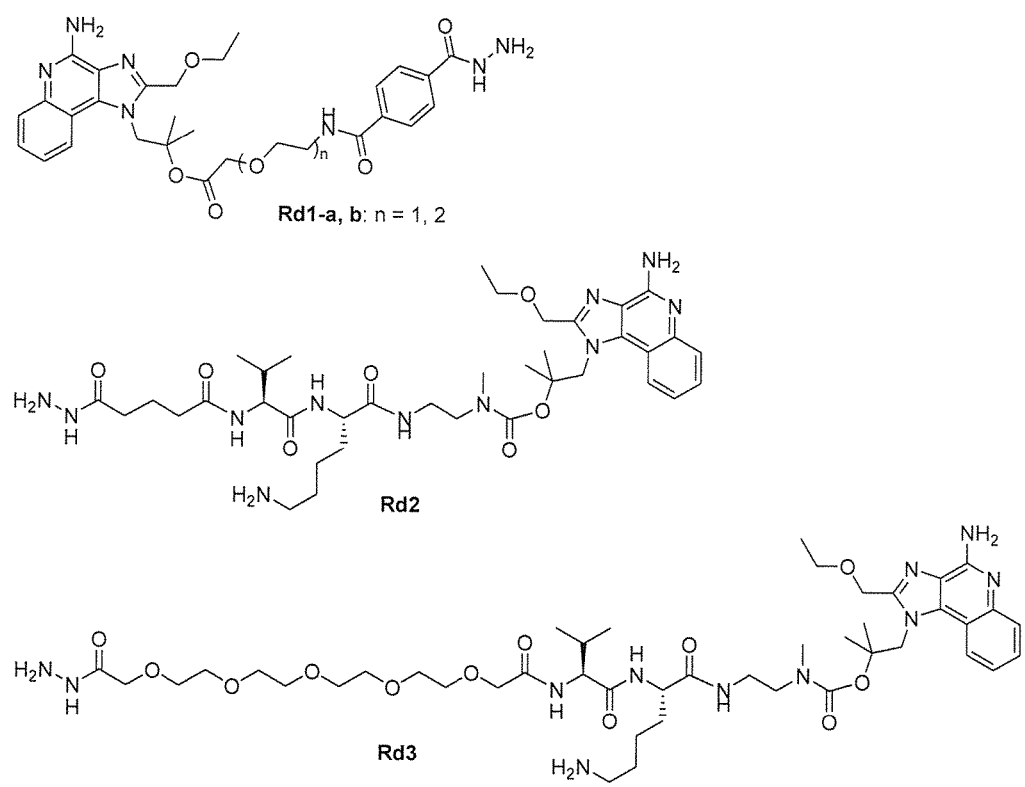
Figure 38A:
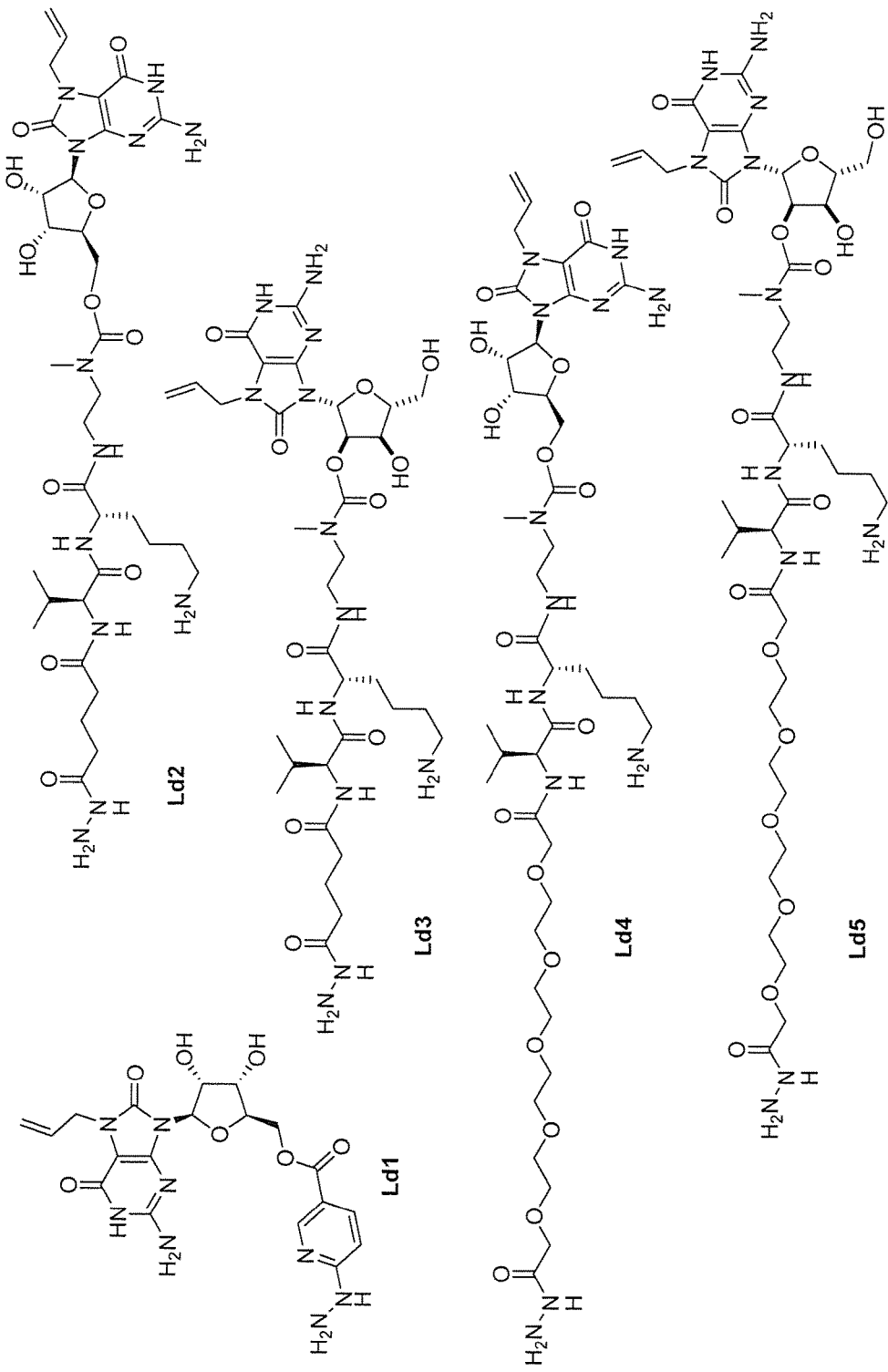
Figure 38B:
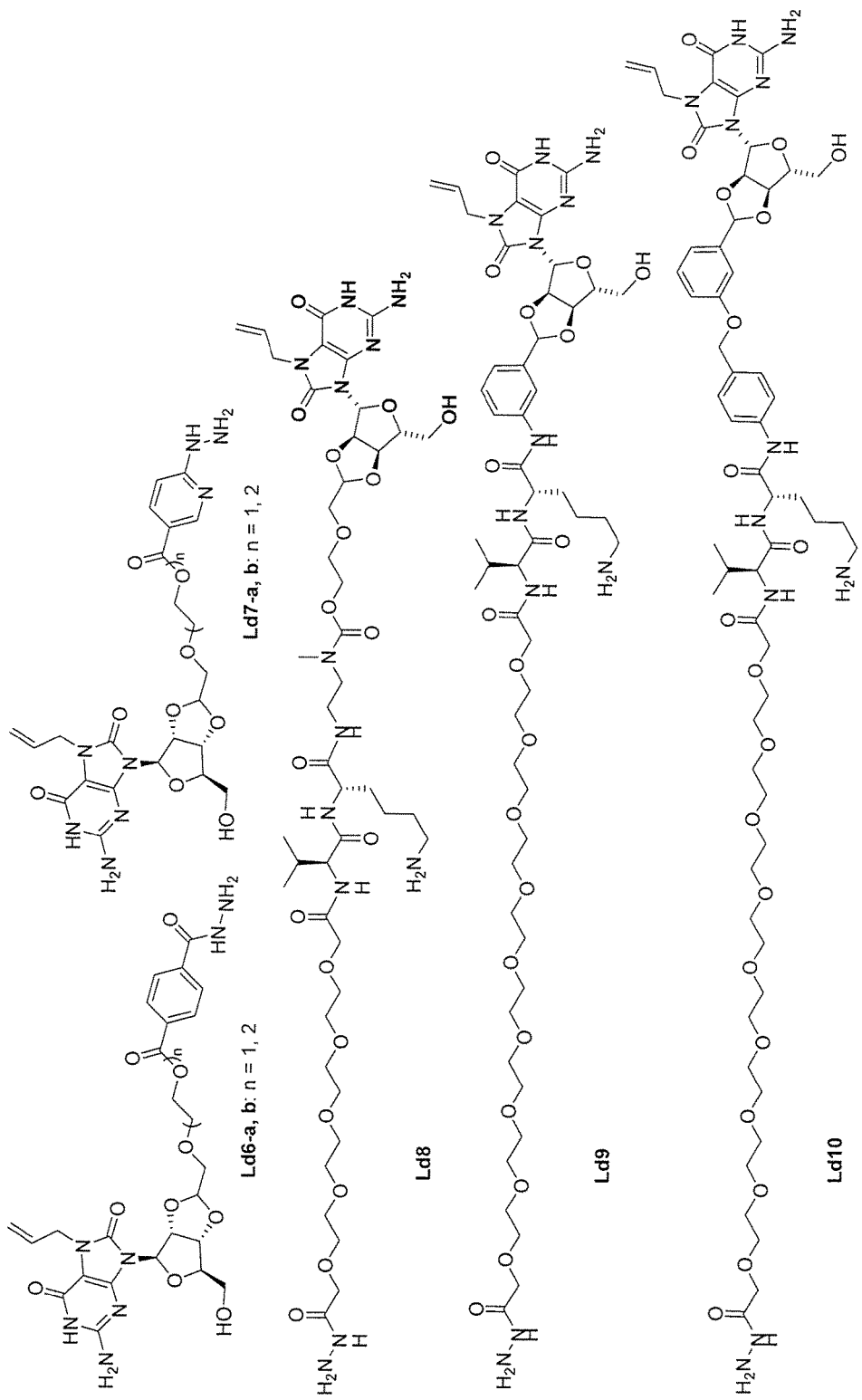
Figure 39:
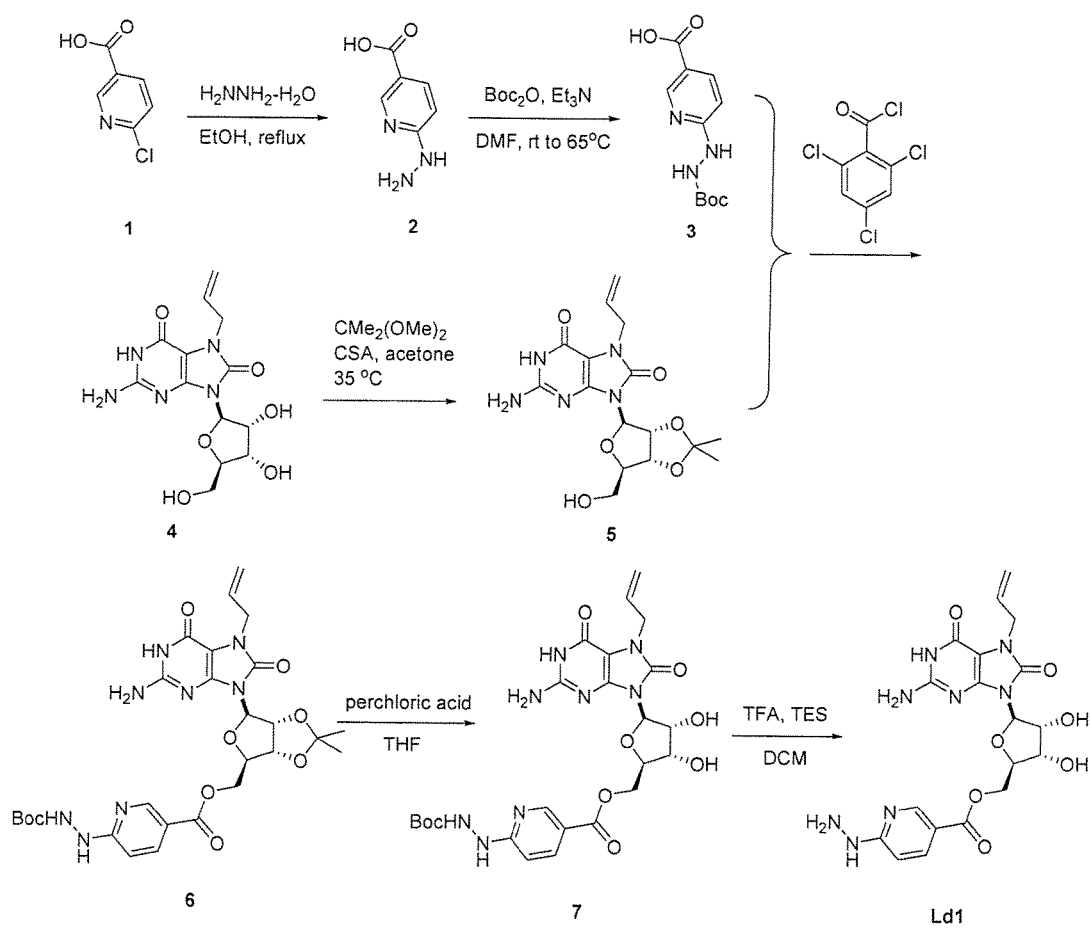
Figure 40A:
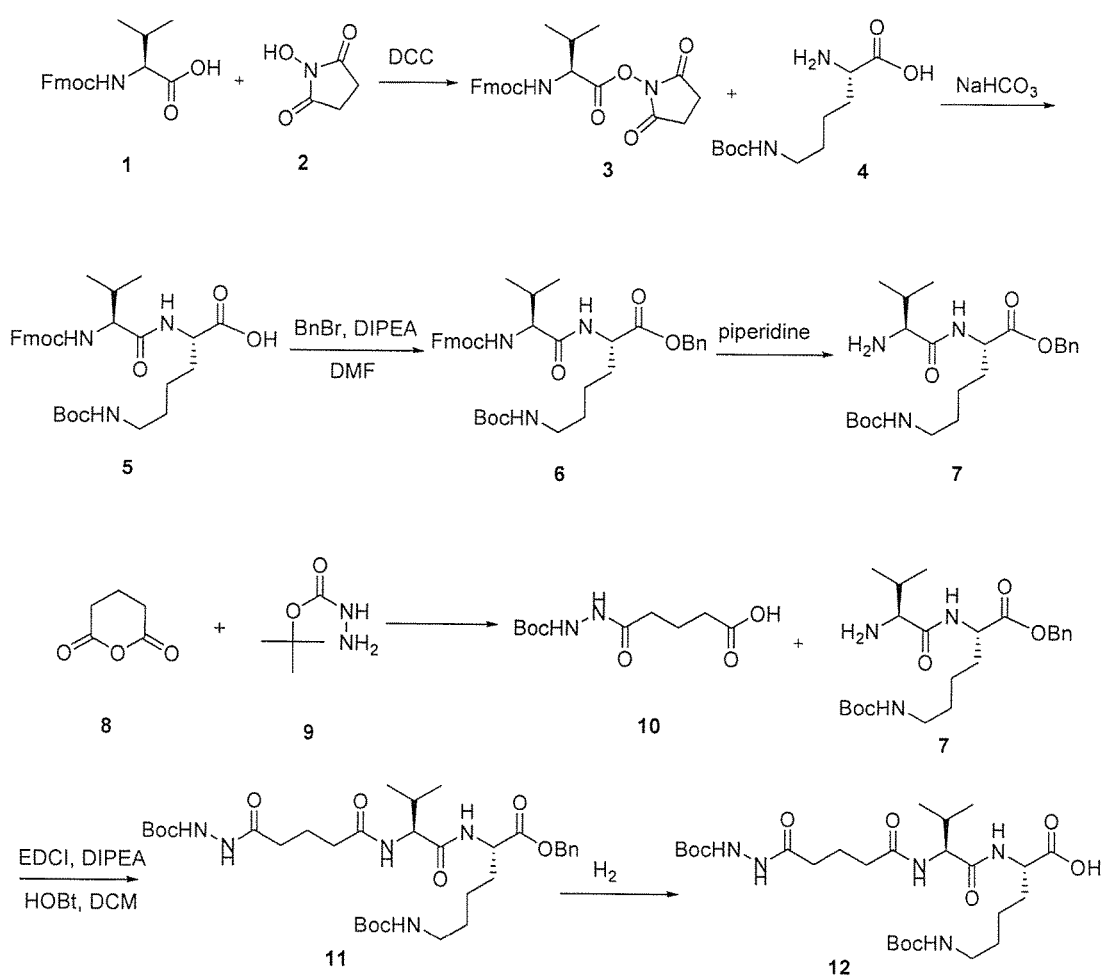
Figure 40B:
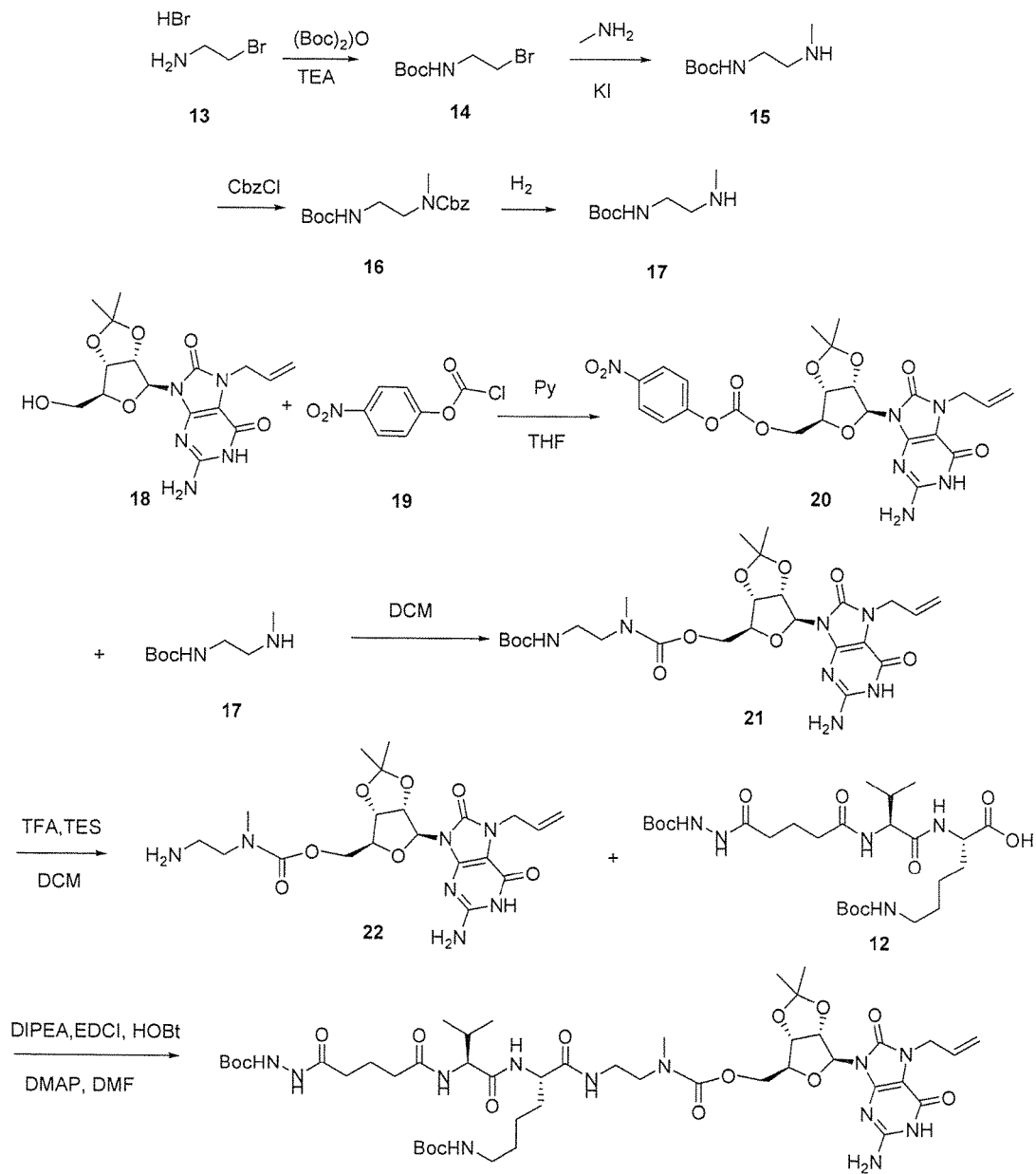
Figure 40C:
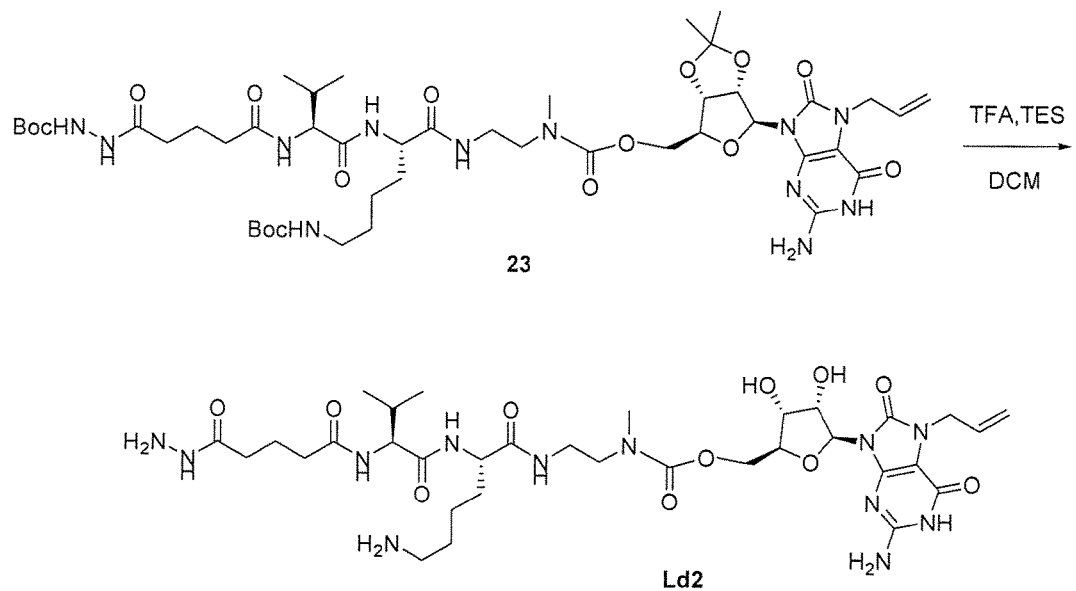
Figure 41:
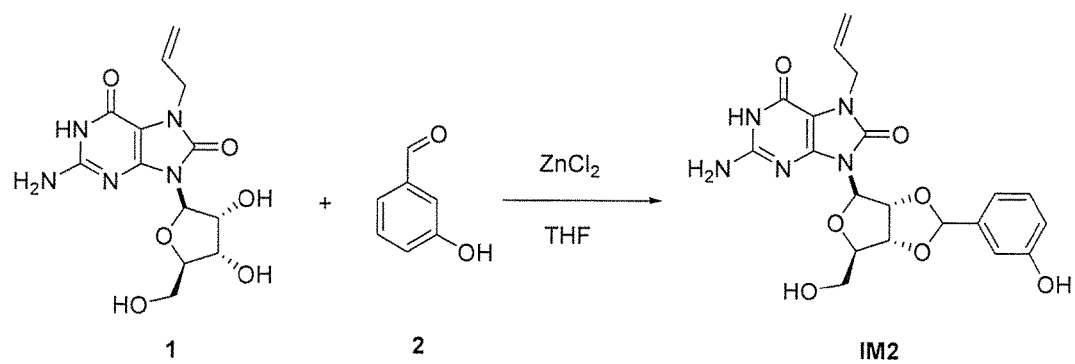
Figure 42:
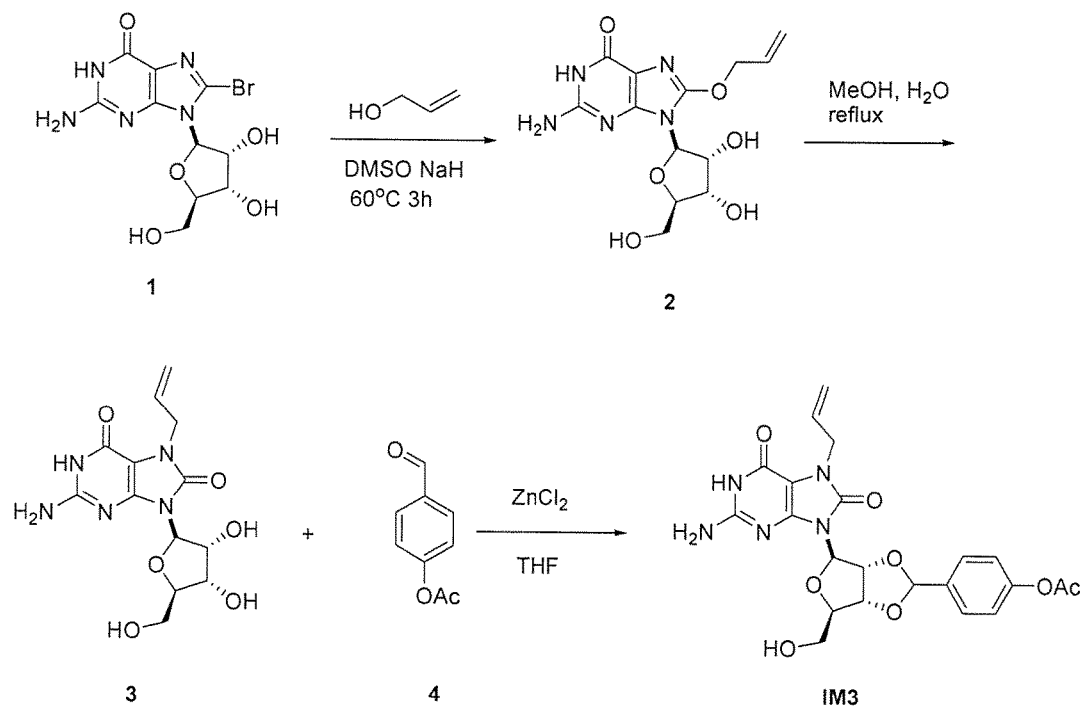

FIG. 22: Synthesis of polyethylene glycol linkers.
FIG. 23: Synthesis of Resiquimod (R-848).
FIG. 24: Synthesis of a functionalized derivative.
FIG. 25: Synthesis of a functionalized derivative.
FIG. 26: Synthesis of a functionalized derivative.
FIG. 27: Synthesis of a functionalized derivative.
FIG. 28: Synthesis of a functionalized derivative.
FIG. 29: Generic synthesis of immune modulator-carbohydrate polymer conjugates.
FIG. 30: Functionalized derivatives 1-5.
FIG. 31: Alternative synthesis of Resiquimod (R-848).
FIG. 32: Synthesis of PEG-A.
FIG. 33: Alternative synthesis of L-1 and Linker-1.
FIG. 34: Synthesis of Loxoribine.
FIG. 35: Synthesis of derivative 4-3.
FIG. 36: Synthesis of derivatives 5-2 and 5-3.
FIG. 37: Functionalized Resiquimod derivatives Rd1-Rd3.
FIG. 38: Functionalized Loxoribine derivatives Ld1-Ld10.
FIG. 39: Synthesis of Ld1.
FIG. 40: Synthesis of Ld2.
FIG. 41: Synthesis of IM2.
FIG. 42: Synthesis of IM3.

Figure 43:
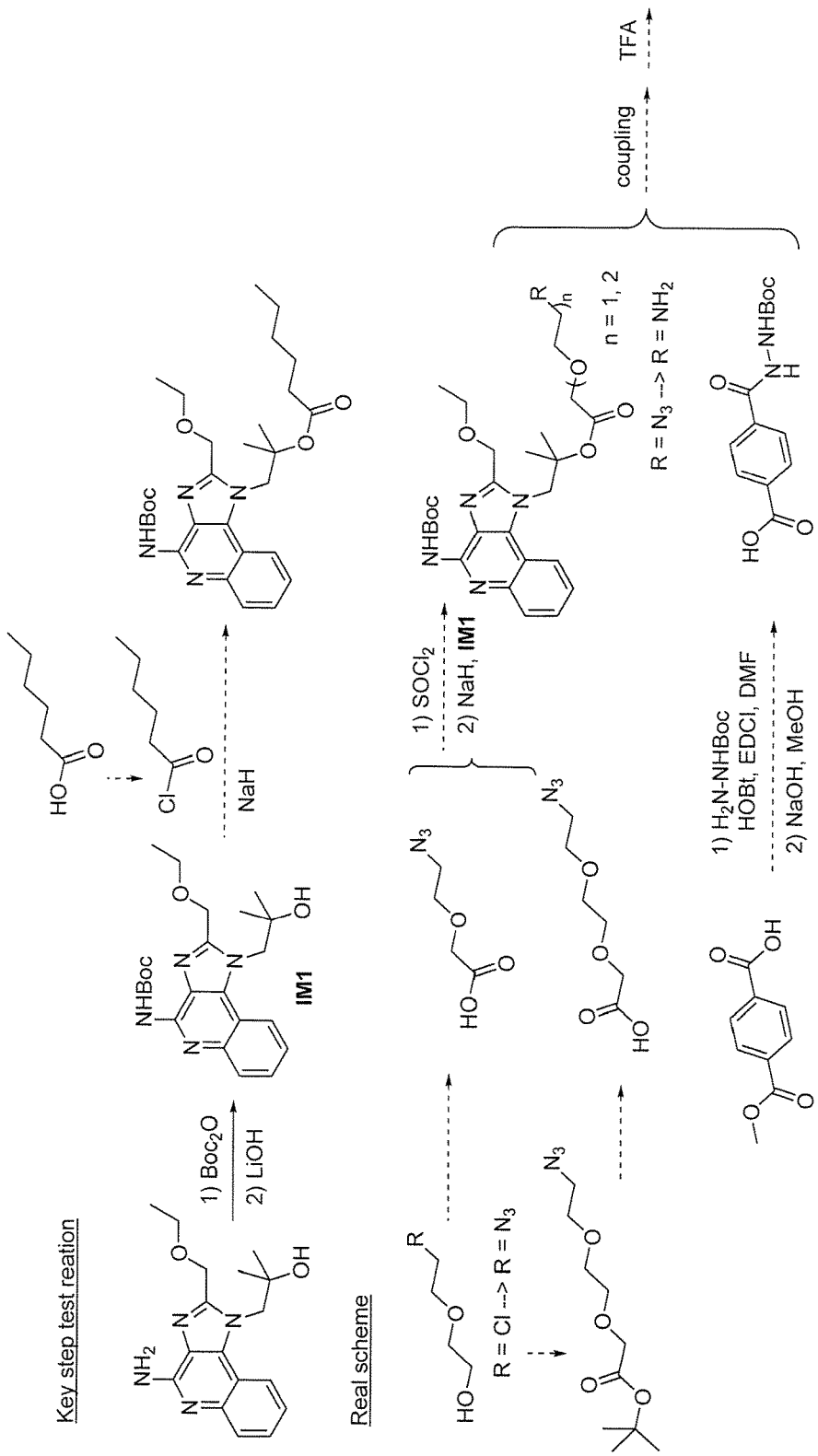

FIG. 43: Synthesis of Rd1.

Figure 44:
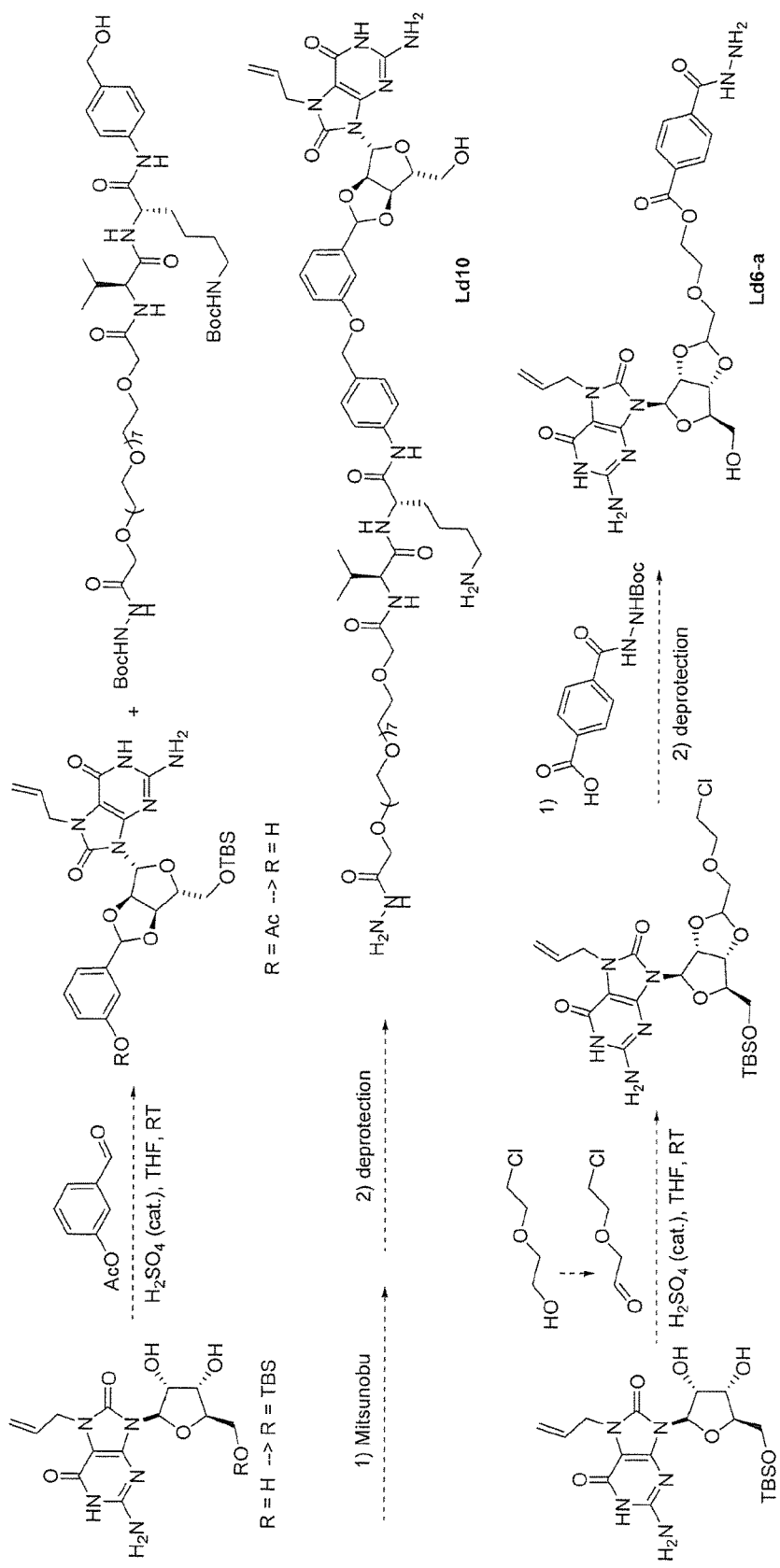

FIG. 44: Synthesis of Ld6/Ld10.

Figure 45:
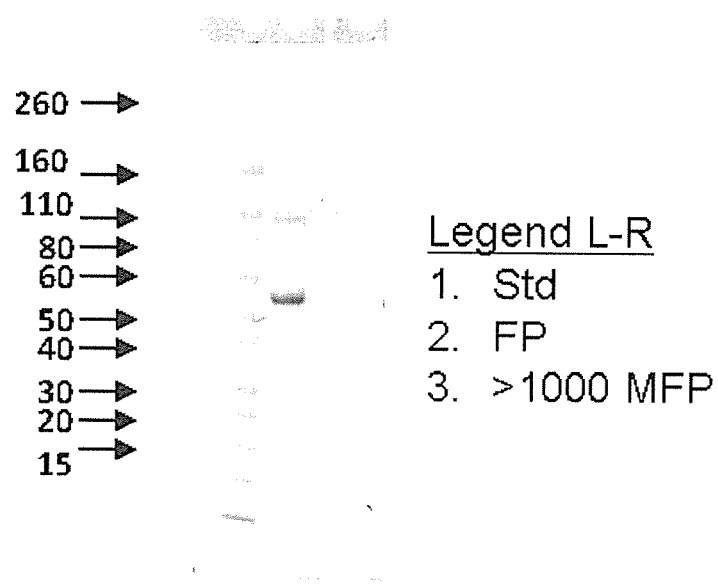

FIG. 45: Conjugation of FP to >1000 kDa oxidized mannan. Molecular weight standards, FP and >1000 MFP were run on SDS-PAGE gels (4-20%) and stained with coomassie blue.

Figure 46:
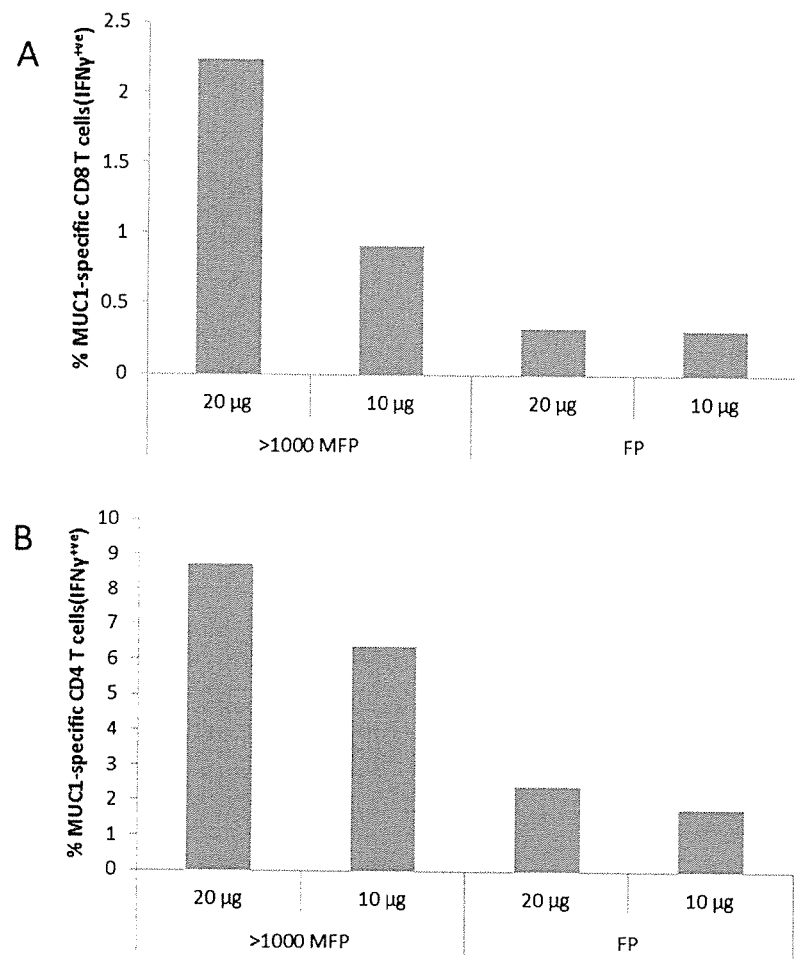

FIG. 46: Recall of MUC1-specific T cell responses. Allogeneic DCs (BC16) were pulsed with 10 and 20 µg/ml of >1000 MFP or FP and used to recall CD8 (FIG. 46A) and CD4 (FIG. 46B) intracellular IFNγ responses in a MUC1-specific T cell line.

Figure 47:
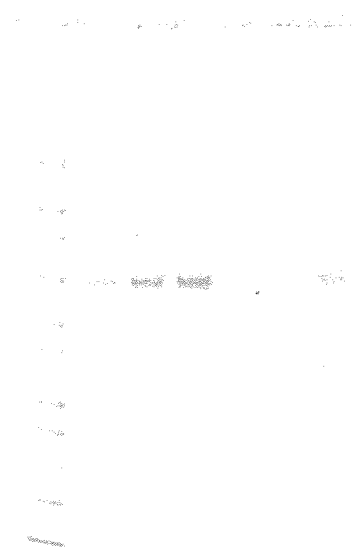

FIG. 47: Conjugation of pTrc (MUC1-VNTR) to >1000 kDa oxidized mannan. Molecular weight standards, pTrc, and >1000 kDa pTrc were run on SDS-PAGE gels (4-20%) and stained with coomassie blue.

Figure 48:
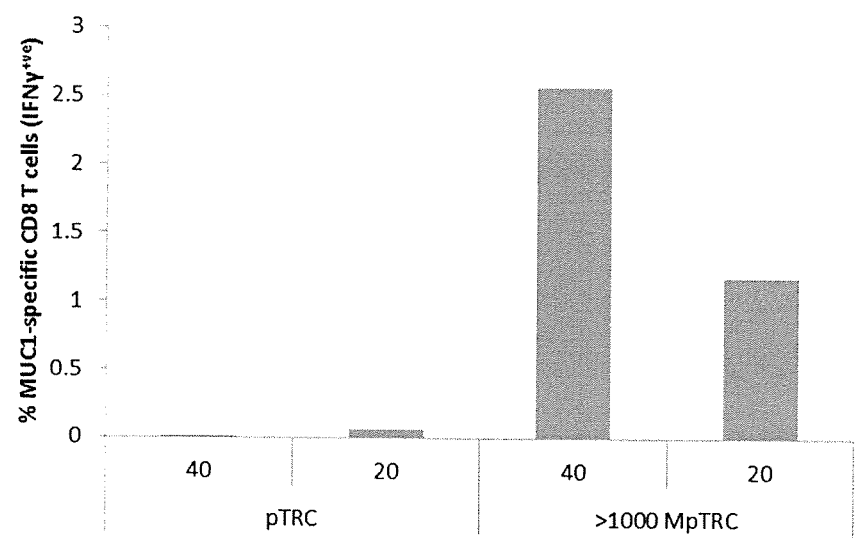

FIG. 48: Recall of MUC1-specific T cell responses. Allogeneic DCs (BC17A) were pulsed with 20 and 40 µg/ml of >1000 kDa pTrc or pTrc and used to recall CD8 intracellular IFNγ responses in a pTrc (MUC1)-specific T cell line from donor BC13.

Figure 49:
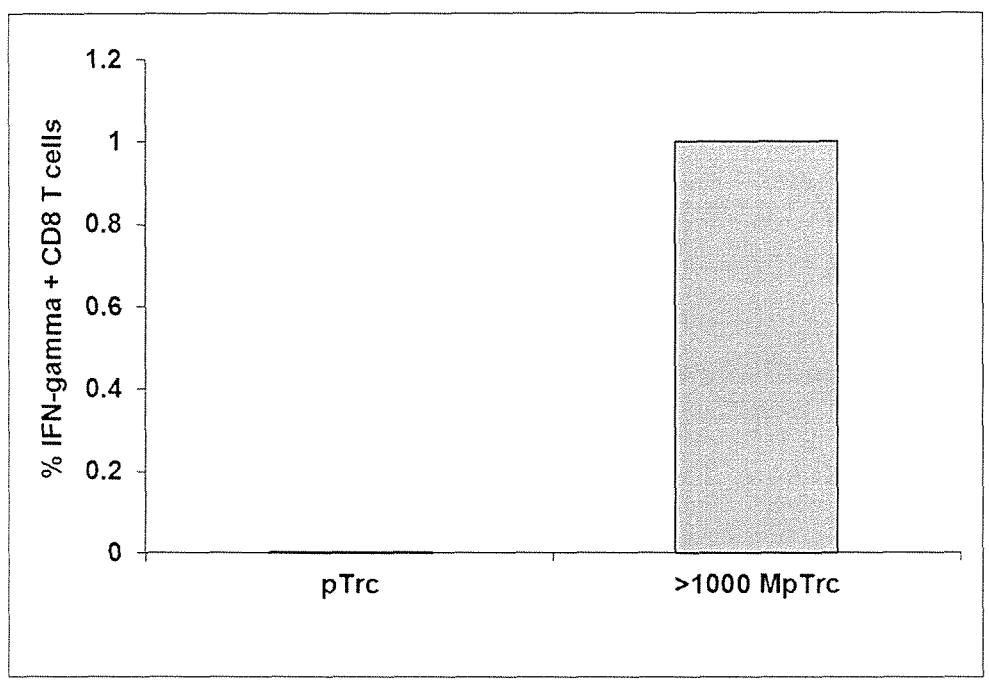

FIG. 49: Recall of MUC1-specific T cell responses. Autologous DCs were pulsed with 20 µg/ml of >1000 kDa oxidized mannan-pTrc or pTrc and used to recall CD8 intracellular IFNγ responses in a MFP-specific T cell line from donor BC17K.

Figure 50:
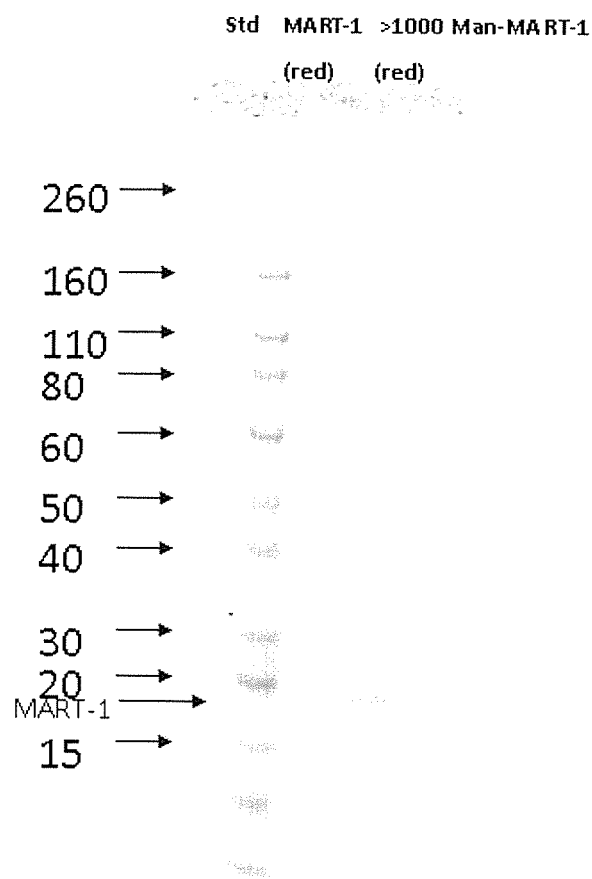

FIG. 50: Conjugation of MART-1 to >1000 kDa oxidized mannan. Molecular weight standards, MART-1, >1000 Mannan-MART-1 were run on SDS-PAGE gels (4-20%) and stained with coomassie blue.

Figure 51:
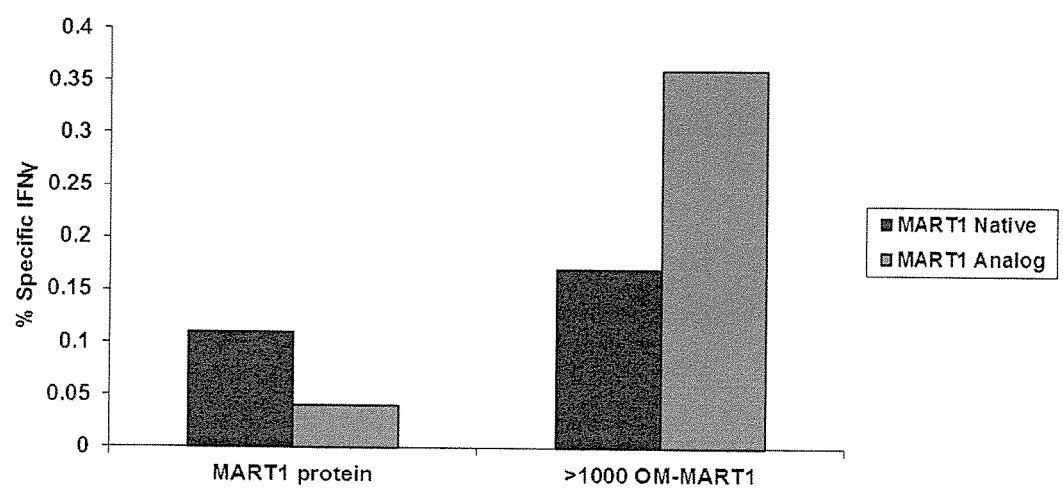

FIG. 51: Priming of MART-1-specific responses (1 stimulation). PBMCs from donor BC28 were primed with MART-1 protein or MART-1 >1000 kDa oxidized mannan conjugate as described in Example 1. Recall of MART-1-specific CD8 intracellular IFNγ responses by MART-1 analog and analog peptide pulsed T2 cells are shown.

Figure 52:
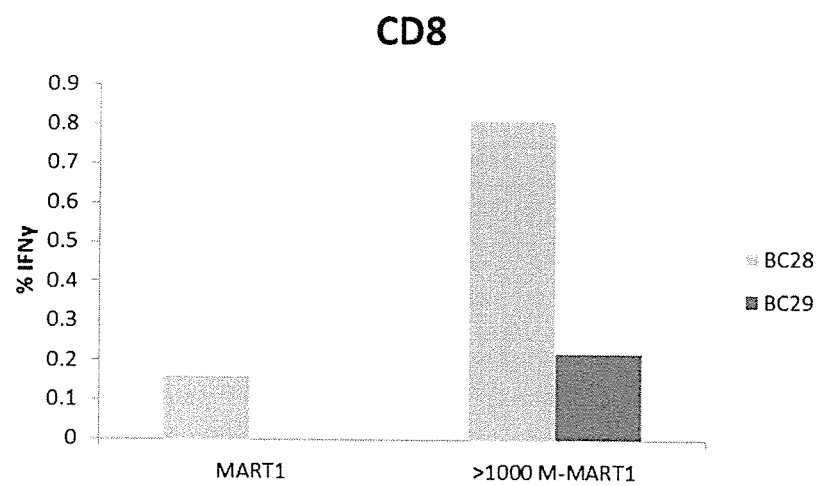

FIG. 52: Priming of MART-1-specific responses (2 stimulation). PBMCs from donor BC28 and BC29 were primed with MART-1 protein or MART-1 >1000 kDa oxidized mannan conjugate as described in Example 1. Recall of MART-1-specific CD8 intracellular IFNγ responses by MART-1 protein and >1000 kDa oxidized mannan conjugate are shown.

Figure 53:
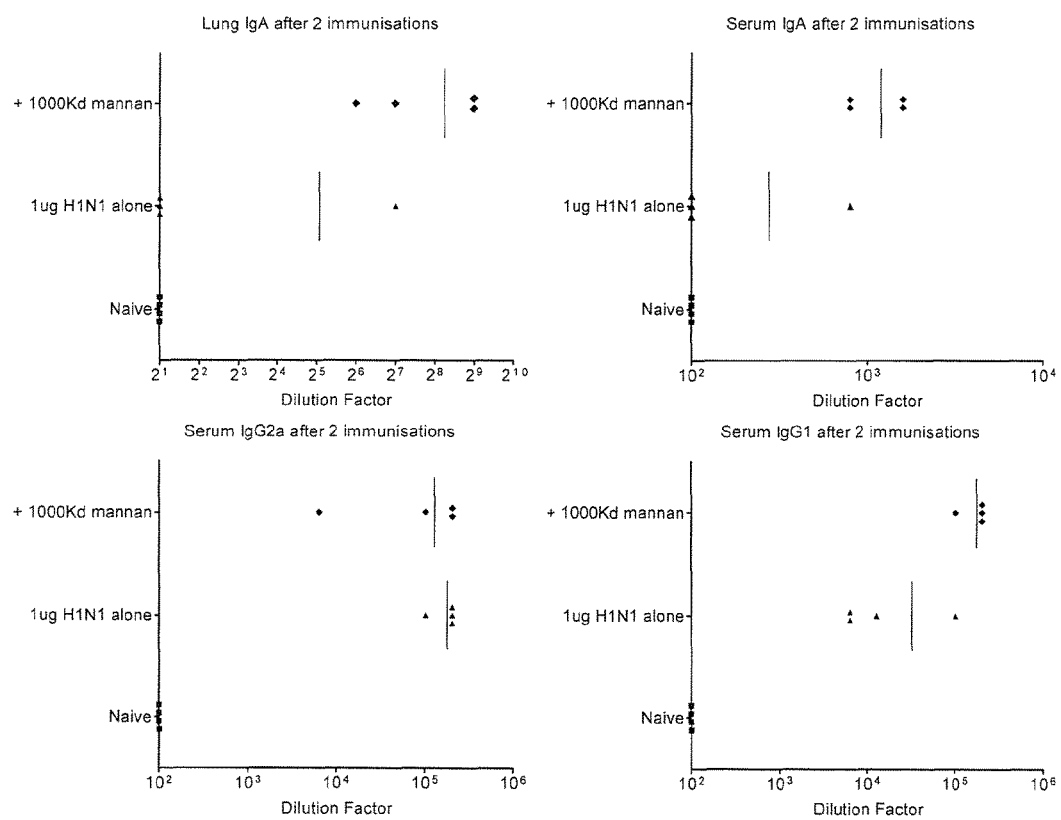

FIG. 53: H1N1-specific antibody responses to H1N1 and a mixture of H1N1+>1000 kDa mannan. Mice were immunized intranasally on days 0 and 14 with 1 µg of H1N1 either alone, or mixed with >1000 kDa mannan. Ten days after the final immunisation, serum samples and lung-wash samples were harvested and tested for anti-H1N1 IgG1, IgG2a and IgA activity by ELISA assay.

Figure 54:
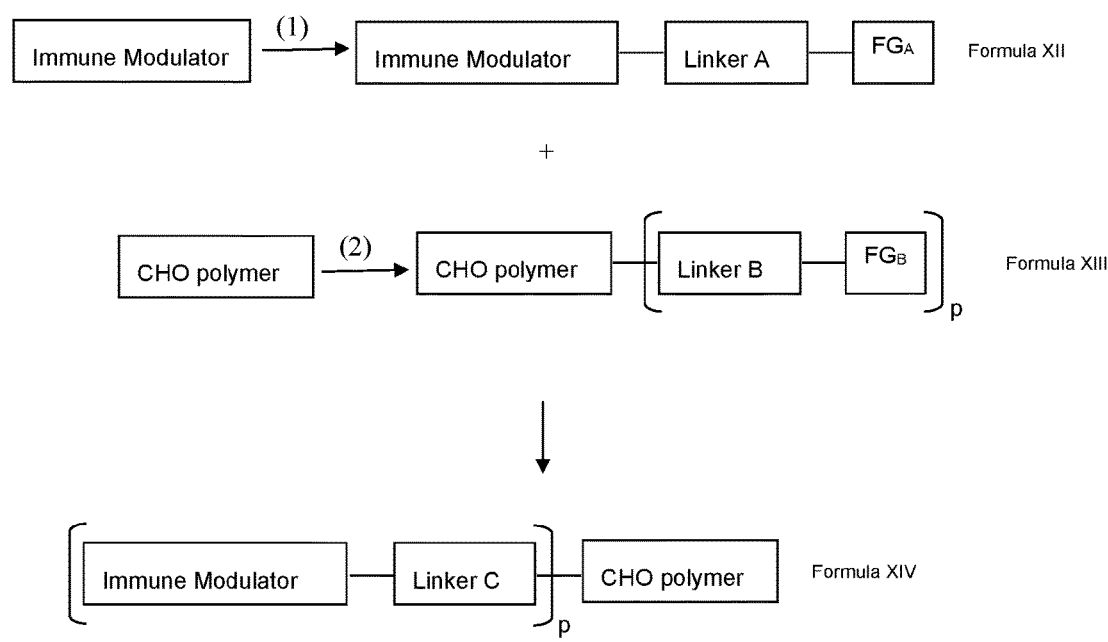

FIG. 54: Reaction scheme for preparing conjugates.

KEY TO SEQUENCE LISTING

SEQ ID NO:1: HLA-A2 epitope peptide specific for Melan/MART-1 (native).

SEQ ID NO:2: HLA-A2 epitope peptide specific for Melan/MART-1 (analog).

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, vaccine technology, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), Maniatis et al., Molecular Cloning: A Laboratory Manual, Cold Spring Harbour Laboratory Press (1982), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), F. M. Ausubel et al., (editors), Current Protocols in Molecular Biology, Greene Pub. Associates and Wiley-Interscience (1988, including all updates until present), E. Harlow and D. Lane (editors), Antibodies: A Laboratory Manual, Cold Spring Harbour Laboratory (1988), and J. E. Coligan et al. (editors), Current Protocols in Immunology, John Wiley & Sons (1991, including all updates until present).

As used herein, "about" or "approximately" shall generally mean within 20%, more preferably within 10%, and even more preferably within 5%, of a given value or range.

The term "and/or", for example, "X and/or Y" shall be understood to mean either "X and Y" or "X or Y" and shall be taken to provide explicit support for both meanings or for either meaning.

The "subject" can be any organism whereby upon administration with a compound or composition of the invention an immune response is induced and/or enhanced. In a preferred embodiment, the subject is an animal, more preferably a mammal or a bird. In a particularly preferred embodiment, the subject is a human.

Other preferred embodiments include companion/domestic animals such as cats and dogs; livestock animals such as horses, cattle, sheep, pigs and goats, poultry, or feral animals.

Immune Modulators

The compounds of the invention include an immune modulator conjugated to a carbohydrate polymer comprising mannose.

The term "immune modulator", as used herein, means a substance which modulates the immune system of a subject. The immune modulator may adjust the immune response to a desired level, as in immunopotentiation, immunosuppression, or induction of immunologic tolerance. Immune modulators for use in compounds of the invention include, but are not limited to, proteins, peptides, antibodies, antibody fragments, small molecules, cytokines, hormones, enzymes, nucleic acids, antisense oligonucleotides such as siRNA, toxins, anti-angiogenic agents, cytotoxic agents, pro-apoptotic agents and other known therapeutic agents. Preferred immune modulators include small molecules (for example, R848, Loxoribine, Stat-3 inhibitors, TGFβ inhibitors, Rapamycin/FK506), cytokines (for example, IL-2, TGFβ), antibody fragments (for example, CTLA-4 agonist scFv), nucleic acids (for example, CpG, siRNA).

The immune modulator may modulate cytokine and/or chemokine biosynthesis. For example, the immune modulator may induce the production and/or secretion of cytokines such as, for example, Type I interferons (IFN-α, IFN-β), Type II interferon (IFN-γ), TNF-α, IL-1, IL-6, IL-10, and/or IL-12, and/or chemokines, IL-8, MIP-I, MCP-I, and/or RANTES. Alternatively, the immune modulator may inhibit production and/or secretion of cytokines, such as, for example, TNF-α, IL-1, IL-4, IL-5, and/or IL-13.

The immune modulator may modulate native and/or adaptive immunity.

The immune modulator may induce a humoral, cellular, Th1 or Th2 response, or combinations thereof.

The immune modulator may act as an adjuvant. Immune modulator compounds that activate a strong CTL response may be particularly desirable as vaccine adjuvants, especially for therapeutic viral and/or cancer vaccines because a therapeutic effect in these settings is typically dependent on the activation of cellular immunity.

The immune modulator may modulate mucosal and/or systemic immunity.

In a preferred embodiment, the immune modulator is an agonist of at least one toll-like receptor (TLR).

As used herein, an "agonist" refers to an agent that binds to at least one TLR and is capable of increasing TLR signaling. In this respect, the level of TLR signaling may be enhanced over a pre-existing level of signaling or it may be induced over a background level of signaling. TLR signaling may mediate an immune response.

As used herein, the term "TLR signaling" refers to any aspect of intracellular signaling associated with signaling through a TLR. Exemplary TLR agonists are shown in Table 1.

For purposes of the present invention, one way to determine if an immune modulator is considered to be an agonist for a particular TLR is if it activates an NFkB/luciferase reporter construct through that TLR from the target species more than about 1.5 fold, and usually at least about 2 fold, in TLR transfected host cells such as, for example, HEK293 or Namalwa cells, relative to control transfectants. For information regarding TLR activation, see for example, U.S. Pat. Nos. 7,375,180, 7,485,432, US 20040014779, US 20040132079, US 20040197865 and WO 03/043588.

Suitable TLR agonists include natural TLR ligands and several classes of small molecules, including the guanosine analogs (e.g., Loxoribine and Isatoribine), the deaza-adenosine analogs (e.g., the Sumitomo compounds) and the imidazoquinolines (e.g., Imiquimod, Resiquimod, 3M-001, 3M-002, 3M-003).

Immune modulator compounds that are agonists for TLRs selected from, TLR7, 8, and/or 9 may be particularly useful for certain applications.

A TLR7-mediated immune response is generally characterized by the induction of IFN-α and IFN-inducible cytokines such as EP-10 and I-TAC. The levels of cytokines IL-1αβ, IL-6, IL-8, MIP-1α/β and MIP-3α/β induced in a TLR7-mediated immune response are typically less than those induced in a TLR8-mediated immune response.

A TLR8-mediated immune response is generally characterized by the induction of pro-inflammatory cytokines such as IFN-γ, IL-12p40/70, TNF-α, IL-1α/β, IL-6, IL-8, MIP-1α/β and MIP-3α/β.

A TLR9-mediated immune response is generally characterized by the production and/or secretion of at least IFN-γ and IL-12, albeit typically at levels lower than are achieved via a TLR8-mediated immune response.

TABLE 1

Exemplary immune modulators

| Compound | Company | Target | Drug Class | Indication[s:[ |
|---|---|---|---|---|
| SMP-105 | Dainippon Sumitomo Pharma | TLR2 | Autoclaved *mycobacteria* | Cancer |
| OM-174 | OM Pharma | TLR2, TLR4 | Lipid-A derivative | Cancer |
| Rinatolimod | Hemispherx Biopharma | TLR3 | dsRNA molecule | Cancer; Viral infection |
| IPH-3102 | Innate Pharma | TLR3 | dsRNA mimic | Cancer |
| Pollinex Quattro | Allergy Therapeutics | TLR4 | MPL plus pollen | Allergy |
| CBLB502 | Cleveland Biolabs Inc | TLR5 | Flagellin | Cancer |
| VAX-102 | VaxInnate Corp. | TLR5 | M2e peptide/Flagellin from *Salmonella tryphimurin* | Influenza |
| ANA773 | Anadys Pharmaceuticals | TLR7 | ssRNA molecule | Cancer; Hepatitis C |
| 852A | 3M Pharmaceuticals | TLR7 | Small-molecule ssRNA | Cancer |
| Imiquimod | 3M Pharmaceuticals | TLR7 | Small-molecule ssRNA | Cancer; Keratosis; Papillomavirus infection |
| Resiquimod | 3M Pharmaceuticals | TLR7, TLR8 | ssRNA molecule | Hepatitis C, Herpes |
| AZD8848 (DSP-3025) | Astra-Zeneca | TLR7 | ssRNA based molecule | Allergy, Asthma |
| VTX-1463 | VentiRx Pharmaceuticals Inc. | TLR8 | ssRNA-based molecule | Allergy |
| IMO-2055 | Idera Pharmaceuticals | TLR9 | CpG oligonucleotdie | Cancer |
| MGN-1706 | Mologen | TLR9 | Non-coding stem-loop DNA | Cancer |
| ISS1018 | Dynavax Technologies | TLR9 | Short DNA oligonucleotide | Cancer |
| Agatolimod | Pfizer | TLR9 | CpG oligonucleotide | Cancer |
| SD-101 | Dynavax Technologies | TLR9 | CpG oligonucleotide | Hepatitis C |
| IMO-2125 | Idera Pharmaceuticals | TLR9 | CpG oligonucleotide | Hepatitis C |
| Biothrax plus CpG-7909 | Coley Pharmaceuticals | TLR9 | CpG oligonucleotide | Anthrax |
| HEPLISAV | Dynavax Technologies | TLR9 | CpG DNA plus Hepatits B antigen | Hepatitis |
| AVE0675 | Sanofi-Aventis/Coley Pharmaceuticals | TLR9 | CpG oligonucleotide | Asthma, Allergic Rhinitis |
| QAX-935 | Idera Pharmaceuticals/ Novartis | TLR9 | CpG oligonucleotide | Allergy, Asthma |
| SAR-21609 | Sanofi-Aventis/Coley Pharmaceuticals | TLR9 | CpG oligonucleotide | Asthma |
| DIMS0150 | InDex Pharmaceuticals | TLR9 | CpG oligonucleotide | Inflammatory Bowel Disease |
| Cadi-05 | Cadila Pharmaceuticals | polyTLR | Autoclaved *myobacterium* | Cancer; *Mycobacterium tuberculosis* infection |

Immune modulator compounds that are TLR8 agonists may be particularly desirable for use with therapeutic cancer vaccines because antigen presenting cells that express TLR8 have been shown to produce IL-12 upon stimulation through TLR8. IL-12 is believed to play a significant role in activation of CTLs which are important for mediating therapeutic efficacy.

Immune modulator compounds that are TLR7 agonists and/or TLR9 agonists may be particularly desirable for use with prophylactic vaccines because the type I interferons induced by stimulation through these TLRs are believed to contribute to the formation of neutralizing Th1-like humoral and cellular responses.

Immune modulator compounds that are both TLR7 and TLR8 agonists may be particularly desirable for use with therapeutic viral vaccines and/or cancer vaccines because TLR7 stimulation is believed to induce the production of type I interferons and activation of innate cells such as macrophages and natural killer (NK) cells, and TLR8 stimulation is believed to activate antigen presenting cells to initiate cellular adaptive immunity as described above. These cell types are able to mediate viral clearance and/or therapeutic growth inhibitory effects against neoplasms.

Immune modulator compounds that are not TLR7 agonists and do not induce substantial amounts of IFNα, may be desirable for use with certain vaccines, such as, bacterial vaccines, because TLR7 induces type I interferon production, which down-regulates the production of IL-12 from macrophages and DCs. IL-12 contributes to the subsequent activation of macrophages, NK cells and CTLs, all of which contribute to anti-bacterial immunity. Therefore the induction of anti-bacterial immunity against some kinds of bacteria may be enhanced in the absence of IFNα.

TLR7 agonists include, for example, guanosine analogs such as C8-substituted guanosines, mixtures of ribonucleosides consisting essentially of G and U, guanosine ribonucleotides and RNA or RNA-like molecules (WO 2003/086280), and adenosine-based compounds (e.g., 6-amino-9-benzyl-2-(3-hydroxy-propoxy)-9H-purin-8-ol (CL-029, Sumitomo), 6-amino-9-benzyl-2-butoxy-9H-purin-8-ol, and other related compounds such as those described in U.S. Pat. No. 6,310,070). TLR7 agonists are also disclosed in Gorden et al. (2005) (e.g., 3M-001, N-[4-(4-amino-2-ethyl-1H-imidazo[4,5-c]quinolin-1-yl)butyl-]methanesulfonamide; $C_{17}H_{23}N_5O_2S$; mw 361).

TLR8 agonists include, for example, mixtures of ribonucleosides consisting essentially of G and U, guanosine ribonucleotides and RNA or RNA-like molecules (WO 2003/086280). Additional TLR8 agonists are also disclosed in Gorden et al. (2005) (e.g., 3M-002, 2-propylthiazolo[4,5-c]quinolin-4-amine; $C_{13}H_{13}N_3S$; mw 243).

Agonists of both TLR7 and TLR8 include, for example, imidazoquinolines, mixtures of ribonucleosides consisting essentially of G and U, guanosine ribonucleotides, and RNA or RNA-like molecules (WO 2003/086280). Additional TLR7/8 agonists are also disclosed in Gorden et al. (2005) (e.g., 3M-003, 4-amino-2-(ethoxy methyl)-α,α-dimethyl-6,7,8,9-tetrahydro-1H-imidazo[4,5-c]quinoline-1-ethanol hydrate: $C_{17}H_{26}N_4O_2$; MW 318).

TLR9 agonists include, for example, immunomodulatory nucleic acids, and in particular, CpG immunomodulatory nucleic acids.

Guanosine Analogs

As used herein, the term "guanosine analog" refers to a guanosine-like nucleoside (excluding guanosine) having a chemical modification involving the guanine base, guanosine nucleoside sugar, or both the guanine base and the guanosine nucleoside sugar. In one example, the guanosine analogue is a 7-deaza-guanosine.

In another example, the guanosine analog is a C8 substituted guanosine. Examples of C8-substituted guanosine include 7-allyl-7,8-dihydro-8-oxo-guanosine (loxoribine), 7-thia-8-oxoguanosine (Immunosine, Isatoribine, ANA245, 7-thia-8-oxo-7,8-dihydroguanosine, 5-amino-3-(β-D-ribofuranosyl)-3H,6H-thiazol[4,5-d]pyrimidine-2,7-dione), 8-mercaptoguanosine, 8-bromoguanosine, 8-methylguanosine, 8-oxo-7,8-dihydroguanosine, C8-arylamino-2'-deoxyguanosine, C8-propynyl-guanosine, C8- and N7-substituted guanine ribonucleosides, 7-methyl-8-oxoguanosine, 8-aminoguanosine, 8-hydroxy-2'-deoxyguanosine, 7-deaza-8-substituted guanosine, and 8-hydroxyguanosine.

Adenosine Analogs

As used herein, the term "adenosine analog" refers to an adenosine-like nucleoside (excluding adenosine) having a chemical modification involving the adenine base, adenosine nucleoside sugar, or both the adenine base and the adenosine nucleoside sugar. Adenosine-based compounds include, for example, 6-amino-9-benzyl-2-(3-hydroxy-propoxy)-9H-purin-8-ol and 6-amino-9-benzyl-2-butoxy-9H-purin-8-ol.

2-aminopyridine fused to a five-membered nitrogen-containing heterocyclic ring

Compounds having a 2-aminopyridine fused to a five-membered nitrogen-containing heterocyclic ring may be imidazoquinoline amines, including but not limited to, substituted imidazoquinoline amines, such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, hydroxylamine substituted imidazoquinoline amines, oxime substituted imidazoquinoline amines, 6-, 7-, 8-, or 9-aryl, heteroaryl, aryloxy, or arylalkyleneoxy substituted imidazoquinoline amines, and imidazoquinoline diamines; tetrahydroimidazoquinoline amines, including but not limited to, amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, thioether substituted tetrahydroimidazoquinoline amines, hydroxylamine substituted tetrahydroimidazoquinoline amines, oxime substituted tetrahydroimidazoquinoline amines, and tetrahydroimidazoquinoline diamines; imidazopyridine amines, including but not limited to, amide substituted imidazopyridine amines, sulfonamido substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; pyrazolopyridine amines; pyrazoloquinoline amines; tetrahydropyrazoloquinoline amines; pyrazolonaphthyridine amines; tetrahydropyrazolonaphthyridine amines; and 1H-imidazo dimers fused to pyridine amines, quinoline amines, tetrahydroquinoline amines, naphthyridine amines, or tetrahydronaphthyridine amines, such as those disclosed in U.S. Pat. Nos. 4,689,338, 4,929,624, 4,988,815, 5,037,986, 5,175,296, 5,238,944, 5,266,575, 5,268,376, 5,346,905, 5,352,784, 5,367,076, 5,389,640, 5,395,937, 5,446,153, 5,482,936, 5,693,811, 5,741,908, 5,756,747, 5,939,090, 6,039,969, 6,083,505, 6,110,929, 6,194,425, 6,245,776, 6,331,539, 6,376,669, 6,451,810, 6,525,064, 6,545,016, 6,545,017, 6,558,951, 6,573,273, 6,656,938, 6,660,735, 6,660,747, 6,664,260, 6,664,264, 6,664,265, 6,667,312, 6,670,372, 6,677,347, 6,677,348, 6,677,349, 6,683,088, 6,894,060, EP 0 394 026, US 20020055517, US20020110840, US 20030133913, US 20030199538, US 20040014779, WO 02/102377 and WO 03/103584.

Other Immune Modulators

Suitable immune modulator compounds also include purine derivatives (such as those disclosed in U.S. Pat. Nos. 6,376,501 and 6,028,076), imidazoquinoline amide derivatives such as those disclosed in U.S. Pat. No. 6,069,149), benzimidazole derivatives (such as those disclosed in U.S. Pat. No. 6,387,938), adenine derivatives (such as those disclosed in U.S. Pat. Nos. 6,376,501, 6,028,076, 6,329,381 and WO 2002/08905), aminoalkyl glucosaminide phosphates (such as those disclosed in U.S. Pat. Nos. 6,113,918, 6,303,347, 6,525,028 and 6,649,172), small molecule immuno-potentiator compounds (such as those disclosed in US 2005/0136065), and cytosine-guanine (CpG) containing oligonucleotide sequences (such as those disclosed in U.S. Pat. Nos. 6,194,388, 6,207,646, 6,239,116, 6,339,068 and 6,406,705). Some CpG containing oligonucleotide include synthetic immunomodulatory structural motifs (such as those disclosed in U.S. Pat. Nos. 6,426,334 and 6,476,000).

Carbohydrate Polymers Comprising Mannose

As used herein, a "carbohydrate polymer comprising mannose" is any multi-subunit compound comprising, more preferably consisting of, mannose subunits (i.e., mannose monomer units) or variants thereof. Examples include, but are not limited to, mannan, galactomannan and acemannan. In one embodiment, the carbohydrate polymer comprises aldehyde groups.

In a preferred embodiment, the carbohydrate polymer is oxidized to give a poly-aldehyde. In a further preferred embodiment, the carbohydrate polymer comprises 150 aldehyde groups prior to being conjugated to at least one immune modulator and/or at least one antigen or nucleic acid encoding therefor. In compositions comprising the carbohydrate polymer to be conjugated to the at least one immune modulator and/or at least one antigen or nucleic acid encoding therefor, preferably at least 75%, more preferably at least 80%, more preferably at least 90%, more preferably at least 95%, more preferably at least 97%, more preferably at least 99%, and even more preferably all, of the carbohydrate polymer in the composition each have at least 150 aldehyde groups.

In one embodiment, the carbohydrate polymer comprising mannose has a molecular weight greater than about 1000 kDa prior to being conjugated to the at least one immune modulator and/or at least one antigen or nucleic acid encoding therefor. In compositions comprising the carbohydrate polymer to be conjugated to the at least one immune modulator and/or at least one antigen or nucleic acid encoding therefor, preferably at least 75%, more preferably at least 80%, more preferably at least 90%, more preferably at least 95%, more preferably at least 97%, more preferably at least 99%, and even more preferably all, of the carbohydrate polymer in the composition is greater than about 1000 kDa.

As used herein "mannan" refers to a linear or branched polysaccharide formed exclusively of mannose and does not refer to a polysaccharide of modified, for example, acetylated mannose (acemannan), or substituted mannan having a mannose backbone but non-mannose side groups (for example, galactomannan consisting of a mannose backbone with galactose side groups).

Mannans useful in the compounds of the invention are found in, for example, fungi, more preferably yeast. In the branched mannans from *Saccharomyces cerevisiae* (baker's yeast), the mannans consist of an α-(1→6) linked mannopyranosyl backbone structure substituted on the O-2 atoms by side-chains of α-D-mannopyranosyl, α-D-mannopyranosyl-α-(1→2)-α-D-mannopyranosyl and α-D-mannopyranosyl α-(1→3)-α-D-mannopyranosyl-α-(1→2)-α-D-mannopyranosyl. In addition, the *S. cerevisiae* mannans can also be phosphorylated (Barreto-Bergter and Gorin, 1983; Vinogradov et al., 1998).

The mannans are preferably isolated from cell walls of fungi, more preferably, yeast. In an embodiment, the mannans may be isolated from genetically modified yeasts that have been engineered to preferentially express high molecular weight mannans, preferably mannans greater than 1000 kDa.

Mannans comprising aldehyde groups can be produced by the oxidation of mannans obtained from, for example, yeast. The most common method for introducing aldehydes into a carbohydrate polymer is by periodate-mediated (NaIO$_4$) oxidation of vicinal diols (see schematic of FIG. 2). For other methods of oxidation see generally, M. L. Wolfrom (editor), Periodate oxidation of carbohydrates, Advances in Carbohydrate Chemistry, Volume 11, pages 1-40 (1956).

In a preferred embodiment, the mannans are oxidized using NaIO$_4$ to produce polyaldehydes which are then conjugated to at least one immune modulator and/or at least one antigen or nucleic acid encoding therefor.

In an embodiment, high molecular weight mannans (i.e., greater than about 1000 kDa) are obtained by size fractionation of whole mannan extract from, for example, yeast such as *Saccharomyces cerevisiae*. In this example, whole mannan may be derived from *S. cerevisiae* by methods known in the art, including hot water extraction of cultured cells or spray dried cells and solvent extraction methods. Mannans derived from *S. cerevisiae* may be obtained from a supplier, for example, Sigma (St. Louis, Mo.) and in an embodiment, subsequently fractionated to give a high molecular weight mannan composition. In an embodiment, the high molecular weight mannan composition is substantially free of ribose, nucleic acids, ribonucleic acids, protein and/or other carbohydrates.

Preparation of a Carbohydrate Polymers Comprising Mannose

Methods for the separation of carbohydrates and sugars are well known in the art (see generally, Z. El Rassi (editor), Carbohydrate analysis by modem chromatography and electrophoresis, Journal of Chromatography, volume 66, Elsevier Science (2002)).

Size Fractionation

In an embodiment, size fractionation of a composition comprising a carbohydrate polymer comprising mannose, more preferably, a composition comprising mannans, is performed by tangential flow filtration (TFF), also called cross flow filtration (CFF). TFF is a process whereby product flow (feed) is directed tangentially along the surface of a membrane with most of the solution circulated back to the feed tank. The rapid flow of feed solution across the membrane acts to "sweep" the surface, reducing concentration polarization (product concentration at the membrane surface). It also prevents build-up of foulants that can plug the pores at the membrane surface. The rapid cross flow creates a pressure drop, which forces some of the feed solution and dissolved molecules that are smaller than the pores in the membrane, through the membrane filter. The solution that passes through the membrane is referred to as filtrate or permeate. Molecules or particles larger than the membrane pores are retained in the feed solution and effectively concentrated.

Membrane filtration can be classified as either a "microfiltration" or "ultrafiltration" process. Microfiltration membranes, with pore sizes typically between 0.1 micron and 1 micron, are generally used for clarification, sterilization and removal of micro-particulates or for cell harvesting. Ultrafiltration membranes, with much smaller pore sizes between 0.001 and 0.1 micron, are used for concentrating and desalting dissolved molecules (protein, peptides, nucleic acids, carbohydrates and other biomolecules), exchanging buffers, fractionation and water purification. Ultrafiltration membranes are typically classified by molecular weight cut off (MWCO), rather than pore size.

In another embodiment, size fractionation of a composition comprising a carbohydrate polymer comprising mannose is performed by size exclusion chromatography.

The basic principles of size exclusion chromatography are well known to those in the art, and are explained in "Gel filtration: Principles and Methods, GE Healthcare". The appropriate columns for fractionating particular ranges can be readily selected and effectively used to resolve the above fractions, for example, Sephacryl S-100 HR, Sephacryl S-200 HR, Sephacryl S-300 HR, Sephacryl S-400 HR and Sephacryl S-500 HR or their equivalents. In an analogous fashion, Sepharose media or their equivalents, for example, Sepharose 6B, 4B, 2B, could be used. In an embodiment, Sephacryl S-400 HR is used to fractionate the composition comprising the carbohydrate polymer comprising mannose.

In yet another embodiment, size fractionation of a composition comprising a carbohydrate polymer comprising mannose is performed by ultrafiltration.

Ultrafiltration of the sample could be performed using molecular membranes with appropriate molecular mass cut-offs. The specific membranes and procedures used to effect fractionation are widely available to those skilled in the art.

Those skilled in the art will also appreciate that the size fractionation of a composition comprising a carbohydrate polymer comprising mannose may also be performed by density gradient centrifugation.

In preferred embodiments, the sample is at least partially purified before fractionation to remove contaminants, such as, for example, ribose, nucleic acids including DNA and RNA, protein and/or carbohydrates not comprising mannose. Purification could be achieved in combination with other chromatography techniques, including affinity, ion exchange, and hydrophobic interaction chromatography. The purity of a composition could be determined by measuring its mannose content as described below.

One method of removal of non-carbohydrate components is the use of digestion enzymes to cleave the non-carbohydrate components, followed by size fractionation to remove the cleaved products. Digestion enzymes including pronase, ribonuclease, DNase and proteases, are well known in the art and described in various text books, one example of which is Maniatis et al. (1982), supra. Proteases useful for digestion of proteins include endo- and exopeptidases, pronase, serine proteases such as trypsin, chymotrypsin and subtilisin, thiol proteases such as papain, and calcium-requiring proteases such as thermolysin.

Alternatively, non-carbohydrate components may be removed by affinity chromatography, for example by use of DNA- or RNA-binding matrices (Maniatis et al., 1982, supra). Another option is to purify the carbohydrate polymer away from the contaminating components by use of polysaccharide binding matrices such as lectins.

According to the processes of the invention, the size distribution, aldehyde and/or mannose content of the carbohydrate polymer comprising mannose in a selected fraction can be determined. This validation may be important in gaining regulatory approval for use in humans.

Size Distribution

The size distribution of a sample prior to and/or following fractionation can be determined. When carried out prior to fractionation, this analysis aids in the selection of a starting composition of the carbohydrate polymer for fractionation. For example, if a majority of the molecular weight species of the polymer in the starting composition is below 1000 kDa, the composition can be discarded and another batch having a higher distribution of high molecular weight species of the carbohydrate polymer selected for fractionation. In contrast, analysis of the size distribution of the recovered fraction acts to confirm or validate the fractionation process. This will be important when gaining regulatory approval for use of these carbohydrate polymers in humans.

The size distribution of the carbohydrate polymers of a composition may be determined by reacting an oxidized sample with ANTS (see schematic of FIG. 3), and resolving the ANTS labelled sample by SDS-PAGE. Comparison of the resolved ANTS labelled sample against protein and/or carbohydrate standards will allow for the size distribution of said sample to be determined.

As used herein "protein and/or carbohydrate standards" refers to a composition of known proteins or carbohydrates of various molecular weights for use as molecular weight standards in SDS-PAGE. The composition is designed to give sharp, well-separated bands that serve as markers for estimating the molecular weight of samples electrophoresed in neighbouring lanes of the same gel. The standards may be prestained (to allow for easy visualization of molecular weight ranges during electrophoresis) or unstained. A variety of standards are available for electrophoresis applications and can be purchased from, for example, Invitrogen or Bio-rad. Typically, the standards are supplied in ready-to-use format, eliminating the need to reduce, pre-mix or add loading dyes. These standards are consistent from lot to lot and strictly quality controlled on appropriate gels to ensure consistent band migration and intensity.

Aldehyde Content

The aldehyde content of a sample may also be determined prior to and/or after fractionation to aid in batch selection and/or fraction validation.

In an embodiment, the aldehyde content of a sample is determined by quantitating the number of aldehyde residues in the sample following oxidation with $NaIO_4$. For example, a composition comprising mannans may be selected for fractionation if the mannans each comprise approximately 90-200 aldehyde residues.

The method involves first oxidizing the sample by for example, reacting 1.4 mg sample in 100 µl in 0.1 M phosphate buffer pH 6.0 with 0.01 M $NaIO_4$ for 1 hour on ice in the dark. The reaction is then quenched with 10 µl ethanediol and allowed to react for a further ½ hour before being loaded on a PD10 column pre-equilibrated with 0.1 M acetate buffer pH 4.8 to remove excess NaIO$_4$.

The number of aldehyde groups can subsequently be measured by spectrophotometry by measuring the release of pyridine-2-thione when treated with PDPH.

As understood by those skilled in the art, several other methods may be used for the quantitation of aldehydes. For example, oximes, hydrazides, semicarbazide, and carbohydrazides readily react with aldehydes and can be attached to reporter molecules (e.g., fluorescent compounds) for the quantitation of aldehyde groups in the carbohydrate polymer. A selection of fluorescent compounds that can be used is detailed in www.invitrogen.com/site/us/en/home/References/Molecular-Probes-The-Handbook/Reagents-for-Modifying-Groups-Other-Than-Thiols-or-Amines/Hydrazines-Hydroxylamines-and-Aromatic-Amines-for-Modifying-Aldehydes-and-Ketones.html. Examples include fluorescein-5-thiosemicarbazide, Alexa Fluor 488, Alexa Fluor 555, Alexa Fluor 568, Alexa Fluor 594, Alexa Fluor 633, Alexa Fluor 647 and Texas Red.

In addition, 2,4-dinitrophenylhydrazine reacts with aldehydes to form a red hydrazone which can also be used to quantitate the number of aldehyde groups in the carbohydrate polymer by absorbance spectrophotometry (Apostolopoulos et al., 2000).

Mannose Content

In an embodiment the mannose content of the composition is determined by a colorimetric assay for neutral sugars, in which neutral sugars react with resorcinol in the presence of a hydrated sulphuric acid solution.

For example, 200 µl of 6 mg/ml resorcinol and 1 ml 75% sulphuric acid is added to an assay tube containing a sample (dissolved in 0.01 M acetic acid) having 5 to 100 nmol of neutral sugars in a volume of 200 µl. The solutions are then vortexted and heated at 90° C. in a temperature-regulated water bath for 30 minutes and subsequently placed in a cold-water bath for 30 minutes in the dark. The optical density of the mixture is then determined at 430 or 480 nm. The same assay can be conducted by using the half volumes indicated above with similar results.

Alternatively, the assay can be conducted in microplate format. In this embodiment, 20 µl of 6 mg/ml resorcinol and 100 µl 75% sulphuric acid and 50 µl pristine is added to a U-shaped well of a 96-well microtiter plate containing a sample (dissolved in 0.01 M acetic acid) having 1 to 100 nmol of neutral sugars in a volume of 20 µl. The solutions are then mixed by shaking the plate with a vortex apparatus and heated at 90° C. in an incubator for 30 minutes and subsequently kept at room temperature for 30 minutes in the dark. The optical density of the mixture is then determined at 430 or 480 nm using a microtiter plate reader. For quantitative purposes, blanks, neutral sugar standards, and samples are assayed in duplicate, more preferably, triplicate, more preferably, quadruplicate.

The mannose content can also be determined by enzymatic or acid hydrolysis of the carbohydrate polymers followed by analysis by HPLC, mass spectrometry, capillary electrophoresis or thin layer chromatography (Wang et al., 2007; Anumula, 1994; R. Townsend, Chromatography in Biotechnology, C. Horvath and L. S. Ettre (editors), American Chemical Society, Washington, D.C. (1993) pp. 86-101).

Immune Modulator-Carbohydrate Polymer Conjugates and their Preparation

The present invention relates to immune modulator-carbohydrate polymer conjugates and methods used to make said immune modulator-carbohydrate polymer conjugates.

In one embodiment, the immune modulator is conjugated to the carbohydrate polymer via a linker. The carbohydrate polymer may possess a functional group that can form a covalent bond with the linker while preserving at least a portion of the biological activity of the carbohydrate polymer. Alternatively, such a functional group may be easily generated or added, in some cases, by a chemical reaction such as, for example, oxidation of the carbohydrate polymer to give a polyaldehyde, or linkage of the carbohydrate polymer to a moiety which has a functional group, for example, a malonyl or sulfonyl.

In one embodiment, a linker having a first functional group is covalently linked to an immune modulator having immunomodulatory activity, at a site on the immune modulator selected to preserve at least a portion of the immunomodulatory activity of the immune modulator, thereby forming an immune modulator-linker. The immune modulator-linker is then reacted with a carbohydrate polymer, allowing a second functional group of the linker to covalently bond at a site on the carbohydrate polymer, thereby forming an immune modulator-carbohydrate polymer conjugate that possesses immune modulator activity and the biological activity of the carbohydrate polymer. Alternatively, the linker may be first conjugated to the carbohydrate polymer and the resultant conjugate subsequently reacted with the immune modulator. Still further, both the immune modulator and carbohydrate polymer may be each first conjugated to a linker and the resultant conjugates subsequently reacted.

Suitable methods for the preparation of conjugates of the invention are described in US 2009/0035323. US 2009/0035323 teaches conjugation of an immune modulator to a second active moiety. However, US 2009/0035323 does not teach conjugation of the immune modulator to a carbohydrate polymer comprising mannose, for example, mannnan. Further, US 2009/0035323 does not teach or suggest conjugation of the immune modulator to a high molecular weight carbohydrate polymer.

Conjugates of the invention can be prepared using the general method illustrated in the Reaction Scheme shown in FIG. 54.

In the Reaction Scheme shown in FIG. 54, the carbohydrate (CHO) polymer and the immune modulator are as described above, while $FG_A$, $FG_B$, Linkers A, B and C are as defined in US2009/0035323. Persons skilled in the art will appreciate that p varies depending on the length of the carbohydrate polymer. In one embodiment, p is an integer from 1 to 100.

In step (1) of the Reaction Scheme shown in FIG. 54, an immune modulator is modified to provide a functionalized immune modulator of Formula XII. Functionalized immune modulator compounds of Formula XII can be prepared using a heterobifunctional linker. As used herein, a "heterobifunctional linker" includes two different reactive functional groups at either end and a spacer of various length and composition. Useful functional groups on the immune modulator that may be modified by a heterobifunctional linker include, but are not limited to, amines, thiols (—SH), ketones, hydrazides (—C(O)NHNH$_2$), hydrazines (—NHNH$_2$), hydroxylamines (—NHOH), and O-alkylhydroxylamines (—O—NH$_2$). Functionalized immune modulator compounds of Formula XII may be synthesized by means other than employing a heterobifunctional linker.

In some embodiments, the immune modulator may be used without the incorporation of Linker A. For example, an immune modulator that contains a functional group $FG_A$ can react with a functionalized moiety of Formula XIII to form the immune modulator-carbohydrate conjugate of Formula XIV. Preferred functional groups $FG_A$ in the immune modulator include, but are not limited to, amines, thiols (—SH), ketones, hydrazides (—C(O)NHNH$_2$), hydrazines (—NHNH$_2$), hydroxylamines (—NHOH), and O-alkylhydroxylamines (—O—NH$_2$).

In step (2) of the Reaction Scheme shown in FIG. 54, the carbohydrate polymer is modified to provide a functionalized moiety of Formula XIII. Functionalized moieties of Formula XIII can be prepared using a heterobifunctional linker by employing a similar strategy to that described in step (1) above. Useful functional groups $FG_B$ on the carbohydrate polymer include, but are not limited to, amines (—NH$_2$), thiols (—SH), and aldehydes (—CHO). In some instances, useful functional groups $FG_B$ may be easily generated on the carbohydrate polymer. For example, carbohydrate residues on the polymer can be oxidized using sodium periodate to form reactive aldehydes. Functionalized moieties of Formula XIII may be synthesized by means other than employing a heterobifunctional linker.

In a preferred embodiment, the carbohydrate polymer may be used without the incorporation of Linker B. For example, a carbohydrate polymer that contains a functional group $FG_B$, can react with a functionalized immune modulator of Formula XII to form an immune modulator-carbohydrate polymer conjugate of Formula XIV. Useful functional groups $FG_B$ on the carbohydrate polymer include, but are not limited to, amines (—NH$_2$), thiols (—SH), and aldehydes (—CHO). In some instances, useful functional groups $FG_B$ may be easily generated on the carbohydrate polymer. For example, carbohydrate residues on the polymer can be oxidized using sodium periodate to form reactive aldehydes.

The reaction can be carried out by adding a solution of the functionalized immune modulator of Formula XII in a suitable solvent such as dimethyl sulfoxide (DMSO) or N,N-dimethylformamide to a solution of a functionalized moiety of Formula XIII in a suitable buffer such as phosphate buffered saline (PBS). The reaction can be carried out at ambient temperature. The resulting conjugate can be purified using conventional methods such as, for example, size exclusion chromatography.

The functionalized immune modulator of Formula XII and the functionalized moiety of Formula XIII are selected such that functional groups $FG_A$ and $FG_B$ react with each other to form a new covalent bond in the immune modulator-carbohydrate polymer conjugate of Formula XIV.

In some embodiments, the functional group $FG_A$ on the immune modulator which is intended to react with an appropriate functional group $FG_B$ on the carbohydrate polymer, may not be compatible with certain functional groups in the immune modulator, for example, an amino group or an hydroxyl group.

In these cases, it may be necessary to use a protecting group or prodrug group, to temporarily mask the reactivity of, for example, an amino or hydroxyl group. The protecting group may then be removed at the appropriate step in the synthetic route.

Suitable amino protecting groups are described in US 2009/0035323 and include acetyl, trifluoroacetyl, tert-butoxycarbonyl (BOC), benzyloxycarbonyl, and 9-fluorenylmethoxycarbonyl (FMOC). Suitable hydroxy protecting groups are described in US 2009/0035323 and include acetyl and silyl groups such as the tert-butyl dimethylsilyl group.

In some embodiments of the invention, a prodrug of the immune modulator can be used. The term "prodrug" means a compound that can be transformed in vivo to yield an immune response modifying compound. The prodrug itself, may be an immune response modifying compound. The transformation may occur by various mechanisms, such as through a chemical (e.g., solvolysis or hydrolysis, for example, in the blood) or enzymatic biotransformation. Suitable prodrugs are described in US 2009/0035323.

Linker

In one embodiment, the linker comprises:
  i) a first functional group that can be conjugated to the carbohydrate polymer (type (i) group);
  ii) a second functional group that can be conjugated to the immune modulator (type (ii) group); and
  iii) a spacer.

The first and second groups may optionally comprise a suitable leaving group or protecting group.

The first group may be, for example, an aldehyde, ketone, formyl, hydrazine, hydrazide, amine, amide, carboxylic acid, alkyne, or halogen.

The second group may be for example, an aldehyde, ketone, formyl, hydrazine, hydrazide, amine, amide, carboxylic acid, alkyne, or halogen.

The linker may be branched so that multiple immune modulator compounds may be covalently attached to the linker. When multiple immune modulator compounds are attached to the linker, the immune modulator compounds may be the same compound or different compounds.

More than one linker may be covalently attached to the carbohydrate polymer, so that multiple immune modulator compounds can be conjugated to the carbohydrate polymer. When multiple linkers are attached to the carbohydrate polymer, the linkers may be the same or different. Further, the immune modulator compounds attached to each linker may be the same compound or different compounds.

In one embodiment, the linker is heterobifunctional and has a formula of Formula I:

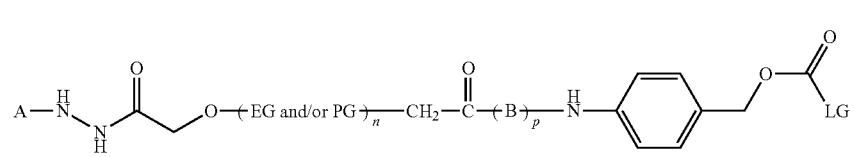

Formula I wherein,
A is a protecting group;
EG is —CH$_2$—CH$_2$—O—:
PG is —CH$_2$—CH$_2$—CH$_2$—O—;
B is an amino acid residue or derivative thereof,
n is an integer between 1 and 10;
p is an integer between 1 and 5; and
LG is a leaving group.

In another embodiment, the linker is heterobifunctional and has a formula of Formula II:

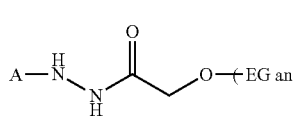 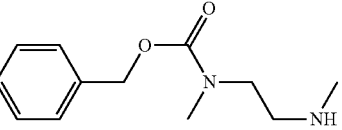

Formula II wherein,
A is a protecting group;
EG is —CH$_2$—CH$_2$—O—;
PG is —CH$_2$—CH$_2$—CH$_2$—O—;
B is an amino acid residue or derivative thereof;
n is an integer between 1 and 10; and
p is an integer between 1 and 5.

The linker's length, rigidity or flexibility, and hydrophobicity or hydrophilicity can be optimized for each immune modulator-carbohydrate polymer conjugate. Furthermore, the linker can be designed and synthesized to include a branching point so that multiple immune modulator compounds may be attached to a single linker.

Finally, the linker can be designed and synthesized such that the immune modulator is released from the immune modulator-carbohydrate polymer conjugate in vivo. For example, the linker may contain labile linkages that include, but are not limited to, a disulfide bond, a hydrazone moiety, or the amide bond of a peptide unit used with or without a self-immolative spacer, such as those described in the literature (Toki et al., 2002; Jeffrey et al., 2005; Sun et al., 2005; WO2005/082023).

The labile bond is readily cleaved in vivo. The cleavage may occur by various mechanisms, such as through a chemical (e.g., hydrolysis at physiological pH or hydrolysis at the lower pH environment found within certain tumors) or enzymatic (e.g. reaction with an esterase) biotransformation.

Such conjugates may be useful for allowing an administered conjugate to reach a target tissue before inducing and/or enhancing or suppressing or tolerizing an immune response. This may provide a therapeutic benefit by providing a more highly localized immune response. The immune modulator moiety may be kept inactive until the conjugate reaches the targeted tissue where the immunotherapy is needed, thereby reducing, even preventing, a systemic immune response.

Immunomodulatory Compounds and Compositions

As used herein, the term "immunomodulatory compound" refers to the capability of the compound to induce and/or enhance or suppress or tolerize an immune response.

Similarly, as used herein, the term "immunomodulatory composition" refers to the capability of the composition to induce and/or enhance or suppress or tolerize an immune response.

The term "immune response" has its ordinary meaning in the art, and includes both humoral and cellular immunity. An immune response can manifest as one or more of, the development of anti-antigen antibodies, expansion of antigen-specific T cells, increase in tumor infiltrating-lymphocytes (TILs); development of an anti-tumor or anti-tumor antigen delayed-type hypersensitivity (DTH) response, clearance of the pathogen, suppression of pathogen and/or tumor growth and/or spread, tumor reduction, reduction or elimination of metastases, increased time to relapse, increased time of pathogen or tumor free survival, and increased time of survival. An immune response may be mediated by one or more of, B-cell activation, T-cell activation, natural killer cell activation, activation of antigen presenting cells (e.g., B cells, DCs, monocytes and/or macrophages), cytokine production, chemokine production, specific cell surface marker expression, in particular, expression of co-stimulatory molecules. The immune response may be characterized by a humoral, cellular, Th1 or Th2 response, or combinations thereof.

Humoral Response

In an embodiment, administration of the compound, composition, or vaccine of the invention results in a humoral response, wherein one or more of IgA, IgG, IgM and optionally, IgE antibody production is stimulated.

The immunoglobulins may include one or more of the subclasses within each class of antibody, for instance IgG2a and IgG1.

In one embodiment, IgG1 and/or IgA production is stimulated.

In some instances, stimulation of IgE production may be beneficial, for example, to immunize against worm infections.

In other instances, a reduction in total IgE production, or a reduction in the level of IgE relative to other antibody classes, can be beneficial, for example, to prevent or reduce type I hypersensitivity or atopy, for example, hayfever, asthma attacks or food and other allergies. IgE binding to its receptor and subsequent cross-linking with allergen is responsible for triggering immune responses underlying conditions such as asthma including atopic asthma, allergic rhinitis and atopic dermatitis, which are health problems of epidemic proportions. Thus, in an embodiment, the immune response is such that IgE production is reduced.

In another embodiment, the IgE titre relative to one or more of IgA, IgG, IgM or subclasses of these is reduced. IgE production may be unchanged, whilst the production of one or more of the other antibodies is increased upon immunization with the composition.

In an embodiment, the immunization selectively stimulates production of one or more of IgA, IgG and IgM over IgE.

In an embodiment, IgA production is stimulated, and the titre of IgA at one or more mucosal areas, and/or in the serum, is increased.

In an embodiment, IgA production upon immunization is greater when compared with production of IgG, IgM and IgE.

In another embodiment, immunization results in greater production of IgA relative to the increase in IgG1 and/or IgG2a production.

In yet another embodiment, IgG production is stimulated, and the titre of IgG at one or more systemic areas and/or in the serum, is increased.

In an embodiment, IgG production upon immunization is greater when compared with production of IgA, IgM and IgE.

In another embodiment, immunization results in greater production of IgG relative to the increase in IgA.

In an embodiment, immunization results in greater production of IgG2a relative to the increase in IgG1.

Cellular Immune Response

In an embodiment, administration of the compound, composition, or vaccine of the invention results in a cellular response, wherein one or more antigen presenting cells are activated.

In an embodiment, macrophages and/or DCs are activated.

Activation of DCs may result in elevated surface expression of co-stimulatory molecules including, for example, CD40, CD80 and 86 and/or an increase in pro-inflammatory cytokines, for example, IL-12 and/or IL-4 and/or an increase in MHC class I and/or II molecules.

In a further embodiment, immunization results in CD8 and/or CD4 T cell responses.

In a further embodiment, immunization results in the production of cytotoxic T lymphocyte (CTL) responses.

In an embodiment, the DCs activate naïve T cells. Dendritic cells are thought to play at least three distinct roles in priming the immune system to vaccine antigen:
1) MHC class II-restricted presentation of vaccine antigen processed in the exogenous pathway following endocytosis thereof,
2) MHC class I and/or class II-restricted presentation of vaccine antigen following direct transfection of DCs with for example, plasmid DNA encoding the antigen,
3) MHC class-I restricted "cross" presentation of vaccine antigen.

Th1/Th2

In an embodiment, administration of the compound, composition, or vaccine of the invention stimulates mediators of humoral and/or cellular immunity.

In an embodiment, administration of the compound, composition, or vaccine of the invention results in a cell mediated, Th1-type response.

In another embodiment, administration of the compound, composition, or vaccine of the invention results in an antibody mediated, Th2-type response.

In an embodiment, administration of the compound, composition, or vaccine of the invention results in the production of Th1-inducing cytokines, such as IL-2, IL-12, IL-15, IL-18 and IFN-γ. These cytokines typically promote cell mediated immunity.

In another embodiment, administration of the compound, composition, or vaccine of the invention results in the production of Th2-inducing cytokines, such as IL-4, IL-5 and IL-10. These cytokines typically promote humoral immunity.

In an embodiment, activation of macrophages results in the production of IL-12 and/or IL-18. This in turn may activate IFN-γδ production by NK cells, inducing differentiation to a Th1 mediated immune response which supports cellular mediated immunity and/or production of complement fixing antibodies.

Vaccine

The term "vaccine composition" refers to a composition that can be used to elicit protective immunity in a recipient subject. It should be noted that to be effective, a vaccine of the invention can elicit immunity in a portion of the population, as some individuals may fail to mount a robust or protective immune response, or in some cases, any immune response to the vaccine. This inability may stem from the individual's genetic background or because of an immunodeficiency condition (either acquired or congenital) or immunosuppression (e.g., treatment with immunosuppressive drugs to prevent organ rejection or suppress an autoimmune condition). Efficacy can be established in animal models.

The vaccine may be "monovalent" (also called univalent) or "multivalent" (also called polyvalent). A monovalent vaccine comprises a single antigen. A multivalent or polyvalent vaccine comprises two or more antigens that may, for example, immunize against two or more strains of the same pathogen, or against two or more pathogens.

The composition or vaccine can be used to immunize, tolerize, treat or protect a subject against, for example, a pathogen or a tumor.

The term "immunize" is used herein to mean generate a protective immune response in a subject, to provide the subject with resistance against a specific pathogen or disease.

The term "tolerize" is used herein to mean induce immunological tolerance in a subject. To tolerize a subject is to induce avoidance or suppression of a specific immune response in the subject. Immunological tolerance can be used to prevent or ameliorate, for example, transplant rejection, autoimmunity, or allergic reaction.

The term "treat" is used herein to mean partial or total destruction of pathogen infected cells or tumor cells within a subject, preferably with minimal destructive effects on non-infected cells. Therapeutic administration of a composition of the invention can treat the recipient subject infected by a pathogen or having cancer. In an alternate embodiment, antigen presenting cells, for example macrophages and DCs, are contacted in vitro or ex vivo with a composition of the invention, and then administered to the subject. As persons skilled in the art are aware, a procedure performed in vitro is performed not in a living organism but in a controlled environment. Such in vitro procedures may be done in or on tissue(s) or cells originating from an organism, and are typically referred to as ex vivo procedures.

The term "protect" is used herein to mean prevent infection by a pathogen or the initiation of tumor growth (i.e., to prevent onset of cancer) or to delay onset of the tumor growth. Prophylactic administration of a composition of the invention can protect the recipient subject from said infection or tumor growth.

Antigens

The present invention provides for use of the immune modulator-carbohydrate polymer conjugate in combination with at least one antigen in a vaccine composition.

The immune modulator-carbohydrate polymer conjugate can be mixed with or conjugated to the at least one antigen to generate a protective immune response following vaccination.

By "at least one antigen" it is meant one or more antigen types or antigenic determinants. Further, it will be appreciated by those skilled in the art, that more than one antigen molecule can be conjugated to the immune modulator-carbohydrate polymer conjugate (i.e., the resultant conjugate may comprise more than a single antigen molecule conjugated to the carbohydrate polymer and may comprise one or more antigen types or antigenic determinants).

Several strategies can be utilized for delivery of an immune modulator and antigen using oxidized mannan. The immune modulator and antigen can be simultaneously or sequentially (in any order) conjugated to oxidized mannan or alternatively, an immune modulator-antigen complex can be generated first and then subsequently conjugated to oxidized mannan. In one example, the aldehyde groups of oxidized mannan can react directly with amino groups of antigens to form Schiff base linkages. In another example, the immune modulator is a TLR agonist that has been modified with linker groups containing maleimide, haloacetyl or activated esters (e.g., N-hydroxysuccinimide) that can react with sulphydryl groups (cysteine) or amino groups (lysine) on antigen. The TLR agonists can also be modified with linkers containing hydrazides or azido groups that can react with antigen functionalized with aldehydes or acetylenic groups, respectively. The TLR-antigen conjugates can then be reacted with the oxidized mannan.

The vaccine can be administered to a subject that has or is susceptible to, or at risk for a disease. The disease may be associated with a pathogen infection. In this embodiment, vaccine administration may prevent or ameliorate the effects of infection by the pathogen.

As used herein, an "antigen" means a substance that has the ability to induce a specific immune response. The antigen may be a whole organism in any of its life cycle stages, inactivated whole organism, fragments or components isolated from the whole organism, lysate of the organism or tumor lysate, specific antigens genetically or synthetically engineered through methods known in the art. In addition, the selected antigen may be derived from either or both a mature whole organism or sporozoites (oocysts).

The antigen for use in the compounds, compositions and methods of the present invention can also consist of whole cells or sub-cellular fractions thereof. Such cells or sub-cellular fractions thereof may be derived from, for example, a tumor or infected tissue.

Preferred selected antigens include, for example, antigens from:
pollens;
allergens, especially those that induce asthma;
viruses, such as influenza, feline leukemia virus, feline immunodeficiency virus, HIV-1, HIV-2, rabies, measles, hepatitis B, hoof and mouth disease, papilloma virus, cytomegalovirus, herpes simplex, hepatitis A, hepatitis C, HTLV-1 and HTLV-2;
bacteria, such as the ethiological agents of anthrax, leprosy, tuberculosis, diphtheria, Lyme disease, syphilis, typhoid fever, and gonorrhea;
protozoans, such as *Babeosis bovis, Plasmodium, Leishmania* spp. *Toxoplasma gondii*, and *Trypanosoma cruzi*;
fungi, such as *Aspergillus* sp., *Candida albicans, Cryplococcus neoformans*, and *Histoplasma capsulatum;*
parasites such as helminths; and
tumor antigens, such as mucin-1 (MUC-1), carcinoembryonic antigen, prostate-specific membrane antigen, prostate specific antigen, protein MZ2-E, polymorphic epithelial mucin (PEM), folate-binding-protein LK26, truncated epidermal growth factor receptor (EGRF), Thomsen-Friedenreich (T) antigen, telomerase, survivin, Melan-A/MART-1, WT1, LMP2, human papillomavirus (HPV) E6 E7, human epithelial growth factor receptor (HER-2/neu), Idiotype, melanoma associated antigen 3 (MAGE-3), p53, NY-ESO-1, prostatic acid phosphatase (PAP), cancer testis antigens, 5T4, and GM-2 and GD-2 gangliosides.

The antigen can be a protein, peptide, polysaccharide or oligosaccharide (free or conjugated to a protein carrier), or mixtures thereof. The proteins and peptides may be part of an extract or lysate, purified from a natural source, synthesized by means of solid phase synthesis, or may be obtained by means of recombinant genetics. The polysaccharides and oligosaccharides may be isolated from a natural source, or may be synthesized using enzymatic procedures and/or organic synthesis approaches.

An antigen may form part of a fusion protein in order to facilitate expression and purification on production of the fusion protein in recombinant host cells. The non-antigen portion of the fusion protein would generally represent the N-terminal region of the fusion polypeptide with the carboxy terminal sequences comprising antigen sequences. Fusion proteins may be selected from glutathione-S-transferase, β-galactosidase, or any other protein or part thereof, particularly those which enable affinity purification utilizing the binding or other affinity characteristics of the protein to purify the resultant fusion protein. The protein may also be fused to the C-terminal or N-terminal of the carrier protein. The nature of the fusion protein will depend upon the vector system in which fusion proteins are produced. An example of a bacterial expression vector is pGEX, which on subcloning of a gene of interest into this vector produces a fusion protein consisting of glutathione-S-transferase with the protein of interest. Examples of other vector systems which give rise to fusion proteins with a protein of interest are described in Sambrook et al. (1989), supra.

Alternatively, synthetic peptides or polypeptides, optionally coupled to a protein carrier may be used in the invention. Synthetic peptides or polypeptides may be produced in accordance with standard methods.

Useful peptides or polypeptides may comprise an epitope-bearing portion of a polypeptide known to elicit an antibody and/or an antigen-specific CTL response when the whole polypeptide is administered to an animal. The epitope of this polypeptide portion is an immunogenic or antigenic epitope of the polypeptide.

An "immunogenic epitope" is defined as a part of a protein that elicits an antibody and/or an antigen-specific CTL response when the whole protein is the immunogen. On the other hand, a region of a protein molecule to which an antibody or MHC molecule can bind is defined as an "antigenic epitope". The number of immunogenic epitopes of a protein generally is less than the number of antigenic epitopes.

With regard to the selection of peptides or polypeptides bearing an antigenic epitope, it is well known in that art that relatively short synthetic peptides that mimic part of a protein sequence routinely elicit antiserum that reacts with the partially mimicked protein (see, for example, Sutcliffe et al., 1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention preferably contain a sequence of at least seven, more preferably at least nine and most preferably between about 15 to 30 amino acids contained within the amino acid sequence of a particular polypeptide.

Epitopes recognized by the T-cell receptors on CTLs may be different from those seen by antibodies. Usually, CTLs recognize peptides (derived from proteins enzymatically degraded in the cytosol compartment) which are bound to MHC class I molecules and exposed on the cell surface. These CTL-recognized peptides bind selectively to MHC class I molecules according to MHC allele-specific sequence motifs. These peptides can be identified by expression cloning (see, van der Bruggen, et al., 1991) and predicted using various class I and class II binding peptide algorithms (Pietersz et al., 2006).

Alternatively, CTL-recognized peptides can be identified by induction of CTLs by in vitro or ex vivo stimulation with peptides derived from the protein antigen used for immunization. The particular CTL-recognized epitope-bearing peptides and polypeptides of the invention are preferably sequences of at least six amino acids, and more preferably between about 7 to 20 amino acids.

Epitope-bearing peptides and polypeptides may be produced by any conventional means.

Bacterial Antigens

The antigen can be derived from bacteria, including but not limited to, *Helicobacter pylori, Chlamydia pneumoniae, Chlamydia trachomatis, Ureaplasma urealyticum, Mycoplasma pneumoniae, Staphylococcus* spp., *Staphylococcus aureus, Streptococcus* spp., *Streptococcus pyogenes, Streptococcus pneumoniae, Streptococcus viridans, Enterococcus faecalis, Neisseria meningitidis, Neisseria gonorrhoeae, Bacillus anthracis, Salmonella* spp., *Salmonella typhi, Vibrio cholera, Pasteurella pestis, Pseudomonas aeruginosa, Campylobacter* spp., *Campylobacter jejuni, Clostridium* spp., *Clostridium difficile, Mycobacterium* spp., *Mycobacterium tuberculosis, Treponema* spp., *Borrelia* spp., *Borrelia burgdorferi, Leptospira* spp., *Hemophilus ducreyi, Corynebacterium diphtheria, Bordetella pertussis, Bordetella parapertussis, Bordetella bronchiseptica, hemophilus influenza, Escherichia coli, Shigella* spp., *Erlichia* spp., and *Rickettsia* spp.

The bacterial antigen can be native, recombinant or synthetic. Such bacterial antigens include, but are not limited to, selectins or lectins from bacteria that bind to carbohydrate determinants present on cell surfaces, and bacteria receptors for proteins, such as fibronectin, laminin, and collagens.

Viral Antigens

The antigen can be derived from viruses, including but not limited to, Influenza viruses, a Parainfluenza viruses, Mumps virus, Adenoviruses, Respiratory syncytial virus, Epstein-Barr virus, Rhinoviruses, Polioviruses, Coxsackieviruses, Echoviruses, Rubeola virus, Rubella virus, Varicell-zoster virus, Herpes viruses (human and animal), Herpes simplex virus, Parvoviruses (human and animal), Cytomegalovirus, Hepatitis viruses, Human papillomavirus, Alphaviruses, Flaviviruses, Bunyaviruses, Rabies virus, Arenaviruses, Filoviruses, HIV 1, HIV 2, HTLV-1, HTLV-II, FeLV, Bovine LV, FeIV, Canine distemper virus, Canine contagious hepatitis virus, Feline calicivirus, Feline rhinotracheitis virus, TGE virus (swine), and Foot and mouth disease.

Viral antigens can be native, recombinant or synthetic. Such viral antigens include, but are not limited to, viral proteins that are responsible for attachment to cell surface receptors to initiate the infection process, such as (i) envelope glycoproteins of retroviruses (HIV, HTLV, FeLV and others) and herpes viruses, and (ii) the neuramidase of influenza viruses.

Tumor Antigens

In an embodiment of the invention, the subject has cancer or is at increased risk of developing cancer.

By "cancer" it is meant any of various malignant neoplasms, characterized by the proliferation of cells that have the capability to invade surrounding tissue and/or metastasize to new colonisation sites. The cancer may be, for example, breast, gastric, colorectal, pancreatic, bladder or lung cancer. In a preferred embodiment, the cancer is breast cancer.

Many "risk factors" for cancer are well established such as familial history of cancer, personal history of cancer, previous biopsy detection of proliferative disease such as atypical hyperplasia. Particular genetic risk factors are also known, examples for breast cancer include BRCA1, BRCA2, ATM, CHEK-2 and p53 mutations. Lifestyle-related risk factors can also be considered. Lifestyle-related risk factors for breast cancer in women include delayed childbirth until after age 30 and long-term use of hormone replacement therapy. A skilled medical practitioner can evaluate these and other risk factors to determine whether a subject will benefit from prophylactic use of a vaccine composition of the invention.

Cancer vaccines of the invention may comprise one or more tumor associated antigens. Tumor associated antigens can be native, recombinant or synthetic. Such tumor associated antigens include, but are not limited to, MUC-1 and peptide fragments thereof, protein MZ2-E, polymorphic epithelial mucin, folate-binding protein LK26, MAGE-1 or MAGE-3 and peptide fragments thereof, Human chorionic gonadotropin (HCG) and peptide fragments thereof, Carcinoembryonic antigen (CEA) and peptide fragments thereof, Alpha fetoprotein (AFP) and peptide fragments thereof, Pancreatic oncofetal antigen and peptide fragments thereof, CA 125, 15-3,19-9, 549, 195 and peptide fragments thereof, Prostate-specific antigens (PSA) and peptide fragments thereof, Prostate-specific membrane antigen (PSMA) and peptide fragments thereof, Squamous cell carcinoma antigen (SCCA) and peptide fragments thereof, Ovarian cancer antigen (OCA) and peptide fragments thereof, Pancreas cancer associated antigen (PaA) and peptide fragments thereof, Her1/neu and peptide fragments thereof, gp-100 and peptide fragments thereof, mutant K-ras proteins and peptide fragments thereof, mutant p53 and peptide fragments thereof, nonmutant p53 and peptide fragments thereof, truncated epidermal growth factor receptor (EGFR), chimeric protein p210BCR-ABL, telomerase and peptide fragments thereof, suvivin and peptide fragments thereof, Melan-A/MART-1 protein and peptide fragments thereof, WT1 protein and peptide fragments, LMP2 protein and peptide fragments, HPV E6 E7 protein and peptide fragments, HER-2/neu protein and peptide fragments, Idiotype protein and peptide fragments, NY-ESO-1 protein and peptide fragments, PAP protein and peptide fragments, cancer testis proteins and peptide fragments, and 5T4 protein and peptide fragments. Other exemplary tumor antigens are described in Cheever et al., 2009.

Mucin

In a preferred embodiment, the antigen is a mucin or antigenic fragment or immunogenic mutant/derivative thereof. Many cancers are accompanied by overproduction of human mucin. Mucins are heavily glycosylated proteins (greater than about 100 kDa) which are produced by many epithelial cells and tumours. Mucins found on cancer cells are different in some respects to those on normal epithelial cells, in that some mucins have a deficiency in their carbohydrate coat which leaves the protein core exposed. There are 21 forms of known human mucin designated MUC-1, MUC-2, MUC-3, MUC-4, MUC-5 MUC-6 and MUC-7, etc. MUC-1 is the most ubiquitous. The various mucins all have very similar properties, that is, they are transmembrane glycoproteins, all having a variable number of repeated amino acid sequences, which have a high content of serine, threonine and proline. Overproduction of aberrantly glycosylated mucins (either non-glycosylated or a deficiency in glycosylation) is characteristic of tumours of the breast, ovary, pancreas, colon, lungs, prostate and other tumours of secretory tissue. The cDNA sequences of the respective protein cores of the human mucins MUC-1 to MUC-21 have been cloned and characterized and have been found to contain highly repetitive central portions of varying numbers of repeats of particular amino acid motifs (known as VNTR's). By way of example, MUC-1 consists of unique amino and carboxyl terminal sequences separated by a highly repetitive central portion containing forty to eighty tandemly arranged copies or repeats of a twenty amino acid motif.

In an embodiment, the tumor associated antigen is any one ore more of the human mucins MUC-1 through MUC-21 which, as mentioned above, all comprise highly repetitive central portions of repeated amino acid sequences which are high in serine, threonine and proline. In particular, the vaccines of the invention may comprise a human mucin polypeptide (containing a variable number of repeats associated with normal allelic variation), or may comprise one or more of the repeated sequences of human mucin, preferably two to eighty, more preferably two to twenty and even more preferably two to ten repeated subunits of human mucin. The human mucin and subunits thereof are preferably non-glycosylated or aberrantly glycosylated so as to provoke an immune response to the mucins found on cancer cells which have a deficiency in their carbohydrate coat which leaves the protein core exposed. The use of human mucin MUC-1 is particularly preferred although it is to be clearly understood that the invention extends to the use of any antigen and especially to the use of the human mucins MUC-1 through MUC-21.

The MUC-1 antigen may be as described in, for example, WO 95/108145, U.S. Pat. Nos. 6,054,438, 6,222,020, WO 98/50527, WO 01/18035, WO 00/63363, WO 95/03825, WO 00/06723 and WO 04/016643. Use of the MUC-1 T cell epitope-derived peptides or peptide analogues disclosed in WO 2008/011672 is also contemplated.

Immune Modulator-Carbohydrate Polymer Conjugates+Antigen(s)

Delivery of the at least one antigen to, for example, macrophages and DCs can be increased when the at least one antigen is conjugated to the immune modulator-carbohydrate polymer. Although not wishing to be limited by theory, this is most likely because macrophages and DCs have cell surface receptors that recognize carbohydrate moieties (typically from microorganisms) and mediate phagocytosis, as well as in pinocytosis, two processes that are involved in antigen presentation. As such, immune modulator-carbohydrate polymer-antigen conjugates of the invention provide an effective mechanism for APC targeting.

In a preferred embodiment, the carbohydrate polymer is oxidized with, for example, $NaIO_4$ prior to conjugation to the at least one antigen. In an embodiment, the carbohydrate polymer is mannan and the polysaccharide chains of the mannan are oxidized prior to conjugation to at least one antigen. The at least one antigen may be conjugated to the oxidized mannan in a similar manner to that described in WO 95/18145. Reduced mannans may also be used, and a composition containing this may be prepared by adding sodium borohydride or sodium cyanoborohydride to oxidized mannan-antigen conjugates.

In an alternate embodiment, the carbohydrate polymer may be first activated with cyanogen bromide and the activated carbohydrate polymer then reacted with a diamine, followed by conjugation to the at least one antigen to form conjugates which may optionally then be oxidized.

The carbohydrate polymer and the at least one antigen may be derivatized with bifunctional agents in order to cross-link the carbohydrate polymer and the at least one antigen. Commonly used crosslinking agents include 1,1-bis (diazoacetyl)-2-phenylethane, glutaraldehyde, N-hydroxy-succinimide esters, for example, esters with 4-azidosalicyclic acid, homobifunctional imidoesters including disuccinimidyl esters such as 3,3'-dithiobis(succinimidyl-propionate), and bi functional maleimides such as bis-N-maleimido-1,8-octane. Derivatizing agents such as methyl-3-[(p-azido-phenyl)dithio] propioimidate yield photactivitable intermediates which are capable of forming cross-links in the presence of light. Oxidized carbohydrate polymers may be reacted with hydrazine derivatives of antigens to give the conjugates. Alternatively, the carbohydrate polymers may be first reacted with reagents such as carbonyl diimidazole, then reacted with antigen, and oxidized to give the conjugates.

The coupling of the at least one antigen to the carbohydrate polymer involves reacting the functional groups on the carbohydrate with functional groups on the antigen. Carbohydrate polymers are replete with hydroxyl groups. These groups may be activated according to standard chemical procedures. For example, hydroxyl groups may be reacted with hydrogen halides, such as hydrogen iodide, hydrogen bromide and hydrogen chloride to give a functionalized halogenated polysaccharide. Hydroxy groups may be activated with phosphorous trihalides, active metals (such as sodium ethoxide, aluminium isopropoxide and potassium tert-butoxide), or esterified (with groups such as tosyl chloride or acetic acid) to form functional groups which can be then be reacted with functional groups on the polypeptide to form one or more bonds.

Nucleic Acid Encoding for Antigen

In an embodiment, the vaccine composition comprises a nucleic acid encoding the antigen. Multiple nucleic acids can be incorporated into the vaccine to produce a polyvalent antigen vaccine. In an embodiment, the vaccine is a DNA vaccine.

At least one nucleic acid can be linked to the carbohydrate polymer, for example, via polycations such as poly-L-lysine, polyethyleneimine, or a PAMAM dendrimer. In an embodiment, the positive charges of oxidized mannan-polycation interact with negatively charged DNA and form a polyplex that can be used for transfection (Tang et al., 2008; Tang et al., 2007; Tang et al., 2009).

DNA vaccination typically involves the direct in vivo introduction of DNA encoding an antigen into, for example, the muscle or skin of the subject for expression of the antigen by the cells of the subject. Once the DNA encoded antigen is processed and presented by the transfected cells, a cellular and/or humoral immune response may be provoked. DNA vaccines are described in U.S. Pat. Nos. 5,939,400, 6,110,898, WO 95/20660 and WO 93/19183.

To date, most DNA vaccines in mammalian systems have relied upon viral promoters derived from cytomegalovirus (CMV). These have had good efficiency in both muscle and skin inoculation in a number of mammalian species. A factor known to affect the immune response elicited by DNA immunization is the method of DNA delivery, for example, parenteral routes can yield low rates of gene transfer and produce considerable variability of gene expression. High-velocity inoculation of plasmids, using a gene-gun, enhanced the immune responses of mice, presumably because of a greater efficiency of DNA transfection and more effective antigen presentation by DCs. Vectors containing the nucleic acid-based vaccine of the invention may also be introduced into the desired host by other methods known in the art, for example, transfection, electroporation, microinjection, transduction, cell fusion, DEAE dextran, calcium phosphate precipitation, lipofection (lysosome fusion), or a DNA vector transporter. Mechanisms of administration of DNA vaccines are described in more detailed below.

Other Components

The compositions of the invention may include at least one pharmaceutically acceptable carrier. The term "pharmaceutically acceptable carrier" refers to molecular entities and compositions that do not produce an allergic, toxic or otherwise adverse reaction when administered to a subject, particularly a mammal, and more particularly a human. The pharmaceutically acceptable carrier may be solid or liquid. Useful examples of pharmaceutically acceptable carriers include, but are not limited to, diluents, excipients, solvents, surfactants, suspending agents, buffering agents, lubricating agents, vehicles, emulsifiers, absorbants, dispersion media, coatings, stabilizers, protective colloids, adhesives, thickeners, thixotropic agents, penetration agents, sequestering agents, isotonic and absorption delaying agents that do not affect the activity of the active agents of the invention.

The carrier can be any of those conventionally used and is limited only by chemico-physical considerations, such as solubility and lack of reactivity with the active agent, and by the route of administration. Suitable carriers for this invention include those conventionally used, for example, water, saline, aqueous dextrose, lactose, Ringer's solution, a buffered solution, hyaluronan, glycols, starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like. Liposomes may also be used as carriers.

Compounds which may further enhance the immunogenicity or effectiveness of the compounds and compositions of the invention may also be administered. These compounds may be included in compositions of the invention or be co-administered with compounds or compositions of the invention. For instance, the compositions may comprise one or more oils (for example, Freund's Complete and Incomplete), saponins, modified saponins, liposomes, mineral salts (for example, $AIK(SO_4)_2$, $AlNa(SO_4)_2$, $AlNH_4(SO_4)$, silica, alum, $Al(OH)_3$, $Ca_3(PO_4)_2$, kaolin, and carbon), polynucleotides (for example, poly IC and poly AU acids), and certain natural substances (for example, lipid A, wax D from *Mycobacterium tuberculosis*, as well as substances found in *Corynebacterium parvum, Bordetella pertussis*, and members of the genus *Brucella*), bovine serum albumin, diphtheria toxoid, tetanus toxoid, edestin, keyhole-limpet hemocyanin, Pseudomonal Toxin A, choleragenoid, cholera toxin, pertussis toxin, viral proteins, and eukaryotic proteins such as interferons, interleukins, or tumor necrosis factor. Such proteins may be obtained from natural or recombinant sources according to methods known to those skilled in the art. Other known immunogenic macromolecules include polysaccharides, tRNA, non-metabolizable synthetic polymers such as polyvinylamine, polymethacrylic acid, polyvinylpyrrolidone, mixed polycondensates (with relatively high molecular weight) of 4',4-diaminodiphenyl-methane-3, 3'-dicarboxylic acid and 4-nitro-2-aminobenzoic acid or glycolipids, lipids or carbohydrates.

Administration

The compound, composition, or vaccine of the invention can be administered to the subject by an appropriate route, either alone or in combination with a second compound.

In an embodiment, the second compound is an antigen or nucleic acid encoding therefor. In an embodiment, the immune modulator-carbohydrate polymer conjugate and the antigen or nucleic acid encoding therefor, are administered sequentially or simultaneously in different compositions. In a preferred embodiment, they are administered in the same composition.

The immune modulator-carbohydrate polymer conjugate may be administered in admixture with the antigen or nucleic acid encoding therefor, or alternatively, the immune modulator-carbohydrate polymer conjugate can be conjugated to the antigen or to the nucleic acid encoding therefor.

A variety of routes of administration are possible including, but not limited to, oral, dietary, topical, parenteral (e.g., intravenous, intra-arterial, intramuscular, intradermal, intravascular or subcutaneous injection), and inhalation (e.g., intrabronchial, intranasal or oral inhalation, intranasal drops) routes of administration.

In one embodiment, the compound, composition, or vaccine of the invention is administered to a mucosal site. Examples of mucosal sites, include but are not limited to the respiratory tract such as the nasal region (e.g., the nose), the trachea, bronchi and the lungs, the buccal or oral tissues including the oral (e.g., the mouth and gingivae) and oropharyngeal cavities, the throat including the tonsils, the conjunctiva of the eyes, the gastrointestinal tract (e.g., oesophagus, stomach, duodenum, small and large intestines, colon and rectum), the reproductive tract/tissues (including but is not limited to the bladder, ureter, urethra and associated tissues, the penis, the vulva/vagina and cervico-vaginal tissues, as well as the uterus and fallopian tubes).

Formulation of the composition or vaccine to be administered will vary according to the route of administration selected (e.g., solution, emulsion, capsule).

For example, the immune modulator-carbohydrate polymer conjugate can be administered in a formulation of about 0.0001% to about 20% (unless otherwise indicated, all percentages provided herein are weight/weight with respect to the total formulation) to the subject. In one embodiment, the immune modulator-carbohydrate polymer conjugate is administered to the subject in a formulation that includes from about 0.01% to about 1% of the conjugate, for example, a formulation that includes about 0.1% to about 0.5% of the conjugate.

The compound of the invention can be prepared in a physiologically acceptable carrier. For solutions or emulsions, suitable carriers include aqueous or alcoholic/aqueous solutions, emulsions or suspensions, including saline and buffered media. Parenteral carriers include sodium chloride solution, Ringer's dextrose, dextrose and sodium chloride, lactated Ringer's or fixed oils. Intravenous carriers include various additives, preservatives, or fluid, nutrient or electrolyte replenishers and the like (See, generally, Remington's Pharmaceutical Sciences, 1985). For inhalation, a soluble composition or vaccine can be loaded into a suitable dispenser for administration (e.g., an atomizer, nebulizer or pressurized aerosol dispenser).

A nucleic acid can be directly delivered to cells by incorporation into a retroviral, adenoviral or other suitable vector, or various other protein-based or lipid-based gene delivery complexes, as well as through use of techniques facilitating the delivery of "naked" polynucleotides (such as electroporation or "gene gun" delivery). Alternatively, the nucleic acid can be introduced into a host cell capable of expressing the protein for delivery. These transfected or transformed cells can then be implanted (alone or in a barrier device), injected or otherwise introduced in an amount effective to express the antigen in a therapeutically effective amount.

In an alternate embodiment, antigen presenting cells, for example macrophages and/or DCs can be contacted in vitro or ex vivo with a compound or composition of the invention to effect loading with antigen and then be administered to the subject. In one embodiment, the antigen presenting cells are derived from the subject or an autologous donor and loaded with antigen ex vivo. For example, blood may be taken from the subject or autologous donor and enriched for peripheral blood mononuclear cells (PBMCs) by density gradient centrifugation, followed by adherence to a plastic surface to enrich monocytes. Adherent cells can then be cultured with a cytokine mix to induce differentiation to for example, immature DCs, and the resulting immature DCs can be contacted with the vaccine antigen and immune modulator-carbohydrate polymer or alternatively, transfected with nucleic acid encoding said antigen. Aliquots (for example, cryopreserved aliquots) of the resultant mature/activated DC preparations (i.e., having upregulated costimulatory molecules CD40, CD80 and CD86) can then be administered to the subject by, for example, intradermal injection(s) on a protocol defined schedule.

Administration of the compound, composition, or vaccine of the invention may be a single or multiple event, or may be part of a prime-boost protocol, a combination of these, or each of these with other, conventional methods of administration/vaccination. The prime-boost protocol may, for example, comprise priming by, for example, intramuscular, intradermal, intravascular subcutaneous, or intravenous administration, and boosting by for example, intranasal, intramuscular, intradermal, intravascular subcutaneous, or intravenous administration. One or both of the priming and boosting composition may include the antigen or nucleic acid encoding therefor and an immune modulator-carbohydrate polymer conjugate. One of the priming and boosting compositions may omit the immune modulator-carbohydrate polymer conjugate.

The amount and frequency of administration of the immune modulator-carbohydrate polymer conjugate effective for a particular application will vary according to factors known in the art including but not limited to, the physical and chemical nature of the immune modulator-carbohydrate polymer conjugate (e.g., the immune modulator moiety and/or the carbohydrate polymer), the nature of the carrier, the intended dosing regimen, the state of the subject's immune system (e.g., suppressed, compromised, stimulated), the method of administering the immune modulator conjugate, and the species to which the formulation is being administered.

Accordingly, it is not practical to set forth generally the amount of immune modulator conjugate effective for all possible applications. The amount and frequency may be determined by an attending physician or veterinarian.

An effective amount of the composition is administered. An "effective amount" is an amount sufficient to achieve the desired immunomodulatory effect, under the conditions of administration.

By way of example, from about 100 ng/kg to about 50 mg/kg immune modulator may be administered to the subject, preferably from about 10 µg/kg to about 5 mg/kg, more preferably, 100 µg/kg to about 1 mg/kg.

By way of example, from about 100 ng/kg to about 50 mg/kg carbohydrate polymer may be administered to the subject, preferably from about 10 µg/kg to about 10 mg/kg. Even more preferably, a dose of from about 1 mg/kg to about 10 mk/kg carbohydrate polymer is contemplated, particularly for humans.

By way of example, from about 1 µg/kg to about 10,000 µg/kg antigen may be administered to a subject, preferably from about 5 µg/kg to about 5000 µg/kg, more preferably from about 8 µg/kg to about 1000 µg/kg and most preferably, from about 400 µg/kg to about 600 µg/kg. Even more preferably, a dose of from about 100 µg/kg to about 200 µg/kg antigen is contemplated, particularly for humans.

Alternatively, the dose may be calculated using actual body weight obtained just prior to the beginning of a treatment course. For the dosages calculated in this way, body surface area ($m^2$) is calculated prior to the beginning of the treatment course using the Dubois method: $m^2=$(wt $kg^{0.425}$×height $cm^{0.725}$)×0.007184. In one embodiment, the immune modulator is administered to the subject at a dose of, for example, from about 0.01 mg/$m^2$ to about 10 mg/$m^2$.

The compound, composition and vaccine of the invention may also be administered to subjects in conjunction with other immune response modifiers, for example cytokines, HLA class II protein-binding helper molecules, CD40 agonists, antagonists of checkpoint receptors (for example, CTLA-4, PD-1, Stat3), B7 costimulatory molecules, FLt3 agonists, and CD40L agonists.

The presence of a HLA class II protein-binding helper molecule is effective in stimulating helper (CD4$^+$) T cells. The HLA class II protein-binding helper molecule may be any of those well known to persons skilled in the art including, for example, keyhole limpet haemocyanin (KLH), tetanus toxoid (TT), diphtheria toxoid, or smaller T cell helper epitopes, such as PADRE peptides, and combinations thereof.

Compounds which may further enhance the immunogenicity or effectiveness of the compounds or compositions of the invention may also be administered.

The compounds and compositions of the invention can also be used in combination with other immunotherapy strategies, for example, chemotherapy where the subject has cancer and the vaccine is a cancer vaccine.

Conditions that may be treated by administering immune modulator-carbohydrate polymer conjugate include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such *chlamydia,* fungal diseases including but not limited to candidiasis, aspergillosis, histoplasmosis, cryptococcal meningitis, or parasitic diseases including but not limited to malaria, pneumocystis carnii pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, breast cancer, lung cancer, prostate cancer, colon cancer, and other cancers;

(e) Th2-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Immune modulator-carbohydrate polymer conjugate also may be useful to individuals having compromised immune function. For example, certain conjugates may be used for treating the opportunistic infections and tumors that occur after suppression of cell mediated immunity in, for example, transplant patients, cancer patients and HIV patients.

Delivery of a Nucleic Acid to a Cell

In an embodiment, the invention relates to a compound or composition for delivering a nucleic acid to a cell. The at least one nucleic acid may be conjugated to the carbohydrate polymer via polycations.

In an embodiment, the nucleic acid encodes an antigen.

The term "nucleic acid" is synonymous with DNA, RNA and polynucleotides in all their forms, i.e., single and double-stranded DNA, cDNA, mRNA, siRNA and the like.

Means of delivery of nucleic acids to a subject include direct delivery of the nucleic acid and delivery of cells transfected or transformed with the nucleic acid. Cells or nucleic acids can be delivered directly to the desired organ or tumor, for example by injection, catheterization, or endoscopy. They can also be delivered intravenously, intrabronchially, intra-tumorally, intrathecally, intramuscularly, intraocularly, topically, subcutaneously, transdermally or per os.

Examples of nucleic acid delivery vehicles are liposomes, biocompatible polymers, including natural polymers and synthetic polymers, lipoproteins, polypeptides, polysaccharides, lipopolysaccharides, artificial viral envelopes, metal particles, and bacteria, viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy, genetic vaccination (for example, DNA vaccination), as well as for simple protein expression.

As used herein, "vector" refers to discrete elements that are used to introduce heterologous nucleic acid into cells for either expression or replication thereof. For example, a vector may be an artificial chromosome, plasmid, cosmid, bacteriophage or virus, and may be capable of stable integration into a host cell genome, or it may exist as an independent genetic element (e.g., episome, plasmid). A vector may exist as a single polynucleotide or as two or more separate polynucleotides. Vectors may be single copy vectors or multicopy vectors when present in a host cell. Preferred vectors for use in the present invention are expression vectors in which one or more functional genes can be inserted into the vector, in proper orientation and proximity to expression control elements so as to direct expression of one or more proteins in the host cell.

The term "control elements" refers to nucleic acid sequences necessary for the expression of an operably linked nucleotide coding sequence in a particular host cell. The control sequences suitable for expression in prokaryotes, for example, include origins of replication, promoters, ribosome binding sites, and transcription termination sites. The control sequences that are suitable for expression in eukaryotes, for example, include origins of replication, promoters, ribosome-binding sites, polyadenylation signals, and enhancers.

A "promoter" directs transcription of a nucleic acid. As used herein, a "promoter" includes necessary nucleic acid sequences near the start site of transcription, such as, in the case of a polymerase II type promoter, a TATA element.

A promoter also optionally includes distal "enhancer or repressor elements", which can be located as much as several thousand base pairs from the start site of transcription. The promoter can either be homologous or heterologous. A "constitutive" promoter is a promoter that is active in a selected organism under most environmental and developmental conditions. An "inducible" promoter is a promoter that is under environmental or developmental regulation in a selected organism.

The vector may be a viral or non-viral vector, including adenovirus vectors, adeno-associated virus vectors, retrovirus vectors, lentivirus vectors, and plasmid vectors. Exemplary types of viruses include HSV (herpes simplex virus), adenovirus, AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers. Gene delivery, gene transfer, and the like, as used herein, are terms referring to the introduction of a nucleic acid (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of nucleic acids). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

EXAMPLES

Example 1: Materials and Methods

Media & chemicals

Complete RPMI-1640 media was prepared by supplementing with 2% HEPES, 0.1 mM 2-mercaptoethanol, 100 U/ml penicillin, 100 µg/ml streptomycin, 2 mM glutamine and 10% (v/v) fetal calf serum. Recombinant GM-CSF used to culture DCs was purchased from BD-Pharmingen (San Diego, USA) and was reconstituted in PBS. Lipopolysaccharide (LPS) (L3137, Sigma, Castle Hill Australia) was reconstituted in sterile distilled water. Anti-CD11c-APC was purchased from BD Pharmingen (San Diego, Calif.). Anti-CD40, CD80 and CD86 antibodies were prepared in-house. Mannan, NaIO$_4$, ANTS, ethane-1,2-diol were purchased from Sigma.

The mannan used in these studies is from Bakers yeast (*Saccharomyces cerevisae*). Mannan is very heterogeneous incorporating mannose rich polysaccharides with various molecular weights ranging from 50 to >1,000 kDa.

Fractionation Method

Mannan (Sigma) at 20 mg/ml in double distilled water (DDW) was added to 20 ml 300 kDa MWCO Vivaspin concentrators (Sartorius), centrifuged at 2500 rpm for 15-20 minutes and concentrated down to 1-2 ml (FIG. 1). The concentrator was refilled until the entire sample was added. Several spins were needed. The filtrate was collected and 2× DDW washes were done but discarded. The concentrated fraction (retentate) is the >300 kDa fraction. The filtrate was then applied to 15 ml 100 kDa MWCO Amicon spin concentrator (Millipore) and carried out as detailed previously. The mannan was then sequentially fractionated using 2× 15 ml 50 kDa MWCO Amicon spin concentrators (Millipore) followed by 2× 15 ml 30 kDa MWCO Amicon spin concentrators (Millipore). This resulted in fractions of >300, 100-300, 50-100, 30-50 and <30 kDa. The retentate fractions and the final filtrate were freeze dried to a white fluffy powder, except with the <30 kDa fraction which was gummy and so not used. The samples were weighed out and recoveries recorded.

In later fractionation runs, 2× 20 ml 1000 kDa MWCO Vivaspin concentrators from Sartorius were used as the first fractionation step, followed by the sequence of the other concentrators as mentioned above. This results in fractions of >1000, 300-1000, 100-300, 50-100, 30-50 and <30 kDa.

As before the retentate fractions and the final filtrate were freeze dried to a white fluffy powder, and the <30 kDa fraction was not used. The samples were weighed out and recoveries recorded. In some runs, there was no powder in the 300-1000 kDa fraction and so in those runs that particular fraction was not used for analysis.

Quantitation of Aldehyde Residues in Mannans Using the PDPH Quantitation Method

A method for the quantification of the number of aldehyde groups in oxidized mannan is schematically shown in FIG. 2. The same molar concentration of NaIO$_4$ is used such that the extent of oxidation will depend on the molecular weight of mannan. Mannan and mannan fractions 1.4 mg/0.1 ml in 0.1 M phosphate pH 6.0 buffer were oxidized with 0.01 M NaIO$_4$ and allowed to react for 1 hour on ice in the dark. The reaction was quenched with 10 µl ethane-1,2-diol and allowed to react for a further ½ hour, before passing through a PD10 column with 0.1 M acetate buffer pH 4.8.

One ml of the 2 ml of oxidized mannan at 0.7 mg/ml was reacted with 0.1 mg PDPH rotating overnight at room temperature, before passing through a PD10 with DDW. The number of aldehyde groups can be determined by reacting with 0.01 M DTT for 15 minutes and reading Absorbance at OD343 nm. This releases the 2-pyridine which indicates aldehyde groups (FIG. 2).

Number of aldehyde residues = concentration of 2-pyridinethione(M)/ concentration of mannan(M) = [$OD_{343}$/8080]/

[concentration of mannan (mg/ml)/Molecular weight of mannan].

The average molecular weight used for the various fractions are; whole mannan=500 kDa, >1,000=1000 kDa, >300=650 kDa, 100-300=200 kDa, 50-100=75 kDa, 30-50=40 kDa.

Chemical Modification of Mannans with ANTS and Quantitation

Chemical modification of oxidized mannan with ANTS is schematically shown in FIG. 3. Mannan and mannan fractions 1.4 mg/0.1 ml in 0.1 M phosphate pH 6.0 buffer were oxidized with 0.01 M NaIO$_4$ and allowed to react for 1 hour on ice in the dark. The reaction was quenched with ethane-1,2-diol and allowed to react for a further ½ hour, before passing through a PD10 column with 0.1 M acetate buffer pH 4.8.

One ml of the 0.7 mg/ml of oxidized mannan, >300 kDa, 100-300 kDa, 50-100 kDa and 30-50 kDa fractions were reacted with 0.288, 0.184, 0.598, 1.59 and 2.99 mg ANTS (×400 excess) in 3/17 acetic acid/DDW respectively. Sodium cyanoborohydride (50 µl, 1 M; Sigma) was added and the reaction left rotating overnight at room temperature, before passing through a PD10 with DDW. The fluorescence of the ANTS conjugates were read against an ANTS standard at excitation 405 nm emission 520 nm.

Resorcinol Assay for Quantitation of Mannose Residues

Mannan and mannan fractions were quantitated using the resorcinol assay (Monsigny et al., 1988). Mannose was used as a standard. The plate was read at Absorbance at OD 450 nm (since there is no 430 or 480 nm).

Conjugation of Antigens to Mannan

Conjugation of proteins to oxidized mannan is schematically shown in FIG. 4. Mannan and fractions >1000 kDa, 300-1000 kDa (or >300 in earlier runs), 100-300 kDa, 50-100 kDa, 30-50 kDa at 14 mg/ml in 0.1 M phosphate pH 6.0, (except 30-50 fraction which was at 14 mg/0.5 ml) was oxidized with the addition of 0.1 M NaIO$_4$ 100, 77, 250, 600 µl and 1.25 ml respectively and made up to a final volume of 1.6 ml.

The mixture was placed for 1 hour on ice in the dark, quenched with ethane-1,2-diol and further reacted for ½ hour as before. The conjugates were separated on a PD10 column (GE Biosciences) pre-equilibrated with 0.05 M bicarbonate pH 9.0 to remove unreacted material and byproducts. This involved passing the 1.6 ml sample, followed by 0.9 ml buffer through the column and discarded. The next 2 ml was collected and 1 ml of oxidized mannan or fraction was reacted with a calculated amount of 0.35, 0.3, 0.495, 0.735 and 0.59 mg of FP and OVA respectively. The conjugates incubated overnight at room temperature and separated on a 4-12 or 4-20% SDS-PAGE gel to verify successful conjugation. Good conjugation is indicated by a smear and lack of a distinct protein band.

For the final >1000MFP conjugate used in the in vivo studies 0.7 mg FP (5.45 mg/ml, 128 µl) was reacted with 2 ml oxidized mannan. Similarly, for >1000ManRSVg conjugate 0.25 mg RSVg (0.37 mg/ml, 367 µl) was reacted with 2 ml oxidized mannan.

The molar concentration of mannan in the >1000MFP is one half of that in MFP, therefore 10 µg FP was used in the in vivo immunogenicity studies.

Native and Denaturing Gel Electrophoresis

Mannan and fractions were visualized on SDS-PAGE or native gels. Precast (PAGE gel) SDS 4-12% or 4-20% gradient gels (PAGE gel) were run in 1×MOPS SDS running buffer. Alternatively, 12% native gels (basic conditions) were used consisting of a 5% stacking gel made in 0.063 M Tris-HCl pH 6.8 and a resolving gel made in TBE. Electrophoresis was performed in TBE plus 0.19 M glycine (Sharma et al., 2003).

Coomassie stain and PAS stain was used to stain gels for protein and sugars respectively.

Molecular Weight Determination of Mannan Fractions by Densitometry Mannan fractions were oxidized with $NaIO_4$ and labelled with ANTS as above. Samples of ANTS-labelled mannan were analysed by SDS-PAGE after PAS staining. Dried gels were scanned and analysed by densitometry using Quantity One (Bio-Rad) software.

Generation of bone-marrow derived dendritic cells Murine DCs were generated as described previously (Apostolopoulos et al., 2006). Briefly, bone marrow cells were extracted from the lumen of femurs and tibias. Bone marrow cells were then treated with sterile 0.73% (w/v) $NH_4Cl$ for 10 minutes at 37° C. to lyze erythrocytes. Cells were washed and resuspended in complete media ($2 \times 10^6$ cells/3 ml) supplemented with 10 ng/ml of GM-CSF. These cells were cultured for 4 days in a 24 well plate (1 ml/well). Cells were harvested by gentle pipetting of the culture media. GM-CSF cultured bone marrow cells yields large numbers of MHC class II expressing DCs that are potent mixed lymphocyte reaction (MLR) stimulator cells.

In Vitro Dendritic Cell Maturation Studies

C57BL/6 mice derived DCs were used in maturation studies. Dendritic cells were removed from culture plates and $1 \times 10^5$ DCs were resuspended in 150 µl of complete RPMI supplemented with 10 ng/ml GM-CSF and seeded into 48 well plates. Mannan and various mannan fractions were added such that final concentrations of 800, 400, and 200 µg/ml were added to wells. LPS (1 µg/ml) was used as a positive control and was also added into respective wells and incubated at 37° C. for 18 hours. Cells were harvested and stained with anti-CD11c-APC together with anti-CD86, anti-CD40 or anti-CD80 that was conjugated with fluorescein isothiocyanate (FITC). $CD11c^{high}$ cells were gated and intensity of FITC was determined by histogram analysis to determine DC maturation states.

In Vivo Mouse Inununogenicity Studies
Mice and Immunizations

HLA-A2/$K^b$ mice were purchased from the Animal Resources Centre, Perth, Australia. To determine effector immune responses induced by the MFP, >1000MFP and unconjugated FP, HLA-A2/$K^b$ mice were immunized intradermally in the base of tail with a volume of 100 µl on days 0, 10 and 17 and immune responses assessed 10-14 days later using ELISpot assay. Mice were bled after $2^{nd}$ and $3^{rd}$ injection and MUC1-specific total Ig, IgG2a and IgG1 detected by ELISA assay.

Antigen-Specific T Cell Responses In Vivo

Spleen cells from immunized HLA-A2/$K^b$ mice were isolated and assessed by ELISpot for antigen-specific IFN-γ secretion. Mixed acetate plates (MAIP Millipore) were coated overnight with anti-mouse IFN-γ (AN18, 5 µg/ml, Mabtech, Germany). $5 \times 10^5$ spleen cells/well were added and incubated in 10% FCS RPMI 1640 media in the presence of MUC-FP (20 µg/ml) for 18 hour. ConA (1 µg/ml) or cells alone were used as positive and negative controls, respectively. Cells were discarded and after washing (0.05% Tween 20/PBS), anti-mouse IFN-γ antibody-biotin (R4-6A2, Mabtech, Calif., USA) was added for 2 hours followed by extravidin-alkaline phosphatase (AP) at 0.1 µg/ml (Sigma, UK) for 2 hours at room temperature. Spots of activity were detected using a colorimetric AP kit (Biorad, Hercules, Calif., USA). Cytokine spots were counted with an AID ELISpot Reader system (Autoimmun Diagnostika GmbH, Germany). Data is presented as mean spot forming units (SFU) per $0.5 \times 10^6$ cells +/− standard deviation of the mean (SD).

Human in vitro immunogenicity studies of protein antigens linked to >1000 kDa oxidized mannan
Protein/peptide antigens MART-1 protein was purchased from Biovision, USA. GST-MUC1-VNTR (FP) was prepared as described in Apostolopoulos et al. (1993). His tagged MUC1-VNTR (pTrc) was prepared in house in the pTrcB vector (Invitrogen) (Loveland et al., 2006). The HLA-A2 epitope peptides specific for Melan-A/MART-1 [EAAGIGILTV (native) (SEQ ID NO: 1), ELAGIGILTV (analog) (SEQ ID NO:2)] were synthesized by Genscript, USA.

Conjugation of GST-MUC1-VNTR (FP), MUC1-VNTR (pTrc) and MART-1 to >1000 kDa oxidized mannan.

The conjugation of antigens to periodate >1000 kDa oxidized mannan was carried out as described above. The ratio of >1000 kDa mannan to antigen was 40:1.

Generation of peptide-specific CD8 T cells.

PBMCs were separated from buffy coats via density gradient centrifugation using Ficoll-Paque PLUS (GE Healthcare). HLA-A2 status was assessed by flow cytometry. PBMC were resuspended at $5 \times 10^6$/ml in complete AB medium (RPMI1640, 10% AB serum, Pen/Strep, HEPES, L-GLUT, NEAA. Sodium Pyruvate (Invitrogen), 2-mercaptoethanol) and stimulated with 10 µg/ml of MART-I analog peptide (ELAGIGILTV) (SEQ ID NO:2) and 3 µg/ml R848 (InvivoGen) in a 24 well plate. Three days later, another 1 ml complete AB medium supplemented with 50 U/ml IL-2 (R & D Systems), 20 ng/ml IL-15 and 20 ng/ml IL-7 (Peprotech) was added. Seven-ten days after initial priming, cells were re-stimulated with irradiated autologous PBMCs (1:100) pulsed with 2 µg/ml FMP or 10 µg/ml MART1 analog peptide (ELA). On the following day, 1 ml supernatant was exchanged for fresh complete AB medium containing 25 U/ml IL-2. This was repeated every 3-4 days.

MART-1-specific T cells clones were generated by FACS sorting. IFNγ secreting cells specific for ELAGIGILTV peptide (SEQ ID NO:2) were sorted using the FACS Aria following a 4 hour incubation with irradiated (6000 cGy) T2 cells pulsed with peptide. IFNγ secreting cells were identified using the IFNγ secretion and detection assay (Miltenyi Biotech) performed according to manufacturer's protocol.

Priming Protein Antigen-Specific T Cell Responses.

Monocytes were purified from PBMC by AutoMACS separation using CD14 microbeads (Miltenyi Biotech). Monocyte-derived dendritic cells (MoDC) were generated by culturing monocytes ($5 \times 10^5$/ml) in complete FCS medium (RPMI1640+10% FCS+L-GLUT, Pen/Strep, HEPES, non-essential amino acids, sodium pyruvate, 2-mercaptoethanol) containing 50 ng/ml GM-CSF and 20 ng/ml IL-4 (R & D Systems) for 5-6 days in a T75 flask.

MoDC at $2 \times 10^5$/ml (for 1:20 MoDC:T cell) in complete AB medium were added to a 24 well plate (1 ml per test condition) followed by protein or >1000 kDa oxidized mannan conjugate (10-20 µg/ml). Four hours later, $4 \times 10^6$ CD14 depleted PBMC were added to the wells in 1 ml complete AB medium. After 3 days, 25 U/ml IL-2, 10 ng/ml IL-7 and 10 ng/ml IL-15 was added. The T cells were re-stimulated 7-10 days later with $1 \times 10^5$ MoDC loaded with antigen. Twenty four hours following re-stimulation, cultures were supplemented with 25 U/ml IL-2 and again 3-4 days after. T cell cultures were typically analysed after 1 or 2 re-stimulations.

Analysis of antigen-specific T cell responses

For T cell epitope peptides—Peptide loaded T2 cells ($2\times10^5$/well) were prepared by pulsing with an irrelevant peptide (e.g., CAP-1 10 µg/ml or no peptide) and one with the peptide of interest (5 µl/ml) for 1 hour in serum free medium with 1.25 µg/ml β2-microglobulin. T2 cells were added at about a 1:5 ratio ($4\times10^4$/well) in 100 µl to the duplicate T cell wells and incubate for 1 hour at 37° C. 5% $CO_2$. 50 µl media containing Golgi-Stop (0.1 µl per 200 µl T cell/MoDC co-culture) was added and cells incubated for a further 3-4 hours at 37° C. 5% $CO_2$.

For protein antigen and conjugates—Antigen or >1000 kDa mannan conjugates (20 µg/ml) were added to v-bottom 96 well cluster plate containing $2\times10^4$ MoDC/well (autologous or A2 matched) in 75-100 µl complete medium and incubated for 2 hours. $2\times10^5$ stimulated T cells in 75-100 µl complete medium were added to each well and cells incubated for 15-16 hours at 37° C. 5% $CO_2$. 50 µl media containing Golgi-Stop (0.1 µl per 200 µl T cell/MoDC co-culture) was added and cells incubated for a further 4-5 hours at 37° C. 5% $CO_2$.

Analysis of intracellular interferon-gamma (IFNγ) responses

Cells were stained for surface markers CD8 and CD4, fixed and permeabilised, then stained for accumulation of intracellular IFNγ using CD4 APC-Cy7, CD8 FITC and IFNγ PE-Cy7 (BD) with the Cytofix/CytoPerm Kit (BD). Antigen-specific T cells were identified by flow cytometry comparing IFNγ+CD4 and CD8 T cells in the presence of the peptide/protein of interest with the irrelevant peptide/protein controls.

Isolation of Peripheral Blood Mononuclear Cells (PBMC) from Fresh Blood

Fresh blood was collected from healthy volunteers and stored in Heparin Sodium tubes. 15 mL of blood was subsequently transferred to a 50 ml centrifugal tube and gently mixed with equal volume of DPBS. 10 ml Ficoll was slowly underlayed using pipette. The tube was centrifuged for 30 minutes at 800 g at RT without break. The buffy coat (containing PBMC) was aspirated at the interface between serum and Ficoll. The PBMC were washed with sufficient DPBS and centrifuged at 900 g to remove the Ficoll. RPMI-1640 Medium was added to the collected PBMC and the number of PBMC determined by counting. 1 ml of blood typically yields at least 1 million of PBMC.

Cytokine Release Assay to Measure IL-6

PBMC were counted and cell densities adjusted. 100 µl of cells were added into the required number of wells such that the cell density for the IL-6 assay was 5,000/well. LD1-oxidized mannan conjugates for screening were serially diluted in DMSO. The LD1 solution was added to each well (final concentration of DMSO in assay was not more than 0.03%). The plates were incubated in a $CO_2$ incubator at 37° C. and supernatants collected at 6 and 24 hours. At each time point of collection, the plates were centrifuged at 900 rpm for 4 minutes and the supernatents transferred to another 96 well plate. These were labelled and stored at −80° C. ELISA kits for IL-6 (Invitrogen) were used for quantitation of cytokine released. The ELISAs were performed as described in the manufacturer's instructions. The absorbances were measured by FlexStation 3. A standard curve for each cytokine was drawn each time for analyzing the data.

Example 2: Fractionation of Mannan

Initially, mannan was sequentially passed through membranes as described in the Materials and Methods to isolate >300 kDa, 100-300 kDa, 50-100 kDa, 30-50 kDa, 4-30 kDa mannan fractions. Subsequently, mannan fractions >1,000 kDa, 100-300 kDa, 50-100 kDa and 30-50 kDa were isolated. The 4-30 kDa fraction was like a gum like residue so not included in the subsequent studies.

Separation was done by sequentially fractionating a known volume of mannan at a known concentration through 300 kDa, 100 kDa, 50 kDa, 30 kDa membranes (FIG. 1). The flow through and washings from each were passed through the next membrane. All separations were done in water and at the end, all samples were lyophilized and weights of the white powders recorded (Table 2).

TABLE 2

A representative sample of fractionation runs showing recovery various fractions and aldehyde residues on oxidized mannan

| | mannan | >300 | 100-300 | 50-100 | 30-50 | <30 |
|---|---|---|---|---|---|---|
| Run 5 240 mg | | | | | | |
| % recovery | | 11.2 | 7.2 | 17.2 | 16.08 | 7.2 | 58.88 |
| Aldehyde residues | 113 | 135 | 113 | 30.7 | 15.9 | |
| | 112 | 135 | 63 | 31 | 16 | |
| Run 6 480 mg | | | | | | |
| % recovery | | 8.75 | 8.89 | 5.3 | 7.8 | ND | 30.74 |
| Aldehyde residues | 74 | 84 | 38 | 21 | 11 | |
| Run 7 960 mg | | | | | | |
| % recovery | | 6 | 8.5 | 10.3 | 7.2 | ND | 32 |
| Aldehyde residues | 73 | 82 | 35 | 19 | 9 | |

The various fractions were analysed for aldehyde residues generated after reaction with 0.01 M $NaIO_4$ as described in the methods. As shown in Table 2, the whole mannan, >300 kDa, 100-300 kDa, 50-100 kDa and 30-50 kDa fractions yield 73, 82, 35, 19 and 9 aldehyde residues respectively (e.g., run 7).

Example 3: Binding of Various Mannan Fractions to Mannose Receptor

Huh-7 cells are human hepatocellular carcinoma cells that express mannose receptors. Mannose-BSA is known to bind the mannose receptor and was included as a positive control in these studies. Whole mannan and the various fractions were labelled with FITC and the binding to huh-7 cells observed by flow cytometry (FIG. 5).

Whole mannan and all fractions bound huh-7 cells in a dose dependent manner. Therefore, regardless of the size all mannan fractions bind the mannose receptor or other mannose binding lectins.

Example 4: Activation of BMDC by Mannan and Various Fractions of Mannan

To ascertain if the various fractions of mannan activate BMDC and if any fraction is superior to whole mannan, fractions were incubated with DCs at different doses and for different times, and maturation markers CD40, CD80 and CD86 was monitored by flow cytometry (FIG. 6). As shown in FIG. 6 all fractions activated DCs in a dose and time dependent manner. The >300 kDa fraction was superior to whole mannan.

Example 5: Isolation of >1000 kDa Mannan Fraction

Since the >300 kDa fraction of mannan activated BMDCs more effectively than whole mannan, a higher molecular weight fraction was isolated for analysis. In order to isolate an even higher molecular weight fraction, the whole mannan was passed through a Centriprep concentrator with 1,000 kDa cut-off membrane. The yield of the various fractions are shown in Table 3. Interestingly, the 300-1,000 kDa fraction was vastly reduced indicating that >1,000 kDa mannans dominate the previously isolated >300 kDa mannan fraction.

Example 6: Comparison of the Activity of the >1000 kDa Mannan Fraction with Whole Mannan and the >300 kDa Mannan Fraction The ability of the various doses of the >1000 kDa fraction to stimulate BMDC was measured by observing the upregulation of CD40 and CD86 after a 48 hour period by flow cytometry (FIGS. 7A and 7B, respectively). The >1000 kDa fraction was compared to the >300 kDa fraction and whole mannan and it was apparent that the >1000 kDa fraction was superior to whole mannan and similar to the >300 kDa fraction.

cal properties of the fractions, as well as obtain relative molecular weights of the fractions so that a set of specifications can be set. The present inventors have already shown that the various mannans generate different numbers of aldehyde groups when oxidized with $NaIO_4$ (Tables 2 and 3).

The resorcinol assay that measures the mannose content of mannan can also be used as a means of identification of the different fractions of mannan (FIG. 8).

Mannans are carbohydrates without charges and highly hydrophilic and as a result do not migrate on SDS-PAGE gels used for protein analysis. Frequently, carbohydrates are chemically modified to incorporate charges and hydrophobic properties for analysis. To incorporate these properties, the oxidized mannans were reacted with ANTS. Analysis of the mannan fractions labelled with ANTS on native PAGE gel (FIG. 9) did not resolve the mannans based on their relative molecular weights.

However, when the ANTS labelled fractions were analysed by SDS-PAGE, they migrated in a pattern similar to the fractionated molecular weight (membrane cut-off) (FIG. 10). The SDS-PAGE gels were scanned and used for densitometric analysis (FIG. 11). Regular protein standards were also used. This enables molecular weight ranges to be assigned to bands which unlike defined proteins are spread (broad bands). Mannans from several fractionation runs were analyzed to validate the analysis. Standard curves were generated from known molecular weight (protein or mannan fractions) and the relative front (Rf). The Rf is defined as the total distance migrated divided by the distance migrated by the specific band (FIG. 12). Based on the standard curves, the relative molecular weights of the various mannan fractions were calculated (FIGS. 13 and 14).

Example 8: Conjugation of MUC1-FP to Mannan

The various fractions of mannan were conjugated to MUC1-FP as described in the methods. Since the molecular

TABLE 3

Representative example of a fractionation run isolating a >1000 kDa mannan fraction

| Fractionation | Bottle/Batch | | mannan | >1000 | 300-1000 | 100-300 | 50-100 | 30-50 | <30 | Recovery |
|---|---|---|---|---|---|---|---|---|---|---|
| 8 | Batch 2 | 985.5 mg | | | | | | | | |
| | 102K37781 | % recovery | | 3.6 | 0 | 4.9 | 10.4 | 7.3 | | 26.1 |
| | | Aldehyde residues | 106 | 205 | | 44 | 16 | 8.8 | | |
| 9 | Batch 2 | 1019 mg | | | | | | | | |
| | 102K37781 | % recovery | | 6.7 | 0 | 20 | 14.7 | 7.5 | | 48.9 |
| | | Aldehyde residues | 108 | 228.9 | N/A | 42 | 19.7 | 10.6 | | |
| 10 | Batch 7 | 1007 mg | | | | | | | | |
| | 048K3810 | % recovery | | 31 | 0.26 | 20 | 0.49 | 2.3 | | 53.7 |
| | | Aldehyde residues | 115 | 219 | 111 | 39.8 | 21 | 8.1 | | |
| 11 | Batch 7 | 1063 mg (end-) | | | | | | | | |
| | 048K3810 | % recovery | | 37 | 0 | 12 | 0.87 | 0.36 | | 53 |
| | | Aldehyde residues | 95 | 218 | N/A | 39.8 | 15 | 7.2 | | |

Example 7: Analysis of Molecular Weight of Mannan Fractions

As seen above, the various fractions of mannan can activate BMDC, bind to the mannose receptor and the >1000 kDa mannan fraction is the most biologically active fraction. However, it is important to be able to analyze the biochemiweights and the number of aldehyde groups generated are different in the whole mannan compared with the fractions, the amount of FP used was standardized as the molar ratio of MUC1-FP to the aldehydes. In addition, a range of amounts of MUC1-FP was conjugated and analysed by SDS-PAGE (FIG. 15).

Example 9: In Vivo Activity of >1000MFP and MFP in Mice

Whole mannan and >1000 kDa mannan were prepared as described above and used for in vivo immunogenicity studies.

To ascertain the immunogenicity of MUC1 linked to whole mannan, >1000 kDa mannan, conjugates or MUC1-FP were injected intradermally into mice at a dose of 10 μg on day 0, 10, 17 and 14 days. Mice were euthanized to analyze cellular responses by ELISpot analysis (FIG. 16). Antigen specific IFN-γ responses to various doses of MUC1-FP were measured in splenocyte cultures from immunized mice. As shown in FIG. 16, the cellular responses were not significantly different between the MUC1-FP, MFP and >1000MFP immunized mice. The serum from immunized mice was tested for anti-MUC1-specific total IgG, IgG1 and IgG2a antibodies (FIG. 17). Interestingly, the mice immunized with the >1000MFP had a ~10 fold higher titre of anti-MUC1-specific IgG2a in comparison to the other groups. A similar IgG2a bias was demonstrated in serum from mice after 2 immunizations (data not shown).

Example 10: Characterisation of Mannan and Possible Quality Control Assays

Mannan is currently sourced from Sigma. It is not of good manufacturing practice (GMP) standard and the only information given is shown in FIG. 18. It will be important to the yeast mannan if it is bought from a manufacturer to ensure it meets a particular standard. The PDPH assay could be used to measure aldehydes, the resorcinol assay to measure mannose content and ANTS assay to characterize the various batches of mannan.

Five batches of mannan from Sigma were analyzed using the resorcinol assay. As showed in FIG. 19A, all batches displayed the same absorbance versus concentration curve, indicating the same mannose content in mannans. FIG. 19B shows the standard curve using mannose in the resorcinol assay. Similarly all 5 batches were analyzed for aldehyde residues after oxidation with NaIO$_4$ (FIG. 20).

From three independent measurements, it can be seen that the number of aldehyde residues vary between 90-155 residues. Therefore, the specification for mannan could be set as pass, if the aldehyde residues generated is 125±20%. In a similar manner, the oxidized mannan can be reacted with ANTS instead of PDPH for measurement of fluorescence (FIG. 21). Interestingly, the variation in all the batches in this assay is also ~±20%.

Example 11: Synthesis of Carbohydrate Polymer-Immune Modulator Conjugates

Conjugates of the invention can be prepared using the general methods illustrated in FIGS. 22 to 44.

In one embodiment, the immune modulator is Resquimod. In an alternate embodiment, the immune modulator is Loxribine.

The immune modulator can be conjugated to oxidized mannan via a linker having a first functional group capable of reacting with a functional group on oxidized mannan and a second functional group capable of reacting with a functional group on the immune modulator The immune modulator can be conjugated to oxidized mannan using Linker 1 or Linker 2. Linkers 1 and 2 can be prepared using the method illustrated in FIG. 22 or FIG. 33.

Resquimod can be conjugated to a linker through its free amino group or free hydroxyl group. Linker 1 and Linker 2 can be used for reaction with the free amino group of Resquimod and the hydroxyl activated derivative of Resquimod, respectively (see FIGS. 24 and 25). Such a derivative may incorporate a protected hydrazide group on Resquimod that can be deprotected and reacted with the aldehyde groups of oxidized mannan.

For example, a Resquimod-oxidized mannan conjugate can be prepared by:
i) oxidizing mannan with 0.01M NaIO$_4$ in 0.1 M phosphate pH 6.0 buffer as detailed previously;
ii) passage through a gel filtration column (e.g., PD10 column) equilibrated with acetate buffer pH 4.5-6.5 to remove unwanted bi-products;
iii) dropwise addition of the hydrazide functionalised Resquimod in a suitable solvent to the oxidized mannan;
iv) passage (2-16 hours following step iii)) through a gel filtration column equilibrated with phosphate buffered saline to remove unreacted Resquimod.

The number of Resquimod molecules reacted with the oxidized mannan can be quantitated by spectrophotometry. The Resquimod-oxidized mannan conjugate may then be used in biological assays, or methods of treatment.

Loxribine can be conjugated to a linker through its amino group or its primary or secondary hydroxyl group. The hydroxyl groups can be suitably activated. However, it is not necessary to suitably protect the other hydroxyl groups from reaction. Linker 1 and Linker 2 can be used for reaction with the free amino group of Loxribine and the hydroxyl activated derivative of Loxribine, respectively (see FIGS. 26 to 28). Once the hydrazide derivatives are obtained, they can be used for conjugating to oxidized mannan as described above for Resquimod.

Synthesis of R-848

R-848 can be prepared using the method illustrated in FIG. 31 and as described below.

1. Preparation of Compound 2-a

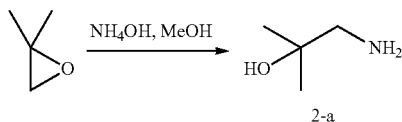

To a round-bottomed flask charged with a magnet-bar NH$_4$OH (60 mL), isobutylene oxide (10.0 g, 138.6 mmol) and MeOH (125 g) were added. The mixture was stirred at r.t. for 12 hrs, and then it was slowly heated to 60° C. and stirred for 2-3 hrs. The solvent was removed under reduced pressure, and the residue was distilled under atmospheric pressure to get the desired product (3.0 g, 33%).

2. Preparation of Compound 2-2

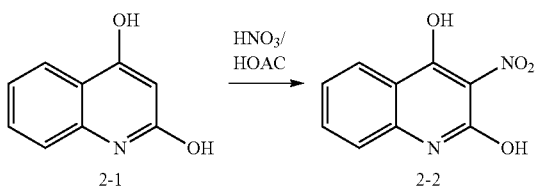 [SMILES: Oc1cc(O)c2ccccc2n1 ; O=[N+]([O-])c1c(O)nc2ccccc2c1O]

A mixture of compound 2-1 (80 g, 0.5 mol) in HNO₃ (130 mL) and HOAc (500 mL) was stirred for 1 hr at 105° C. Then it was cooled down to r.t., and the reaction was quenched by the addition of water. Solid was precipitated, and filtered to get yellow product 2-2 (60 g, 58%).

3. Preparation of Compound 2-3

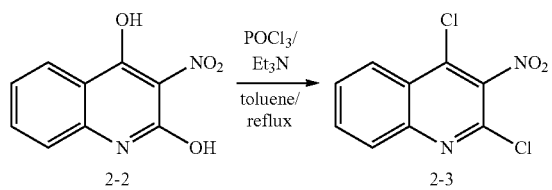 [SMILES: O=[N+]([O-])c1c(O)nc2ccccc2c1O ; O=[N+]([O-])c1c(Cl)nc2ccccc2c1Cl]

To a solution of 2-2 (10 g, 48.5 mmol) in POCl₃ (80 mL) was added Et₃N (4.85 g, 48.5 mmol). The solution was heated to 120° C. and stirred for 3 hrs, and then the solvent was removed in vacuum. The residue was poured into ice-water, and extracted with DCM. The organic phase was washed with NaHCO₃ and brine, and dried over anhydrous Na₂SO₄ and filtered. The filtration was concentrated and the desired product was obtained (30 g, 68%).

4. Preparation of Compound 2-4

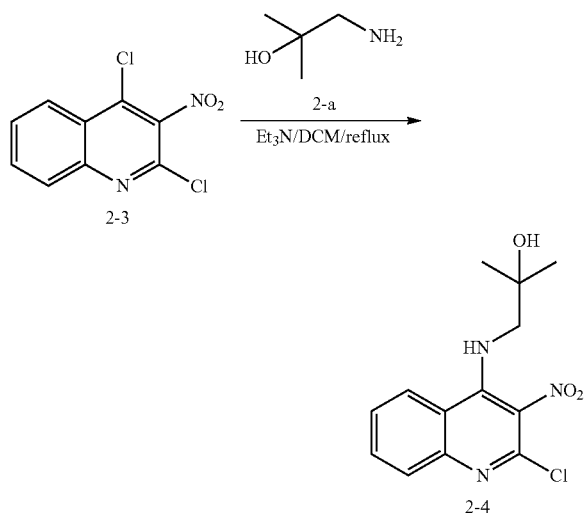

To a solution of 2-3 (10 g, 41 mmol) and TEA (5 g, 49 mmol) in DCM was added 2-a (3 g, 34 mmol) dropwise. The mixture was stirred for 12 hrs at 40° C. The solution was cooled down to r.t., and washed with brine, dried over anhydrous Na₂SO₄ and filtered. The filtration was concentrated and crude product was obtained. Further purification by silica gel column chromatography (PE: EA=1:1) afforded 6.0 g desired product, yield 50%.

5. Preparation of Compound 2-5

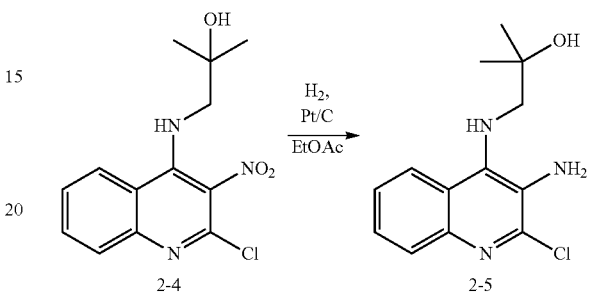

A mixture of compound 2-4 (6 g, 20 mmol), Pt/C (800 mg) in EA was hydrogenated at r.t. for 4 hrs. Then the mixture was filtered and the filtration was concentrated to give the desired product 2-5 (5.7 g).

6. Preparation of Compound 2-6

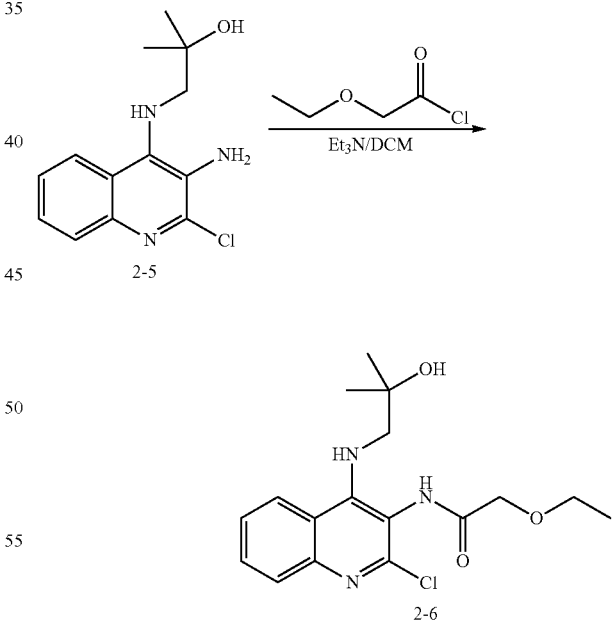

To a solution of 2-5 (5.7 g, 21.5 mmol) and TEA (4 g, 40 mmol) in DCM(100 mL) was added compound 2-ethoxyacetyl chloride (3 g). The mixture was stirred for 3 hrs, and then it was washed with sat. brine. The organic layer was concentrated and the residue was purified by silica gel column chromatography (EA: PE=1:2). The desired product was obtained (3.7 g, 50%).

7. Preparation of R-848

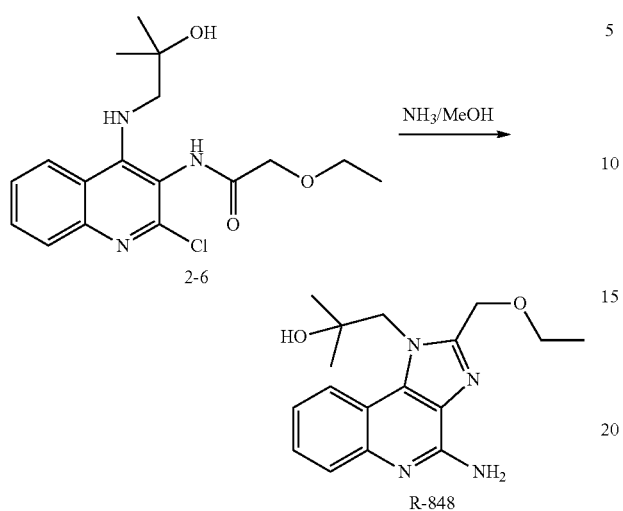

A mixture of compound 2-6 (1.87 g, 5.3 mmol) in NH₃/MeOH was sealed in an autoclave and stirred at 160° C. for 8 hrs. Then the solvent was removed and the residue was purified by silica gel column chromatography (EA/TEA 95: 5). The desired product R-848 (1.5 g) was obtained.

Synthesis of PEG-A

PEG-A can be prepared using the method illustrated in FIG. 32 and as described below.

1. Preparation of PEG-A-2

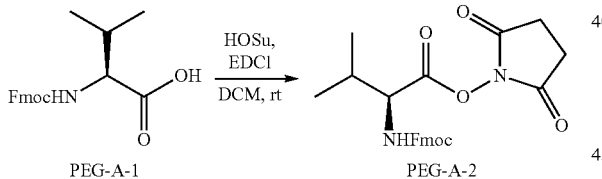

To a stirred solution of PEG-A-1 (30 g, 93 mmol) and EDCI (36.52 g, 138 mmol) at 0° C. in DCM, HOSu (12.72 g, 111.7 mmol) was added. The mixture was stirred in ice bath for 30 mins. Then the solution was allowed to warm up to r.t. and stirred for 15 hrs. The mixture was washed with H₂O, 1N aq. HCl and sat. NaHCO₃, then dried over Na₂SO₄, the solvent was evaporated to give 36.5 g crude PEG-A-2.

2. Preparation of PEG-A-3

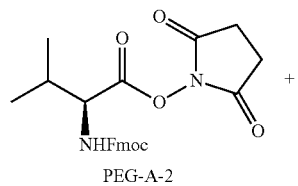

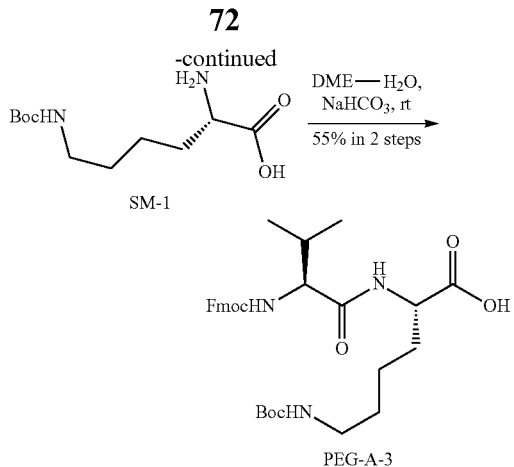

To a solution of SM-1 (24.71 g, 100.32 mmol) and NaHCO₃ (8.43 g, 100.32 mmol) in 50 mL H₂O was added PEG-A-2 (83.6 g, 36.5 mmol) which was dissolved in 50 mL DME. The mixture was stirred at r.t. for 15 hrs, evaporated in vacuo. The residue was dissolved in 100 mL EA, the pH was adjusted to 2-3 by addition of 1N aq. HCl and the reaction mixture was washed with H₂O, then dried over Na₂SO₄, evaporated under reduced pressure and purified by column chromatography eluting with PE/EA=1:1 to give a light yellow solid PEG-A-3 (15.2 g, 70%).

3. Preparation of PEG-A-4

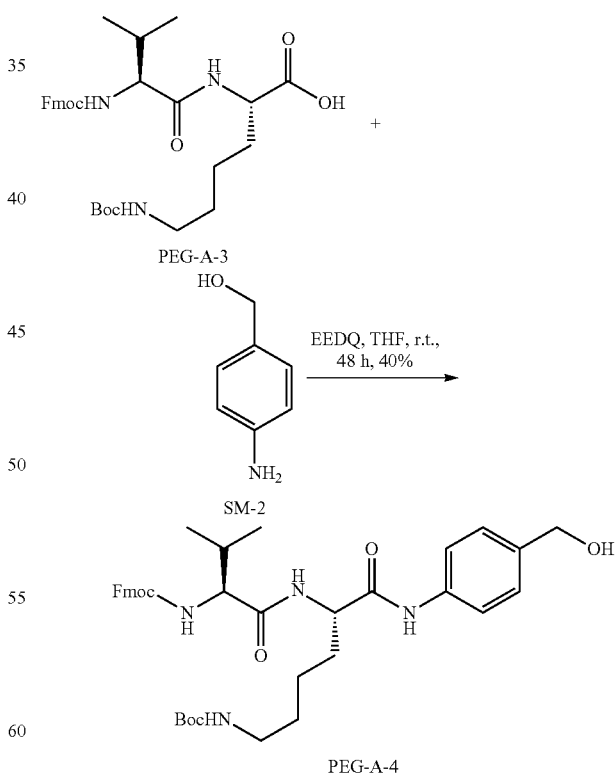

A 1 L round-bottomed flask was charged with PEG-A-3 (9.5 g, 16.7 mmol), SM-2 (4.04 g, 33.4 mmol), EEDQ (8.26 g, 33.4 mmol), DCM (300 mL) and MeOH (100 mL). The mixture was stirred at r.t. for overnight, washed with 1N aq.

HCl and dried over Na₂SO₄. The solvent was evaporated and purified by column chromatography to give a light yellow solid PEG-A-4 (4 g, 40%).

4. Preparation of PEG-A

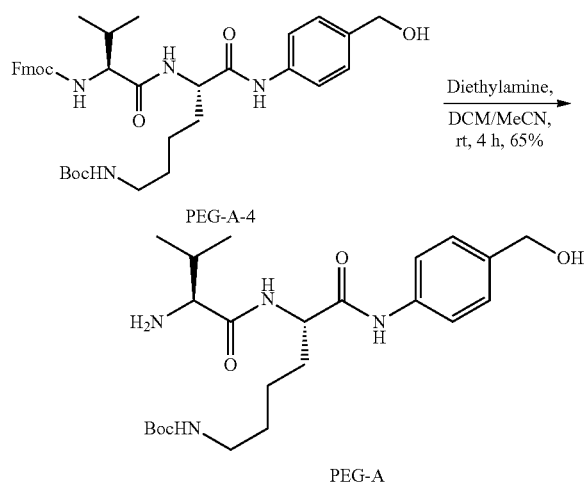

A 1 L round-bottomed flank was charged with PEG-A-4 (4.5 g, 6.68 mmol), diethylamine (7.33 g, 100.2 mmol), DCM (200 mL), MeCN (200 mL). The mixture was stirred at 0° C. for 2 hrs, then stirred at r.t. for 15 hrs. TLC showed the starting material was trace, the mixture was washed with 1N aq. HCl, H₂O and dried over Na₂SO₄. The solvent was evaporated and the residue was purified by column chromatography to give PEG-A (1.5 g, 65%).

5. Preparation of PEG-A-4a

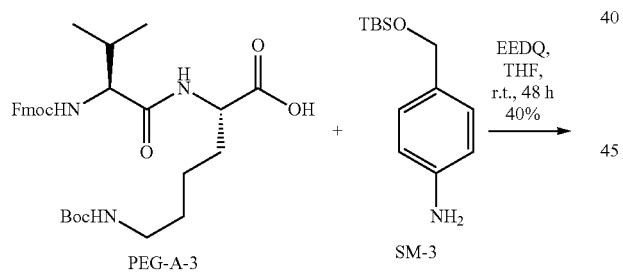

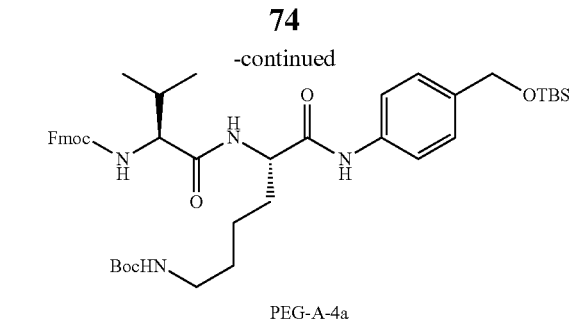

The procedure was the same as PEG-A-4.

6. Preparation of PEG-Aa

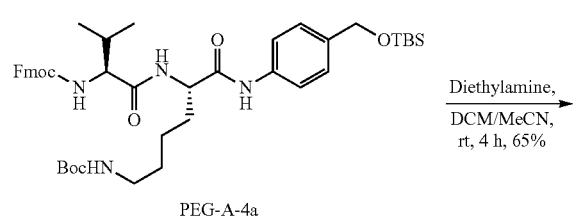

The procedure was the same as PEG-A.

Synthesis of L-1 and Linker-1

L-1 and Linker-1 can be prepared using the method illustrated in FIG. 33 and as described below.

1. Preparation of PEG-B-2

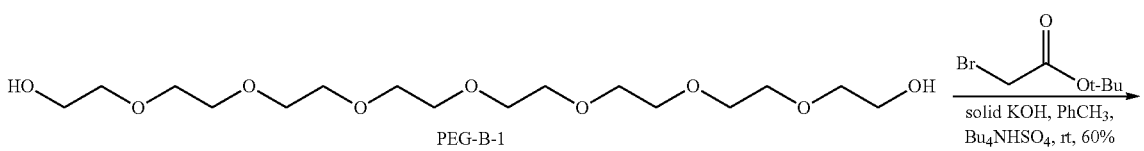

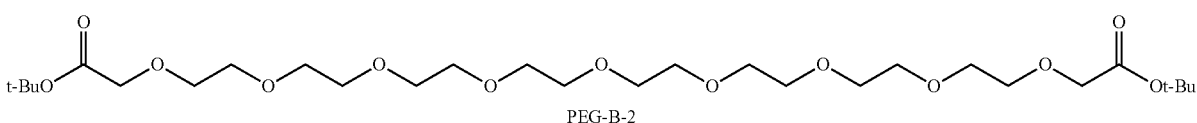

To a solution of PEG-B-1 (11 g, 30 mmol), solid KOH (6.72 g, 120 mmol) and n-Bu₄NHSO₄ (1.3 g, 3.6 mmol) in toluene (160 mL), t-Butyl bromoacetate (18 mL, 120 mmol) was added dropwise at 0° C. The reaction mixture was stirred at 0° C. for 1 hr, then rt for 4 hrs, filtered, washed with water, sat. NH₄Cl, sat. NaHCO₃, sat. brine and dried with Na₂SO₄, evaporated to provide PEG-B-2 (12 g, yield 70%).

2. Preparation of PEG-B-3

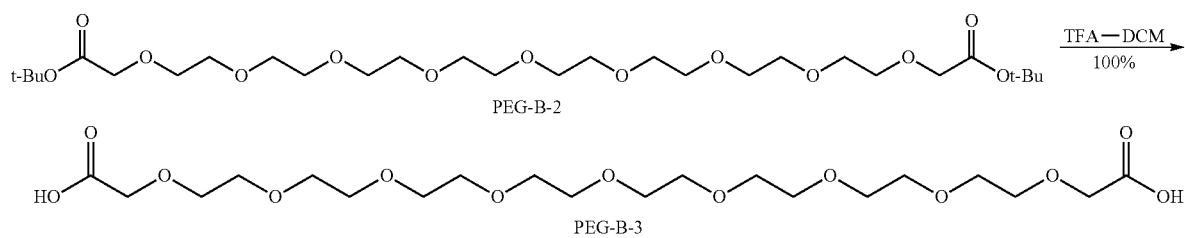

A mixture of PEG-B-2 (6 g, 10 mmol) in TFA/DCM (5 mL/5 mL) was stirred at r.t. for 2 hrs. TLC showed that the reaction was over. Evaporated to give PEG-B-3, quantitatively and used directly for the next step.

3. Preparation of L-2 & L-2a

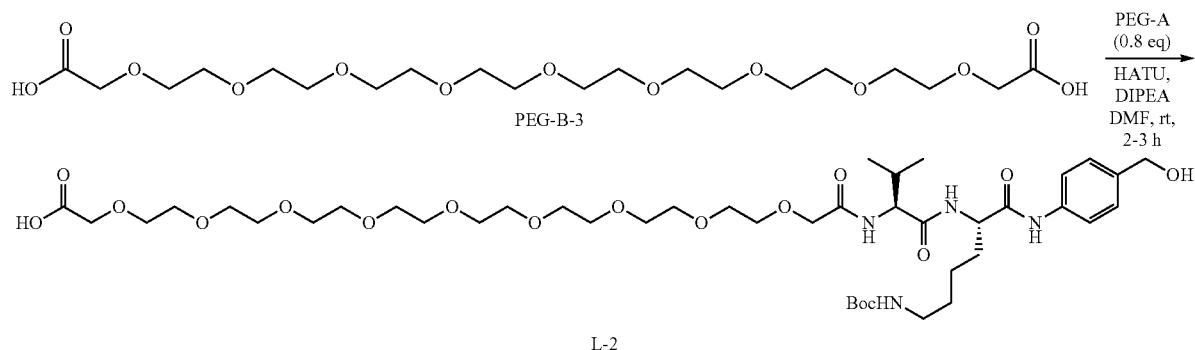

To a solution of PEG-B-3 (1.2 g, 2.4 mmol) and HATU (0.8 g, 2.1 mmol) in 10 mL THF, PEG-A (0.9 g, 2 mmol) and DIPEA (0.47 g, 3.6 mmol) was added. The mixture was stirred at r.t. for 2 hrs, evaporated in vacuo and the residue was dissolved in 100 mL EA. The solution was washed with sat. NH₄Cl, sat. NaHCO₃, sat. NaCl, then dried over Na₂SO₄, evaporated under reduced pressure to provide crude L-2 which was used directly for the next step.

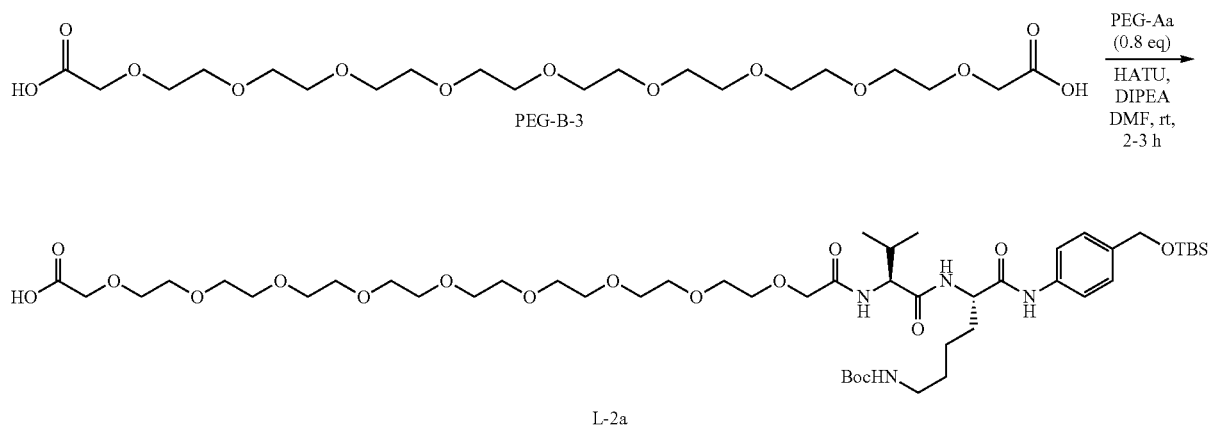

The preparation of L-2a is the same as L-2.

4. Preparation of L-1 & L-1a

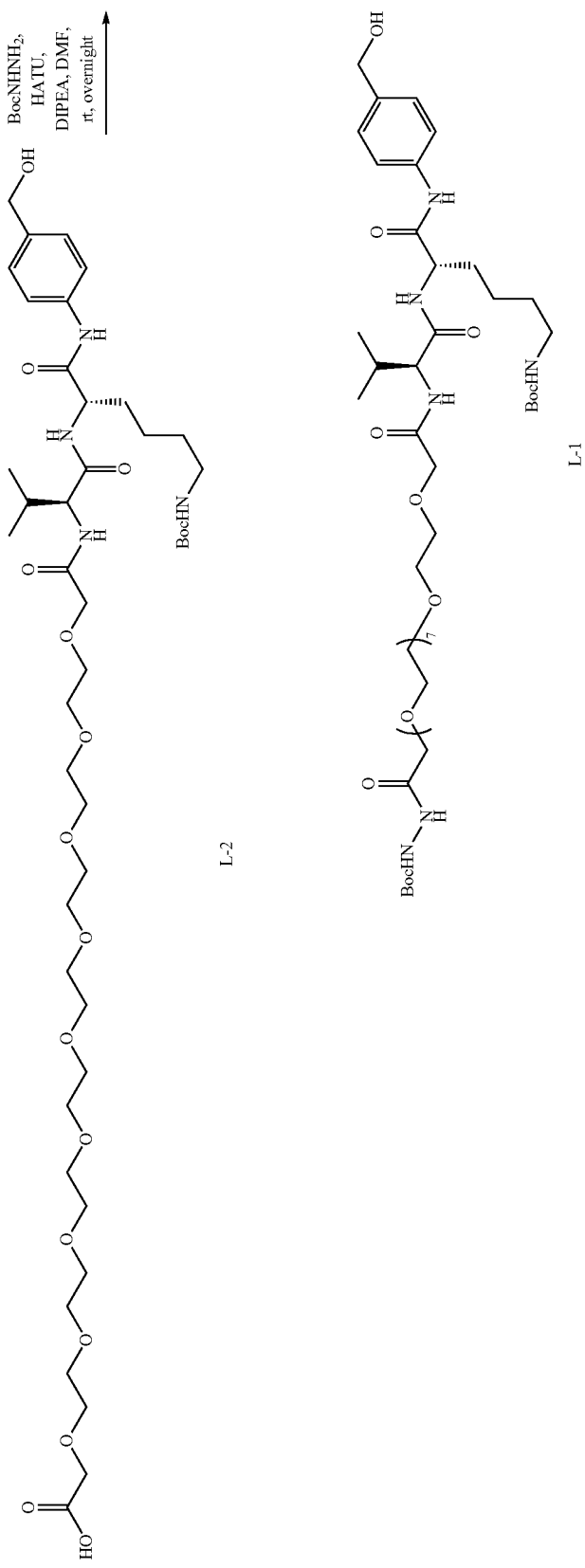

To a solution of L-2 (4.6 g, 5 mmol) and HATU (2.3 g, 6 mmol) in 20 mL DMF, BocNHNH$_2$ (1.32 g, 10 mmol) and DIPEA (0.77 g, 6 mmol) was added. The mixture was stirred at r.t. for 2 hrs. The mixture was evaporated in vacuo and the residue was dissolved in 100 mL EA. The mixture was washed with sat. NH$_4$Cl, sat. NaHCO$_3$, sat. NaCl, then dried over Na$_2$SO$_4$, evaporated under reduced pressure to provide the crude L-1, which was used directly for the next step.

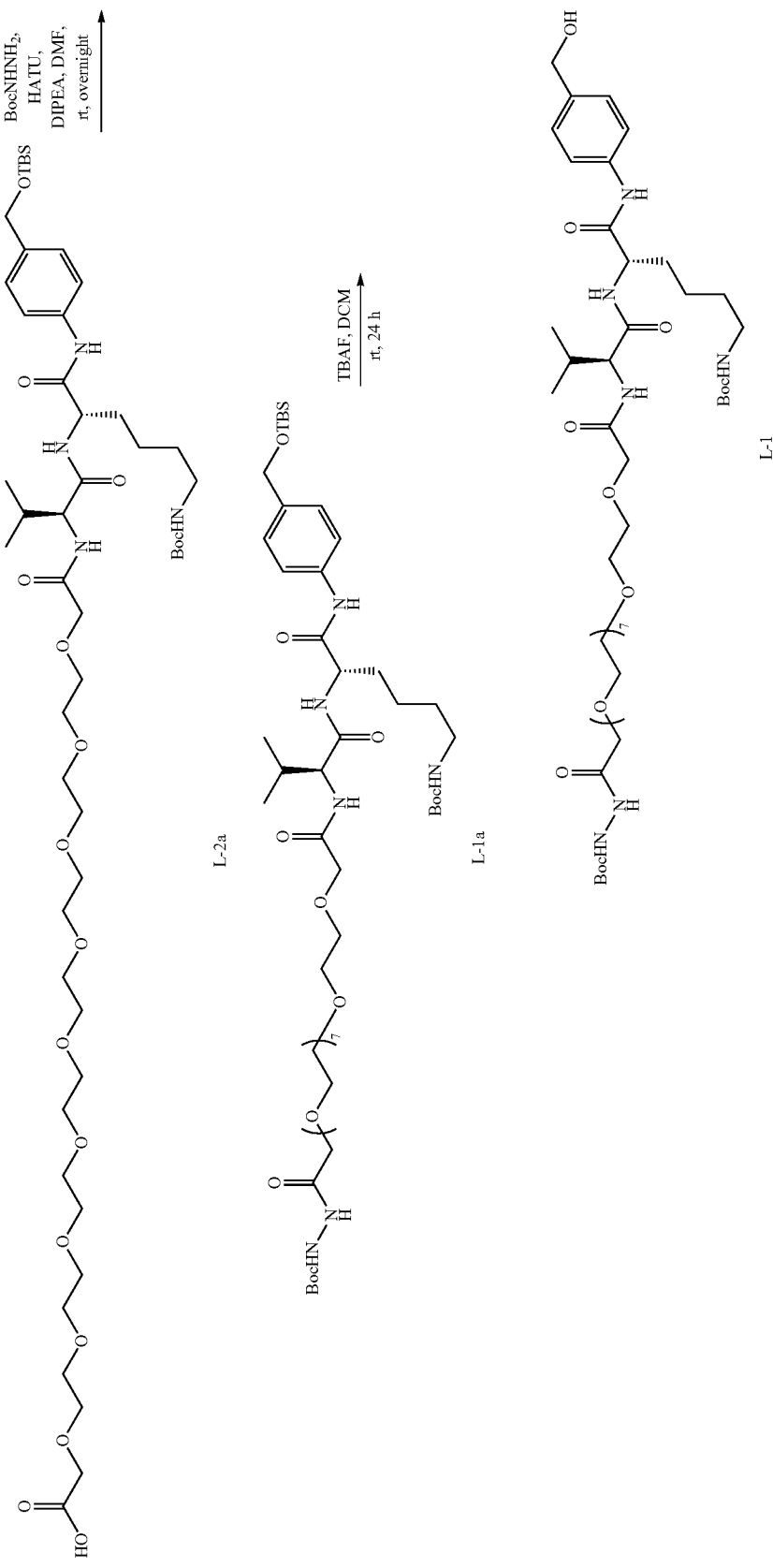

The preparation of L-1a is the same as L-1.
The procedure from L-1a to L-1:
To a solution of L-1a (4 g crude, 1 mmol) in 20 mL DCM, TBAF (2.2 g, 8 mmol) was added. The reaction mixture was stirred at rt for 24 h, then was washed with sat. NaCl, dried over Na$_2$SO$_4$, evaporated and purified by column chromatography to give L-1 (1.1 g).

The mixture was stirred for 30 min, filtrated and the solid (3-0) was used for the next step without purification.

The above solid (3-0) was dissolved in H$_2$O and MeOH (1:1, 300 mL). The mixture was reflux for 5 hrs, then evaporated to provide crude Loxoribine (10.7 g, yield 76% for two steps).

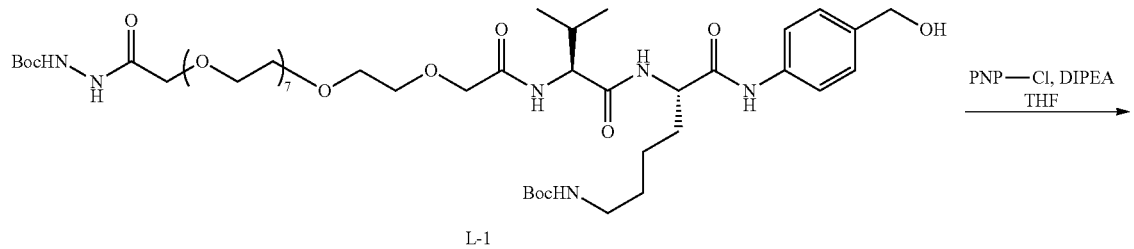

L-1

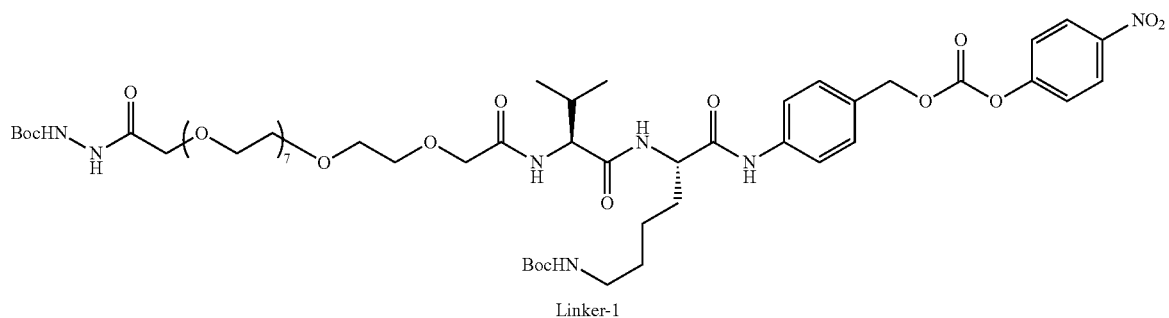

Linker-1

5. Preparation of Linker-1

To a solution of L-1 (310 mg, 0.3 mmol), pyridine (237 mg, 3 mmol) in 2 mL DCM at 0° C. was added a solution of PNP-Cl (485 mg, 2.4 mmol) in 2 mL DCM dropwise. The mixture was stirred at r.t. for 20 hrs. The solution was washed with brine, then dried over Na$_2$SO$_4$, evaporated and purified by column chromatography (DCM: MeOH=25: 1) to provide Linker-1 (100 mg).

Synthesis of Loxoribine

Loxoribine A can be prepared using the method illustrated in FIG. 34 and as described below.

1. Preparation of Loxoribine

To a solution of NaH (4.2 g, 176 mmol) in DMSO (300 mL) was added prop-2-en-1-ol (30 mL) and 8-bromoguanosine (15 g, 41.4 mmol) in one portion. The mixture was stirred at 65° C. for 3 h, cooled, then EA (1000 mL) was added, filtrated. The solid was collected, washed with EA, then dissolved in H$_2$O and AcOH (5:1, 90 mL) at ice-bath.

Synthesis of d4-3

Derivative 4-3 can be prepared using the method illustrated in FIG. 35 and as described below.

1. Preparation of d4-1

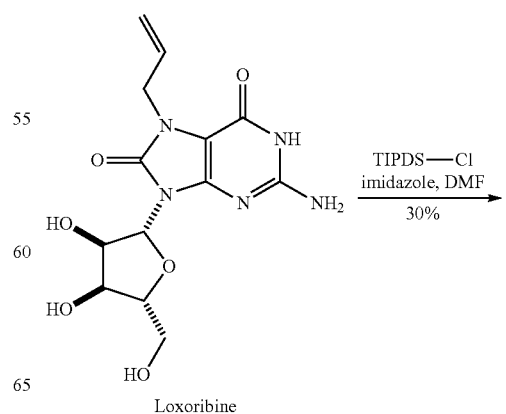

Loxoribine

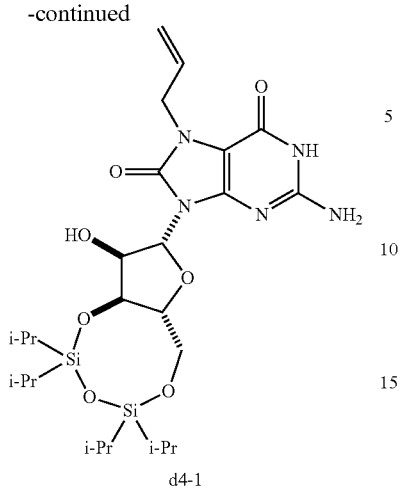

d4-1

To a solution of Loxoribine (2 g, 6 mmol) and imidazole (820 mg, 12 mmol) in DMF (10 mL, dried) was added TIPDS-Cl (2 mL) dropwise. Then the mixture was stirred at r.t. for 4 hrs. EA was added, the organic phase was washed with sat. NaHCO$_3$, sat. brine, then dried over Na$_2$SO$_4$, evaporated and purified by column chromatography (PE: EA=1:1) to provide d4-1 (900 mg).

2. Preparation of d4-2

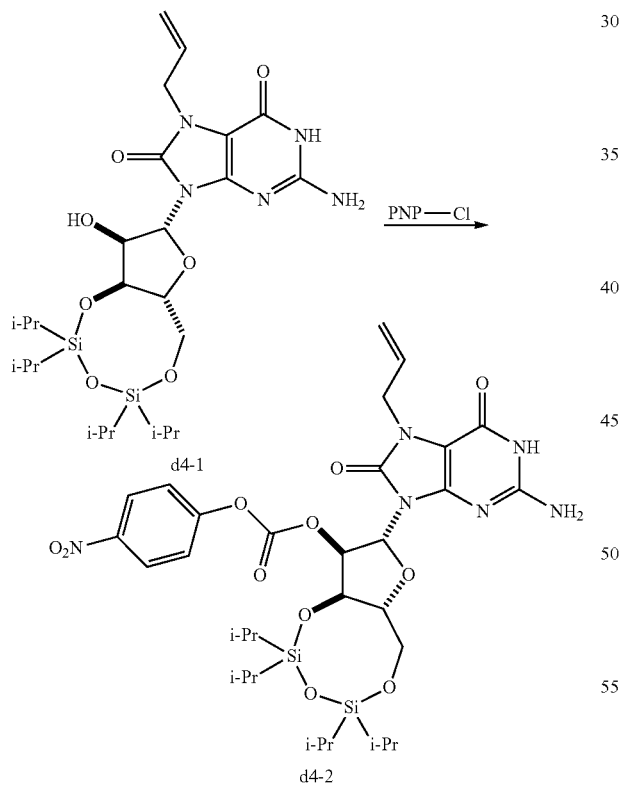

d4-2

To a solution of d4-1 (870 mg, 1.5 mmol) and pyridine (1.2 g, 15 mmol) in 15 mL DCM at 0° C. was added a solution of PNP-Cl (3 g, 15 mmol) in 5 mL DCM dropwise. The mixture was stirred at r.t. for 10 hrs, washed with sat. NaCl, then dried over Na$_2$SO$_4$, evaporated to provide the crude desired product which was used directly for the next step.

3. Preparation of d4-3

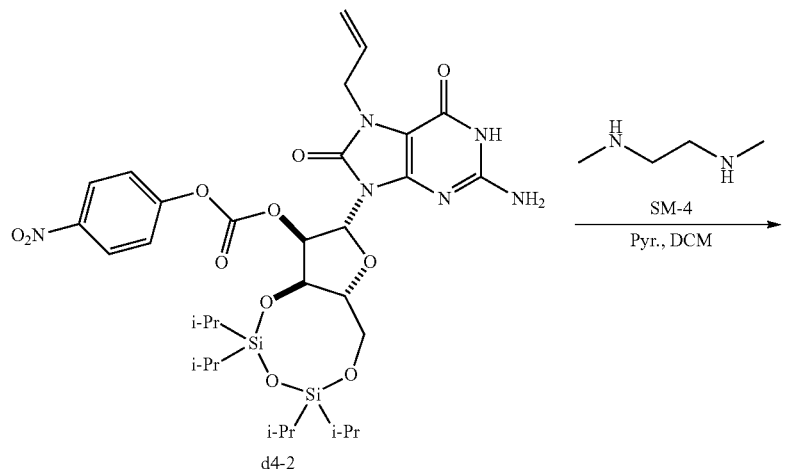

d4-2

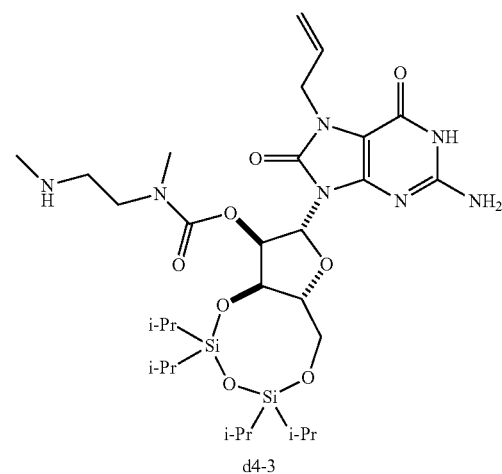

d4-3

To a solution of d4-2 (380 mg, 0.5 mmol) and pyridine (400 mg, 5 mmol) in 5 mL DCM was added SM-4 (530 mg, 6 mmol). The mixture was stirred at r.t. for 4 hrs, washed with $H_2O$, sat. brine, then dried over $Na_2SO_4$, evaporated and purified by column chromatography (DCM: MeOH=5:1) to provide d4-3 (100 mg).

Reaction of d4-3 with Linker 1 and deprotection will give derivative 4.

Synthesis of d5-2 and d5-3

Derivatives 5-2 5-3 and can be prepared using the method illustrated in FIG. 36 and as described below.

1. Preparation of d5-1

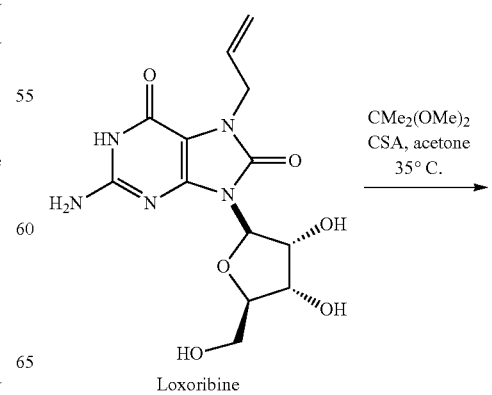

Loxoribine

3. Preparation of d5-3

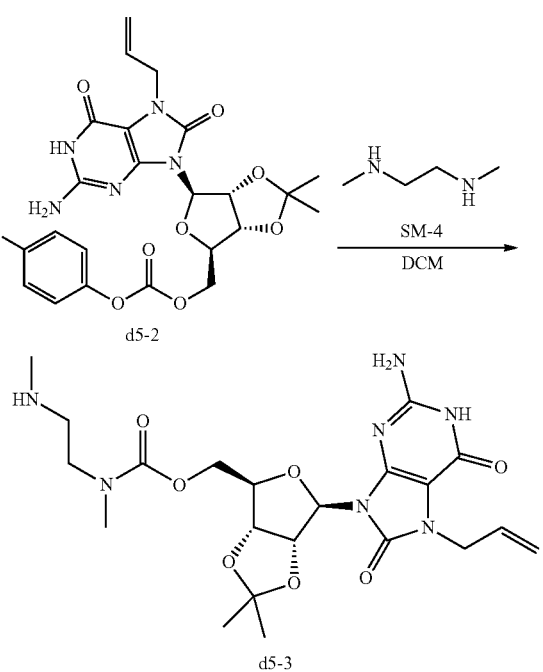

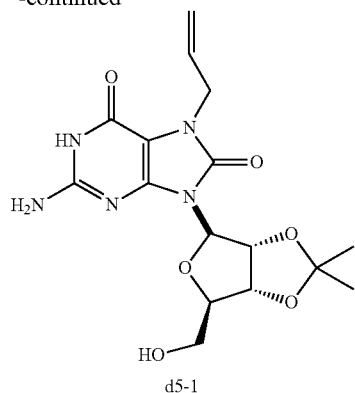

A mixture of loxoribine (2.5 g, 7.4 mmol), 2,2-dimethoxypropane (14.1 g, 134.7 mmol) and CSA (1.89 g, 8.2 mmol) in 50 mL acetone was stirred at 35° C. for 5 h, evaporated and purified by column chromatography (DCM: MeOH=10:1) to provide d5-1 (1.5 g, yield 55%).

2. Preparation of d5-2

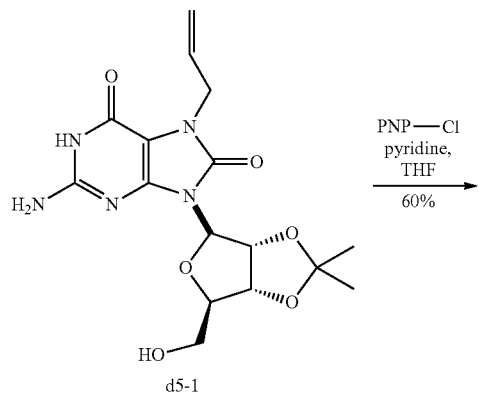

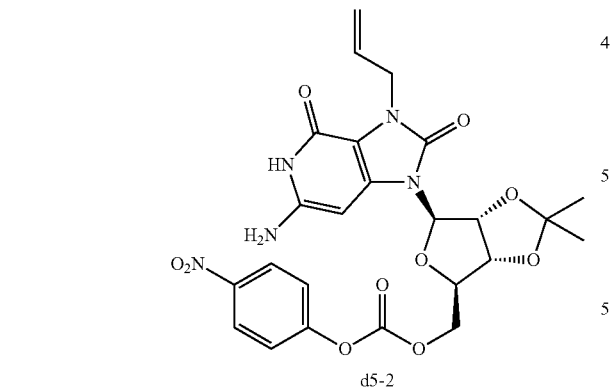

To a solution of d5-1 (860 mg, 2.27 mmol) and pyridine (1.8 g, 22.7 mmol) in 25 mL DCM at 0° C. was added a solution of PNP-Cl (2.83 g, 14 mmol) in 15 mL DCM dropwise. The mixture was stirred at r.t. for 10 hrs. The solution was washed with brine, then dried over $Na_2SO_4$, evaporated and purified by column chromatography (DCM: MeOH=300:1~100:1) to provide d5-2 (620 mg, yield 50%).

To a solution of d5-2 (640 mg, 1.18 mmol) in 15 mL DCM was added SM-4 (210 mg, 2.36 mmol). The mixture was stirred at r.t. for 1 hr. The solution was washed with $H_2O$, brine, then dried over $Na_2SO_4$, evaporated and purified by column chromatography (DCM: MeOH=5: 1) to provide d5-3 (300 mg).

Reaction of d5-3 with Linker 1 and deprotection will give derivative 5.

Example 12: Synthesis of Carbohydrate Polymer-Immune Modulator Conjugates

Further Resquimod derivatives (referred to as Rd1-Rd3) and Loxoribine derivatives (referred to as Ld1-Ld10) are illustrated in FIGS. 37 and 38, respectively.

Synthesis of Ld1

Ld1 can be prepared using the method illustrated in FIG. 39 and as described below.

1. Synthesis of 6-hydrazinylnicotinic Acid

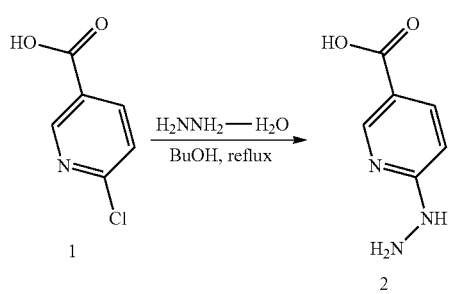

To a solution of 6-chloronicotinic acid (5 g, 32 mmol)) in EtOH (50 mL) was added hydrazine hydrate (3.7 mL, 80 mmol). The mixture was heated to reflux with stirring for 48 hrs. The mixture was allowed to cooled to r.t. to give a gray precipitate which was collected by filtration and then washed with EtOH and petroleum ether/EtOAc (2:1) to give 2 g solid (40%)

LC-MS: CP-0007023-001: (ES, m/z): 154 [M+H]$^+$

2. Synthesis of 6-(2-(tert-butoxycarbonyl)hydrazinyl)nicotinic Acid

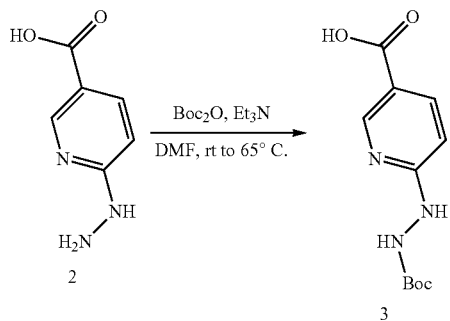 [SMILES: NNc1ccc(C(=O)O)cn1 ; CC(C)(C)OC(=O)NNc1ccc(C(=O)O)cn1]

To a suspension of 6-hydrazinylnicotinic acid (3 g, 19.6 mmol) in DMF (20 mL) was added TEA (2.97 g, 29.4 mmol) and Boc$_2$O (4.7 g, 21.6 mmol). The suspension was heated to 65° C. with stirring for 15 hrs. The suspension was poured into water (20 mL) and adjusted pH to 6 with HCl (1 M) and then purified by reverse phase biotage to give 1.2 g solid (24%).

LC-MS: CP-0007023-008: (ES, m/z): 254 [M+H]$^+$

3. Synthesis of 7-allyl-2-amino-9-((3aR,4R,6R,6aR)-6-(hydroxymethyl)-2,2-dimethyl-tetrahydrofuro[3,4-d][1,3]dioxol-4-yl)-1H-purine-6,8(7H,9H)-dione

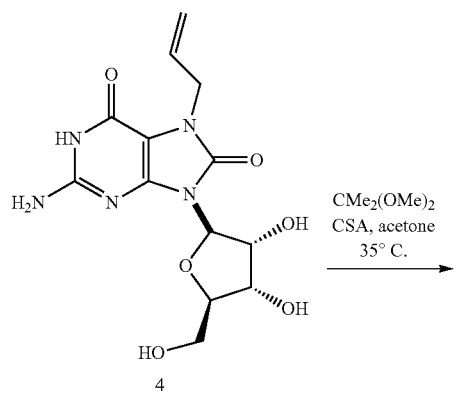

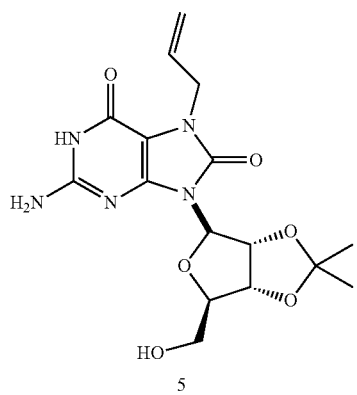

To a suspension of 7-allyl-2-amino-9-((2R,3R,4S,5R)-3,4-dihydroxy-5-(hydroxymethyl)-tetrahydrofuran-2-yl)-1H-purine-6,8(7H,9H)-dione (1.1 g, 3.24 mmol) and 2,2-dimethoxypropane (6.75 g, 64.9 mmol) in acetone (40 mL) was added (+/−)-Camphor-10-sulfonic acid (301 mg, 1.3 mmol). The suspension was heated to 35° C. with stirring for 2 hrs. The mixture was concentrated purified by column chromatography (MeOH/CH2Cl2=20:1) to give a white solid product (710 mg, 58%).

LC-MS: CP-0007023-045: (ES, m/z): 380 [M+H]$^+$

4. Synthesis of ((3aR,4R,6R,6aR)-6-(7-allyl-2-amino-6,8-dioxo-1,6,7,8-tetrahydropurin-9-yl)-2,2-dimethyl-tetrahydrofuro[3,4-d][1,3]dioxol-4-yl)methyl 6-(2-(tert-butoxycarbonyl)hydrazinyl)nicotinate

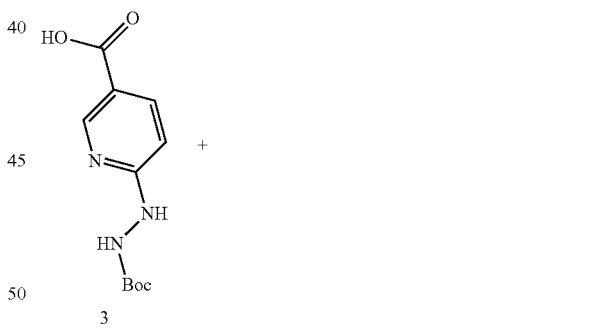

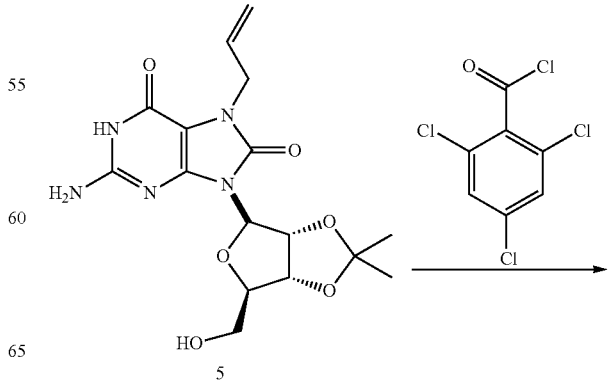

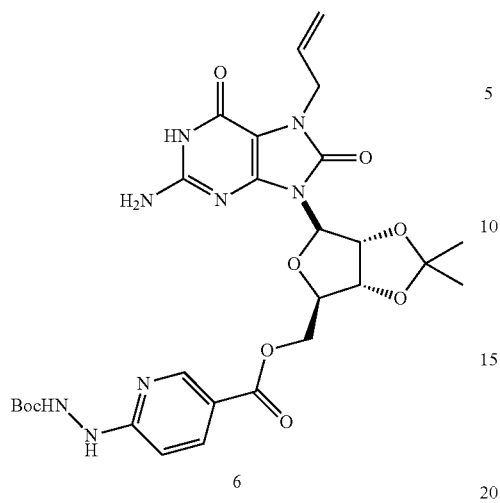

6

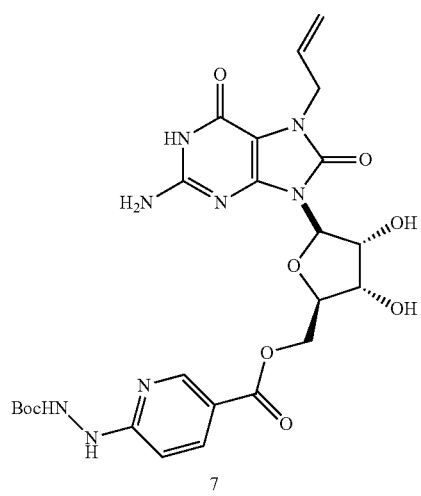

7

To a suspension of 6-(2-(tert-butoxycarbonyl)hydrazinyl) nicotinic acid (668 mg, 2.63 mmol) in toluene (10 mL, anhydrous) was added 2,4,6-trichlorobenzoyl chloride (959 mg, 3.95 mmol) and DIPEA (679 mg, 5.62 mmol). The suspension was stirred for 10 min and then a suspension of 7-allyl-2-amino-9-((3aR,4R,6R,6aR)-6-(hydroxymethyl)-2,2-dimethyl-tetrahydrofuro[3,4-d][1,3]dioxol-4-yl)-1H-purine-6,8(7H,9H)-dione (500 mg, 1.32 mmol) and DMAP (321 mg, 2.63 mmol) in toluene (10 mL, anhydrous) was added. The suspension was stirred for 15 hrs then quenched with brine. The aqueous phase was extracted with EtOAc (20 mL*3). The organic phase was combined, dried over Na$_2$SO$_4$, filtered and concentrated. The residue was purified by reverse phase biotage to give a white solid product (390 mg, 48%).

LC-MS: CP-0007023-070: (ES, m/z): 615 [M+H]$^+$

5. Synthesis of ((2R,3S,4R,5R)-5-(7-allyl-2-amino-6,8-dioxo-, 6,7,8-tetrahydropurin-9-yl)-3,4-dihydroxy-tetrahydrofuran-2-yl)methyl 6-(2-(tert-butoxycarbonyl)hydrazinyl)nicotinate ((3aR,4R,6R,6aR)-6-(7-allyl-2-amino-6,8-dioxo-1,6,7,8-tetrahydropurin-9-yl)-2,2-dimethyl-tetrahydrofuro[3,4-d][1,3]dioxol-4-yl)methyl 6-(2-(tert-butoxycarbonyl)hydrazinyl) nicotinate (220 mg, 0.36 mmol) was added to a mixture of perchloric acid (6.6 mL, 10%) and THF (13.2 mL). The mixture was reacted by microwave at 40° C. for 1 h. The mixture was poured into water (10 mL) and adjusted pH to 8 with NaHCO$_3$(aq), extracted with EtOAc (15 mL*3). The organic phase was combined and dried over Na$_2$SO$_4$, filtered and concentrated. The residue was purified by reverse phase biotage to give a white solid product (56 mg, 27%).

LC-MS: CP-0007023-109: (ES, m/z): 575 [M+H]$^+$

6. Synthesis of ((2R,3S,4R,5R)-5-(7-allyl-2-amino-6,8-dioxo-1,6,7,8-tetrahydropurin-9-yl)-3,4-dihydroxy-tetrahydrofuran-2-yl)methyl 6-hydrazinylnicotinate

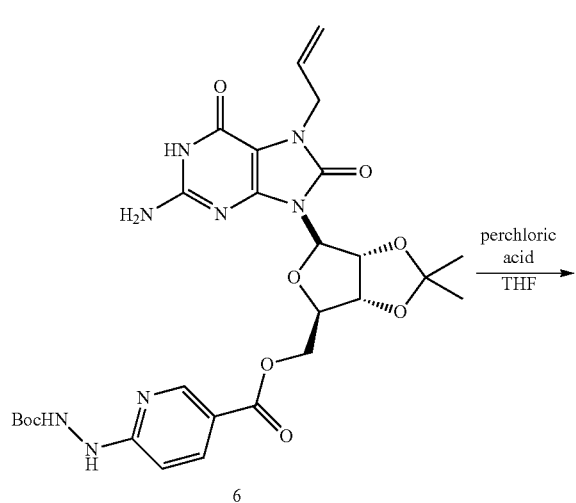

6

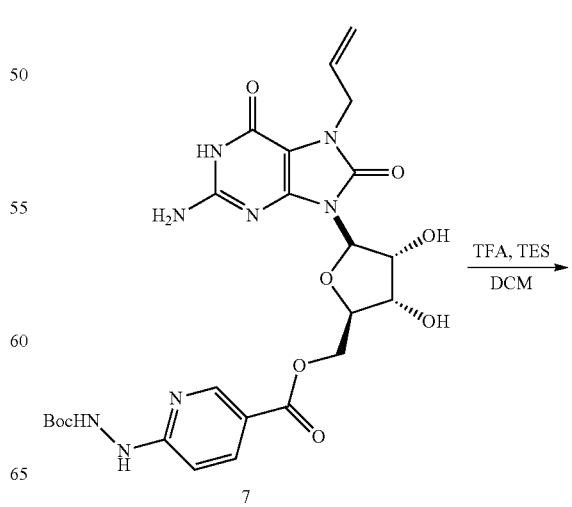

7

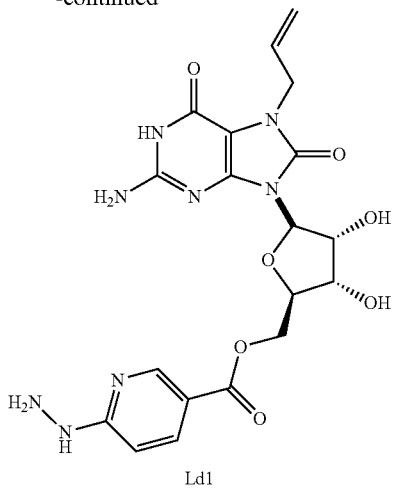

Ld1

To a solution of ((2R,3S,4R,5R)-5-(7-allyl-2-amino-6,8-dioxo-1,6,7,8-tetrahydropurin-9-yl)-3,4-dihydroxy-tetrahydrofuran-2-yl)methyl 6-(2-(tert-butoxycarbonyl)hydrazinyl)nicotinate (250 mg, 0.44 mmol) and TES (12.5 mL) in CH$_2$Cl$_2$ (25 mL) was added TFA (10 mL) dropwise at 0° C. The mixture was stirred at 0° C. for 2.5 hours and then concentrated under reduce pressure. The residue was purified by reverse phase biotage to give a white solid product (40 mg, 17%).

LC-MS: CP-0007023-117: (ES, m/z): 475 [M+H]$^+$ $^1$H NMR: CP-0007023-117: $^1$H-NMR (DMSO-d$_6$, 500 MHz): δ (ppm) 10.953 (s, 1H), 8.585-8.581 (d, J=2 Hz, 1H), 8.408 (s, 1H), 7.895-7.874 (dd, J=2, 9 Hz, 1H), 6.721-6.707 (d, J=7 Hz, 1H), 6.587 (s, 2H), 5.923-5.857 (m, 1H), 5.627-5.619 (d, J=4 Hz, 1H), 5.379-5.368 (d, J=5.5 Hz, 1H), 5.135-5.016 (m, 3H), 4.811-4.872 (m, 1H), 4.429-4.355 (m, 6H), 4.295-4.259 (m, 1H), 4.020-3.988 (m, 1H).

Synthesis of Ld2

Ld2 can be prepared using the method illustrated in FIG. 40 and as described below.

1. Synthesis of (S)-2,5-dioxopyrrolidin-1-yl 2-(((9H-fluoren-9-yl)methoxy)carbonylamino)-3-methylbutanoate

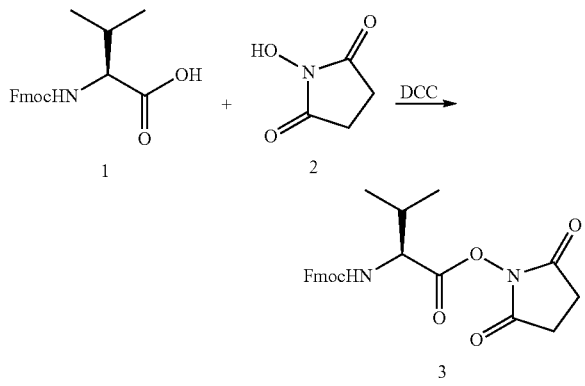

(S)-2-(((9H-fluoren-9-yl)methoxy)carbonylamino)-3-methylbutanoic acid (5 g, 15 mmol) and 1-hydroxypyrrolidine-2,5-dione (1.8 g, 17 mmol)) were dissolved in dry THF (40 mL). DCC (3.4 g, 17 mmol) in dry THF (20 mL) was added at 0° C. and the suspension was stirred at 0° C. for 4 hours. The solid was filtered off and the filtrate was purified by column chromatography (PE:EtOAc=3:1) to give 2.56 g solid (40%)

LC-MS: CP-0007349-011: (ES, m/z): 459 [M+Na]$^+$

2. Synthesis of (S)-2-((S)-2-(((9H-fluoren-9-yl)methoxy) carbonylamino)-3-methylbutanamido)-6-(tert-butoxycarbonylamino)hexanoic Acid

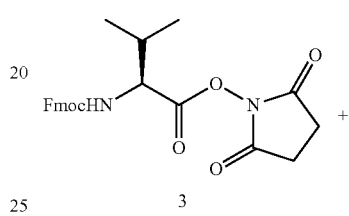

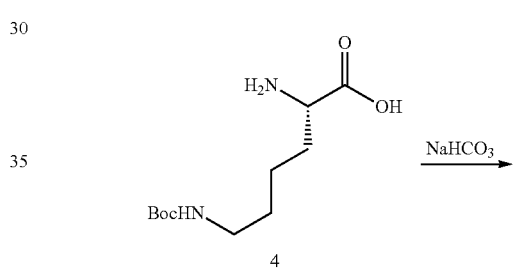

To a suspension of (S)-2-amino-6-(tert-butoxycarbonylamino)hexanoic acid (524 mg, 2.2 mmol)) in acetone (10 mL) and NaHCO$_3$ (616 mg, 7.34 mmol in H2O (10 mL) was added (S)-2,5-dioxopyrrolidin-1-yl 2-(((9H-fluoren-9-yl)methoxy)carbonylamino)-3-methylbutanoate (800 mg, 1.83 mmol). The suspension was stirred for 18 hours and then washed with Et$_2$O (10 mL). EtOAc (20 mL) was added to the mixture and adjusted pH to 5 with HCl (1M). The organic phase was collected and washed with water, dried over Na$_2$SO$_4$, filtered and concentrated to give 820 mg solid (78%)

LC-MS: CP-0007023-104: (ES, m/z): 568 [M+H]$^+$

3. Synthesis of (S)-benzyl 2-((S)-2-(((9H-fluoren-9-yl)methoxy)carbonylamino)-3-methylbutanamido)-6-(tert-butoxycarbonylamino)hexanoate

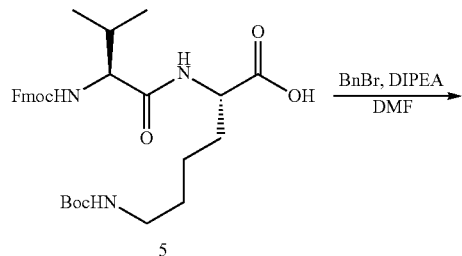

To a solution of (S)-2-((S)-2-(((9H-fluoren-9-yl)methoxy)carbonylamino)-3-methylbutanamido)-6-(tert-butoxycarbonylamino)hexanoic acid (1 g, 1.76 mmol) and DIPEA (1.14 g, 8.82 mmol) in DMF (20 mL) was added BnBr (899 mg, 5.29 mmol) dropwise at 0° C. The mixture was stirred at r.t. for 3 hours. The mixture was poured into water (150 mL) and extracted with EtOAc (100 mL*3). The organic phase was combined and washed with water (50 mL), then dried over Na$_2$SO$_4$, filtered and concentrated. The residue was purified by column chromatography (MeOH/CH$_2$Cl$_2$=1:99) to give a white solid product (980 mg, 84%).

LC-MS: CP-0007349-062: (ES, m/z): 658 [M+H]$^+$

4. Synthesis of (S)-benzyl 2-((S)-2-amino-3-methylbutanamido)-6-(tert-butoxycarbonylamino)hexanoate

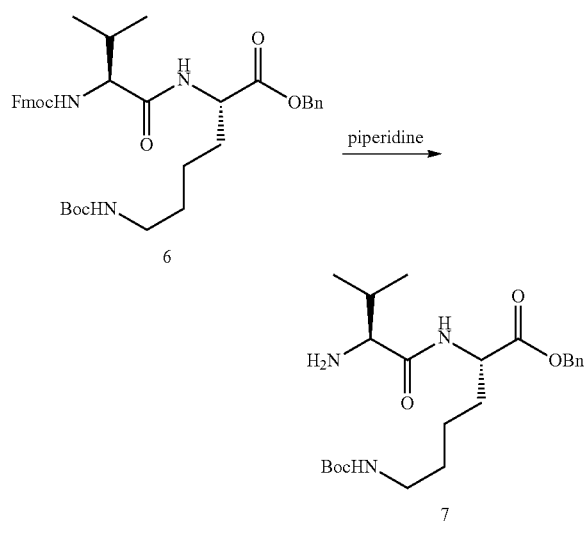

To a solution of (S)-benzyl 2-((S)-2-(((9H-fluoren-9-yl)methoxy)carbonylamino)-3-methylbutanamido)-6-(tert-butoxycarbonylamino)hexanoate (950 mg, 1.45 mmol) in CH$_2$Cl$_2$ (30 mL) was added piperidine (1.23 g, 14.5 mmol). The mixture was stirred for 3 hours and then concentrated under reduce pressure and the residue was purified by column chromatography to give a white solid product (330 mg, 52%).

LC-MS: CP-0007349-067: (ES, m/z): 436 [M+H]$^+$

5. Synthesis of 5-(2-(tert-butoxycarbonyl)hydrazinyl)-5-oxopentanoic Acid

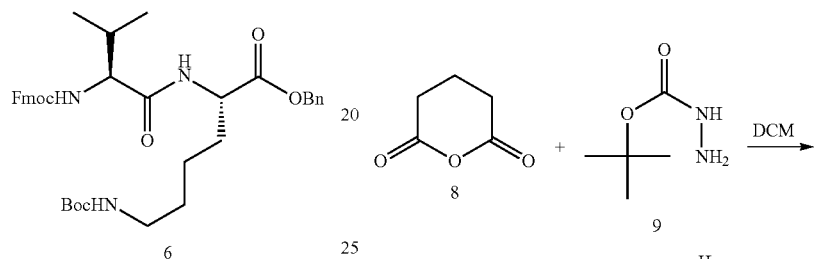

To a solution of dihydro-3H-pyran-2,6-dione (250 mg, 2.19 mmol) in CH2Cl2 (4 mL) was added a solution of tert-butyl hydrazinecarboxylate (290 mg, 2.19 mmol) in CH$_2$Cl$_2$ (1 mL) dropwise. The mixture was stirred for 2 hours and then concentrated under reduce pressure and the residue was purified by column chromatography to give an oil product (190 mg, 35%).

$^1$H-NMR-CP-0007023-169: $^1$H-NMR (DMSO-d$_6$, 500 MHz): δ(ppm) 12.052 (s, 1H), 9.480 (s, 1H), 8.654 (s, 1H), 2.249-2.218 (t, J=7.5, 15.5 Hz, 2H), 2.105-2.007 (t, J=7, 14 Hz, 2H), 1.741-1.682 (m, 2H), 1.391 (s, 9H).

6. Synthesis of Compound 11

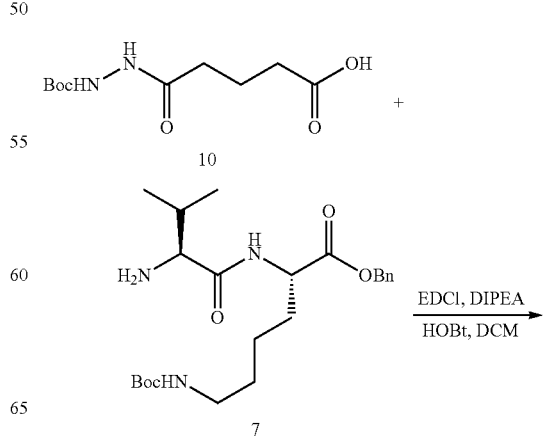

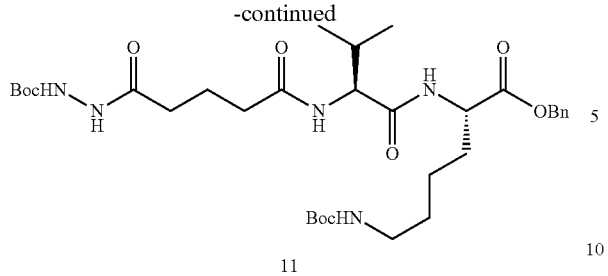

11

To a solution of 5-(2-(tert-butoxycarbonyl)hydrazinyl)-5-oxopentanoic acid (339 mg, 1.38 mmol) in DMF (8 mL) was added DIPEA (1.33 g, 10.3 mmol), EDCI (397 mg, 2.07 mmol) and HOBt (186 mg, 1.38 mmol). The mixture was stirred for 1.5 hours and then (S)-benzyl 2-((S)-2-amino-3-methylbutanamido)-6-(tert-butoxycarbonylamino)hexanoate (300 mg, 0.69 mmol) and DMAP (168 mg, 1.38 mmol) were added. The mixture was stirred at r.t. for 16 hours. The mixture was poured into water (100 mL) and extracted with EtOAc (30 mL*3). The organic phase was combined and washed with water (15 mL), then dried over Na$_2$SO$_4$ concentrated and purified by column chromatography (MeOH/CH2Cl2=3:97) to give a white solid product (150 mg, 33%).

LC-MS: CP-0007349-069: (ES, m/z): 664 [M+H]$^+$

7. Synthesis of (13S,16S)-13-isopropyl-2,2,24,24-tetramethyl-4,7,11,14,22-pentaoxo-3,23-dioxa-5,6,12,15,21-pentaazapentacosane-16-carboxylic Acid

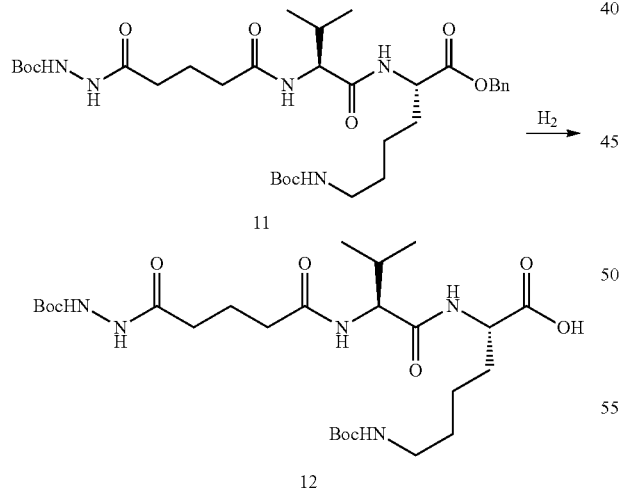

To a solution of 11 (140 mg, 0.21 mmol) in THF (10 mL) was added Pd/C (40 mg, 10%). The suspension was agitated under an H$_2$ atmosphere with stirring for 3 hours. The catalyst was removed by filtration and the filtrate was concentrated under reduce pressure to give a white solid product (96 mg, 80%).

LC-MS: CP-0007349-069: (ES, m/z): 574 [M+H]$^+$

8. Synthesis of tert-butyl 2-bromoethylcarbamate

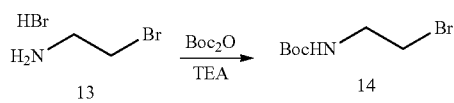

To a suspension of 2-bromoethanamine hydrobromide (10 g, 48.8 mmol) in CH2Cl2 (190 mL) was added TEA (12.34 g, 121.95 mmol) and Boc$_2$O (11.72 g, 53.7 mmol). The mixture was stirred for 16 hours and washed with water and brine, dried over Na$_2$SO$_4$, filtered and concentrated under reduced pressure to give 8.7 g oil (used for next step without purification).

9. Synthesis of tert-butyl 2-(methylamino)ethylcarbamate

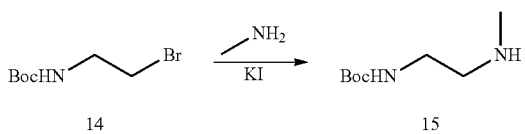

To a solution of tert-butyl 2-bromoethylcarbamate (9 g, 40.3 mmol) and methylamine (41.7 g, 403 mmol, 30% in EtOH) in EtOH (80 mL) was added KI (140 mg, 0.8 mmol). The mixture was heated to 50° C. with stirring for 5 hours and then concentrated under reduce pressure, the residue was poured into water and extracted with EtOAc (3*80 mL). The organic phase was dried over Na$_2$SO$_4$, filtered and removal of solvent to give 4.3 g oil (used for next step without purification).

LC-MS: CP-0007023-128: (ES, m/z): 175 [M+H]$^+$

10. Synthesis of Compound 16

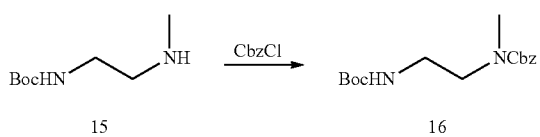 [SMILES: "CbzCl" ; CNCCNC(=O)OC(C)(C)C ; CN(CCNC(=O)OC(C)(C)C)C(=O)OCc1ccccc1]

To a solution of tert-butyl 2-(methylamino)ethylcarbamate (4.3 g, 0.44 mmol) in THF (60 mL) was added TEA (5.49 g, 54.3 mmol) and CbzCl (4.62 g, 27.1 mmol) at 0° C. The mixture was stirred at 0° C. for 4 hours and then poured into water (100 mL) and extracted with EtOAc (3*80 mL). The organic phase was dried over Na$_2$SO$_4$, filtered and the residue was purified by reverse phase biotage to give an oil product (2.5 g, 33%).

LC-MS: CP-0007023-130: (ES, m/z): 331 [M+Na]$^+$

11. Synthesis of tert-butyl 2-(methylamino)ethylcarbamate

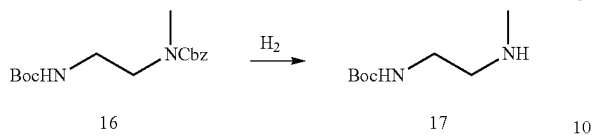

To a solution of compound 16 (1.3 g, 4.22 mmol) in MeOH (30 mL) was added Pd/C (150 mg, 10%). The suspension was agitated under an H2 atmosphere with stirring for 2 hours. The catalyst was removed by filtration and the filtrate was concentrated under reduce pressure to give an oil product (720 mg, 98%).

$^1$H NMR: CP-0007023-117: $^1$H-NMR (DMSO-$d_6$, 500 MHz): δ (ppm) 6.707 (s, 1H), 2.999-2.962 (q, J=6.5, 12.5 Hz, 2H), 2.488-2.461 (t, J=7, 13.5 Hz, 2H), 2.247 (s, 3H), 1.369 (s, 9H).

12. Synthesis of ((3aS,4S,6S,6aS)-6-(7-allyl-2-amino-6,8-dioxo-1,6,7,8-tetrahydropurin-9-yl)-2,2-dimethyl-tetrahydrofuro[3,4-d][1,3]dioxol-4-yl) methyl 4-nitrophenyl carbonate

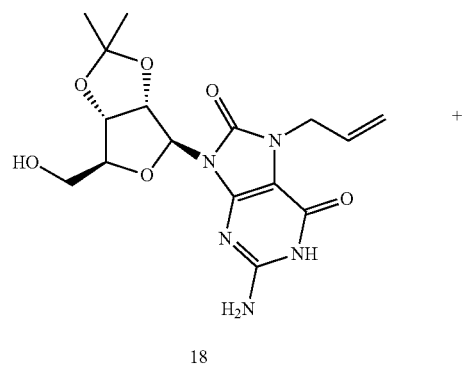

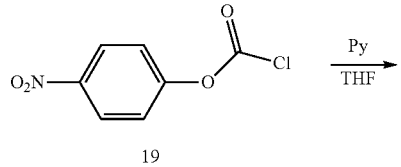

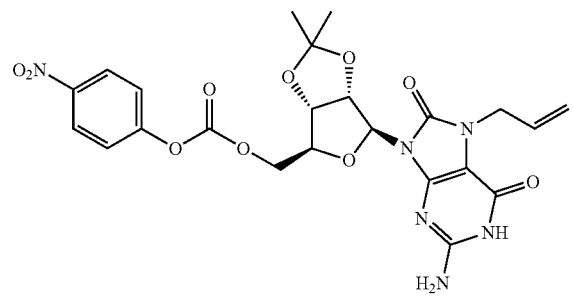

To a suspension of 7-allyl-2-amino-9-((3aS,4S,6S,6aS)-6-(hydroxymethyl)-2,2-dimethyl-tetrahydrofuro[3,4-d][1,3]dioxol-4-yl)-1H-purine-6,8(7H,9H)-dione (1.4 g, 3.7 mmol) in dry THF (36 mL) was added pyridine (2.92 g, 37 mmol), the suspension was stirred for 0.5 h and then added a solution of 4-nitrophenyl carbonochloridate (4.48 g, 22.2 mmol) in dry THF (24 mL) dropwise at 0° C. The mixture was stirred at r.t. for 5 hours and then concentrated under reduce pressure. The residue was dissolved in CH2Cl2 (70 mL) and washed with brine (satd.), the organic phase was dried over Na$_2$SO$_4$, filtered and concentrated. The residue was purified by reverse phase biotage to give a yellow solid product (1.2 g, 55%).

LC-MS: CP-0007023-172: (ES, m/z): 545 [M+H]+

13. Synthesis of Compound 21

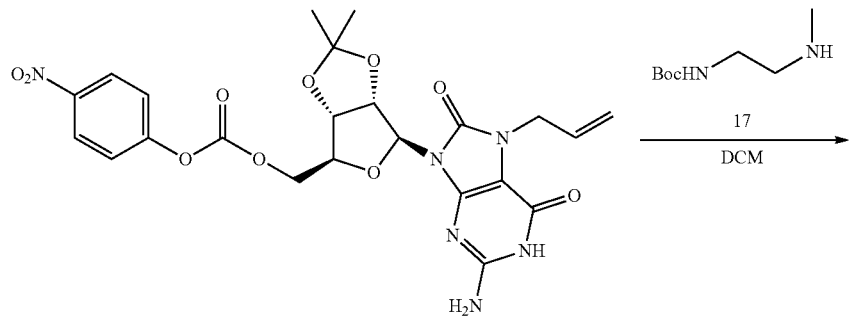

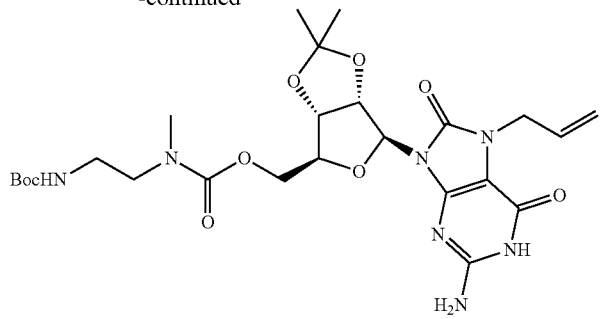

21

To a solution of ((3aS,4S,6S,6aS)-6-(7-allyl-2-amino-6,8-dioxo-1,6,7,8-tetrahydropurin-9-yl)-2,2-dimethyl-tetrahydrofuro[3,4-d][1,3]dioxol-4-yl)methyl 4-nitrophenyl carbonate (1.1 g, 2 mmol) in CH2Cl2 (10 mL) was added tert-butyl 2-(methylamino)ethylcarbamate (704 mg, 4 mmol). The mixture was stirred for 2 hours at r.t. and then washed with brine (satd). The organic phase was dried over Na$_2$SO$_4$ and purified by reverse phase biotage to give a yellow solid product (910 mg, 78%).

LC-MS: CP-0007023-175: ES, m/z): 580[M+H]$^+$

14. Synthesis of ((3aS,4S,6S,6aS)-6-(7-allyl-2-amino-6,8-dioxo-1,6,7,8-tetrahydropurin-9-yl)-2,2-dimethyl-tetrahydrofuro[3,4-d][1,3]dioxol-4-yl) methyl 2-aminoethyl(methyl) carbamate

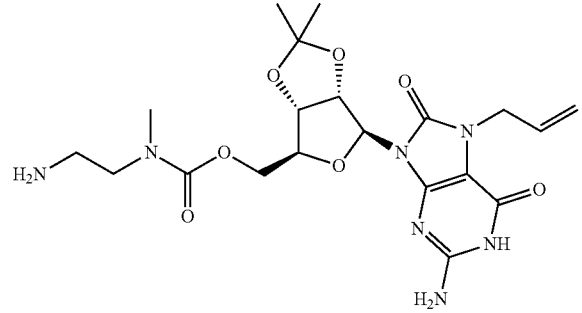

22

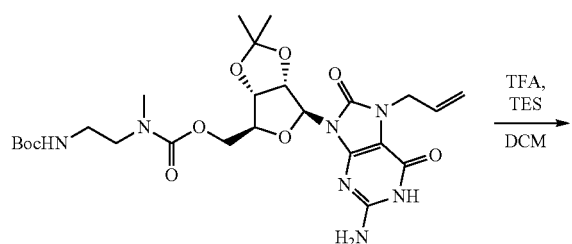

21

To a solution of 21 (1 g, 1.73 mmol) and TES (3.4 mL) in CH2Cl2 (16.5 mL) was added TFA (3.4 mL) dropwise at 0° C. The mixture was stirred at 0° C. for 2 hours and then concentrated under reduce pressure. The residue was washed with Et$_2$O to give a white solid product (920 mg, 90%).

LC-MS: CP-0007023-179: (ES, m/z): 480[M+H]$^+$

15. Synthesis of Compound 23

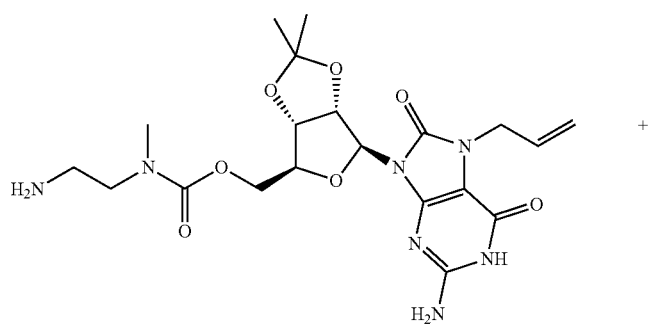

22

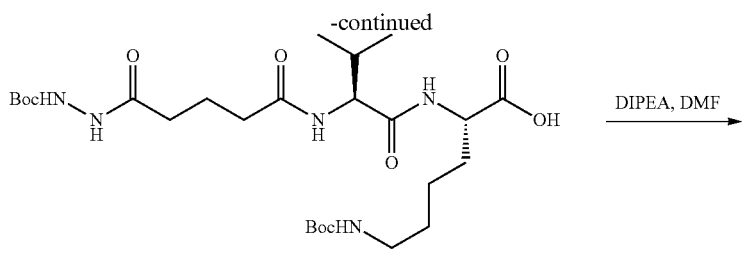

12

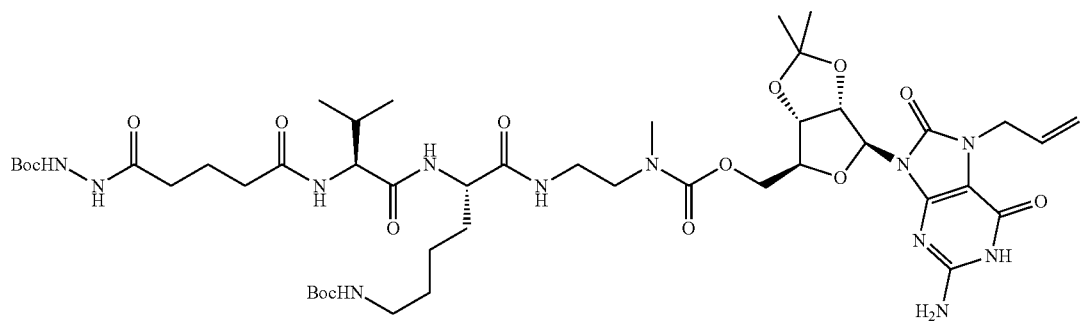

23

To a solution of (13S,16S)-13-isopropyl-2,2,24,24-tetramethyl-4,7,11,14,22-pentaoxo-3,23-dioxa-5,6,12,15,21-pentaazapentacosane-16-carboxylic acid (197 mg, 0.34 mmol) in DMF (5 mL) was added DIPEA (296 mg, 2.3 mmol), EDCI (132 mg, 0.69 mmol) and HOBt (62 mg, 0.46 mmol). The mixture was stirred for 1.5 hours and then added ((3aS,4S,6S,6aS)-6-(7-allyl-2-amino-6,8-dioxo-1,6,7,8-tetrahydropurin-9-yl)-2,2-dimethyl-tetrahydrofuro[3,4-d][1,3]dioxol-4-yl)methyl 2-aminoethyl(methyl)carbamate (110 mg, 0.23 mmol) and DMAP (56 mg, 0.46 mmol), the mixture was stirred at r.t. for 16 hours. The mixture was poured into water (50 mL) and extracted with EtOAc (30 mL*3). The organic phase was combined and washed with water (15 mL), then dried over Na$_2$SO$_4$, filtered and concentrated. The residue was purified by Pre-HPLC to give a white solid product (43 mg, 23%).

LC-MS: CP-0007349-069: (ES, m/z): 1035 [M+H]$^+$

16. Synthesis of ((2S,3R,4S,5S)-5-(7-allyl-2-amino-6,8-dioxo-1,6,7,8-tetrahydropurin-9-yl)-3,4-dihydroxy-tetrahydrofuran-2-yl)methyl 2-((S)-6-amino-2-((S)-2-(5-hydrazinyl-5-oxopentanamido)-3 methylbutanamido)hexanamido)ethyl(methyl)carbamate

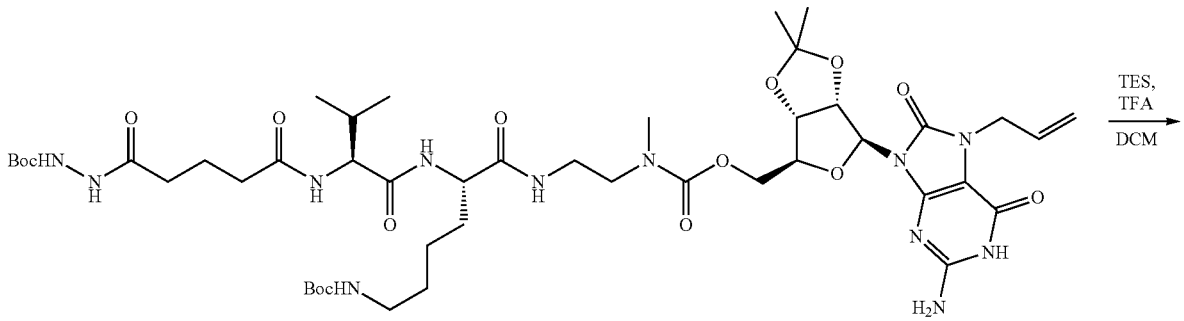

23

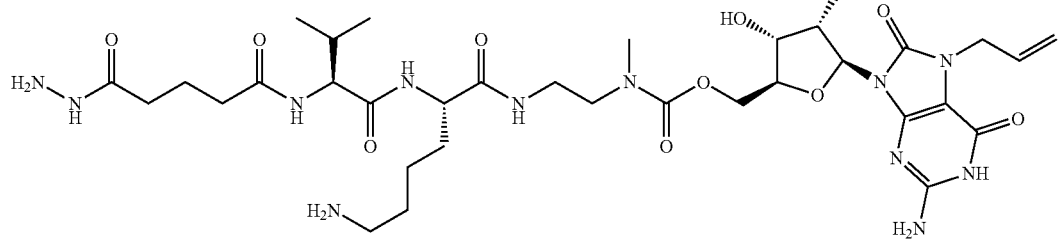

Ld2

To a solution of compound 23 (30 mg, 0.03 mmol) and TES (0.5 mL) in CH2Cl2 (1 mL) was added TFA (0.5 mL) dropwise at 0° C. The mixture was warmed to r.t. with stirring for 4 hours and then concentrated under reduced pressure. The residue was purified by Pre-HPLC to give a white solid product (4 mg, 17%).

LC-MS: CP-0007023-117: (ES, m/z): 795 [M+H]$^+$

Synthesis of Ld3

Ld3 can be prepared by reacting a derivative of Loxorubicin with a linker as shown below using similar methods to those described in this specification.

Synthesis of Ld6

Ld6 can be prepared using the method illustrated in FIG. 44.

Synthesis of LD7

Ld7 incorporates a hydrazine nicotinic acid instead of a carbohydrazide benzoic acid and can be prepared using the same method used to prepare Ld6.

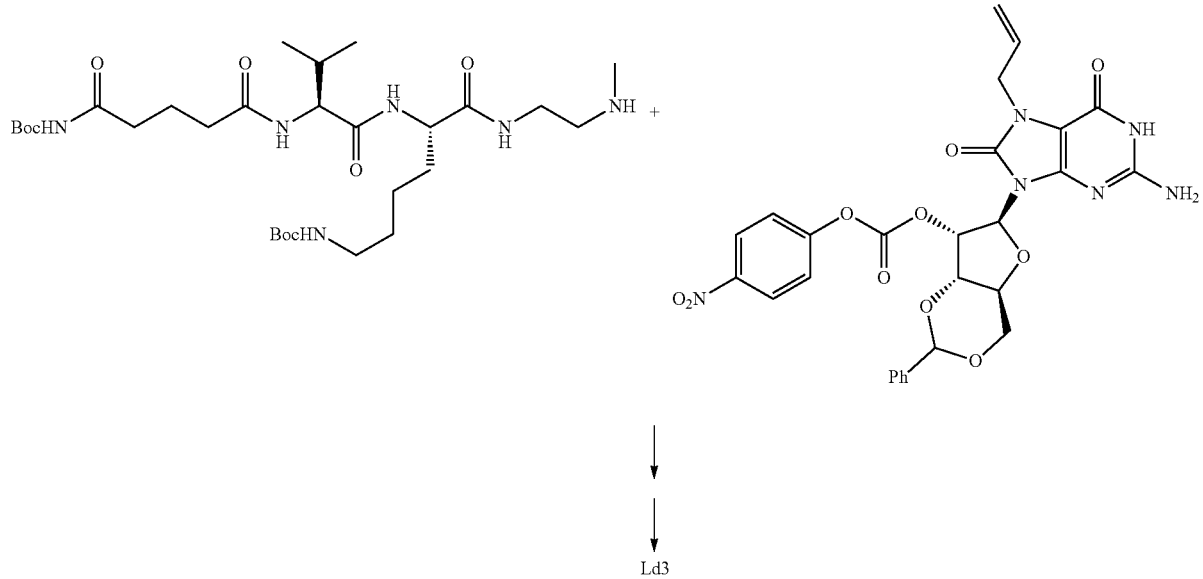

Ld3

Synthesis of Ld4

Ld4 can be prepared using a similar method to that illustrated in FIG. 28, using a shorter PEG chain.

Synthesis of Ld5

Ld5 can be prepared using a similar method to that illustrated in FIG. 27, using a shorter PEG chain.

Synthesis of Ld8

Similar strategies used to synthesize PEG-based linkers can be used to synthesize the required PEG linker with an acetal group for Ld8. This linker can be condensed with the Loxorubine as shown below to form Ld8 incorporating the cyclic acetal.

111    112
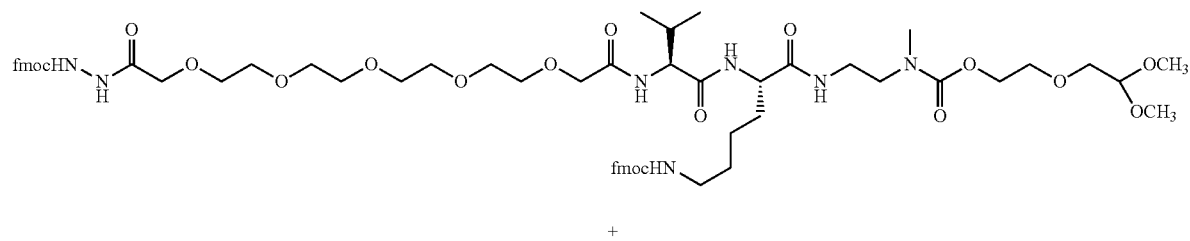
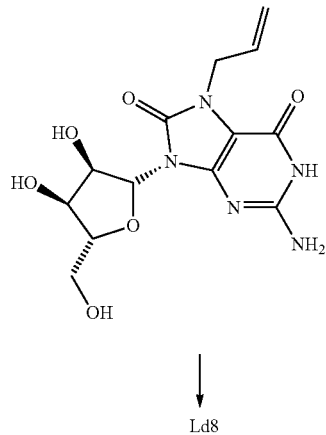
Ld8
Synthesis of Ld9                                    Synthesis of Ld10
Similar strategies used to synthesize PEG-based linkers can be used to synthesize the required PEG linker for Ld9. This linker can be condensed with the acetal of Loxorubine as shown below to form Ld9.
Ld10 can be prepared using the method illustrated in FIG. 44.
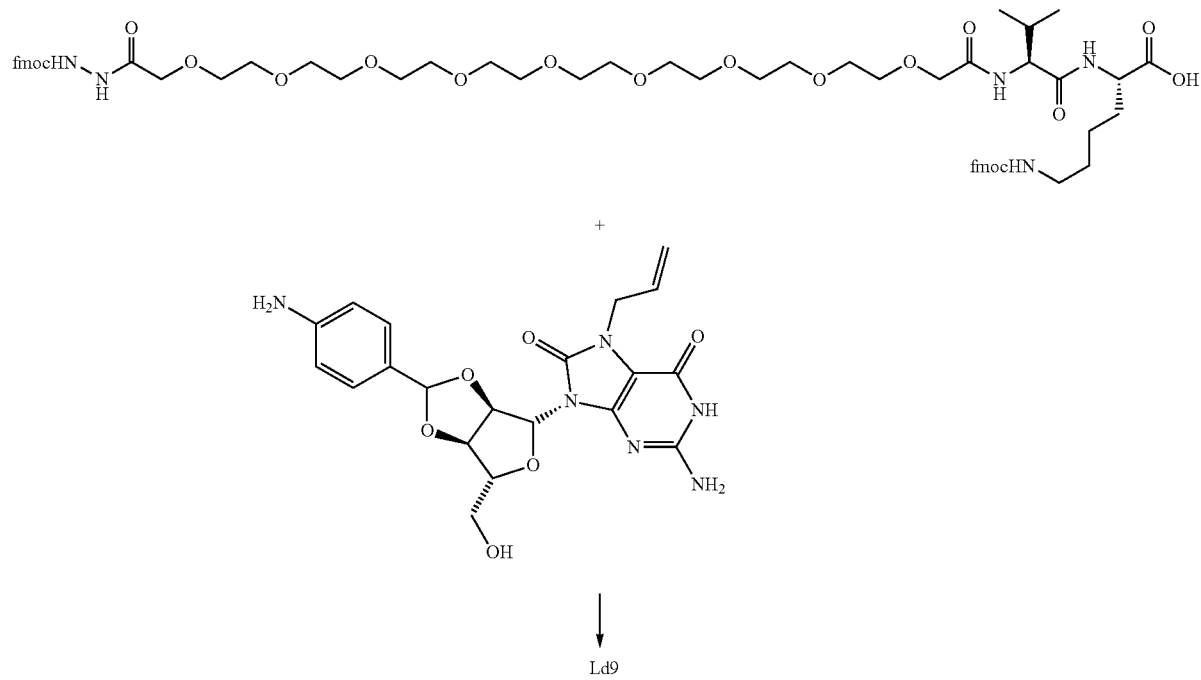
Ld9

Synthesis of IM2

IM2 (intermediate compound in the synthesis of Ld10) can be prepared using the method illustrated in FIG. 41 and as described below.

1. Synthesis of 7-allyl-2-amino-9-((3aR,4R,6R,6aR)-6-(hydroxymethyl)-2-(3-hydroxyphenyl)-tetrahydrofuro[3,4-d][1,3]dioxol-4-yl)-1H-purine-6,8(7H,9H)-dione

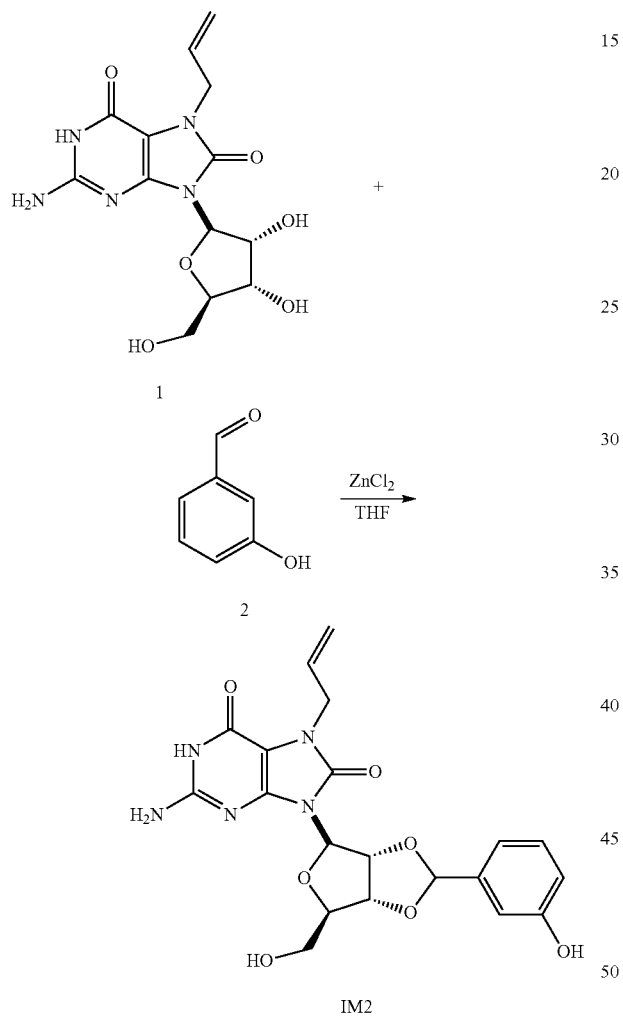

To a suspension of 7-allyl-2-amino-9-((2R,3R,4S,5R)-3,4-dihydroxy-5-(hydroxymethyl)-tetrahydrofuran-2-yl)-1H-purine-6,8(7H,9H)-dione (500 mg, 1.47 mmol) and 3-hydroxybenzaldehyde (1.8 g, 14.7 mmol) in THF (40 mL, anhydrous) was added $ZnCl_2$ (7.37 mL, 7.37 mmol, in $Et_2O$). The suspension was heated to reflux with stirring for 48 hours. The suspension was cooled to r.t. and poured into $Et_2O$ (300 mL) to give a gray precipitate and then purified by Pre-TLC to give a gray solid product (45 mg, 7%).

LC-MS: CP-0007023-040: (ES, m/z): 444 [M+H]+
$^1$H-NMR-CP-0006708-040: $^1$H-NMR (DMSO-$d_6$, 500 MHz): δ (ppm) 11.06 (s, 1H), 9.597 (s, 1H), 7.239-7.207 (t, J=8, 16 Hz, 1H), 6.943-6.907 (m, 2H), 6.831-6.811 (dd, J=2, 8 Hz, 1H), 6.677 (s, 2H), 5.946-5.870 (m, 3H), 5.436-5.420 (dd, J=1, 7 Hz, 1H), 5.124-5.100 (dd, J=1.5, 10.5 Hz, 1H), 5.058-5.020 (m, 2H), 4.890-4.866 (t, J=6, 24 Hz, 1H), 4.411-4.400 (d, J=5.5 Hz, 2H), 4.157-4.125 (m, 1H), 3.619-3.571 (m, 1H), 3.504-3.457 (m, 1H).

Synthesis of IM3

IM3 (intermediate compound in the synthesis of an analog of Ld10) can be prepared using the method illustrated in FIG. 42 and as described below.

1. Synthesis of 8-(allyloxy)-2-amino-9-((2R,3R,4S,5R)-3,4-dihydroxy-5-(hydroxymethyl)-tetrahydrofuran-2-yl)-1H-purin-6(9H)-one

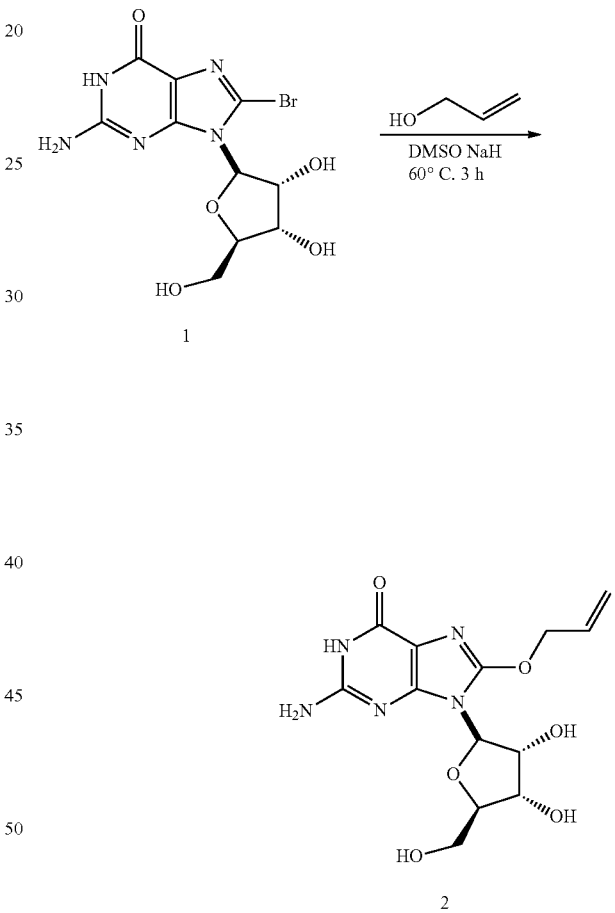

To a solution of prop-2-en-1-ol (120 ml) in DMSO (160 mL, anhydrous) was added sodium hydride (11 g, 276 mmol) in portions at 0° C. The mixture was allowed to warm to 25° C. with stirring for 1 h, and then 2-amino-8-bromo-9-((2R,3R,4S,5R)-3,4-dihydroxy-5-(hydroxymethyl)-tetrahydrofuran-2-yl)-1H-purin-6(9H)-one was added. The mixture was stirred for 0.5 h and then heated to 60° C. with stirring for 4 hours. The mixture was allowed to cooled to r.t. and then added to diethyl ether (2.5 L) to give a gray precipitate and purified by reverse phase biotage to give a white solid product (4.8 g, 51%).

LC-MS: CP-0007023-020: (ES, m/z): 340 [M+H]+

2. Synthesis of 7-allyl-2-amino-9-((2R,3R,4S,5R)-3,4-dihydroxy-5-(hydroxymethyl)-tetrahydrofuran-2-yl)-1H-purine-6,8(7H, 9H)-dione

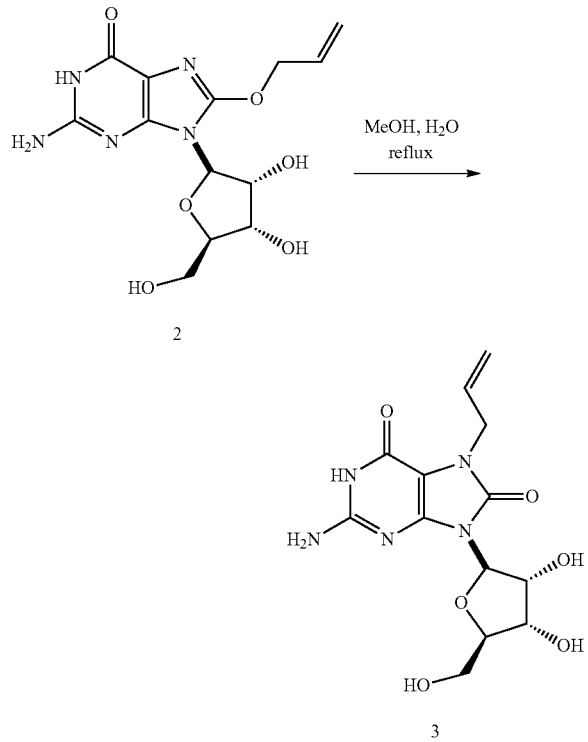

8-(allyloxy)-2-amino-9-((2R,3R,4S,5R)-3,4-dihydroxy-5-(hydroxymethyl)-tetrahydrofuran-2-yl)-1H-purin-6(9H)-one (2.6 g, 7.7 mmol) was suspended in MeOH (25 mL) and water (25 mL). The suspension was heated to reflux with stirring for 20 hours (the mixture became clear). The organic solvent was removed and the aqueous solution was freezing-dried to give a white solid product (2.6 g, 100%).

LC-MS: CP-0007023-031: (ES, m/z): 340 [M+H]+

3. Synthesis of 4-((3aR,4R,6R,6aR)-4-(7-allyl-2-amino-6,8-dioxo-1,6,7,8-tetrahydropurin-9-yl)-6-(hydroxymethyl)-tetrahydrofuro[3,4-d][1,3]dioxol-2-yl)phenyl acetate

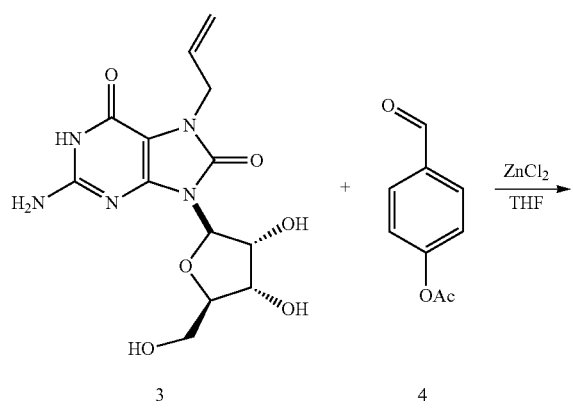

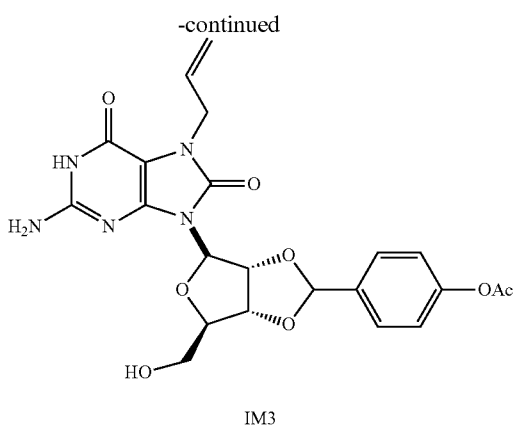

IM3

To a suspension of 7-allyl-2-amino-9-((2R,3R,4S,5R)-3,4-dihydroxy-5-(hydroxymethyl)-tetrahydrofuran-2-yl)-1H-purine-6,8(7H,9H)-dione (400 mg, 1.18 mmol) and 4-formylphenyl acetate (1.93 g, 11.8 mmol) in THF (30 mL, anhydrous) was added $ZnCl_2$ (5.9 mL, 5.9 mmol, in $Et_2O$). The suspension was heated to reflux with stirring for 48 hours. The suspension was cooled to r.t. and poured into $Et_2O$ (300 mL) to give a gray precipitate and then purified by Pre-TLC to give a gray solid product (45 mg, 8%).

LC-MS: CP-0007023-034: (ES, m/z): 486 [M+H]+

1H-NMR-CP-0006708-034: 1H-NMR (DMSO-$d_6$, 500 MHz): δ (ppm) 11.00 (s, 1H), 7-575-7.558 (d, J=8.5 Hz, 2H), 7.221-7.204 (d, J=8.5 Hz, 2H), 6.684 (s, 2H), 5.988 (s, 1H), 5.945-5.879 (m, 2H), 5.466-5.450 (dd, J=1, 7 Hz, 1H), 5.119-5.018 (m, 3H), 4.890-4.867 (t, J=6, 11.5 Hz, 1H), 4.408-4.397 (d, J=5.5 Hz, 2H), 4.179-4.147 (m, 1H), 3.616-3.568 (m, 1H), 3.502-3.455 (m, 1H), 2.287 (s, 3H).

Synthesis of Rd1

Rd1 can be prepared using the method illustrated in FIG. 43.

Synthesis of Rd2

Rd2 can be prepared using a similar method to that illustrated in FIG. 25, using a non PEG linker similar to that used for Ld2 and Ld3.

Synthesis of Rd3

Rd3 incorporates a PEG linker present in Ld4 and Ld5 and can be prepared using a similar strategy.

Conjugation of LD1 to oxidized mannan
Oxidization of mannan
1. Mannan, 28 mg was dissolved in 2 ml 0.1 M PB, pH 6.0.
2. Sodium periodate, 0.213 g was dissolved in 10 ml dd$H_2O$ (0.1 M).
3. Reaction: periodate was added last. Two reactions were set up.
   >1000 kDa mannan, 1.0 ml (14 mg)
   0.1 M phosphate buffer (pH 6.0), 550 μl
   0.1 M sodium periodate, 50 μl
   Total 1.6 ml
4. The mixture was incubated on ice for 1 hr in the dark.
5. The reaction was quenched with 10 μl Ethanediol.
6. The mixture was incubated on ice for a further 0.5 hr in the dark.

7. A PD-10 column was washed with 50 ml 0.2 M NaOH followed by 50 ml DDW.
8. Sample was passed through a PD10 (G25, GE Healthcare, 8.3 ml) column pre-equilibrated with 0.2 M acetate buffer, pH 5.0. 1.6 ml sample was loaded and run in. Another 0.9 ml acetate buffer was added and allowed to flow through without collection.
9. 2 ml acetate buffer was added and fraction collected. The oxidized mannan was about 7 mg/ml in acetate buffer assuming recovery to be 100%.
10. Steps 7-9 were repeated to get the rest of the sample desalted.

Conjugation with LD1
1. 5.3 mg LD1 (M.W 474, 90% pure) was dissolved in 0.83 ml DMSO (10 mM).
2. Conjugation started according to Table 4.

TABLE 4

Conjugation of LD1 to oxidized mannan

| | Ox mannan | LD1 (10 mM) | DMSO | note |
|---|---|---|---|---|
| Conj x100 | 1.0 ml (7 mg/ml) | 70 µl | 130 µl | 100 times excess of LD1 |
| Conj x50 | 1.0 ml (conc. to 14 mg/ml) | 70 µl | 130 µl | 50 times excess of LD1 |

3. A PD-10 column was washed with 50 ml 0.2 M NaOH followed by 50 ml DDW.
4. After 4 hr incubation at RT, the sample was passed through a PD10 column. 1.2 ml sample was loaded and run in. 1.3 ml DDW added and allowed to flow through without collection.
5. 2 ml DDW was added and sample collected.
6. Sample was stored at 4° C. Concentration was determined by OD300.

Removal of endotoxin
1. The sample was incubated with 1% Triton x-114 at 4° C. for 1 hr.
2. A 1 ml Q Sepharose FF column was packed.
3. A Q Sepharose column was washed with 10 ml 1.0 M NaOH followed by 10 ml $H_2O$.
4. Sample was loaded onto the column and washed with 10 ml 1% Triton x-114.
5. The column was washed with 10 ml water.
6. The sample was eluted with 2 ml of 0.5 M NaCl.
7. 100 µl fractions collected and OD300 determined.
8. Fractions containing the conjugate were pooled.

Endotoxin Determination
Endotoxin level of the samples was determined by LAL assay.

Concentration
1. The sample was concentrated by Millipore Amicon Ultra (0.5 ml, cutoff 30 kDa). The Amicon ultra tubes were treated with 0.1 M NaOH before use.
2. To change buffer, samples were diluted 10 times with water during concentration.
3. Samples were stored at −80° C.

Quantitation
Since both mannan and its oxidized form don't have absorption under visible light, quantization of the conjugate can be easily simplified by checking concentration of LD1. LD1 has maximum absorption around 300 nm and OD300 is proved to be linear with LD1 concentration.

To determine concentration of the conjugate, a standard curve for LD1 was obtained by serial dilution. The OD300 for the conjugate was measured and then its concentration calculated according to the standard curve.

TABLE 5

Concentration of final products

| | LD1 Vs OM ratio | concentration | Amount (µl) | Endotoxin |
|---|---|---|---|---|
| OM-LD1, conjx50 | 63 | 5.9 mM | 30 µl | <1 ng/ml |
| OM-LD1, conjx100 | 120 | 7.9 mM | 25 µl | <1 ng/ml |

Conjugation of LD2 to oxidized mannan
Oxidation of mannan
1. Sodium periodate, 0.213 g was dissolved in 10 ml ddH2O (0.1 M).
2. 28 mg mannan was dissolved in 2 ml 0.1M phosphate buffer, pH 6.0.
3. Reaction: periodate was added last.
   >1000 kDa mannan, 2.0 ml (28 mg)
   0.1 M phosphate buffer (pH 6.0), 1.1 ml
   0.1 M sodium periodate, 100 µl
   Total 3.2 ml
4. The mixture was incubated on ice for 1 hr in the dark.
5. The reaction was quenched with 10 µl Ethanediol.
6. The mixture was incubated on ice for a further 0.5 hr in the dark.
7. A PD-10 column was washed with 50 ml 0.2 M NaOH followed by 50 ml DDW.
8. Sample passed through a PD10 (G25, GE Healthcare, 8.3 ml) column pre-equilibrated with 0.2 M acetate buffer, pH 5.0.1.6 ml sample was loaded and run in. 0.9 ml acetate buffer added and allowed to flow through without collection.
9. 2 ml acetate buffer added and fraction collected.
10. Steps 8-9 were repeated to get the rest of the sample desalted.
11. The oxidized mannan was about 7 mg/ml in acetate buffer. Recovery assumed to be 100%. Endotoxin level determined by LAL method.

Conjugation with LD2
1. 4 mg LD2-#195 or #197 (M.W 794) was dissolved in 0.5 ml DMSO (10 mM).
2. Conjugation set up according Table 6.

TABLE 6

Conjugation of LD2 to oxidized mannan

| | Ox mannan | LD2 (10 mM) | note |
|---|---|---|---|
| OM-LD2-#195 | 2.0 ml | 225 µl | 150 times excess of LD2 |
| OM-LD2-#197 | 2.0 ml | 450 µl | 300 times excess of LD2 |

3. A PD-10 column was washed with 50 ml 0.2 M NaOH followed by 50 ml DDW.
4. After 4 hr incubation at RT, sample was passed through the PD10 column. Sample loaded and run in. 2.5 ml DDW added and allowed to flow through without collection.
5. Column washed with 3.5 ml DDW and sample collected. Endotoxin level determined by LAL method.
6. Samples stored at 4° C. Concentration was determined by OD300.

Endotoxin removal
1. A 1 ml Q Sepharose FF column was packed.
2. The Q Sepharose column was washed with 10 ml 1.0 M NaOH followed by 10 ml $H_2O$.

3. The sample was loaded onto the column and washed with 2.5 ml water (flow through collected) followed by 10 ml 1% Triton x-114.
4. The column was washed with 10 ml water.
5. The sample was eluted with 5 ml of 0.5 M NaCl and 100 µl fractions collected.
6. The OD300 for each fraction determined and fractions containing the conjugate pooled.
   Note, for OM-LD2-#195, about ⅓ conjugate was in the flow through and a second Q Sepharose column with fresh resin was used.

Endotoxin Determination

Endotoxin level of the samples was determined by LAL assay.

Concentration
1. Sample was concentrated by Millipore Amicon Ultra (0.5 ml, cutoff 3 kDa). The Amicon ultra tubes were treated with 0.1 M NaOH before use.
2. To change buffer, samples were diluted 10 times with water during concentration.
3. Samples were stored at −80° C.

Quantitation

The concentration of LD2 and the number of residues were determined as described for LD1 using a standard curve of LD2 and optical density at 300 nm.

TABLE 7

Concentration of final products

| | LD2 Vs OM ratio | concentration | Amount (µl) | Endotoxin |
|---|---|---|---|---|
| OM-LD2-#195 | 100 | 13.3 mM | 45 µl | <1 ng/ml |
| OM-LD2-#197 | 60 | 21.3 mM | 45 µl | <1 ng/ml |

Example 13: Stimulation of Cytokine Release (IL-6) from PBMC by Loxorubine (LOX) Oxidized Mannan Conjugates The Loxorubine (LOX) derivative, LD1, was synthesised and conjugated to oxidized mannan (LD1-OM) as described above. The LOX derivative, LD1, incorporates a hydrazide linkage for conjugation to aldehyde residues of oxidized mannan and an ester linkage between the linker and the LOX. LD1 oxidized mannan conjugates were used to stimulate PBMCs isolated from human donors and IL-6 cytokine release measured by ELISA.

IL-6 assays were validated by testing the cytokine stimulatory effect of free LOX. As shown in Table 8, LOX was able to stimulate IL-6 release at a dose of 500 µM.

TABLE 8

Cytokine stimulation in PBMC by LOX

| | IL-6 (pg/ml) |
|---|---|
| Control unstimulated | 4.37 |
| LOX (500 µM) | 103.58 |
| LOX (500 µM) | 218.48 |

LD1 oxidized mannan conjugates with 2 different drug loadings (LD1-OM60 and LD1-OM120) were tested for IL-6 release by PBMCs at 6 and 24 hours. The LD1 oxidized mannan conjugates successfully stimulated IL-6 release by PBMC at both 6 and 24 hours (Table 9).

TABLE 9

Cytokine stimulation in PBMC by LOX oxidized mannan conjugates

| | $EC_{50}$ of IL-6 | | Amount IL-6 (pg/ml) | |
|---|---|---|---|---|
| Compound | 6 hr | 24 hr | 6 hr | 24 hr |
| LOX | / | / | / | 10 |
| LD1 | / | / | / | / |
| LD1-OM60 | 54.8 µM | 107.3 µM | 86 | 91 |
| LD1-OM120 | 74.8 µM | 146.7 µM | 105 | 111 |

"/" $EC_{50}$ defined as 50% of maximum cytokine release was not reached

Since free LOX did not achieve an EC50 value, the stimulation of IL-6 by the free LOX was compared to the conjugates using the amount of induced IL-6 (pg/ml) calculated from the IL-6 standard curve. Unconjugated LD1 did not stimulate IL-6. At the 24 hour time point, a dose of 500 µM LOX stimulated 10 pg/ml of IL-6 from PBMC whilst LD1 oxidized mannan conjugates with 60 and 120 residues stimulated 91 and 111 pg/ml IL-6, respectively. Similarly, at the 6 hour time point, LD1 conjugates induced 86 (60 residues) and 105 pg/ml (120 residues) IL-6 whilst free LOX failed to induce IL-6 from human PBMC.

The in vitro data clearly indicates that LD1 oxidized mannan conjugates are more effective than free LOX in inducing IL-6 secretion by PBMC. Clearly, the linkage of the LOX derivative, LD1, via an ester linkage to oxidized mannan can lead to more efficient stimulation of IL-6 from PBMC.

Example 14: GST-MUC1-VNTR (FP)

Conjugation

FP was conjugated to >1000 kDa oxidized mannan (>1000 MFP) as described previously (FIG. 45).

Immunogenicity of FP linked to >1000 kDa oxidized mannan

A MUC1-specific T cell line was generated by repeated stimulation with oxidized mannan-pTrc followed by sorting of MUC1-specific T cell and expansion. The ability of allogeneic DCs (BC16) pulsed with mannan conjugates to present MUC1 to the MUC1-specific T cell line was investigated. >1000 MFP was able to stimulate a MUC1-specific T cell line as shown in FIG. 46. >1000 MFP was more effective in stimulating the T cells than unconjugated FP at the 10 and 20 µg/ml doses.

Example 15: MUC1-VNTR (pTrc)

Conjugation

MUC1-VNTR (pTrc) was conjugated to >1000 kDa oxidized mannan (FIG. 47). Various amounts of pTrc was reacted with >1000 kDa oxidized mannan to ascertain optimal ratio. Conjugates with antigen:mannan ratio 1:40 (½×, lane 5) was used for immunogenicity studies.

Immunogenicity of MUC1-VNTR conjugated to >1000 kDa oxidized mannan

The in vitro immunogenicity of pTrc linked to >1000 kDa oxidized mannan was ascertained via a pTrc (MUC1) T cell line (from donor BC13) recalled with frozen MoDC (frozen, BC17K) (FIG. 48). As shown, pTrc was not effectively processed and presented to the MUC1-specific T cells. However, the >1000 kDa conjugate stimulated MUC1 specific T cells more effectively than unconjugated pTrc. Autologous MoDC pulsed with 20 µg/ml pTrc, >1000 kDa pTrc conjugates were used to recall MUC1 specific CD8 responses from a MUC1-specific T cell line derived from healthy donor BC17K (FIG. 49). >1000 kDa oxidized mannan conjugates efficiently stimulated intracellular IFNγ secretion in CD8 T cells compared to non-conjugated antigen.

Example 16: MART-1

Conjugation

Recombinant MART-1 protein was also linked to >1000 kDa oxidized mannan as described above (FIG. 50). Two types of conjugates were made with MART-1 protein, normal and reduced. The MART-1 protein has several cysteines and is therefore prone to air oxidation and aggregation. To facilitate conjugation, MART-1 was first reduced with DTT and then used in conjugation.

Immunogenicity of MART-1 >1000 kDa oxidized mannan conjugates

T cell priming and recall with peptides

PBMC and MoDC from 2 donors (BC28 and BC29) were used for priming with MART-1 and >1000 kDa oxidized mannan conjugates (20 µg/ml) as described in Example 1. After 1 stimulation, analog and native MART-1 peptide-specific T cell responses were measured using pulsed T2 cells (FIG. 51). BC28 donor T cells primed with >1000 kDa oxidized mannan-MART-1 efficiently responded to analog or native MART-1 peptides presented by T2 cells (FIG. 51). The BC28 and BC29 cultures were re-stimulated with the respective proteins and conjugates and tested for MART-1 protein-specific T cell responses using autologous pulsed MoDC as antigen presenting cells (FIG. 52). The pulsed MoDC were able to recall MART-1-specific CD8 T cell responses in BC28 and BC29 donor T cells primed with >1000 kDa oxidized mannan conjugate. The priming with MART-1 >1000 kDa oxidized mannan was more efficient in priming than unconjugated protein.

Example 17: In Vivo Immunogenicity Studies with a Mixture of Inactivated Influenza Virus (H1N1) and >1000 kDa Mannan Influenza Virus and Mice Egg-grown H1N1 (A/New Caledonia/20/1999) virus was purified by sucrose gradient, concentrated and inactivated with β-propiolactone, to create an influenza zonal pool (IZP) preparation which was kindly provided by Dr Ian Barr, Deputy Director of the WHO Collaborating Centre for Reference and Research on Influenza (North Melbourne, Australia). All mice were female BALB/c supplied by WEHI (Melbourne, Australia), and were 8-10 weeks of age at first immunization.

Generation of H1N1/>1000 kDa mannan mixes

H1N1/>1000 kDa mannan mixes were generated by diluting the H1N1 stock (from 2.7 mg/ml) and the >1000 kDa mannan stock (from 14 mg/ml) in sterile PBS, such that the desired dose of each was contained in 50 µl. The >1000 kDa mannan was isolated as described previously.

Immunisations

All immunisations were administered via the intranasal route. While completely anaesthetized (via methoxyfluorane inhalation) and held upright, approximately 5 µl drops were gently pipetted alternately into each nostril.

Serum and BAL (bronchio-alveolar-lavage/lung-wash) collection

Serum was collected by retro-orbital bleed as described. Before collection of BAL, mice were euthanised with a cocktail of ketamine and xylazil. Tissue was removed to expose the upper trachea, and a small incision made therein. With the aid of a blunt needle attached to a 1 ml syringe, 1 ml of PBS was gently flushed into the lungs, and drawn back out.

ELISA determination of antibody titre

ELISAs were performed using the HRP/TMB system. Plates were coated with whole inactivated H1N1 (A/New Caledonia/20/1999) at a concentration of 1 µg/ml. Total anti H1N1 IgG was detected using directly conjugated rat anti-mouse IgG-HRP (GE healthcare, product # RPN1231V) and IgG1, IgG2a and IgA were detected using biotin labeled primary antibodies from Pharmingen (product numbers 553441, 553388 and 556978), and secondary streptavidin-HRP from GE healthcare (product #346480). End-titre was measured as the last value in the titration to remain above the corresponding control value, where the control was calculated as the mean OD values+2SD of näive mouse sera (3-5 mice) at each titration point.

Groups of 4 BALB/c mice were immunized intranasally with H1N1 (1 µg), or H1N1 mixed with >1000 kDa mannan (100 µg) on days 0, 14. Ten-fourteen days after last immunization, mice serum and lung secretions were analysed for H1N1 specific IgG, IgG2a and IgA antibodies. As seen in FIG. 53, >1000 kDa mannan enhanced serum IgG1 responses. More importantly >1000 kDa mannan was effective in enhancing serum and lung H1N1-specific IgA.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

The present application claims priority from AU 2011904656 filed 9 Nov. 2011, the entire contents of which are incorporated herein by reference.

REFERENCES

Anumula, Analytical Biochemistry (1994) 220(2):275
Apostolopoulos et al., Br. J. Cancer (1993) 67:713
Apostolopoulos et al., Vaccine (2000) 18:3174
Apostolopoulos et al., Vaccine (2006) 24:3191
Barreto-Bergter and Gorin, Adv. Carbohydr. Chem. Biochem. (1983) 41:67
Cheever et al., Clin. Cancer Res (2009) 15:5323
Gorden et al., J. Immunol. (2005) 174:1259
Jeffrey et al., J: Med. Chem. (2005) 48:1344 Loveland et al., Clin. Cancer Res (2006) 123:869
Monsigny et al., Analytical Biochemistry (1988) 175:525
Pietersz et al., Current Medicinal Chemistry (2006) 13(14):1591
Sharma et al., Electrophoresis (2003) 24:2733-2739
Sun et al., Bioconjugate Chem. (2005) 16:1282
Sutcliffe et al., Science (1983) 219:660
Tang et al., Immunology (2007) 120(3):325
Tang et al., Vaccine (2008) 26(31):3827
Tang et al., Biomaterials (2009) 30(7):1389
Toki et al., J. Org. Chem. (2002) 67:1866
van der Bruggen, et al., Science (1991) 245:1643
Vinogradov et al., Carbohydr. Res. (1998) 307:177
Wang et al., Journal of Chromatographic Science (2007) 45(4):200

The invention claimed is:

1. An immunomodulatory compound comprising a carbohydrate polymer comprising mannose, and at least one immune modulator conjugated to the polymer, wherein the molecular weight of the polymer is greater than 1000 kDa.

2. The compound of claim 1, wherein the carbohydrate polymer is oxidized.

3. The compound of claim 2, wherein the carbohydrate polymer is further conjugated to at least one antigen or at least one nucleic acid encoding the at least one antigen.

4. The compound of claim 3, wherein the oxidized carbohydrate polymer included at least 150 aldehyde groups prior to conjugation to (A) the immune modulator, or (B) the at least one antigen or the nucleic acid encoding the at least one antigen, or (C) both (A) and (B).

5. The compound of claim 1, wherein the carbohydrate polymer is mannan.

6. The compound of claim 5, wherein the mannan is a yeast mannan.

7. The compound of claim 1, wherein the at least one immune modulator is a Toll-like receptor (TLR) agonist.

8. The compound of claim 7, wherein the at least one TLR agonist is selected from the group consisting of imidazoquinolines, guanosine analogs, deaza-adenosine analogs, and derivatives of any of the foregoing.

9. The compound of claim 7, wherein the TLR agonist is selected from the group consisting of Resiquimod, Loxoribine, Isatoribine, Imiquimod, and derivatives thereof.

10. The compound of claim 1, wherein each of the at least one immune modulator is conjugated to the carbohydrate polymer via a linker which comprises:
   i) a functional group conjugated to the carbohydrate polymer (type (i) group);
   ii) a functional group conjugated to the immune modulator (type (ii) group); and
   iii) a spacer between (i) and (ii);
and wherein each linker may be the same as or different from each other linker.

11. The compound of claim 10, wherein the type (i) group is a hydrazone and the type (ii) group is a carbamate.

12. The compound of claim 10, wherein the spacer is a polymer comprising 1 to 100 units of ethylene glycol, propylene gycol, or a combination of ethylene gycol and propylene gylcol.

13. The compound of claim 12, wherein the spacer is a polymer comprising 1-10 units of ethylene glycol or propylene glycol, 1-5 amino acid residues or 1-5 derivatives of amino acid residues, or a phenyl group containing a chemical moiety.

14. The compound of claim 10, wherein the linker comprises one or more cleavable groups selected from the group consisting of esters, carbamates, hydrazones, amides and acetals.

15. A compound of claim 1 represented by Formula V wherein the carbohydrate polymer is an oxidized mannan:

Formula V

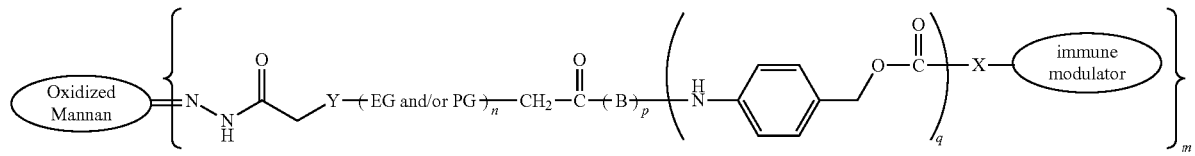

wherein,
  Y is —CH$_2$—CH$_2$—, —CH$_2$—, or —O—;
  EG is —CH$_2$—CH$_2$—O—;
  PG is —CH$_2$—CH$_2$—CH$_2$—O—;
  B is an amino acid residue or a derivative of an amino acid residue;
  n is an integer from 0 to 10;
  p is an integer from 1 to 5;
  q is 0 or 1;
  m is an integer equal to or greater than 1; and X is a group capable of binding to one or more hydroxyl groups or to a free amino group present in the immune modulator.

16. A compound of claim 15, wherein each amino acid residue is independently valine or lysine.

17. A compound of claim 15, wherein X is —R$^3$N(CH$_2$)$_2$NR$^4$C(O)— connected to the immune modulator via at least one hydroxyl group or free amino group present on the immune modulator, and R$^3$ and R$^4$ are each independently H or C$_{1-4}$alkyl.

18. A compound of claim 15, wherein the structure X-immune modulator includes the following functionality:

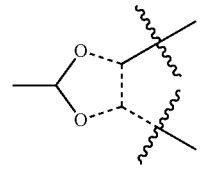

wherein the two oxygens and dotted bonds are part of the immune modulator.

19. A compound of claim 1, wherein the at least one immune modulator conjugated to the carbohydrate polymer is conjugated by reacting a terminal hydrazine group to form a hydrazone group and is selected from the group consisting of:

derivative 1

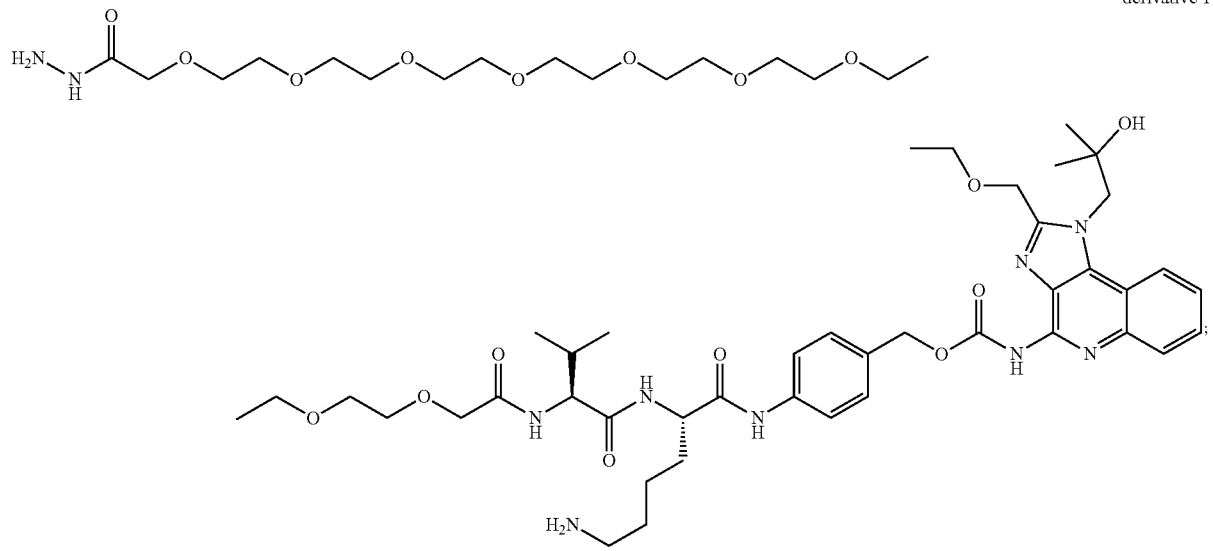

derivative 2

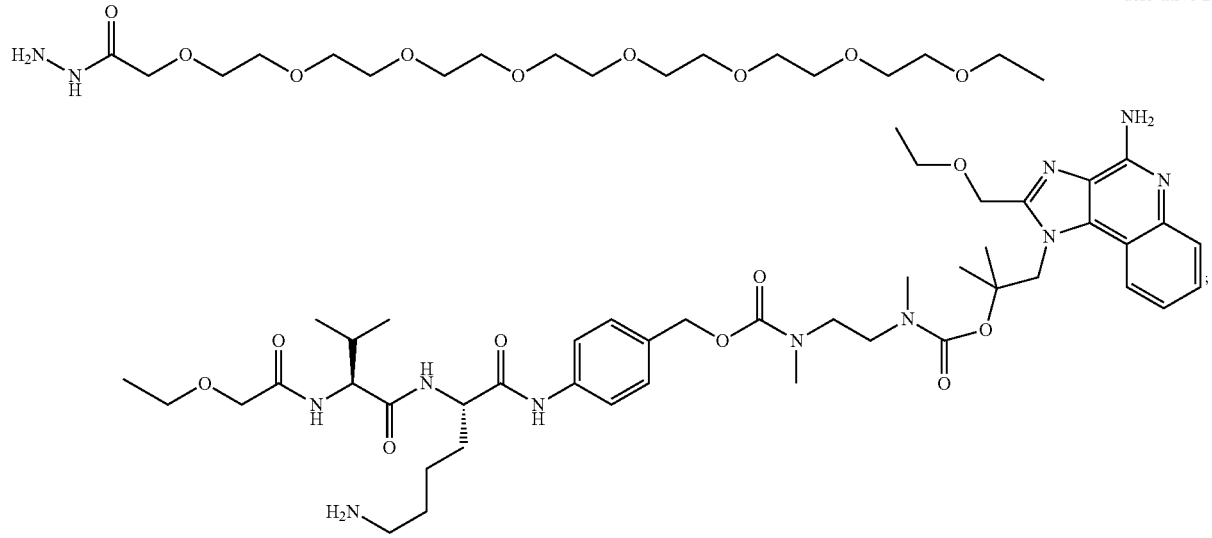

-continued
derivative 3
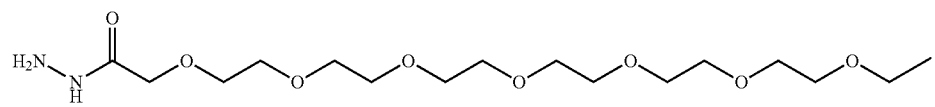
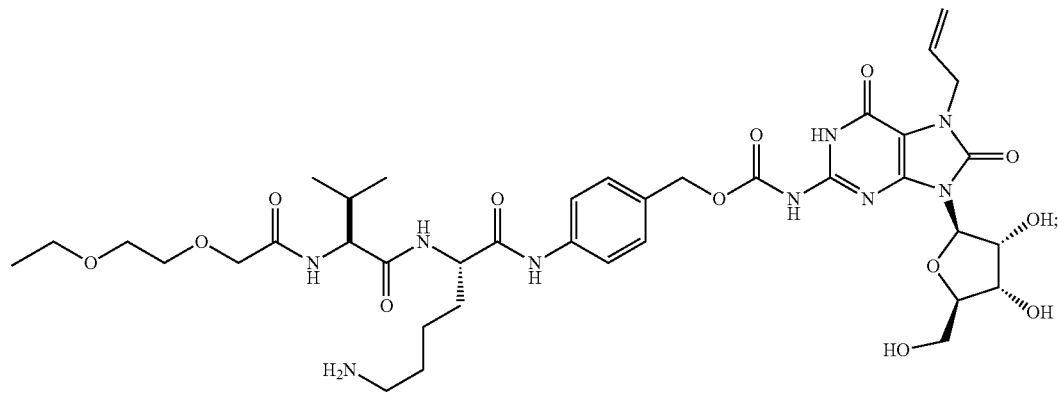
derivative 4
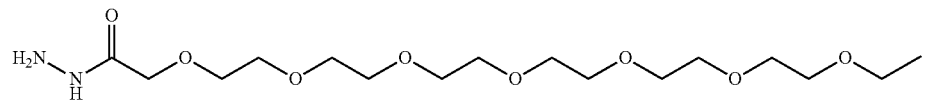
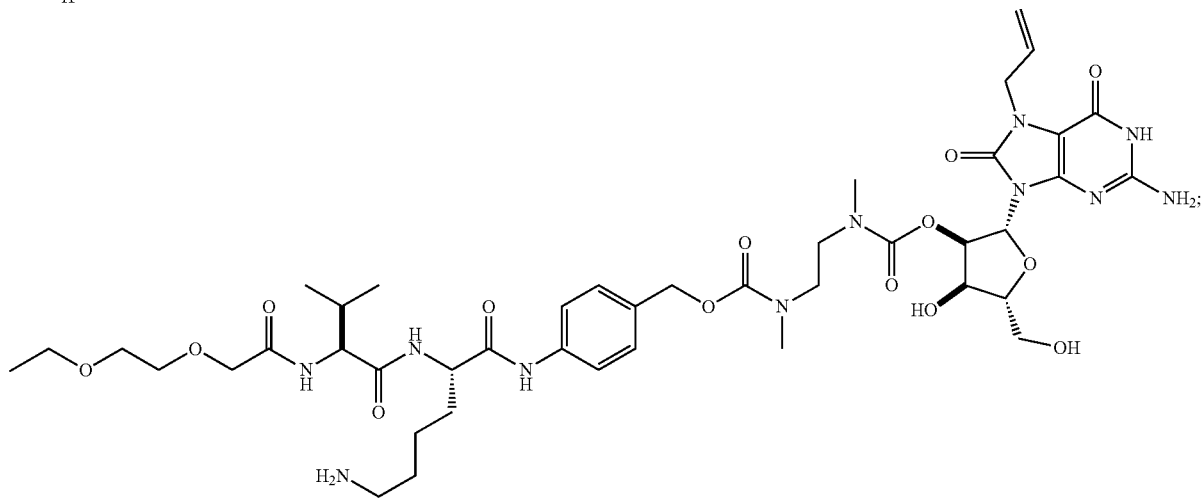
derivative 5
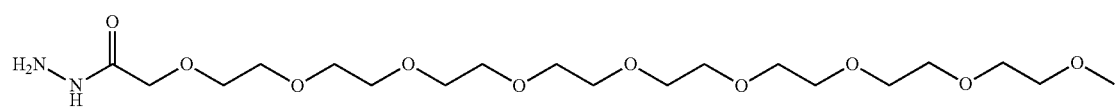
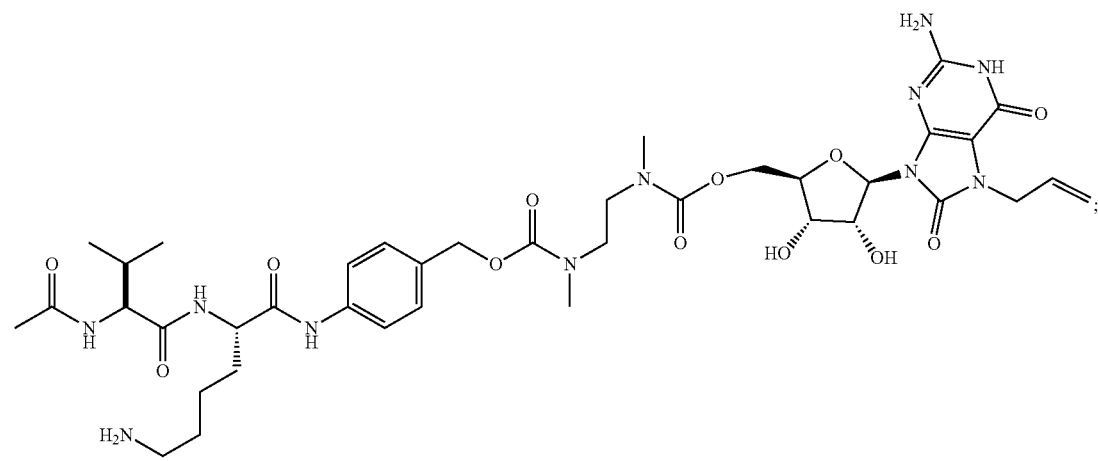

-continued
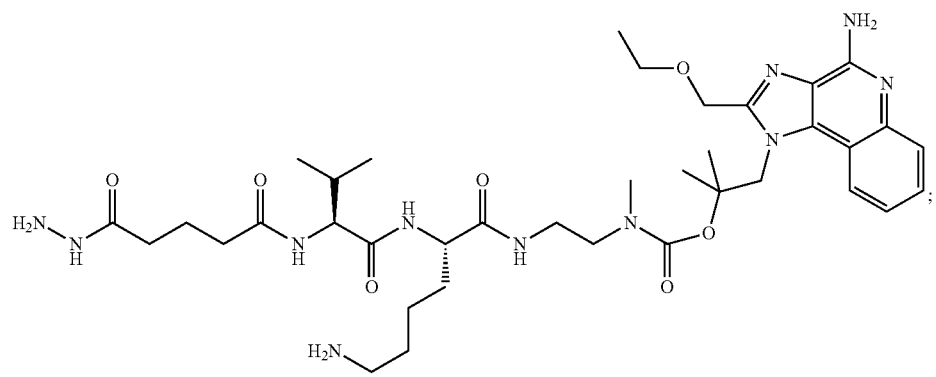
Rd2
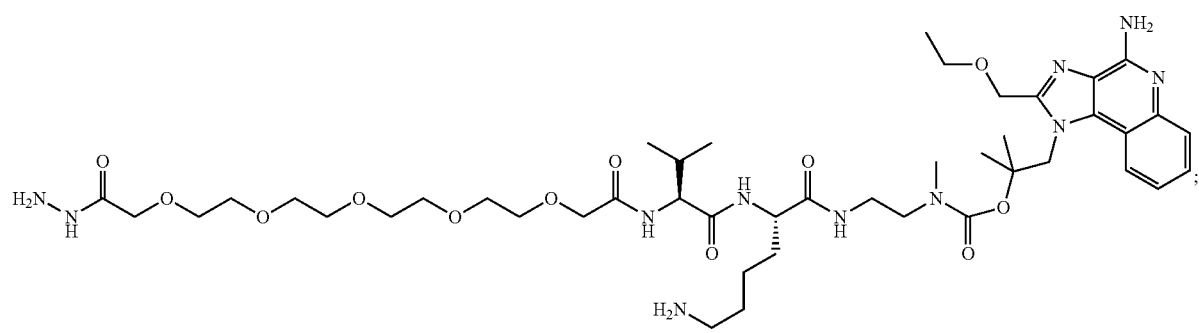
Rd3
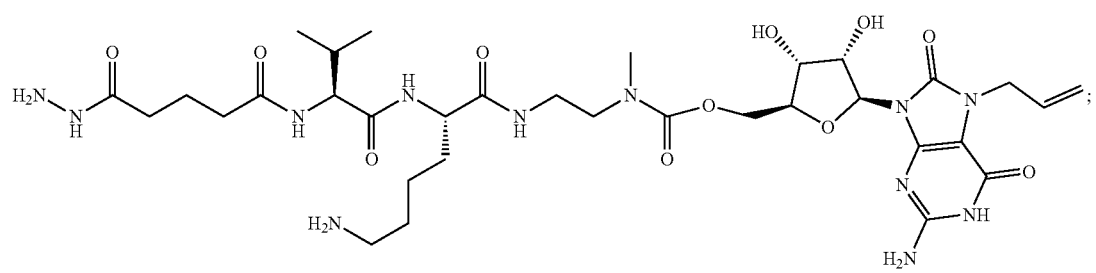
Ld2
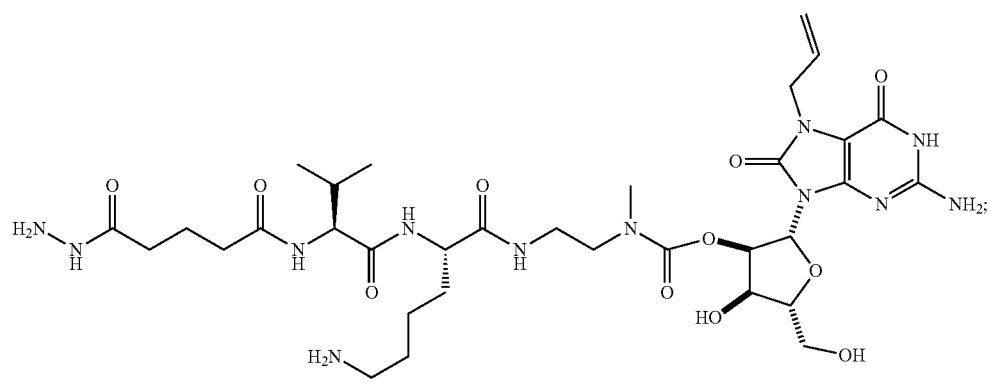
Ld3
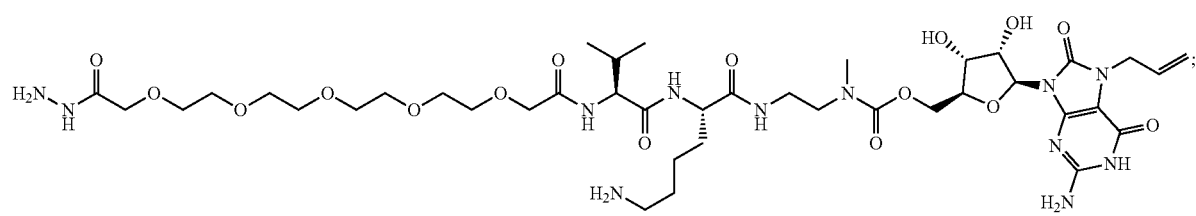
Ld4

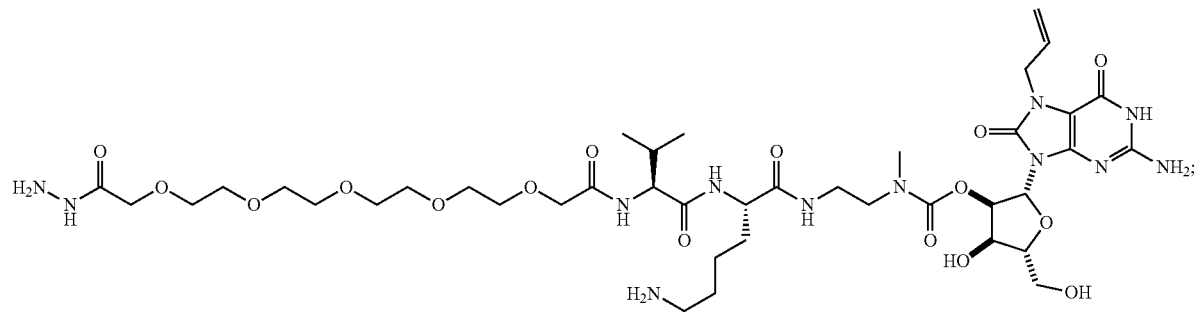
Ld5
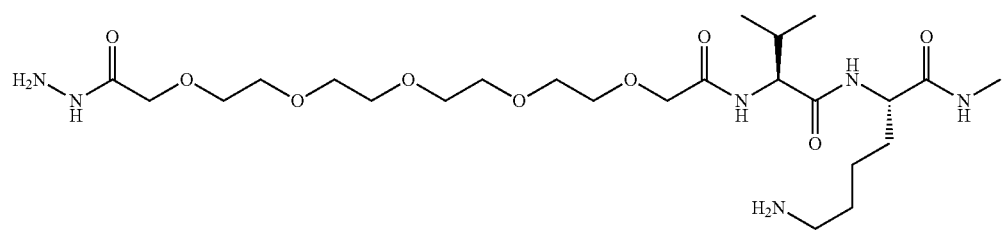
Ld8
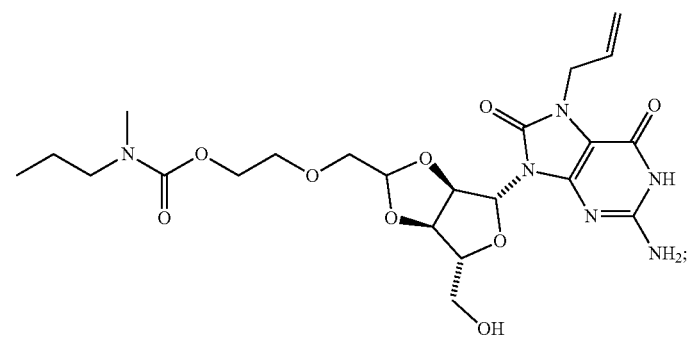
Ld9
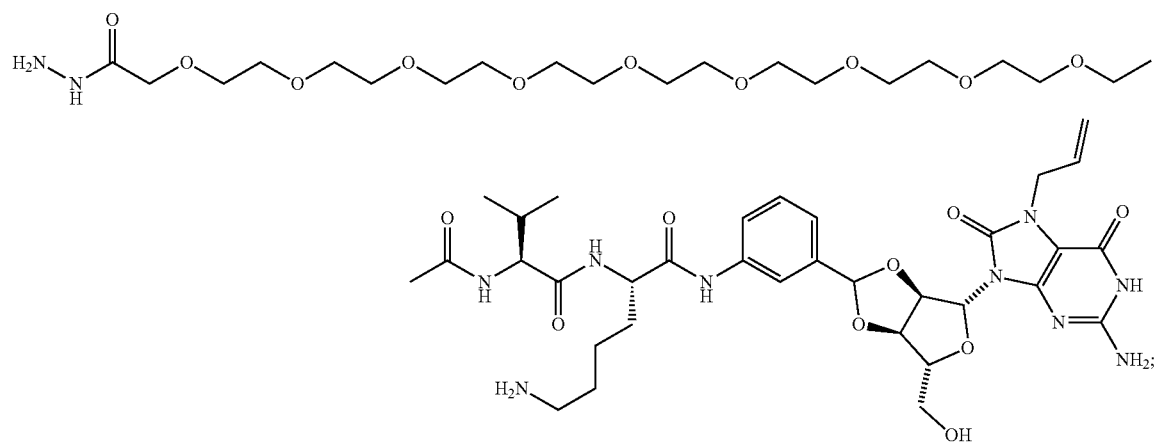
and
Ld10
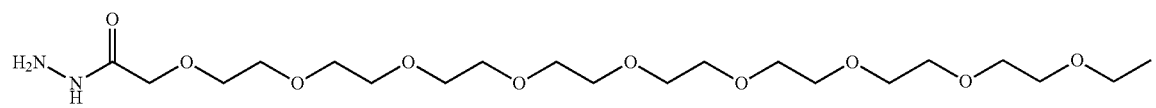

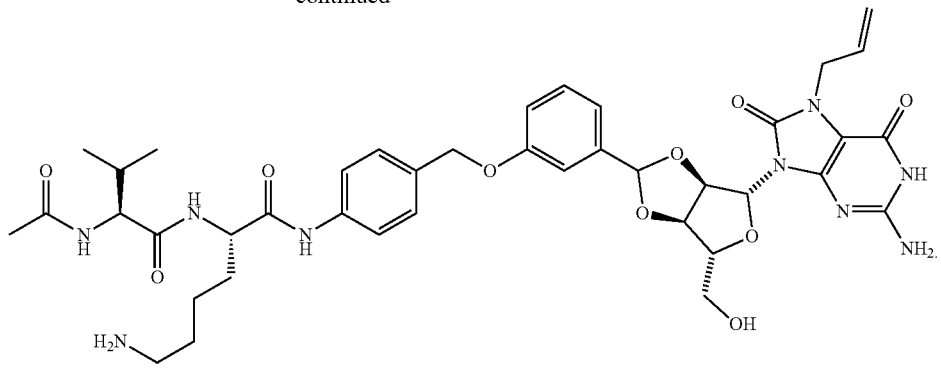

20. A compound of claim 1 represented by Formula VII wherein the carbohydrate polymer is an oxidized mannan:

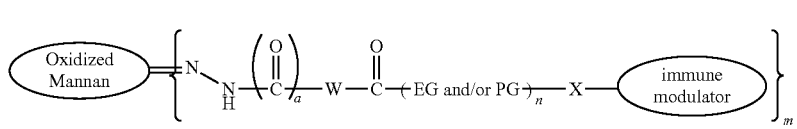

wherein
- W is a connecting group comprising an aromatic or heteroaromatic ring comprising 1 to 3 heteroatoms selected from the group consisting of N, O and S;
- EG is —$CH_2$—$CH_2$—O—;
- PG is —$CH_2$—$CH_2$—$CH_2$—O—;
- n is an integer from 0 to 10;
- a is 0 or 1;
- m is an integer equal to or greater than 1; and
- X is a group capable of binding to one or more hydroxyl groups or to a free amino group present in the immune modulator.

21. A compound of claim 20, wherein the structure X-immune modulator includes the following functionality:

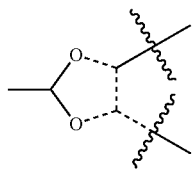

wherein the two oxygens and dotted bonds are part of the immune modulator.

22. A compound of claim 20, wherein X is selected from the group consisting of a bond and —$CH_2$—C(O)—.

23. A compound of claim 22, wherein W is a pyridine ring or a benzene ring.

24. A compound of claim 1, wherein the at least one immune modulator is selected from the group consisting of:

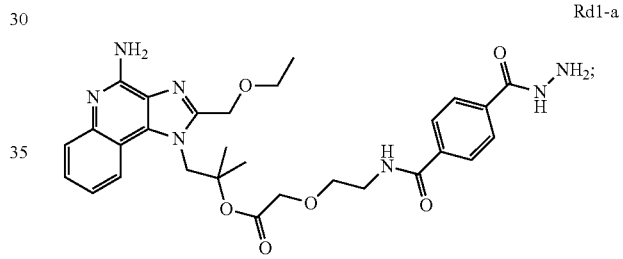

Rd1-a

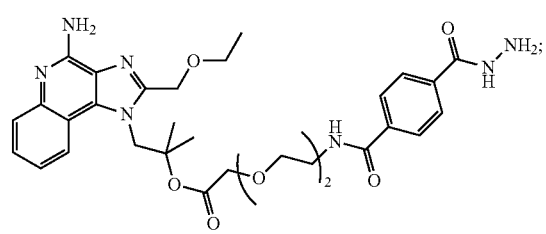

Rd1-b

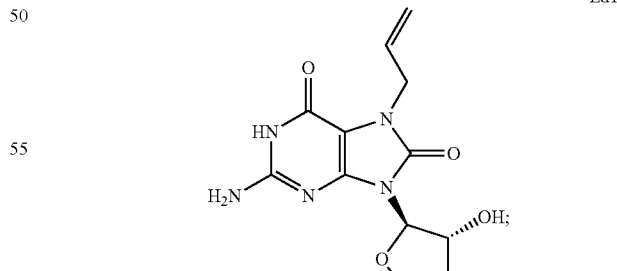

Ld1

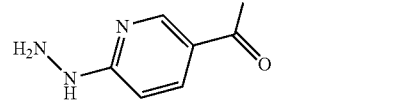

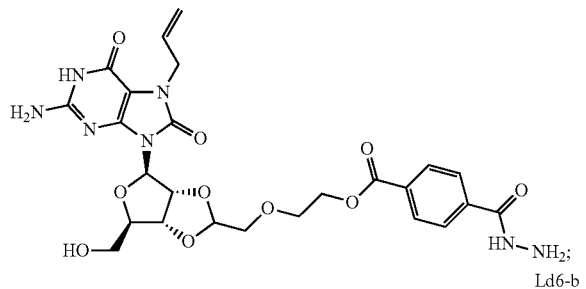
Ld6-a

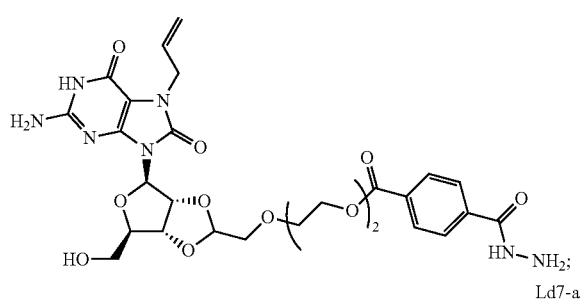
Ld6-b

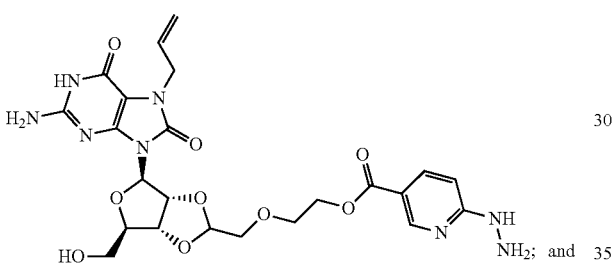
Ld7-a; and

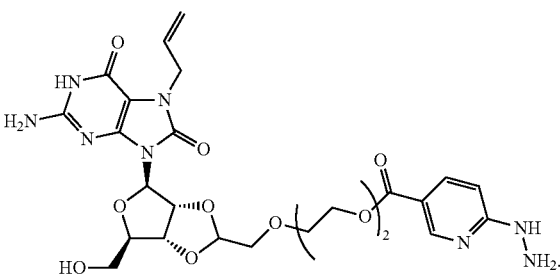
Ld7-b

25. An immunomodulatory composition comprising the compound of claim 1 and a pharmaceutically acceptable excipient.

26. A vaccine composition comprising the compound of claim 2.

27. The compound of claim 10, wherein each type of functional group is independently selected from the group consisting of aldehydes, ketones, formyls, hydrazines, hydrazides, amines, amides, carboxylic acids, alkynes, maleimides, sulphydryls and halogens.

28. The compound of claim 5, wherein the mannan is oxidised mannan.

* * * * *